US008765376B2

(12) United States Patent
Fischer et al.

(10) Patent No.: US 8,765,376 B2
(45) Date of Patent: Jul. 1, 2014

(54) METHODS FOR IDENTIFYING AND COMPOUNDS USEFUL FOR INCREASING THE FUNCTIONAL ACTIVITY AND CELL SURFACE EXPRESSION OF CF-ASSOCIATED MUTANT CYSTIC FIBROSIS TRANSMEMBRANE CONDUCTANCE REGULATOR

(75) Inventors: David Frederik Fischer, Leiden (NL); Richard Antonius Jozef Janssen, Leiden (NL); Marjet Roseboom, Haarlem (NL); Amelia Katie Scaffidi, Hillarys (AU); Michela Tessari, Leiden (NL)

(73) Assignee: Galapagos NV, Mechelen (BE)

( * ) Notice: Subject to any disclaimer, the term of this patent is extended or adjusted under 35 U.S.C. 154(b) by 268 days.

(21) Appl. No.: 13/063,333

(22) PCT Filed: Sep. 10, 2009

(86) PCT No.: PCT/EP2009/061732
§ 371 (c)(1),
(2), (4) Date: Jun. 6, 2011

(87) PCT Pub. No.: WO2010/029118
PCT Pub. Date: Mar. 18, 2010

(65) Prior Publication Data
US 2011/0245322 A1 Oct. 6, 2011

Related U.S. Application Data

(60) Provisional application No. 61/191,809, filed on Sep. 11, 2008.

(51) Int. Cl.
*A61K 31/70* (2006.01)
*A61K 31/7088* (2006.01)
*A61P 1/16* (2006.01)
*C12N 15/11* (2006.01)
*G01N 33/68* (2006.01)
*C07H 21/02* (2006.01)
*C12Q 1/68* (2006.01)
*C07H 21/04* (2006.01)

(52) U.S. Cl.
CPC .......... *C12N 15/111* (2013.01); *G01N 33/6872* (2013.01); *C12N 2310/14* (2013.01); *C12N 2330/31* (2013.01); *G01N 2800/382* (2013.01)
USPC ......... 435/6.11; 435/7.1; 435/7.21; 536/24.5; 514/1.1; 514/44 A; 514/1.8

(58) Field of Classification Search
None
See application file for complete search history.

(56) References Cited

U.S. PATENT DOCUMENTS

2007/0213357 A1 9/2007 Becq et al.

FOREIGN PATENT DOCUMENTS

WO 02066654 8/2002
WO 2007002972 1/2007

OTHER PUBLICATIONS

Antonin, et al., A Snare complex mediating fusion of late endosomes defines conserved properties of SNARE structure and function, Embo J., 2000; 19:6543-64.
Bilan, et al., Syntaxin 8 impairs trafficking of cystic fibrosis transmembrane conductance regulator CFTR and inhibits its channel activity, J Cell Sci, 2004; 117: 1923-35.
Buckley, et al., Tissue- and gender-specific mRNA expression of UDP-glucuronosyltransferases (UGATs) in mice, Drug metabolism and Disposition, 2007; 35(1): 121-127.
Carolan, et al., Up-regulation of expression of the ubiquitin carboxyl-terminal hydrolase L1 gene inhuman airway epithelium of cigarette smokers, Cancer Res., 2006; 66: 10729-40.
Cheng, et al., Defective intracellular transport and processing of CFTR is a molecular basis of most cycstic fibrosis, Cell., 1990; 63: 827-34.
Denning, et al., Processing of mutant cystic fibrosis transmembrane conductance regulator is temperature-sensitive, Nature, 1992; 358: 761-4.
Devor, et al., Pharmacological modulation of ion transport across wild-type and DeltaF508 CFTR-expressing human bronchial epithelia, Am J Physiol Cell Physiol, 2000; 279: C461-479.
Fischer, et al., Identification of novel drug targets to treat cystic fibrosis using adenoviral knock-down technology, Ped Pulmonol., 2006; 41: Suppl. 29, p. 209.
Galietta, et al., Green fluorescent protein-based halide indicators with improved chloride and iodide affinities, FEBS Lett., 2001a; 499: 220-4.
Galietta, et al., Cell-based assay for high-throughput quantitative screening of CFTR chloride transport agonists, 2001b; 281: C1734-42.
Gruenert, et al., Established cell lines used in cystic fibrosis research, J Cyst Fibros., 2004; 3S2:191-6.
Guggino, et al., New insights into cystic fibrosis: molecular switches that regulate CFTR, Nat Rev Mol Cell Biol., 2006; 7: 426-36.
Hwang, et al., Genistein potentiates wild-type and delta F508-CFTR channel activity, Am J. Physiol, 1997; 273: C988-98.
Lambert, et al., Control of Cystic Fibrosis Transmembrane Conductance Regulator Expression by BAP31, J Biol Chem., 2001; 276: 20340-20345.
Li, et al., Transepithelial electrical measurements with the Ussing chamber, J Cyst Fibros, 3S2: 123-6 , 2004.
Ma, et al., Rapid determination of adenoviral vector titers by quantitative real-time PCR, J Virol Methods, 2001; 93: 181-8.
Ma, et al Thiazolidinone CFTR inhibitor identified by high-throughput screening blocks cholera toxin-inducsed intestinal fluid secretion, J Clin. Invest., 2002; 110: 1651-1658.

(Continued)

*Primary Examiner* — Sean McGarry
(74) *Attorney, Agent, or Firm* — Klauber & Jackson, LLC

(57) ABSTRACT

The present invention relates to agents, and methods for identifying compounds, which agents and compounds result in the modulation of cellular trafficking of proteins in particular that of CF-associated mutant Cystic Fibrosis Transmembrane Conductance Regulator (CFTR). In addition, the invention relates to compositions and methods for the use thereof in treating conditions that are characterized by an ER-associated protein misfolding and abnormal cellular trafficking of disease-associated proteins, including cystic fibrosis (CF).

10 Claims, 5 Drawing Sheets

(56) References Cited

OTHER PUBLICATIONS

Myerburg, et al., Airway surface liquid volume regulates ENaC by altering the serine protease-protease inhibitor balance: a mechanism for sodium hyperasbsorption in cystic fibrosis, J. Biol. Chem., 2006; 281: 27942-27949.

Myerburg, et al., Prostasin expression is regulated by airway surface liquid volume and is increased in cycstic fibrosis, Am J Physiol Lung Mol Physiol, 2008; 294: L932-941.

Prince, et al., Rapid endocytosis of the cystic fibrosis transmembrane conductance regulator chloride channel, Proc Natl Acad Sci USA, 1994; 91: 5192-6.

Quinton, Cystic fibrosis: a disease in electrolyte transport, Faseb J., 1990; 4: 2709-17.

Riordan, et al., Identification of the cystic fibrosis gene: cloning and characterization of complementary DNA, Science, 1989; 245: 1066-73.

Rowe, et al., Cystic Fibrosis, N Engl J Med., 2005; 352: 1992-2001.

Sheppard, et al., Mutations in CFTR associated with mild-disease-form Cl—channels with altered pore properties, Nature, 1993; 362: 160-164.

Thoreau, et al., Molecular cloning, expression analysis and chromosomal localization of human syntaxin 8 (STX8), Biochem Biophys Res Commun., 1999; 257: 577-83.

Ulloa-Aguirre, et al., Pharmacologic rescue of conformationally-defective proteins: implications for the treatment of human disease, Traffic, 2004; 5:821-37.

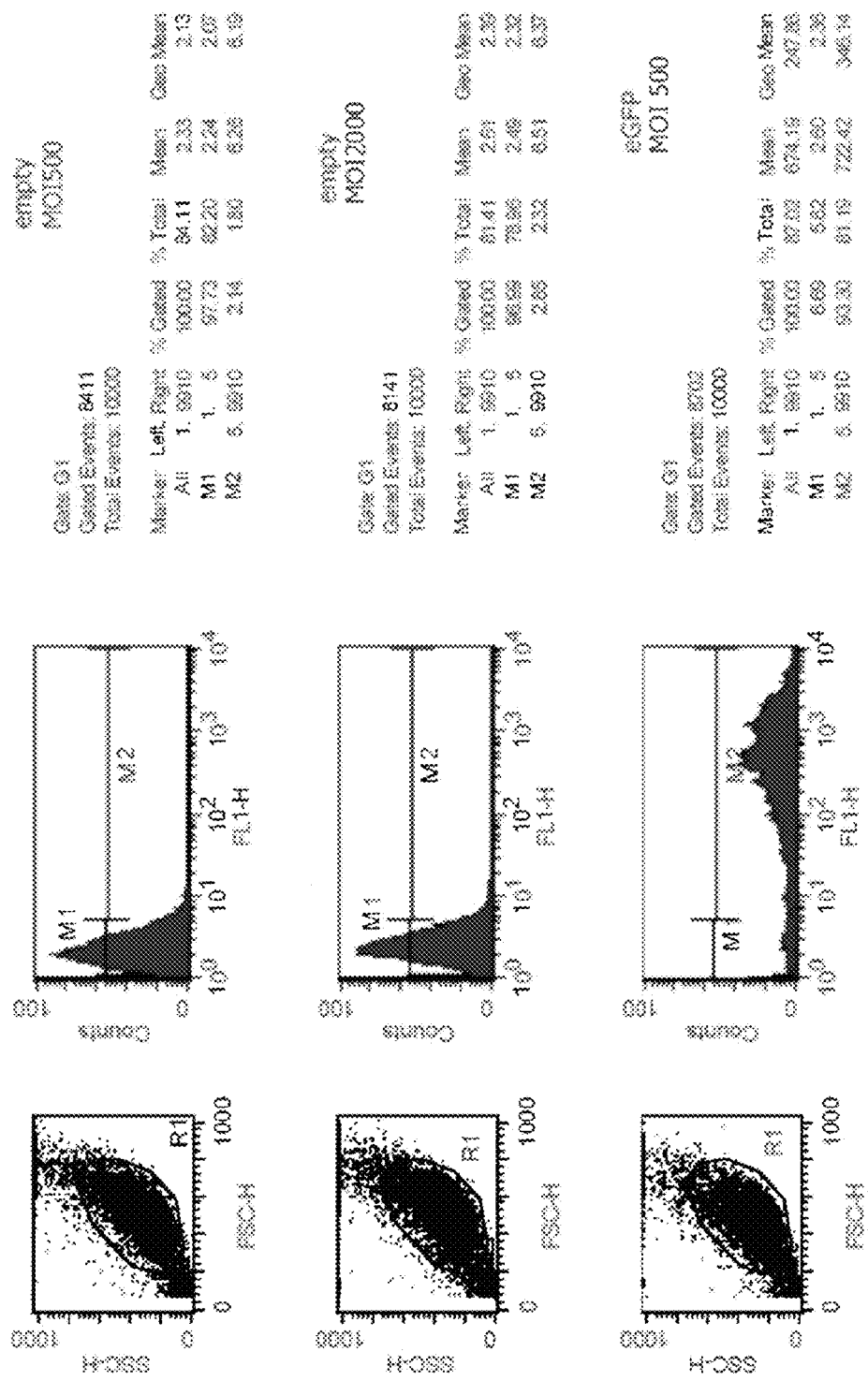

SEQUENCE LISTING

<160> NUMBER OF SEQ ID NOS: 103

<210> SEQ ID NO 1
<211> LENGTH: 2824
<212> TYPE: DNA
<213> ORGANISM: Homo sapiens

<400> SEQUENCE: 1

```
daacgaacag aagggcgaga gaattggcag gatccgtctc ctacctcttc ctaggcccac    60
agccagtgcc tttggagtac tgaggcgcgc acagagtcct tagcccggcg cagggcgcgc   120
agcccaggct gagatccgct gcttctgtgg aagtgagcat ggttgggcag cgggtgctgc   180
ttctagtggc cttccttctt tctggggtcc tgctctcaga ggctgccaaa tcctgacaa    240
tatctacact gggtggaagc cattacctac tgttggaccg ggtgtctcag attcttcaag   300
agcatggtca taatgtgact atgcttcatc agagtggaaa gttttttgatc ccagatatta  360
aagaggagga aaaatcatac caagttatca ggtggttttc acctgaagat catcaaaaaa   420
gaattaagaa gcattttgat agctacatag aaacagcatt ggatggcaga aaagaatctg   480
aagcccttgt aaagctaatg gaaatatttg ggactcaatg tagttatttg ctaagcagaa   540
aggatataat ggattcctta aagaatgaga actgtgatct ggtatttgtt gaagcatttg   600
atttctgttc tttcctgatt gctgagaagc ttgtgaaacc atttgtggcc attcttccca   660
ccacattcgg ctctttggat tttgggctac caagccccctt gtcttatgtt ccagtattcc   720
cttccttgct gactgatcac atggacttct ggggccgagt gaagaatttt ctgatgttct   780
ttagtttctc caggagccaa tgggacatgc agtctacatt tgacaacacc atcaaggagc   840
atttcccaga aggctctagg ccagttttgt ctcatcttct actgaaagca gagttgtggt   900
ttgttaactc tgattttgcc tttgatttg cccggcccct gcttcccaac actgtttata    960
ttggaggctt gatggaaaaa cctattaaac cagtaccaca agacttggac aacttcattg  1020
ccaactttgg ggatgcaggg tttgtccttg tggcctttgg ctccatgttg aacacccatc  1080
agtcccagga agtcctcaag aagatgcaca atgcctttgc ccacctccct caaggagtga  1140
tatggacatg tcagagttct cattggccca gagatgttca tttggccaca aatgtgaaaa  1200
ttgtggactg gcttcctcag agtgacctcc tggctcaccc cagcatccgt ctttttgtca  1260
ctcatggtgg gcagaacagc gtaatggaga ccatccgtca tggtgtgccc atggtgggat  1320
taccagtcaa tggagaccag catggaaaca tggtccgagt agtagccaaa aattatggtg  1380
tctctatccg gttgaatcag gtcacagccg acacactgac acttacaatg aaacaagtca  1440
tagaagacaa gaggtacaag tcggcagtgg tggcagccag tgtcatcctg cactctcagc  1500
ccctgagccc cgcacagcgg ctggtgggct ggatcgacca catcctccag actgggggag  1560
cgacgcacct caagcctat gtcttccagc agccttggca tgagcagtac ctcattgatg   1620
tcttttgtgtt tctgctgggg ctcactctgg gcactatgtg gctttgtggg aagctgctgg  1680
gtgtggtggc caggtggctg cgtggggcca ggaaggtgaa gaagacatga ggctaggtgt  1740
agccttgggt gaggggaggg catccctggt cctttgaagg ttctccccac ccagcacac    1800
gccaccccctc tgttctctct tcagctccac ccgccactga tcctgcaact tgcttctttc  1860
tattctctgc ctctgtttag aaatcttcac acaccactga ggcttcttga cttgcccctt  1920
gtgacttgaa accccagctc agatacaaat tttcacctgc cagccctgcc tcctccttc    1980
tccctttttcc tagacacagg actctgacaa cttcatcctc cttgtttaga tgacttccca  2040
gtttccagtc cccattctc cttctatcac ttttcataaa aaaactcagg aaatatttga    2100
catatcttcc atttcaaatt cttccatttt atgcagatat cttgcccttc ctataagctc   2160
tcctcaaagc tcaggaaacc tggtctgctc tcctgcattt agggaaggag aaccctgcc    2220
aagacctttg ctcactgcct gagacccctt ccttagagag cacctccttt gctggtcaga  2280
```

```
catggagcct gcagttggtc acagatgata ctgctttatt tcagttttta cagttgcctt    2340
cttaagattc ccgtcttata aatggagtac agggaacctc aagtagtgaa gtggaaatcc    2400
atgtgtaagg ctttgtggct tcaggtacca gtggctaagg tagttttaaa gactttgttg    2460
attttagaaa aagtccatct tccatcccct acatggcagt taatacccct ctatatggta    2520
aaaccttaga gattacctta atctgctagg aacagaagca agaaaaacca tggcgtaaac    2580 accccagag ttttgttca tttgtttcat ctttcttgat aaagcccgaa ggtagcccat    2640
tcagggctgt tgtggttggt tgctccatca tgtcatcaat agcccatatc ttttcttttt    2700
tatcttcctt agtataacac caaactacct ctctgatagc tggtgttcat gaaatatttt    2760
accttcaaat gattgtacct ttttatttgc tttagagttc tgaaataaaa tgaaattcca    2820
ctgt                                                                 2824
```

<210> SEQ ID NO 2
<211> LENGTH: 2341
<212> TYPE: DNA
<213> ORGANISM: Homo sapiens

<400> SEQUENCE: 2

```
agtgcctttg gcgcactgag gtgcacaggg tcccttagcc gggcgcaggg cgcgcagccc      60
aggctgagat ccgcggcttc cgtagaagtg agcatggctg ggcagcgagt gcttcttcta     120
gtgggcttcc ttctccctgg ggtcctgctc tcagaggctc ccaaaatcct gacaatatct     180
acagtaggtg gaagccatta tctactgatg gaccgggttt ctcagattct tcaagatcac     240
ggtcataatg tcaccatgct taaccacaaa gaggtccttt tatgccaga ttttaaaaag     300 gaagaaaaat catatcaagt tatcagttgg cttgcacctg aagatcatca aagagaattt     360
aaaaagagtt ttgatttctt tctggaagaa actttaggtg gcagaggaaa atttgaaaac     420
ttattaaatg ttctagaata cttggcgttg cagtgcagtc atttttttaaa tagaaaggat     480 atcatggatt cctaaagaa tgagaacttc gacatggtga tagttgaaac ttttgactac     540
tgtcctttcc tgattgctga gaagcttggg aagccatttg tggccattct ttccacttca     600
ttcggctctt tggaatttgg gctaccaatc cccttgtctt atgttccagt attccgttcc     660
ttgctgactg atcacatgga cttctggggc cgagtgaaga ttttctgat gttctttagt     720 ttctgcagga ggcaacagca catgcagtct acatttgaca acaccatcaa ggaacatttc     780
acagaaggct ctaggccagt tttgtctcat cttctactga aagcagagtt gtggttcatt     840
aactctgact ttgcctttga ttttgctcga cctctgcttc ccaacactgt ttatgttgga     900
ggcttgatgg aaaaacctat taaaccagta ccacaagact tggagaactt cattgccaag     960
tttgaggact ctggttttgt ccttgtgacc ttgggctcca tggtaacac ctgtcagaat    1020 ccggaaatct tcaaggagat gaacaatgcc tttgctcacc taccccaagg ggtgatatgg    1080
aagtgtcagt gttctcattg gcccaaagat gtccacctgg ctgcaaatgt gaaaattgtg    1140
gactggcttc ctcagagtga cctcctggct cacccaagca tccgtctgtt tgtcacccac    1200
ggcgggcaga atagcataat ggaggccatc cagcatggtg tgcccatggt ggggatccct    1260
ctctttggag accagcctga aaacatggtc cgagtagaag ccaaaaagtt tggtgttttct    1320 attcagttaa agaagctcaa ggcagagaca ttggctctta agatgaaaca aatcatggaa    1380
gacaagagat acaagtccgc ggcagtggct gccagtgtca tcctgcgctc ccacccgctc    1440
agccccacac agcggctggt gggctggatt gaccacgtcc tccagacagg gggcgcgacg    1500 caccctcaagc cctatgtctt tcagcagccc tggcatgagc agtacctgct cgacgttttt    1560
```

| | |
|---|---|
| gtgtttctgc tgggctcac tctggggact ctatggcttt gtgggaagct gctgggcatg | 1620 |
| gctgtctggt ggctgcgtgg ggccagaaag gtgaaggaga cataaggcca ggtgcagcct | 1680 |
| tggcggggtc tgtttggtgg gcgatgtcac catttctagg gagcttccca ctagttctgg | 1740 |
| cagccccatt ctctagtcct tctagttatc tcctgttttc ttgaagaaca ggaaaaatgg | 1800 |
| ccaaaaatca tcctttccac ttgctaattt tgctacaaat tcatccttac tagctcctgc | 1860 |
| ctgctagcag aattctttcc agtcctcttg tcctcctttg tttgccatca gcaagggcta | 1920 |
| tgctgtgatt ctgtctctga gtgacttgga ccactgaccc tcagatttcc agccttaaaa | 1980 |
| tccaccttcc ttctcatgcg cctctccgaa tcacaccctg actcttccag cctccatgtc | 2040 |
| cagacctagt cagcctctct cactcctgcc cctactatct atcatggaat aacatccaag | 2100 |
| aaagacacct tgcatattct ttcagtttct gttttgttct cccacatatt ctcttcaatg | 2160 |
| ctcaggaagc ctgccctgtg cttgagagtt cagggccgga cacaggctca caggtctcca | 2220 |
| cattgggtcc ctgtctctgg tgcccacagt gagctccttc ttggctgagc aggcatggag | 2280 |
| actgtaggtt tccagatttc ctgaaaaata aaagtttaca gcgttatctc tccccaacct | 2340 |
| c | 2341 |

```
<210> SEQ ID NO 3
<211> LENGTH: 1968
<212> TYPE: DNA
<213> ORGANISM: Homo sapiens

<400> SEQUENCE: 3
```

| | |
|---|---|
| gaggaggagg aggagatgac tggggagcgg gagctcgaga atactgccca gttactctag | 60 |
| cgcgccaggc cgaaccgcag cttcttggct taggtacttc tactcacagc ggccgattcc | 120 |
| gaggccaact ccagcaatgg cttttgcaaa tctgcggaaa gtgctcatca gtgacagcct | 180 |
| ggacccttgc tgccggaaga tcttgcaaga tggaggctg caggtggtgg aaaagcagaa | 240 |
| ccttagcaaa gaggagctga tagcggagct gcaggactgt gaaggcctta ttgttcgctc | 300 |
| tgccaccaag gtgaccgctg atgtcatcaa cgcagctgag aaactccagg tggtgggcag | 360 |
| ggctggcaca ggtgtggaca atgtggatct ggaggccgca acaaggaagg gcatcttggt | 420 |
| tatgaacacc cccaatggga acagcctcag tgccgcagaa ctcacttgtg aatgatcat | 480 |
| gtgcctggcc aggcagattc cccaggcgac ggcttcgatg aaggacggca aatgggagcg | 540 |
| gaagaagttc atgggaacag agctgaatgg aaagaccctg ggaattcttg gcctgggcag | 600 |
| gattgggaga gaggtagcta cccggatgca gtcctttggg atgaagacta tagggtatga | 660 |
| ccccatcatt tccccagagg tctcggcctc ctttggtgtt cagcagctgc cctggagga | 720 |
| gatctggcct ctctgtgatt tcatcactgt gcacactcct ctcctgccct ccacgacagg | 780 |
| cttgctgaat gacaacacct tgcccagtg caagaagggg gtgcgtgtgg tgaactgtgc | 840 |
| ccgtggaggg atcgtggacg aaggcgccct gctccgggcc ctgcagtctg ccagtgtgc | 900 |
| cggggctgca ctggacgtgt ttacggaaga gccgccacgg gaccgggcct tggtggacca | 960 |
| tgagaatgtc atcagctgtc cccacctggg tgccagcacc aaggaggctc agagccgctg | 1020 |
| tgggaggaa attgctgttc agttcgtgga catggtgaag gggaaatctc tcacgggggt | 1080 |
| tgtgaatgcc caggccctta ccagtgcctt ctctccacac accaagcctt ggattggtct | 1140 |
| ggcagaagct ctggggacac tgatgcgagc ctggctggg tccccaaag ggaccatcca | 1200 |
| ggtgataaca cagggaacat ccctgaagaa tgctgggaac tgcctaagcc ccgcagtcat | 1260 |

-continued

```
tgtcggcctc ctgaaagagg cttccaagca ggcggatgtg aacttggtga acgctaagct    1320
gctggtgaaa gaggctggcc tcaatgtcac cacctcccac agccctgctg caccagggga    1380
gcaaggcttc ggggaatgcc tcctggccgt ggccctggca ggcgcccctt accaggctgt    1440
gggcttggtc caaggcacta cacctgtact gcagggctc aatggagctg tcttcaggcc     1500
agaagtgcct ctccgcaggg acctgcccct gctcctattc cggactcaga cctctgaccc    1560
tgcaatgctg cctaccatga ttggcctcct ggcagaggca ggcgtgcggc tgctgtccta    1620
ccagacttca ctggtgtcag atggggagac ctggcacgtc atgggcatct cctccttgct    1680
gcccagcctg gaagcgtgga agcagcatgt gactgaagcc ttccagttcc acttctaacc    1740
ttggagctca ctggtccctg cctctggggc ttttctgaag aaacccaccc actgtgatca    1800
atagggagag aaaatccaca ttcttgggct gaacgcgggc ctctgacact gcttacactg    1860
cactctgacc ctgtagtaca gcaataaccg tctaataaag agcctacccc caaaaaaaaa    1920
aaaaaaaaaa aaaaaaaaaa aaaaaaaaaa aaaaaaaaa aaaaaaaa                 1968

<210> SEQ ID NO 4
<211> LENGTH: 2720
<212> TYPE: DNA
<213> ORGANISM: Homo sapiens

<400> SEQUENCE: 4
agaggggcgg gagctctggc tcaggtaaaa actctttctt cggctcgcga gctgagagga      60
gcaggtagag gggcagaggc gggactgtcg tctggggggag ccgcccagga ggctcctcag    120
gccgacccca gaccctggct ggccaggatg aagtatctcc ggcaccggcg gcccaatgcc    180
accctcattc tggccatcgg cgctttcacc ctcctcctct tcagtctgct agtgtcacca    240
cccacctgca aggtccagga gcagccaccg gcgatcccg aggccctggc ctggcccact     300
ccacccaccc gcccagcccc ggccccgtgc catgccaaca cctctatggt cacccacccg    360
gacttcgcca cgcagccgca gcacgttcag aacttcctcc tgtacagaca ctgccgccac    420
tttccctgc tgcaggacgt gccccctct aagtgcgcgc agccggtctt cctgctgctg      480
gtgatcaagt cctcccctag caactatgtg cgccgcgagc tgctgcggcg cacgtggggc    540
cgcgagcgca aggtacgggg tttgcagctg cgcctcctct tcctggtggg cacagcctcc    600
aacccgcacg aggcccgcaa ggtcaaccgg ctgctggagc tggaggcaca gactcacgga    660
gacatcctgc agtgggactt ccacgactcc ttcttcaacc tcacgctcaa gcaggtcctg    720
ttcttacagt ggcaggagac aaggtgcgcc aacgccagct tcgtgctcaa cggggatgat    780
gacgtctttg cacacacaga caacatggtc ttctacctgc aggaccatga ccctggccgc    840
cacctcttcg tggggcaact gatccaaaac gtgggcccca tccgggcttt ttggagcaag    900
tactatgtgc cagaggtggt gactcagaat gagcggtacc cacctattg tgggggtggt    960
ggcttcttgc tgtcccgctt cacggccgct gccctgcgcc gtgctgccca tgtcttggac   1020
atcttcccca ttgatgatgt cttcctgggt atgtgtctgg agcttgaggg actgaagcct   1080
gcctcccaca gcggcatccg cacgtctggc gtgcgggctc atcgcaacg cctgtcctcc    1140
tttgaccccct gcttctaccg agacctgctg ctggtgcacc gcttcctacc ttatgagatg   1200
ctgctcatgt gggatgcgct gaaccagccc aacctcacct gcggcaatca gacacagatc   1260
tactgagtca gcatcagggt ccccagcctc tgggctcctg tttccatagg aagggggcgac   1320
accttcctcc caggaagctg agacctttgt ggtctgagca aagggagtg ccaggaaggg    1380
tttgaggttt gatgagtgaa tattctggct ggcgaactcc tacacatcct tcaaaaccca   1440
```

```
cctggtactg ttccagcatc ttccctggat ggctggagga actccagaaa atatccatct    1500 tcttttgtg  gctgctaatg gcagaagtgc ctgtgctaga gttccaactg tggatgcatc    1560
cgtcccgttt gagtcaaagt cttacttccc tgctctcacc tactcacaga cgggatgcta   1620
agcagtgcac ctgcagtggt ttaatggcag ataagctccg tctgcagttc caggccagcc   1680
agaaactcct gtgtccacat agagctgacg tgagaaatat ctttcagccc aggagagagg   1740
ggtcctgatc ttaaccccttt cctgggtctc agacaactca gaaggttggg gggataccag   1800
agaggtggtg aataggacc  gcccctcct tacttgtggg atcaaatgct gtaatggtgg    1860
aggtgtgggc agaggaggga ggcaagtgtc ctttgaaagt tgtgagagct cagagtttct   1920
ggggtcctca ttaggagccc ccatccctgt gttccccaag aattcagaga acagcactgg   1980
ggctggaatg atctttaatg ggcccaaggc caacaggcat atgcctcact actgcctgga   2040
gaagggagag attcaggtcc tccagcagcc tccctcaccc agtatgtttt acagattacg   2100
gggggaccgg gtgagccagt gaccccctgt agccccagc ttcaggcctc agtgtctgcc    2160
agtcaagctt cacaggcatt gtgatggggc agccttgggg aatataaaat tttgtgaaga   2220
cttggagatc ttttttttt  tttaagcaaa tttacaagtt tcaacagaca agtccacatt   2280
catccctaaa agtctcattt tccagtagaa aatatacact ggtaaaaacg gggcatgggg   2340
ccgtggctca gggctgtaat tctagcacat tgggagacca agtgggagg  atcacttgag   2400 cccaggagtt ctggatcctg tctctgcaca aaataaaaaa ttactcaggc gtggtggtgc   2460
tcacatgcct gtagtcccag ctatacttgg gaggctgagg cgagaggatc gcttgagccc   2520
aggagttgga ggctgcagtg aaccatgatt gcgccactgt actccactgg gcggcaataa   2580
gaagacaaaa acataaaaca ggacatgtgt gaggcaaaag ctgcaggaat ttctatcagg   2640
cagatctgac ctcatcccac ccacccctg  ctcagatacc cttcatagct ccttattgct   2700
ttcagctcat aaccccacat                                              2720
```

<210> SEQ ID NO 5
<211> LENGTH: 813
<212> TYPE: DNA
<213> ORGANISM: Homo sapiens

<400> SEQUENCE: 5

```
gaaatccgcg gaccgggctt taggttcgcc ggaatcccac gctcccgact tctgcttccg     60
ggtcggagcc atggcggtgg caaattcaag tcctgttaac cccgtggtgt tctttgatgt    120
cagtattggc ggtcaggaag ttggccgcat gaagatcgag ctctttgcag acgttgtgcc    180
taagacggcc gagaacttta ggcagttctg caccggagaa ttcaggaaag atggggttcc    240
aataggatac aaaggaagca ccttccacag ggtcataaag gatttcatga ttcagggtgg    300
agattttgtt aatggagatg gtactggagt cgccagtatt taccgggggc catttgcaga    360
tgaaaatttt aaacttagac actcagctcc aggcctgctt ccatggcga  acagtggtcc   420 aagtacaaat ggctgtcagt tctttatcac ctgctctaag tgcgattggc tggatgggaa   480
gcatgtggtg tttggaaaaa tcatcgatgg acttctagtg atgagaaaga ttgagaatgt   540
tcccacaggc cccaacaata agcccaagct acctgtggta atctcgcagt gtggggagat   600
gtagtccaga caaagactga atcaggcctt cccttcttct tggtggtgtt cttgagtaag   660
ataatctgga ctgccccccg tctttgcttc cctgcctgct gctgccccat tgatcaaga    720 gaccatggaa gtgtcagaga ttcagaatcc aagattgtct ttaagttttc aactgtaaat   780
```

```
aaagtttttt tgtatgcgta aaaaaaaaaa aaa                                    813
```

<210> SEQ ID NO 6
<211> LENGTH: 11974
<212> TYPE: DNA
<213> ORGANISM: homo sapiens

<400> SEQUENCE: 6

```
agcgaaccat cggggcggcc gggagccatg ttggagcggc gggaggcggc agcagcgtcg     60
gggatgctgt ggtgggggcg gaaaaagcca gggccgcacg ccggaggggc tccggccgcg    120
gagtagatgg tgcccagagg gcggcggggg tgcggagaga caggcggagg ggcggggggcc   180
cggggcggcg gcaggggccc gggaggggggc ccgagcggcg gggccagccc aaggcccgga   240
ccggggcggg gggcggtgga ggccgtgcag ggaggcgggg gatgatggcg aggcggccgc    300
cgtggcgggg cctcggggga cggtcgaccc ccatactcct gctccttctc ctctctttgt    360
tcccccctcag ccaggaggag ctgggggggcg gtgggcacca gggctgggac ccaggcttag   420
ctgccactac ggggccaagg gcgcatatcg gtggcggagc cttagctctt tgtccggagt    480
cttccgggt ccggaggat ggggggcctg gcctgggggt cagggagcct atcttcgtgg      540
ggctccgagg gagaaggcaa agcgcccgga atagtcgagg gcccctgag cagccgaatg     600
aggagctggg gattgaacac ggcgtccagc cattgggcag ccgcgaacga gagacaggac    660
agggaccagg gtctgtgtta tactggcgcc cagaggtctc ctcttgcggg cggacaggac    720
cttgcaaag aggtagtctg tcaccagggg ctctgtcctc aggggtcccg ggctcgggga     780
acagctcgcc cctcccttca gactttttga ttcggcacca cggtcccaag ccggtgtcct    840
cccagcggaa cgctgggaca ggctcccgca aaagagtggg caccgcgcgc tgctgtgggg    900
aattatgggc aacagggagc aagggtcagg gcgagagagc cacgacatcc ggagcagaaa    960
ggacagccccc ccggcggaac tgtcttccag gggcctcggg atctggcccc gagctggatt   1020
cagcaccacg cacggcgagg acagctcctg catcaggttc agcaccccgc gagtctcgga   1080
cagctcccga gccggcgccc aagcgcatgc gctcccgggg tctcttccgc tgccgcttcc   1140
tcccgcagcg ccccggggccg cgtccccggg gactcccggc ccgtcctgaa gccaggaaag  1200
taacctcggc gaaccgggca cgctttcgtc gcgccgcaaa ccgccacccg cagtttccgc   1260
agtacaacta ccagacgctg gtgccggaga atgaggcagc aggcaccgcg gtgctacgcg   1320
tggttgctca ggacccggac gccggcgagg ccgggcgcct agtctactcg ctggcggcac   1380
tcatgaacag ccgctcgctg gagctgttca gcatcgaccc gcagagcggc cttatccgta   1440
cggcggcagc tctggaccgc gagagcatgg agcgtcacta cctgcgtgtg accgcgcagg   1500
accacgggtc gccgcgcctc tcggccacca cgatggtggc cgtgacagta gccgaccgca   1560
acgaccactc gccggtttt gagcaagcgc agtaccggga gacccttcgc gagaatgtgg    1620
aggagggcta ccctatcctg cagctgcgtg ccactgacgg cgacgcgccc cccaacgcca   1680
acctgcgcta ccgcttcgtg gggccgccag ctgcgcgcgc tgcagctgcc gccgccttcg   1740
agattgatcc acgctccggc ctcatcagca ccagcggccg agtggaccgc gagcacatgg   1800
aaagctatga gctggtggtg gaagccgcg accaggccca ggaacccggg ccgcgctcgg     1860
ccactgtgcg cgtacacata actgtgctag acgagaacga caatgctcct cagttcagcg   1920
agaagcgcta cgtggcgcag gtgcgcgagg atgtgcgccc ccacacagtc gtgctgcgcg   1980
tcacggccac tgaccgggac aaggacgcca acggattggt gcactacaac atcatcagtg   2040
gcaatagccg tggacacttt gccatcgaca gcctcactgg cgagatccag gtggtggcac   2100
```

```
ctctggactt cgaggcagag agagagtatg ccttgcgcat cagggcgcag gatgctggcc    2160
ggccaccgct gtccaacaac acgggcctgg ccagcatcca ggtggtggac atcaatgacc    2220
acattcctat ttttgtcagc acgcccttcc aagtttctgt cttggaaaat gctcccttgg    2280
gtcactcagt catccacatt caggcagtcg atgcagacca ggggagaat gccagattgg     2340
agtactccct aactggtgtg gcacctgata ctccttttgt gataaacagc gccactggct    2400
gggtctctgt gagtggtccc ctggaccgtg agtctgtgga gcattacttc tttggtgtgg    2460
aggctcgaga ccatggctca cccccactct ctgcctcagc cagtgtcacc gtgactgtgc    2520
tggacgttaa tgacaatcgg cctgagttca caatgaagga gtaccaccta cgactgaatg    2580
aggatgcagc tgtgggcacc agtgtggtca gcgtgaccgc agtagaccgt gatgccaaca    2640
gtgccatcag ctaccagatc acaggcggca cacccggaa tcgctttgcc atcagcaccc     2700
agggggtgt gggtctggtg actctggctc tgccactgga ctacaagcag gaacgctact     2760
tcaagctggt actaactgca tctgaccgtg cccttcatga tcactgctat gtgcacatca    2820
acatcacaga tgccaacact catcggccgg tctttcaaag tgcccactac tcagtgagtg    2880
tgaatgaaga tcggccaatg ggtagcacca tagtggtcat cagtgcctct gatgatgacg    2940
tgggtgagaa tgctcgtatc acctatctcc tggaggacaa cctgccccag ttccgcattg    3000
atgcagactc aggagccatt acattacagg ccccattaga ctatgaggac caggtgacct    3060
acacccctggc tatcacagct cgggacaatg gcatcccaca gaaggcagac actacttatg   3120
tggaggtgat ggtcaatgac gtgaatgaca atgctccaca atttgtggcc tcccactata   3180
cagggctggt ctctgaggat gccccacctt tcaccagtgt cctgcagatc tcagccactg    3240
accgggatgc tcatgccaat ggccgggtcc agtacacttt ccagaatggt gaagatgggg    3300
atggagattt taccattgag cccacctctg gaattgtccg tacagtaagg cggctagacc    3360
gggaggcagt atcagtgtat gagttgactg cctacgcagt ggacagaggt gtgccccac    3420
tccggactcc agtcagtatc caggtgatgg tgcaggatgt gaacgacaat gcacctgtct    3480
tcccagctga ggagtttgag gtgcgggtga aagagaatag cattgtgggc tcagtggtgg    3540
cccagatcac tgcagtggac cctgacgaag gccccaatgc ccatataatg taccagatcg    3600
tggaggggaa catccctgag ctgttccaaa tggacatctt ctctggagaa ctgacggcac    3660
tcattgacct agactatgag gctcgccaag aatatgtgat tgtggtgcag gccacatctg    3720
ctcctttggt cagccgggcc actgtgcacg tccgcctggt tgaccagaat gacaacagcc    3780
ctgtgctcaa caacttccag atcctcttca caaactatgt atccaaccgt tcagacacct    3840
tcccgtcggg cattattggg cgcatcccag cttatgaccc cgatgtctcc gaccacctct    3900
tctactcctt tgagcgtggc aatgagctgc agctgctggt agtcaaccag accagtgggg    3960
agctgcgact cagccgaaag ctagacaata accgcccact ggtggcctcc atgttggtga    4020
ctgtcacaga tggcctgcac agcgtgacgg cgcagtgtgt gctgcgcgtg gtcatcatca    4080
cggaggagtt gctggccaac agcctgaccg tgcgccttga aacatgtgg caggagcgct     4140
tcctgtcacc gctgctgggc cgcttcctcg agggcgtggc tgcggtgctc gctacgcccg    4200
ctgaggacgt cttcatcttc aacatccaga acgacacaga cgtaggggc accgtgctca     4260
atgtgagttt ctcggcgcta gctccacgtg gggccggggc gggcgctgca gggccctggt    4320
tcagctccga ggagctgcag gagcagttgt acgtgcgccg ggcggcgctg gcggctcgct    4380
ccctgctcga cgtactgccc ttcgacgaca acgtgtgcct gcgagagccc tgtgagaact    4440
```

```
acatgaaatg cgtgtccgtg ctccgctttg actcgtccgc gcccttcctg gcctcggcct    4500
ccacgctgtt ccgacccatc cagcccatcg ctggcctgcg ctgccgctgc ccgcccggat    4560
tcacgggaga cttttgcgag accgagctcg acctctgcta ctccaaccca tgtcgcaacg    4620
gcggagcctg cgccgcggcg cagggaggct acacgtgcgt ctgccgcccg cgcttcaccg    4680
gagaggactg cgagctggac accgaggccg gccgctgcgt gccgggcgtc tgccgcaacg    4740
ggggcacctg caccgacgcg cccaacggcg gcttcgctg ccagtgcccg gcaggcggcg     4800
ccttcgaggg cccgcgctgc gaggtggctg cgcgctcctt cccgcccagt tcgttcgtca    4860
tgtttcgcgg cctgcggcag cgattccacc ttacgctgtc cctctcgttc gcgacagtgc    4920
agcagagcgg gctgctcttc tacaacgggc gcctgaacga gaagcacgac ttcctggccc    4980
tggaactcgt ggctggccaa gtgcggctca catattccac gggtgaatcc aacaccgtgg    5040
tcagccccac agttccaggg ggcttgagtg acgggcaatg gcatacagtg catctgagat    5100
actacaacaa gccccggaca gatgccctag ggggtgcaca gggcccctcc aaggacaagg    5160
tggctgtgct aagcgtggat gattgtgatg tggccgtggc tctgcagttt ggtgctgaga    5220
ttggcaacta ctcatgcgcg gctgctggtg tgcaaacaag ctccaagaag tccctggacc    5280
tgacgggccc tcttcttctg ggaggtgtcc ccaacctccc cgagaacttc cccgtatccc    5340
ataaggactt catcgctgt atgcgggacc tgcacattga tggccgccga gtggacatgg    5400
cggcttttgt cgcaaataat ggcaccatgg caggctgcca agccaagcta cacttttgtg    5460
actcaggccc ctgcaagaac agtggcttct gctcggagcg ctggggcagc ttcagctgcg    5520
actgccctgt gggcttcggc ggcaaagact gtcagcttac tatggcccat ccccaccatt    5580
tccgtggcaa cggcacactg agctggaact ttggaagtga catggctgtg tctgtgccat    5640
ggtacctggg gctggcattt cggacacggg caacgcaggg ggtcctgatg caagtgcagg    5700
ctgggccaca cagcacgctc cttttgccagc tagatcgggg gttactgtct gtgacagtga    5760
ccaggggctc gggccgtgct tcccatctcc ttctggacca ggtgactgtc agtgatggcc    5820
ggtggcacga tctgcggctg gagttgcagg aggaaccagg tggccggcgg ggccaccatg    5880
tccttatggt ctcactggac tttagcctct tccaggacac catggcggtg gggagtgagc    5940
tgcagggcct gaaggtaaag cagctccacg tgggaggcct gccccccggc agtgcagagg    6000
aggctcctca gggtctggtt ggctgcatcc aggggggtgtg gctcggctcc acaccctctg    6060
gctccccggc cctgctaccc cccagccacc gagtgaatgc ggagcctggc tgtgttgtga    6120
ccaacgcctg tgcctctggg ccctgcccac ctcacgcaga ctgccgggac ctctggcaga    6180
ccttttcttg cacctgccag ccaggttact acggcccagg ctgtgtggat gcctgcctcc    6240
tgaaccctg tcagaaccag ggatcatgcc ggcacctgcc aggagccccc catggctata    6300
cctgtgactg tgtgggtggc tatttcgggc accactgtga gcacaggatg gaccagcagt    6360
gcccacgggg ctggtggggg agcccaacct gtggcccctg caactgtgat gttcacaaag    6420
gttttgatcc caactgcaac aagacaaatg gcagtgtca ctgcaaggag ttccactacc     6480
gaccgcgggg cagtgactct tgcctcccat gtgactgcta cctgtgggc tccacctcgc     6540
gctcatgtgc accccacagc gggcagtgcc cctgtcgccc aggagccctt ggccgccagt    6600
gcaacagctg tgacagtccc ttcgcagagg tgacagccag cggctgccgg gtgctctatg    6660
atgcctgccc taagtccctg agatctggtg tgtggtggcc ccagacaaag tttggcgtcc    6720
tggccacagt gccctgtccc cggggggccc tgggtgctgc tgtgcggctg tgtgatgagg    6780
cccagggttg gctggagccc gacctcttca actgtacctc ccctgccttt cgagagctca    6840
```

```
gtctgctgct ggatggccta gagctgaaca agacggcact ggataccatg gaggccaaga    6900
agctggctca gcggctacgg gaggtgactg gccacactga ccactatttt agccaagatg    6960
ttcgagtcac tgcccgcctg ctggcccacc tgctggcctt cgagagccat cagcagggct    7020
tcgggctgac agccacacag gatgcccact tcaatgagaa tctgctgtgg gccggctctg    7080
cactgcttgc cccagagaca ggggacttgt gggcggcgct ggggcagcgg gcccctgggg    7140 gctcccagg cagcgcggga ctggtgaggc acctggagga gtatgcagcc acactcgcaa    7200
ggaatatgga actcacatac ctgaatccca tggggctggt gacgcctaat atcatgctca    7260
gcattgaccg catggagcac cccagttctc cccgggggc ccgtcgctac cctcgctacc    7320
atagcaacct ctttcgaggc caggatgcct gggatcctca cacccatgtg ctgctgcctt    7380
cccagtcccc acggccatcc ccatctgaag ttctgcccac aagcagcagc atagaaaact    7440
ccaccacctc aagtgtggtc cccccaccag cccgccaga gccagagcct gggatctcca    7500
ttatcattct cctcgtttac cgcaccttag ggggactgct ccctgcccag ttccaggcag    7560
aacgccgagg tgccaggctt cctcagaacc ccgtcatgaa ctccccggtg gtcagcgtgg    7620
ctgtgttcca cggacgcaac ttcctaaggg gaatcctgga gtcccccatc agcctagagt    7680
ttcgcctgct acagacagcg aatcggagca aggcgatctg tgtgcagtgg gacccacctg    7740
gcctggcgga gcagcatggt gtgtggacag cacgggactg cgagctggtg cacaggaatg    7800
ggtcccacgc acggtgtcgc tgcagccgga cagggacctt tggggtcctc atggatgcct    7860
ctccccgtga gaggctggag ggcgacctgg agctgctggc tgtgttcacc cacgtggtcg    7920
tggctgtgtc tgtggctgcg ctggtgctga ctgcagccat cctgctgagc ctgcgcagcc    7980
tcaagtccaa tgtgcgtggg atccatgcca atgtggcagc cgccctgggg gtggcagagc    8040
tcctcttcct gctggggatt cacaggaccc acaatcagct ggtgtgcact gcagtcgcca    8100
tcctcctgca ctacttcttc ctcagcacct tcgcgtggct cttcgtgcag gggctgcacc    8160
tctaccgcat gcaggttgag ccacgcaacg tggaccgcgg cgccatgcgc ttctaccatg    8220
ccctgggctg gggcgtccct gctgtgctgc tgggccttgc tgtgggcctg gaccctgagg    8280
gctatgggaa ccctgacttc tgctggatct cagtccacga gccctcatc tggagctttg    8340 ctggccctgt tgtcctggtc atagtgatga cgggaccat gtttctcctc gctgcccgca    8400
catcctgctc cacagggcag agggaggcca agaagacctc tgcactgacc cttcgcagct    8460
ccttcctgct gcttctgctg gtcagtgcct cctggctctt gggctcctg gcagtcaacc    8520 acagcatcct agccttccac tacctccatg ctggactctg cggcctccag ggcctggcgg    8580
tgctgctgct cttctgtgtc ctaaatgcag atgctcgggc tgcctggatg ccagcctgtc    8640
tgggcaggaa ggcagcgcct gaggaggcaa ggccagcacc tgggctggga cctggggcct    8700
acaacaacac ggctctcttt gaggagagtg gcctcatccg catcactctg ggcgcctcca    8760
ccgtctcctc tgtgagcagt gcccgctccg gccgaccca ggaccaggac agccagcggg    8820
gccgcagcta cctcagggac aatgtcctgg ttcgacatgg ctcagccgct gaccacactg    8880
accacagcct ccaggctcat gctggcccca ctgacctgga cgtggccatg ttccatcgag    8940
atgctggcgc agactccgac tctgacagtg acctgtcctt ggaggaggag aggagtctct    9000
ccattccatc ttcagaaagc gaggacaatg gccggacgcg ggggcgcttc caacggccac    9060
tctgccgagc agcccagagt gagaggctcc tcacccaccc caaagatgtg gatggcaatg    9120
acctcctgtc ctactggcca gccctggggg agtgcgaggc agccccctgt gctctgcaga    9180
```

```
cttggggctc tgaaaggcgc ctggggctgg acaccagcaa ggatgcagct aacaacaacc      9240
agccagaccc ggccctgacc agtggggatg agacttctct gggccgggcc cagcgccaga      9300
ggaaaggcat cctgaagaac cggttgcaat acccactggt gccacagacc cgaggtgccc      9360
ctgagctgtc ctggtgccgt gcagccacct tgggccaccg tgctgtgcca gctgcctctt      9420
acggtcgcat ctatgctggc gggggcacgg gcagcctttc acagccagcc agccgctact      9480
cttctagaga acagctggac ctgctcctcc ggcggcaact gagccgtgag cgactagagg      9540
aagcccctgc ccctgttcta cgtcccctga gccggccagg gtcccaggaa tgcatggatg      9600
ctgcaccagg ccgactggag cccaaagatc ggggcagcac cctgccacgg aggcagccac      9660
ctcgggacta ccctggcgcc atggctggcc gcttcgggtc acgggatgcg ctcgacttag      9720
ggcacctcg agagtggttg agcacgctgc ctccgccccg ccgcacccgg gaccttgacc       9780
cacagccccc acctctgccc ctgtctcccc agcggcaact ctcaagggac cccctcttgc      9840
catcccggcc gctggactct ctgtctagga gctcgaactc tcgggagcag ctggaccagg      9900
tgcctagccg gcacccctca cgagaagccc ttgggcact cccgcagctg ctcagagcta       9960
gggaggactc ggtcagtggc cccagccatg gccctccac agaacagttg gacattcttt       10020
cctccatcct tgcctctttc aactcctcgg ccctctcctc tgtgcaatct tcaagcacac      10080
ccttgggccc tcacaccact gccacacctt ctgccacagc ctctgtgctt gggccctcca      10140
cgccacgttc tgccacgtct cacagcatct cggagctgtc gccagactca gaagttccca      10200
gaagtgaggg tcactcctga ggggatgacg gcgtggacga ggaacagctg agggcgacag      10260
aggatctagg ctaacaggag agactccagg agtgggggca gatcccaagg cagcctcctg      10320
ctccccagtg gtgggtgccc cagctctacc tggtgtggca gggctgaggc tccatgtgca      10380
tctgtgagca tgcgtgtgac aggtgcagag acggggggact ggagggagac ttttatacgt     10440
tttgtacctt tgtaaccaga gagatgctta tgttattttt cagcttttct gtctcctggg      10500
gggtttgagg ctgggctggg aggggaggg agatagaggg agagatgcag tttgaccca        10560
tttgggtcct gagcaaaccc tatgctcatc tctctctcct tcctggggtg gactcagatg      10620
ggtgggacac atgccttcct cccctattc caccccaag ttgatctgag tatcgtcagg        10680
ggcccaaagt acagaattgt tctttgcttt ttattgaatg ctccaaaggc caaacttctg      10740
gggctggggg ttggtcttgg aaacaggggt cctctgactt cctcatgggg gcttgctcat      10800
accgcccctc ctggtggatg tgtgtgttta ttatgtggag tccctgccac ttactgcctt      10860
atgacctagg actgatgctg tggggtgctg gtggagcagc tgatgtcgtg tttacagagc      10920
aaggcttccc tgtctcccac ggggagggc tcgggcctct agtcagacat tcctgcagag       10980
ggtcggtgga ggggtcattc acctgcccct gcagcaagca aaagttgtct gtggtgccat      11040
ttgattccct gacactgccc cctgcttgaa ttgattccga agggtagggt gggaaggtga      11100
gcaaagggag cagaaacaag ggaattcaag acccagaatg taggtgccac tgcctcctat      11160
gtttacagga tcctccgtgg ccctaggcac ctgggctgca ggaagtgact ccgttccact      11220
cctcctttat tcccttaaaa agggaaaaat gactgttacg accctgttca caaaactctt      11280
acttttgcta ttttgtctgc tgtccagaac tgaagacttt aaaattttgt tactgtttac      11340
aagtccagat tcaaaaaatg ttttttacttt gtttacaact caaaactttg agttttacac     11400
tttgtttaca gtagataatt ttttttcctt tgtttccaag tgaaaggtag ggaaagtggg      11460
agagggactt ggaggaccca cctgtgagga ccctgacctg gccatcttga ggggttttct      11520
aaccccagg tctcccaggc cgaaggtcag ccttgagtcc cgtttaacag cagatccaga       11580
```

| | | | | |
|---|---|---|---|---|
| agaccttgag | agtaggcgtc | ctctaaccac | gggggagagt | ggctgtgcag ggctgggggg | 11640 |
| tggtctgtgc | agacacctcc | tcacccacca | ccccatgcat | actcttggga agcagcttcc | 11700 |
| tgggagatta | gaaattctac | ttccctgact | ggagctaaat | cccaccagcc aggacccaaa | 11760 |
| ctctccttac | cgagaaggac | cccagctctt | gaagggctga | gtggcctgct gggggtggga | 11820 |
| gggtgtcttt | actatgtcct | aggtttcgta | gatgcccctc | tctggggttc ccctcctcca | 11880 |
| gcccagcggc | cctcttttcct | gtctgtgtaa | attgttccgt | gaagccgcgc tctgttttgg | 11940 |
| gaataaactt | ctatagaaaa | caaaaaaaaa | aaaa | | 11974 |

<210> SEQ ID NO 7
<211> LENGTH: 3652
<212> TYPE: DNA
<213> ORGANISM: homo sapiens

<400> SEQUENCE: 7

| | | | | |
|---|---|---|---|---|
| attccttctc | attcattttg | cccagaaagt | tcctgcttca | gagctgaagg tgattgggag | 60 |
| attttaactt | agatctccag | caagtgctac | aaggaagaaa | gatcctgaa gaatcaatca | 120 |
| agttttccgt | gaagtcaagt | ccaagtaaca | tccccgcctt | aaccacaagc aggagaaatg | 180 |
| aagcacatta | tcaactcgta | tgaaaacatc | aacaacacag | caagaaataa ttccgactgt | 240 |
| cctcgtgtgg | ttttgccgga | ggagatattt | ttcacaattt | ccattgttgg agttttggag | 300 |
| aatctgatcg | tcctgctggc | tgtgttcaag | aataagaatc | tccaggcacc catgtacttt | 360 |
| ttcatctgta | gcttggccat | atctgatatg | ctgggcagcc | tatataagat cttggaaaat | 420 |
| atcctgatca | tattgagaaa | catgggctat | ctcaagccac | gtggcagttt tgaaaccaca | 480 |
| gccgatgaca | tcatcgactc | cctgtttgtc | ctctccctgc | ttggctccat cttcagcctg | 540 |
| tctgtgattg | ctgcggaccg | ctacatcacc | atcttccacg | cactgcggta ccacagcatc | 600 |
| gtgaccatgc | gccgcactgt | ggtggtgctt | acggtcatct | ggacgttctg cacggggact | 660 |
| ggcatcacca | tggtgatctt | ctcccatcat | gtgcccacag | tgatcacctt cacgtcgctg | 720 |
| ttcccgctga | tgctggtctt | catcctgtgc | ctctatgtgc | acatgttcct gctggctcga | 780 |
| tcccacacca | ggaagatctc | caccctcccc | agagccaaca | tgaaaggggc catcacactg | 840 |
| accatcctgc | tcgggtgtct | tcatcttctgc | tgggccccct | tgtgcttca tgtcctcttg | 900 |
| atgacattct | gcccaagtaa | cccctactgc | gcctgctaca | tgtctctctt ccaggtgaac | 960 |
| ggcatgttga | tcatgtgcaa | tgccgtcatt | gacccctca | tatatgcctt ccggagccca | 1020 |
| gagctcaggg | acgcattcaa | aaagatgatc | ttctgcagca | ggtactggta gaatggctga | 1080 |
| tccctggttt | tagaatccat | gggaataacg | ttgccaagtg | ccagaatagt gtaacattcc | 1140 |
| aacaaatgcc | agtgctcctc | actggccttc | cttccctaat | ggatgcaagg atgatcccac | 1200 |
| cagctagtgt | ttctaatagc | taggttctat | gtgaacagtc | ttattgtagg ggcaacctct | 1260 |
| taactttgtg | actggacaga | taaaacgatg | tagtaaaaga | aggatagaat acaaagtatt | 1320 |
| aggtaggtac | aaaagtaatt | aaggttttttg | ccattacttt | caatgaccaa aaattgcaat | 1380 |
| tacttttgca | ccaatctagt | aaaacagcaa | taaaaattca | agggctttgg gctaaggcaa | 1440 |
| agacttgctt | tcctgtggac | atctaacaag | ccagttctga | ggtggccttt ccaggtggag | 1500 |
| gccattgcag | ccaatttcca | gaagttaagt | acctggacat | gcgactccag gcagaagatg | 1560 |
| tagggtctct | gtaagccaat | aataaattgg | aaggaatgca | ttgctgcagc tgaatttgtc | 1620 |
| tgtctcccac | agccatgtgg | aatctccacc | ctcctctttc | tccctgttag tctgatgtat | 1680 |

```
tgatgccacc tcagtttcag aaagtaggct gagtataaac tataaatgtc aaataacgag     1740
cttcgagttt ccaatgataa atggaccttc tctgttagtc ttctttgctc actcagtatc     1800
ccactggcct taaaacccct tcctgttaca tttcctcatg ctttatgagc atacatttca     1860
aaggaagaaa tgaaaattta atccatttag ttcccatgtg ggaatacata aaggccagat     1920
gaaaattgtc actatttgaa gaagctgtaa ccaaactatg tgtgttacaa tgtagaagta     1980
caagaaaaga gccccaacat gtattttaag aaataaagag agagagacag agacagacag     2040
agagagagag agagagagag agagagagtg tgtgtgtgtg tgtgtgtgtg tgtgtgtgtg     2100
tgtgtgtgtg tgtgtgtgta ttttccccat gcttttggac tatggggaaa accaaaacca     2160
aagcaagaca tcaagcaatg gtgctgttat tatagcccca agtcaaagac ctgagggagg     2220
caaacaccac ctcattctgc agatgaatgt gaaagcagac ccagtcactg ggaaatgtca     2280
tcctcccatc agccaagatg ccagcaatgg aagagtggca accccagtag gaataaaaga     2340
aacataattt gcaagttcat tcattttttaa tagctaaaaa tcagcttaaa ggagaagcac     2400
atcctgattg taagtcccca ctaagttgga gggtgacttg aatggggtga aaggtgaaag     2460
ggacagagga gagcagtggg gcttcagagg ccaccaggct caggatctgc aggatggatg     2520
gtatcttcca gaacaggcaa tgcttttgccc tcaggagaat ttcccagagc tgctgagggg     2580
agaagacagc cacacacagg acagaccatt tggtgatggg tttgatatta gaagtggcag     2640
ggacaggaac ttcagaagca aaggaggcaa ggcagctgga gtcaagtgag gacagtggca     2700
ggcgtgcttt cacatggcct gtcccacaga tggaggtgaa aggtgcacct tcttgtcctc     2760
tgttctgtag aaatccttcc ctgtttgatc cttcccctgc caaatgaact atgttactct     2820
aatactaacc tgtattaatt aatatatgag atatatataa gttaattttt catgaaatct     2880
aaagcacaac cctagaacta atttttaaaa gtgttatttc taccattgaa aaagtaatgt     2940
ataacatatt ttatgtgatt aaagtgcgta ttctcaataa gaggtaaccct tttttttgatg     3000 ctgcaatgct ctgtgatacc acagaggtaa gcaatgccac ttaacctgta tcataaatag     3060
tcccaaactg ctcttcctat aaaattctgc ctttgtcaac agctttgctg tctcctaatc     3120
actctcaagc tctctgctgt gcatgtgact gttgtcagaa ggaaaatcac caagaaactt     3180 caccctctcac tgcctttgat ttgttgcagt taatctaaga aacaaaatga agatggctag     3240
tctaatggtg gatgaaacaa aaatgaagtc tgagtgctaa ttcagagaac ttgcaattcc     3300
agacattttc aattctaggt cttctgctat attccaatca gaacagaagc ttcagggctc     3360
atagttactg agaaaactca cgttttttcta cctctaactt catatagaat tccaaatgaa     3420
agcaccacca aactgcacat atttgtgtga ggaagatcaa caagcttcag acttttccca     3480
tgaggactta attcttttat caaattaccc aattttttaaa ctgctgtgtg gatactgtga     3540
gtgttcagct ttatcgatga cctagccttg gaccagatag ctgaaaatgt tcaggatgtg     3600
tactcaagct gatagtaatt ctgagccctg tctaataaaa aaggaaggat gt              3652

<210> SEQ ID NO 8
<211> LENGTH: 1137
<212> TYPE: DNA
<213> ORGANISM: homo sapiens

<400> SEQUENCE: 8
atggtctggg ggaaaatttg ctggttcagc cagagggctg gatggacagt gtttgctgag       60
tcacagatat ctctctcatg tagcctttgt ctccacagtg gtgaccagga ggcacagaac      120
ccaaacctgg tatctcagct ctgtggcgtc tttcttcaaa atgagacgaa tgaaaccata      180
```

| | |
|---|---|
| catatgcaga tgagcatggc agtgggacag caggccctgc ccttgaatat cattgccccc | 240 |
| aaggctgtgc tggtctccct ctgtggggtc ttattgaatg cactgtctt ctggctgctt | 300 |
| tgctgtgggg ccacgaatcc ctacatggta tacatcctcc acctggtcgc tgctgacgtg | 360 |
| atctatcttt gctgctcggc agtggggttc ttacaggtga ctctgctaac ttatcatgga | 420 |
| gtcgtgtttt ttatccctga tttcctggcc atattgtctc ccttctcctt tgaggtgtgt | 480 |
| ctctgtctcc tggtggccat cagcacagag cggtgtgtgt gtgtcctctt ccccatctgg | 540 |
| tacagatgcc accgcccaaa atacacatct aatgttgtct gcaccctcat ctggggcctg | 600 |
| ccttttttgca tcaacatagt aaaatcactt ttcctaactt actggaaaca tgtaaaggca | 660 |
| tgtgtcatat ttctaaagct ttctgggctc ttccatgcta tcctttcact tgtgatgtgt | 720 |
| gtgtcgagtc tgactctact cattagattc ctgtgctgct cccagcagca aaaggccacc | 780 |
| agggtctatg cggtggtgca gatctcggcc cccatgttcc tactctgggc cctacccctg | 840 |
| agcgtggcac ccctcataac agatttcaaa atgtttgtca ccacctccta tttaatttcc | 900 |
| ttgttcctca ttataaacag cagcgccaac cctatcattt atttctttgt ggggagcctc | 960 |
| agaaagaaaa ggctgaagga atctctcaga gtgattctcc aacgggcgtt agcagataag | 1020 |
| ccagaggtgg ggaggaacaa aaaggcagct ggcatcgacc caatggagca accacactct | 1080 |
| actcagcatg tggagaacct tcttcccagg gagcacaggg tcgatgtgga aacataa | 1137 |

<210> SEQ ID NO 9
<211> LENGTH: 9239
<212> TYPE: DNA
<213> ORGANISM: homo sapiens

<400> SEQUENCE: 9

| | |
|---|---|
| gcgctggctg cgggcggtga gctgagctcg cccccgggga gctgtggccg gcgcccctgc | 60 |
| cggttccctg agcagcggac gttcatgctg ggagggcggc gggttggaag caggtgccac | 120 |
| catggctagt ggcagctgtc aggggtgcga agaggacgag gaaactctga agaagttgat | 180 |
| agtcaggctg aacaatgtcc aggaaggaaa acagatagaa acgctggtcc aaatcctgga | 240 |
| ggatctgctg gtgttcacgt actccgagca cgcctccaag ttatttcaag caaaaatat | 300 |
| ccatgtgcct ctgttgatcg tcttggactc ctatatgaga gtcgcgagtg tgcagcaggt | 360 |
| gggttggtca cttctgtgca aattaataga agtctgtcca ggtacaatgc aaagcttaat | 420 |
| gggaccccag gatgttggaa atgattggga agtccttggt gttcaccaat tgattcttaa | 480 |
| aatgctaaca gttcataatg ccagtgtaaa cttgtcagtg attggactga agaccttaga | 540 |
| tctcctccta acttcaggta aaatcacctt gctgatattg gatgaagaaa gtgatatttt | 600 |
| catgttaatt tttgatgcca tgcactcatt tccagccaat gatgaagtcc agaaacttgg | 660 |
| atgcaaagct ttacatgtgc tgtttgagag agtctcagag gagcaactga ctgaatttgt | 720 |
| tgagaacaaa gattatatga tattgttaag tgcgttaaca aatttaaag atgaagagga | 780 |
| aattgtgctt catgtgctgc attgtttaca ttccctagcg attccttgca ataatgtgga | 840 |
| agtcctcatg agtggcaatg tcaggtgtta taatattgtg gtggaagcta tgaaagcatt | 900 |
| ccctatgagt gaaagaattc aagaagtgag ttgctgtttg ctccataggc ttacattagg | 960 |
| taattttttc aatatcctgg tattaaacga agtccatgag tttgtggtga agctgtgca | 1020 |
| gcagtaccca gagaatgcag cattgcagat ctcagcgctc agctgtttgg ccctcctcac | 1080 |
| tgagactatt ttcttaaatc aagatttaga ggaaaagaat gagaatcaag agaatgatga | 1140 |

```
tgaggggggaa gaagataaat tgttttggct ggaagcctgt tacaaagcat taacgtggca   1200
tagaaagaac aagcacgtgc aggaggccgc atgctgggca ctaaataatc tccttatgta   1260
ccaaaacagt ttacatgaga agattggaga tgaagatggc catttcccag ctcataggga   1320
agtgatgctc tccatgctga tgcattcttc atcaaaggaa gttttccagg catctgcgaa   1380
tgcattgtca actctcttag aacaaaatgt taatttcaga aaaatactgt tatcaaaagg   1440
aatacacctg aatgttttgg agttaatgca gaagcatata cattctcctg aagtggctga   1500
aagtggctgt aaaatgctaa atcatctttt tgaaggaagc aacacttccc tggatataat   1560
ggcagcagtg gtccccaaaa tactaacagt tatgaaacgt catgagacat cattaccagt   1620
gcagctggag gcgcttcgag ctattttaca ttttatagtg cctggcatgc cagaagaatc   1680
cagggaggat acagaatttc atcataagct aaatatggtt aaaaaacagt gtttcaagaa   1740
tgatattcac aaactggtcc tagcagcttt gaacaggttc attggaaatc ctgggattca   1800
gaaatgtgga ttaaaagtaa tttcttctat tgtacatttt cctgatgcat tagagatgtt   1860
atccctggaa ggtgctatgg attcagtgct tcacacactg cagatgtatc cagatgacca   1920
agaaattcag tgtctgggtt taagtcttat aggatacttg attacaaaga agaatgtgtt   1980
cataggaact ggacatctgc tggcaaaaat tctggtttcc agcttatacc gatttaagga   2040
tgttgctgaa atacagacta aaggatttca gacaatctta gcaatcctca aattgtcagc   2100 atcttttct aagctgctgg tgcatcattc atttgactta gtaatattcc atcaaatgtc   2160
ttccaatatc atggaacaaa aggatcaaca gtttctaaac ctctgttgca agtgttttgc   2220
aaaagtagct atggatgatt acttaaaaaa tgtgatgcta gagagagcgt gtgatcagaa   2280
taacagcatc atggttgaat gcttgcttct attgggagca gatgccaatc aagcaaagga   2340
gggatcttct ttaatttgtc aggtatgtga gaaagagagc agtcccaaat tggtggaact   2400
cttactgaat agtggatctc gtgaacaaga tgtacgaaaa gcgttgacga taagcattgg   2460
gaaaggtgac agccagatca tcagcttgct cttaaggagg ctggccctgg atgtggccaa   2520
caatagcatt tgccttggag gattttgtat aggaaaagtt gaaccttctt ggcttggtcc   2580
tttatttcca gataagactt ctaatttaag gaaacaaaca aatatagcat ctacactagc   2640
aagaatggtg atcagatatc agatgaaaag tgctgtggaa gaaggaacag cctcaggcag   2700
cgatggaaat ttttctgaag atgtgctgtc taaatttgat gaatggacct ttattcctga   2760
ctcttctatg gacagtgtgt tgctcaaag tgatgacctg gatagtgaag gaagtgaagg   2820
ctcatttctt gtgaaaaaga aatctaattc aattagtgta ggagaatttt accgagatgc   2880
cgtattacag cgttgctcac caaatttgca aagacattcc aattccttgg ggcccatttt   2940
tgatcatgaa gatttactga agcgaaaaag aaaaatatta tcttcagatg attcactcag   3000
gtcatcaaaa cttcaatccc atatgaggca ttcagacagc atttcttctc tggcttctga   3060
gagagaatat attacatcac tagacctttc agcaaatgaa ctaagagata ttgatgccct   3120
aagccagaaa tgctgtataa gtgttcattt ggagcatctt gaaaagctgg agcttcacca   3180
gaatgcactc acgagctttc cacaacagct atgtgaaact ctgaagagtt tgacacattt   3240
ggacttgcac agtaataaat ttacatcatt tccttcttat ttgttgaaaa tgagttgtat   3300
tgctaatctt gatgtctctc gaaatgacat tggaccctca gtggttttag atcctacagt   3360
gaaatgtcca actctgaaac agtttaacct gtcatataac cagctgtctt ttgtacctga   3420
gaacctcact gatgtggtag agaaactgga gcagctcatt ttagaaggaa ataaaatatc   3480
agggatatgc tcccccttga gactgaagga actgaagatt ttaaaccttc gtaagaacca   3540
```

```
catttcatcc ctatcagaga actttcttga ggcttgtcct aaagtggaga gtttcagtgc   3600
cagaatgaat tttcttgctg ctatgccttt cttgcctcct tctatgacaa tcctaaaatt   3660
atctcagaac aaattttcct gtattccaga agcaatttta aatcttccac acttgcggtc   3720
tttagatatg agcagcaatg atattcagta cctaccaggt cccgcacact ggaaatcttt   3780
gaacttaagg gaactcttat ttagccataa tcagatcagc atcttggact tgagtgaaaa   3840
agcatattta tggtctagag tagagaaact gcatctttct cacaataaac tgaaagagat   3900
tcctcctgag attggctgtc ttgaaaatct gacatctctg gatgtcagtt acaacttgga   3960
actaagatcc tttcccaatg aaatggggaa attaagcaaa atatgggatc ttcctttgga   4020
tgaactgcat cttaactttg attttaaaca tataggatgt aaagccaaag acatcataag   4080
gtttcttcaa cagcgattaa aaaaggctgt gccttataac cgaatgaaac ttatgattgt   4140
gggaaatact gggagtggta aaaccacctt attgcagcaa ttaatgaaaa ccaagaaatc   4200
agatcttgga atgcaaagtg ccacagttgg catagatgtg aaagactggc ctatccaaat   4260
aagagacaaa agaaagagag atctcgtcct aaatgtgtgg gattttgcag gtcgtgagga   4320
attctatagt actcatcccc attttatgac gcagcgagca ttgtaccttg ctgtctatga   4380
cctcagcaag ggacaggctg aagttgatgc catgaagcct ggctcttca atataaaggc   4440 tcgcgcttct tcttcccctg tgattctcgt tggcacacat ttggatgttt ctgatgagaa   4500
gcaacgcaaa gcctgcatga gtaaaatcac caaggaactc ctgaataagc gagggttccc   4560
tgccatacga gattaccact ttgtgaatgc caccgaggaa tctgatgctt ggcaaaact   4620 tcggaaaacc atcataaacg agagccttaa tttcaagatc cgagatcagc ttgttgttgg   4680
acagctgatt ccagactgct atgtagaact tgaaaaaatc attttatcgg agcgtaaaaa   4740
tgtgccaatt gaatttcccg taattgaccg gaaacgatta ttacaactag tgagagaaaa   4800
tcagctgcag ttagatgaaa atgagcttcc tcacgcagtt cactttctaa atgaatcagg   4860
agtccttctt cattttcaag acccagcact gcagttaagt gacttgtact tgtggaacc   4920 caagtggctt tgtaaaatca tggcacagat tttgacagtg aaagtggaag ttgtccaaa   4980 acaccctaag ggcattattt cgcgtagaga tgtggaaaaa tttctttcaa aaaaaaggaa   5040
atttccaaag aactacatgt cacagtattt taagctccta gaaaaattcc agattgcttt   5100
gccaatagga gaagaatatt tgctggttcc aagcagtttg tctgaccaca ggcctgtgat   5160
agagcttccc cattgtgaga actctgaaat tatcatccga ctatatgaaa tgccttattt   5220
tccaatggga ttttggtcaa gattaatcaa tcgattactt gagatttcac cttacatgct   5280
ttcagggaga gaacgagcac ttcgcccaaa cagaatgtat tggcgacaag gcatttactt   5340 aaaattggtct cctgaagctt attgtctggt aggatctgaa gtcttagaca atcatccaga   5400
gagtttctta aaaattacag ttccttcttg tagaaaaggc tgtattcttt tgggccaagt   5460
tgtggaccac attgattctc tcatggaaga atggtttcct gggttgctgg agattgatat   5520
ttgtggtgaa ggagaaactc tgttgaagaa atgggcatta tatagtttta atgatggtga   5580
agaacatcaa aaaatcttac ttgatgactt gatgaagaaa gcagaggaag agatctctt   5640 agtaaatcca gatcaaccaa ggctcaccat tccaatatct cagattgccc ctgacttgat   5700
tttggctgac ctgcctagaa atattatgtt gaataatgat gagttggaat tgaacaagc   5760 tccagagttt ctcctaggtg atggcagttt tggatcagtt taccgagcag cctatgaagg   5820
agaagaagtg gctgtgaaga tttttaataa acatacatca ctcaggctgt taagacaaga   5880
```

```
gcttgtggtg ctttgccacc tccaccaccc cagtttgata tctttgctgg cagctgggat    5940
tcgtccccgg atgttggtga tggagttagc ctccaagggt tccttggatc gcctgcttca    6000
gcaggacaaa gccagcctca ctagaaccct acagcacagg attgcactcc acgtagctga    6060
tggtttgaga tacctccact cagccatgat tatataccga gacctgaaac cccacaatgt    6120
gctgcttttc acactgtatc ccaatgctgc catcattgca aagattgctg actacggcat    6180
tgctcagtac tgctgtagaa tggggataaa aacatcagag ggcacaccag gtttcgtgc     6240 acctgaagtt gccagaggaa atgtcattta taaccaacag gctgatgttt attcatttgg    6300
tttactactc tatgacattt tgacaactgg aggtagaata gtagagggtt tgaagtttcc    6360
aaatgagttt gatgaattag aaatacaagg aaaattacct gatccagtta aagaatatgg    6420
ttgtgcccca tggcctatgg ttgagaaatt aattaaacag tgtttgaaag aaaatcctca    6480
agaaaggcct acttctgccc aggtctttga cattttgaat tcagctgaat tagtctgtct    6540
gacgagacgc attttattac ctaaaaacgt aattgttgaa tgcatggttg ctacacatca    6600
caacagcagg aatgcaagca tttggctggg ctgtgggcac accgacagag acagctctc     6660 atttcttgac ttaaatactg aaggatacac ttctgaggaa gttgctgata gtagaatatt    6720
gtgcttagcc ttggtgcatc ttcctgttga aaaggaaagc tggattgtgt ctgggacaca    6780
gtctggtact ctcctggtca tcaataccga agatgggaaa aagagacata ccctagaaaa    6840
gatgactgat tctgtcactt gtttgtattg caattccttt tccaagcaaa gcaaacaaaa    6900
aaatttcctt ttggttggaa ccgctgatgg caagttagca ttttttgaag ataagactgt    6960
taagcttaaa ggagctgctc ctttgaagat actaaatata ggaaatgtca gtactccatt    7020
gatgtgtttg agtgaatcca caaattcaac ggaaagaaat gtaatgtggg gaggatgtgg    7080
cacaaagatt ttctcctttt ctaatgattt caccattcag aaactcattg agacaagaac    7140
aagccaactg ttttcttatg cagctttcag tgattccaac atcataacag tggtggtaga    7200
cactgctctc tatattgcta agcaaaatag ccctgttgtg gaagtgtggg ataagaaaac    7260
tgaaaaactc tgtggactaa tagactgcgt gcactttta agggaggtaa tggtaaaaga     7320
aaacaaggaa tcaaaacaca aaatgtctta ttctgggaga gtgaaaaccc tctgccttca    7380
gaagaacact gctctttgga taggaactgg aggaggccat attttactcc tggatctttc    7440
aactcgtcga cttatacgtg taatttacaa cttttgtaat tcggtcagag tcatgatgac    7500
agcacagcta ggaagcctta aaaatgtcat gctggtattg ggctacaacc ggaaaaatac    7560
tgaaggtaca caaaagcaga aagagataca atcttgcttg accgtttggg acatcaatct    7620
tccacatgaa gtgcaaaatt tagaaaaaca cattgaagtg agaaaagaat tagctgaaaa    7680
aatgagacga acatctgttg agtaagagag aaataggaat tgtctttgga taggaaaatt    7740
attctctcct cttgtaaata tttatttaa aaatgttcac atggaaaggg tactcacatt     7800
ttttgaaata gctcgtgtgt atgaaggaat gttattattt ttaatttaaa tatatgtaaa    7860
aatacttacc agtaaatgtg tattttaaag aactatttaa aacacaatgt tatatttctt    7920
ataaatacca gttactttcg ttcattaatt aatgaaaata atctgtgaa gtacctaatt     7980 taagtactca tactaaaatt tataaggccg ataattttt gttttcttgt ctgtaatgga     8040
ggtaaacttt attttaaatt ctgtgcttaa gacaggacta ttgcttgtcg attttctag     8100 aaatctgcac ggtataatga aaatattaag acagtttccc atgtaatgta ttccttctta    8160
gattgcatcg aaatgcacta tcatatatgc ttgtaaatat tcaaatgaat ttgcactaat    8220
aaagtccttt gttggtatgt gaattctctt tgttgctgtt gcaaacagtg catcttacac    8280
```

```
aacttcactc aattcaaaag aaaactccat taaaagtact aatgaaaaaa catgacatac    8340
tgtcaaagtc ctcatatcta ggaaagacac agaaactctc tttgtcacag aaactctctg    8400
tgtctttcct agacataata gagttgtttt tcaactctat gtttgaatgt ggatacccctg   8460 aattttgtat aattagtgta aatacagtgt tcagtccttc aagtgatatt tttattttt    8520 tattcatacc actagctact tgttttctaa tctgcttcat tctaatgctt atattcatct    8580
tttccctaaa tttgtgatgc tgcagatcct acatcattca gatagaaacc ttttttttt    8640 tcagaattat agaattccac agctcctacc aagaccatga ggataaatat ctaacacttt    8700
tcagttgctg aaggagaaag gagctttagt tatgatggat aaaaatatct gccaccctag   8760
gcttccaaat tatacttaaa ttgtttacat agcttaccac aataggagta tcagggccaa    8820
atacctatgt aataatttga ggtcatttct gctttaggaa aagtactttc ggtaaattct    8880
ttggccctga ccagtattca ttatttcaga taattccctg tgataggaca actagtacat    8940
ttaatattct cagaacttat ggcatttttac tatgtgaaaa ctttaaattt atttatatta    9000
agggtaatca aattcttaaa gatgaaagat tttctgtatt ttaaaggaag ctatgcttta    9060
acttgttatg taattaacaa aaaaatcata tataatagag ctctttgttc cagtgttatc    9120
tctttcattg ttactttgta tttgcaattt tttttaccaa agacaaatta aaaaaatgaa    9180
taccatattt aaatggaata ataaaggttt tttaaaaact taaaaaaaaa aaaaaaaaa    9239

<210> SEQ ID NO 10
<211> LENGTH: 5100
<212> TYPE: DNA
<213> ORGANISM: homo sapiens

<400> SEQUENCE: 10
cttgttgact aggcgctgtt cttgctggct ggtgccccag ggcctggaga ggtctgaaga     60
aacctgggag ccagcagccc ggggctccac tctgggttct gaaagcccat tccctgctct    120
gcggctcctc ccaccccacc tcttctcagc cttgcagctc aagggttgat ctcaggagtc    180
caggacccag gagagggaag aatctgagga acacagaaca gtgagcgttg cccacacccc    240
atctcccgtc accacatctc ccctcaccct caccctccct gcctggccct ggaccccatc    300
ccaggacctc cctatcagct gacttcttcc agtgtcttgc aggcccctct gggctcctcc    360
ctcccctggc ttttcctacc actccccctc tatcggcgtc tatctgtagg tgccctggga    420
tttataaaac tgggttccga atgctgaata agagacggta agagccaagg caaaggacag    480
cactgttctc tgcctgcctg ataccctcac cacctgggaa catcccccag acaccctctt    540
aactccggga cagagatggc tggcggagcc tggggccgcc tggcctgtta cttggagttc    600
ctgaagaagg aggagctgaa ggagttccag cttctgctcg ccaataaagc gcactccagg    660
agctcttcgg gtgagacacc cgctcagcca gagaagacga gtggcatgga ggtggcctcg    720
tacctggtgg ctcagtatgg ggagcagcgg gcctgggacc tagccctcca tacctgggag    780
cagatggggc tgaggtcact gtgcgcccaa gcccaggaag gggcaggcca ctctccctca    840
ttcccctaca gcccaagtga accccacctg gggtctccca gccaacccac ctccaccgca    900
gtgctaatgc cctggatcca tgaattgccg gcggggtgca cccagggctc agagagaagg    960
gttttgagac agctgcctga cacatctgga cgccgctgga gagaaatctc tgcctcactc   1020
ctctaccaag ctccttccaag ctccccagac catgagtctc caagccagga gtcacccaac   1080
gcccccacat ccacagcagt gctggggagc tgggatcccc cacctcagcc cagcctagca   1140
```

```
cccagagagc aggaggctcc tgggacccaa tggcctctgg atgaaacgtc aggaatttac   1200
tacacagaaa tcagagaaag agagagagag aaatcagaga aaggcaggcc cccatgggca   1260
gcggtggtag gaacgccccc acaggcgcac accagcctac agccccacca ccacccatgg   1320
gagccttctg tgagagagag cctctgttcc acatggccct ggaaaaatga ggattttaac   1380
caaaaattca cacagctgct acttctacaa agacctcacc ccagaagcca agatcccctg   1440
gtcaagagaa gctggcctga ttatgtggag gagaatcgag gacatttaat tgagatcaga   1500
gacttatttg gcccaggcct ggatacccaa gaacctcgca tagtcatact gcagggggct   1560
gctggaattg ggaagtcaac actgccagg caggtgaagg aagcctgggg gagaggccag    1620
ctgtatgggg accgcttcca gcatgtcttc tacttcagct gcagagagct ggcccagtcc   1680
aaggtggtga gtctcgctga gctcatcgga aaagatggga cagccactcc ggctcccatt   1740
agacagatcc tgtctaggcc agagcggctg ctcttcatcc tcgatggtgt agatgagcca   1800
ggatgggtct gcaggagcc gagttctgag ctctgtctgc actggagcca gccacagccg    1860
gcggatgcac tgctgggcag tttgctgggg aaaactatac ttcccgaggc atccttcctg   1920
atcacggctc ggaccacagc tctgcagaac ctcattcctt ctttggagca ggcacgttgg   1980
gtagaggtcc tggggttctc tgagtccagc aggaaggaat atttctacag atatttcaca   2040
gatgaaaggc aagcaattag agcctttagg ttggtcaaat caaacaaaga gctctgggcc   2100
ctgtgtcttg tgccctgggt gtcctggctg gcctgcactt gcctgatgca gcagatgaag   2160
cggaaggaaa aactcacact gacttccaag accaccacaa ccctctgtct acattacctt   2220
gcccaggctc tccaagctca gccattggga ccccagctca gagacctctg ctctctggct   2280
gctgagggca tctggcaaaa aaagacccctt tcagtccag atgacctcag gaagcatggg    2340
ttagatgggg ccatcatctc caccttcttg aagatgggta ttcttcaaga gcaccccatc   2400
cctctgagct acagcttcat tcacctctgt ttccaagagt tctttgcagc aatgtcctat   2460
gtcttggagg atgagaaggg gagaggtaaa cattctaatt gcatcataga tttgaaaaag   2520
acgctagaag catatggaat acatggcctg tttggggcat caaccacacg tttcctattg   2580
ggcctgttaa gtgatgaggg ggagagagag atggagaaca tctttcactg ccggctgtct   2640
caggggagga acctgatgca gtgggtcccg tccctgcagc tgctgctgca gccacactct   2700
ctggagtccc tccactgctt gtacgagact cggaacaaaa cgttcctgac acaagtgatg   2760
gcccatttcg aagaaatggg catgtgtgta gaaacagaca tggagctctt agtgtgcact   2820
ttctgcatta aattcagccg ccacgtgaag aagcttcagc tgattgaggg caggcagcac   2880
agatcaacat ggagccccac catggtagtc ctgttcaggt gggtcccagt cacagatgcc   2940
tattggcaga ttctcttctc cgtcctcaag gtcaccagaa acctgaagga gctgacccta   3000 agtggaaaact cgctgagcca ctctgcagtg aagagtcttt gtaagaccct gagacgccct   3060
cgctgcctcc tggagaccct gcggttggct ggctgtggcc tcacagctga ggactgcaag   3120
gaccttgcct ttgggctgag agccaaccag accctgaccg agctggacct gagcttcaat   3180
gtgctcacgg atgctggagc caaacacctt tgccagagac tgagacagcc gagctgcaag   3240
ctacagcgac tgcagctggt cagctgtggc ctcacgtctg actgctgcca ggacctggcc   3300
tctgtgctta gtgccagccc cagcctgaag gagctagacc tgcagcagaa caacctggat   3360
gacgttggcg tgcgactgct ctgtgagggg ctcaggcatc ctgcctgcaa actcatacgc   3420
ctggggctgg accagacaac tctgagtgat gagatgaggg aggaactgag ggccctggag   3480
caggagaaac ctcagctgct catcttcagc agacggaaac caagtgtgat gaccccctact   3540
```

| | |
|---|---|
| gagggcctgg atacgggaga gatgagtaat agcacatcct cactcaagcg gcagagactc | 3600 |
| ggatcagaga gggcggcttc ccatgttgct caggctaatc tcaaactcct ggacgtgagc | 3660 |
| aagatcttcc caattgctga gattgcaggc aagagccacg aggaaagctc cccagaggta | 3720 |
| gtaccggtgg aactcttgtg cgtgccttct cctgcctctc aagggacct gcatacgaag | 3780 |
| cctttgggga ctgacgatga cttctggggc cccacggggc ctgtggctac tgaggtagtt | 3840 |
| gacaaagaaa agaacttgta ccgagttcac ttccctgtag ctggctccta ccgctggccc | 3900 |
| aacacgggtc tctgctttgt gatgagagaa gcggtgaccg ttgagattga attctgtgtg | 3960 |
| tgggaccagt tcctgggtga gatcaaccca cagcacagct ggatggtggc agggcctctg | 4020 |
| ctggacatca aggctgagcc tggagctgtg gaagctgtgc acctccctca ctttgtggct | 4080 |
| ctccaagggg gccatgtgga cacatccctg ttccaaatgg cccactttaa agaggagggg | 4140 |
| atgctcctgg agaagccagc cagggtggag ctgcatcaca tagttctgga aaaccccagc | 4200 |
| ttctcccct tgggagtcct cctgaaaatg atccataatg ccctgcgctt cattcccgtc | 4260 |
| acctctgtgg tgttgcttta ccaccgcgtc catcctgagg aagtcacctt ccacctctac | 4320 |
| ctgatcccaa gtgactgctc cattcggaag gccatagatg atctagaaat gaaattccag | 4380 |
| tttgtgcgaa tccacaagcc accccgctg acccccactt tatatgggctg tcgttacact | 4440 |
| gtgtctgggt ctggttcagg gatgctgaaa atactcccca aggaactgga gctctgctat | 4500 |
| cgaagccctg gagaagacca gctgttctcg gagttctacg ttggccactt gggatcaggg | 4560 |
| atcaggctgc aagtgaaaga caagaaagat gagactctgg tgtgggaggc cttggtgaaa | 4620 |
| ccaggaagga acaccagcca gccgtggaac ctcaggtgca acagagacgc caggagatac | 4680 |
| tagtgcccag cagcctgcgg cagtaccaat gaagccagag agggcttggt ggatgacaag | 4740 |
| gaggcctgag tagaccgcag gtgggtctga gaaatgggct taggtgaggc aggtctttga | 4800 |
| aggatttgtt cttaatcata tgcgagatgc tcaaaaggct ggatgcctgc ttttgtgggt | 4860 |
| gaagagcaag aagagaaaac aggttgtaca catacagatg cagatggaga gacagagaaa | 4920 |
| aaaaaggaag aaggcagaga aatgcaccaa ttcttgagct gtattatctc tggaccttgg | 4980 |
| gattgtggga ggctttattt tactactgat tttgcctaca ctgttttctc aatttctagt | 5040 |
| tttctacaaa gatgatgtgt tagcttttc acgcattaag attaaaattt aaaacagaaa | 5100 |

<210> SEQ ID NO 11
<211> LENGTH: 5491
<212> TYPE: DNA
<213> ORGANISM: homo sapiens

<400> SEQUENCE: 11

| | |
|---|---|
| cttgttgact aggcgctgtt cttgctggct ggtgccccag ggcctggaga ggtctgaaga | 60 |
| aacctgggag ccagcagccc ggggctccac tctgggttct gaaagcccat tccctgctct | 120 |
| gcggctcctc ccaccccacc tcttctcagc cttgcagctc aagggttgat ctcaggagtc | 180 |
| caggacccag gagagggaag aatctgagga acacagaaca gtgagcgttg cccacacccc | 240 |
| atctcccgtc accacatctc ccctcaccct caccctccct gcctggccct ggaccccatc | 300 |
| ccaggacctc cctatcagct gacttcttcc agtgtcttgc aggcccctct gggctcctcc | 360 |
| ctcccctggc ttttcctacc actccccctc tatcggcgtc tatctgtagg tgccctggga | 420 |
| tttataaaac tgggttccga atgctgaata agagacggta agagccaagg caaaggacag | 480 |
| cactgttctc tgcctgcctg ataccctcac cacctgggaa catcccccag acaccctctt | 540 |

```
aactccggga cagagatggc tggcggagcc tggggccgcc tggcctgtta cttggagttc      600
ctgaagaagg aggagctgaa ggagttccag cttctgctcg ccaataaagc gcactccagg      660
agctcttcgg gtgagacacc cgctcagcca gagaagacga gtggcatgga ggtggcctcg      720
tacctggtgg ctcagtatgg ggagcagcgg gcctgggacc tagccctcca tacctgggag      780
cagatggggc tgaggtcact gtgcgcccaa gcccaggaag gggcaggcca ctctccctca      840
ttcccctaca gcccaagtga accccacctg gggtctccca gccaacccac ctccaccgca      900
gtgctaatgc cctggatcca tgaattgccg gcggggtgca cccagggctc agagagaagg      960
gttttgagac agctgcctga cacatctgga cgccgctgga gagaaatctc tgcctcactc     1020
ctctaccaag ctcttccaag ctccccagac catgagtctc aagccagga gtcacccaac      1080 gcccccacat ccacagcagt gctgggagc tgggatccc cacctcagcc cagcctagca      1140
cccagagagc aggaggctcc tgggacccaa tggcctctgg atgaaacgtc aggaatttac     1200
tacacagaaa tcagagaaag agagagagag aaatcagaga aaggcaggcc cccatgggca     1260
gcggtggtag gaacgccccc acaggcgcac accagcctac agccccacca ccacccatgg     1320
gagccttctg tgagagagag cctctgttcc acatggccct ggaaaaatga ggattttaac     1380
caaaaattca cacagctgct acttctacaa agacctcacc ccagaagcca agatcccctg     1440
gtcaagagaa gctggcctga ttatgtggag gagaatcgag gacatttaat tgagatcaga     1500
gacttatttg gccaggcct ggatacccaa gaacctcgca tagtcatact gcaggggct       1560 gctggaattg ggaagtcaac actggccagg caggtgaagg aagcctgggg gagaggccag     1620
ctgtatgggg accgcttcca gcatgtcttc tacttcagct gcagagagct ggcccagtcc     1680
aaggtggtga gtctcgctga gctcatcgga aaagatggga cagccactcc ggctcccatt     1740
agacagatcc tgtctaggcc agagcggctg ctcttcatcc tcgatggtgt agatgagcca     1800
ggatgggtct gcaggagcc gagttctgag ctctgtctgc actggagcca gccacagccg     1860
gcggatgcac tgctgggcag tttgctgggg aaaactatac ttcccgaggc atccttcctg     1920
atcacggctc ggaccacagc tctgcagaac ctcattcctt ctttggagca ggcacgttgg     1980
gtagaggtcc tggggttctc tgagtccagc aggaaggaat atttctacag atatttcaca     2040
gatgaaaggc aagcaattag agcctttagg ttggtcaaat caaacaaaga gctctgggcc     2100
ctgtgtcttg tgccctgggt gtcctggctg gcctgcactt gcctgatgca gcagatgaag     2160
cggaaggaaa aactcacact gacttccaag accaccacaa ccctctgtct acattacctt     2220
gcccaggctc tccaagctca gccattggga ccccagctca gagacctctg ctctctggct     2280
gctgagggca tctggcaaaa aaagacccctt ttcagtccag atgacctcag gaagcatggg     2340
ttagatgggg ccatcatctc caccttcttg aagatgggta ttcttcaaga gcaccccatc     2400
cctctgagct acagcttcat tcacctctgt ttccaagagt ctttttgcagc aatgtcctat    2460 gtcttggagg atgagaaggg gagaggtaaa cattctaatt gcatcataga tttggaaaag    2520
acgctagaag catatggaat acatggcctg tttgggcat caaccacacg tttcctattg      2580
ggcctgttaa gtgatgaggg ggagagagag atggagaaca tctttcactg ccggctgtct     2640
caggggagga acctgatgca gtgggtcccg tccctgcagc tgctgctgca gccacactct     2700
ctggagtccc tccactgctt gtacgagact cggaacaaaa cgttcctgac acaagtgatg     2760
gcccatttcg aagaaatggg catgtgtgta gaaacagaca tggagctctt agtgtgcact     2820
ttctgcatta aattcagccg ccacgtgaag aagcttcagc tgattgaggg caggcagcac     2880
agatcaacat ggagccccac catggtagtc ctgttcaggt gggtcccagt cacagatgcc     2940
```

```
tattggcaga ttctcttctc cgtcctcaag gtcaccagaa acctgaagga gctggaccta    3000
agtggaaact cgctgagcca ctctgcagtg aagagtcttt gtaagaccct gagacgccct    3060
cgctgcctcc tggagaccct gcggttggct ggctgtggcc tcacagctga ggactgcaag    3120
gaccttgcct ttgggctgag agccaaccag accctgaccg agctggacct gagcttcaat    3180
gtgctcacgg atgctggagc caaacacctt tgccagagac tgagacagcc gagctgcaag    3240
ctacagcgac tgcagctggt cagctgtggc ctcacgtctg actgctgcca ggacctggcc    3300
tctgtgctta gtgccagccc cagcctgaag gagctagacc tgcagcagaa caacctggat    3360
gacgttggcg tgcgactgct ctgtgagggg ctcaggcatc ctgcctgcaa actcatacgc    3420
ctggggctgg accagacaac tctgagtgat gagatgaggc aggaactgag ggccctggag    3480
caggagaaac ctcagctgct catcttcagc agacggaaac caagtgtgat gaccccctact   3540 gagggcctgg atacgggaga tgagtaat agcacatcct cactcaagcg gcagagactc      3600
ggatcagaga gggcggcttc ccatgttgct caggctaatc tcaaactcct ggacgtgagc    3660
aagatcttcc caattgctga gattgcagag gaaagctccc cagaggtagt accggtggaa    3720
ctcttgtgcg tgccttctcc tgcctctcaa ggggacctgc atacgaagcc tttgggggact   3780 gacgatgact tctggggccc cacggggcct gtggctactg aggtagttga caaagaaaag    3840
aacttgtacc gagttcactt ccctgtagct ggctcctacc gctggcccaa cacgggtctc    3900
tgctttgtga tgagagaagc ggtgaccgtt gagattgaat tctgtgtgtg ggaccagttc    3960
ctgggtgaga tcaacccaca gcacagctgg atggtggcag gcctctgct ggacatcaag     4020 gctgagcctg gagctgtgga agctgtgcac ctccctcact tgtggctct ccaagggggc     4080 catgtggaca catccctgtt ccaaatggcc cactttaaag aggagggat gctcctggag     4140 aagccagcca gggtggagct gcatcacata gttctggaaa accccagctt ctccccttg     4200 ggagtcctcc tgaaaatgat ccataatgcc ctgcgcttca ttcccgtcac ctctgtggtg    4260
ttgctttacc accgcgtcca tcctgaggaa gtcaccttcc acctctacct gatcccaagt    4320
gactgctcca ttcggaagga actgagctc tgctatcgaa gccctggaga agaccagctg     4380
ttctcggagt tctacgttgg ccacttggga tcagggatca ggctgcaagt gaaagacaag    4440
aaagatgaga ctctggtgtg ggaggccttg gtgaaaccag gagatctcat gcctgcaact    4500
actctgatcc ctccagcccg catagccgta ccttcacctc tggatgcccc gcagttgctg    4560
cactttgtgg accagtatcg agagcagctg atagcccgag tgacatcggt ggaggttgtc    4620
ttggacaaac tgcatggaca ggtgctgagc caggagcagt acgagagggt gctggctgag    4680
aacacgaggc ccagccagat gcggaagctg ttcagcttga ccagtcctg ggaccggaag     4740 tgcaaagatg gactctacca agccctgaag gagacccatc ctcacctcat tatggaactc    4800
tgggagaagg gcagcaaaaa gggactcctg ccactcagca gctgaagtat caacaccagc    4860
ccttgaccct tgagtcctgg ctttggctga cccttcttg ggtctcagtt tcttttctctg    4920 caaacaagtt gccatctggt ttgccttcca gcactaaagt aatggaactt tgatgatgcc    4980
tttgctgggc attatgtgtc catgccaggg atgccacagg gggcccagt ccaggtggcc     5040 taacagcatc tcaggaatg tccatctgga gctggcaaga cccctgcaga cctcatagag     5100
cctcatctgg tggccacagc agccaagcct agagccctcc ggatcccatc caggcgcaaa    5160
gaggaatagg agggacatgg aaccatttgc ctctggctgt gtcacagggt gagccccaaa    5220
attggggttc agcgtgggag gccacgtgga ttcttggctt tgtacaggaa gatctacaag    5280
```

| | |
|---|---|
| agcaagccaa cagagtaaag tggaaggaag tttattcaga aaataaagga gtatcacagc | 5340 |
| tcttttagaa tttgtctagc aggctttcca gtttttacca gaaacccct ataaattaaa | 5400 |
| aattttttac ttaaatttaa gaattaaaaa aatacaaaaa agaaaaatg aaaataaagg | 5460 |
| aataagaagt tacctactcc aaaaaaaaaa a | 5491 |

<210> SEQ ID NO 12
<211> LENGTH: 5623
<212> TYPE: DNA
<213> ORGANISM: homo sapiens

<400> SEQUENCE: 12

| | |
|---|---|
| cttgttgact aggcgctgtt cttgctggct ggtgccccag ggcctggaga ggtctgaaga | 60 |
| aacctgggag ccagcagccc ggggctccac tctgggttct gaaagcccat tccctgctct | 120 |
| gcggctcctc ccaccccacc tcttctcagc cttgcagctc aagggttgat ctcaggagtc | 180 |
| caggacccag gagagggaag aatctgagga acacagaaca gtgagcgttg cccacacccc | 240 |
| atctcccgtc accacatctc ccctcaccct caccctccct gcctggccct ggaccccatc | 300 |
| ccaggacctc cctatcagct gacttcttcc agtgtcttgc aggcccctct gggctcctcc | 360 |
| ctccctggc ttttcctacc actcccctc tatcggcgtc tatctgtagg tgccctggga | 420 |
| tttataaaac tgggttccga atgctgaata agagacggta agagccaagg caaaggacag | 480 |
| cactgttctc tgcctgcctg ataccctcac cacctgggaa catccccag acaccctctt | 540 |
| aactccggga cagagatggc tggcggagcc tggggccgcc tggcctgtta cttggagttc | 600 |
| ctgaagaagg aggagctgaa ggagttccag cttctgctcg ccaataaagc gcactccagg | 660 |
| agctcttcgg gtgagacacc cgctcagcca gagaagacga gtggcatgga ggtggcctcg | 720 |
| tacctggtgg ctcagtatgg ggagcagcgg gcctgggacc tagccctcca tacctgggag | 780 |
| cagatggggc tgaggtcact gtgcgcccaa gcccaggaag gggcaggcca ctctccctca | 840 |
| ttcccctaca gcccaagtga accccacctg gggtctccca gccaacccac ctccaccgca | 900 |
| gtgctaatgc cctggatcca tgaattgccg gcggggtgca cccagggctc agagagaagg | 960 |
| gttttgagac agctgcctga cacatctgga cgccgctgga gagaaatctc tgcctcactc | 1020 |
| ctctaccaag ctcttccaag ctccccagac catgagtctc caagccagga gtcacccaac | 1080 |
| gcccccacat ccacagcagt gctgggagc tggggatccc cacctcagcc cagcctagca | 1140 |
| cccagagagc aggaggctcc tgggacccaa tggcctctgg atgaaacgtc aggaatttac | 1200 |
| tacacagaaa tcagagaaag agagagagag aaatcagaga aaggcaggcc cccatgggca | 1260 |
| gcggtggtag gaacgccccc acaggcgcac accagcctac agccccacca ccacccatgg | 1320 |
| gagccttctg tgagagagag cctctgttcc acatggccct ggaaaaatga ggattttaac | 1380 |
| caaaaattca cacagctgct acttctacaa agacctcacc ccagaagcca agatcccctg | 1440 |
| gtcaagagaa gctggcctga ttatgtggag gagaatcgag gacatttaat tgagatcaga | 1500 |
| gacttatttg gccaggcct ggatacccaa gaacctcgca tagtcatact gcagggggct | 1560 |
| gctggaattg ggaagtcaac actggccagg caggtgaagg aagcctgggg gagaggccag | 1620 |
| ctgtatgggg accgcttcca gcatgtcttc tacttcagct gcagagagct ggcccagtcc | 1680 |
| aaggtggtga gtctcgctga gctcatcgga aaagatggga cagccactcc ggctcccatt | 1740 |
| agacagatcc tgtctaggcc agagcggctg ctcttcatcc tcgatggtgt agatgagcca | 1800 |
| ggatgggtct tgcaggagcc gagttctgag ctctgtctgc actggagcca gccacagccg | 1860 |
| gcggatgcac tgctgggcag tttgctgggg aaaactatac ttcccgaggc atccttcctg | 1920 |

| | |
|---|---|
| atcacggctc ggaccacagc tctgcagaac ctcattcctt ctttggagca ggcacgttgg | 1980 |
| gtagaggtcc tggggttctc tgagtccagc aggaaggaat atttctacag atatttcaca | 2040 |
| gatgaaaggc aagcaattag agcctttagg ttggtcaaat caaacaaaga gctctgggcc | 2100 |
| ctgtgtcttg tgccctgggt gtcctggctg gcctgcactt gcctgatgca gcagatgaag | 2160 |
| cggaaggaaa aactcacact gacttccaag accaccacaa ccctctgtct acattacctt | 2220 |
| gcccaggctc tccaagctca gccattggga ccccagctca gagacctctg ctctctggct | 2280 |
| gctgagggca tctggcaaaa aaagacccct tcagtccag atgacctcag gaagcatggg | 2340 |
| ttagatgggg ccatcatctc caccttcttg aagatgggta ttcttcaaga gcaccccatc | 2400 |
| cctctgagct acagcttcat tcacctctgt ttccaagagt tctttgcagc aatgtcctat | 2460 |
| gtcttggagt atgagaaggg gagaggtaaa cattctaatt gcatcataga tttggaaaag | 2520 |
| acgctagaag catatggaat acatggcctg tttggggcat caaccacacg tttcctattg | 2580 |
| ggcctgttaa gtgatgaggg ggagagagag atggagaaca tctttcactg ccggctgtct | 2640 |
| caggggagga acctgatgca gtgggtcccg tccctgcagc tgctgctgca gccacactct | 2700 |
| ctggagtccc tccactgctt gtacgagact cggaacaaaa cgttcctgac acaagtgatg | 2760 |
| gcccatttcg aagaaatggg catgtgtgta gaaacagaca tggagctctt agtgtgcact | 2820 |
| ttctgcatta aattcagccg ccacgtgaag aagcttcagc tgattgaggg caggcagcac | 2880 |
| agatcaacat ggagccccac catggtagtc ctgttcaggt gggtcccagt cacagatgcc | 2940 |
| tattggcaga ttctcttctc cgtcctcaag gtcaccagaa acctgaagga gctggaccta | 3000 |
| agtggaaact cgctgagcca ctctgcagtg aagagtcttt gtaagaccct gagacgccct | 3060 |
| cgctgcctcc tggagaccct gcggttggct ggctgtggcc tcacagctga ggactgcaag | 3120 |
| gaccttgcct ttgggctgag agccaaccag accctgaccg agctggacct gagcttcaat | 3180 |
| gtgctcacgg atgctggagc caaacacctt tgccagagac tgagacagcc gagctgcaag | 3240 |
| ctacagcgac tgcagctggt cagctgtggc ctcacgtctg actgctgcca ggacctggcc | 3300 |
| tctgtgctta gtgccagccc cagcctgaag gagctagacc tgcagcagaa caacctggat | 3360 |
| gacgttggcg tgcgactgct ctgtgagggg ctcaggcatc ctgcctgcaa actcatacgc | 3420 |
| ctggggctgg accagacaac tctgagtgat gagatgaggc aggaactgag ggccctggag | 3480 |
| caggagaaac ctcagctgct catcttcagc agacggaaac caagtgtgat gaccccctact | 3540 |
| gagggcctgg atacgggaga gatgagtaat agcacatcct cactcaagcg gcagagactc | 3600 |
| ggatcagaga gggcggcttc ccatgttgct caggctaatc tcaaactcct ggacgtgagc | 3660 |
| aagatcttcc caattgctga gattgcagag gaaagctccc cagaggtagt accggtggaa | 3720 |
| ctcttgtgcg tgccttctcc tgcctctcaa ggggacctgc atacgaagcc tttggggact | 3780 |
| gacgatgact tctggggccc cacggggcct gtggctactg aggtagttga caaagaaaag | 3840 |
| aacttgtacc gagttcactt ccctgtagct ggctcctacc gctggcccaa cacgggtctc | 3900 |
| tgctttgtga tgagagaagc ggtgaccgtt gagattgaat tctgtgtgtg ggaccagttc | 3960 |
| ctgggtgaga tcaacccaca gcacagctgg atggtggcag ggcctctgct ggacatcaag | 4020 |
| gctgagcctg gagctgtgga agctgtgcac ctccctcact ttgtggctct ccaagggggc | 4080 |
| catgtggaca catccctgtt ccaaatggcc cactttaaag aggagggat gctcctggag | 4140 |
| aagccagcca gggtggagct gcatcacata gttctgaaaa accccagctt ctccccctyg | 4200 |
| ggagtcctcc tgaaaatgat ccataatgcc ctgcgcttca ttcccgtcac ctctgtggtg | 4260 |

```
ttgctttacc accgcgtcca tcctgaggaa gtcaccttcc acctctacct gatcccaagt    4320
gactgctcca ttcggaaggc catagatgat ctagaaatga aattccagtt tgtgcgaatc    4380
cacaagccac ccccgctgac cccactttat atgggctgtc gttacactgt gtctgggtct    4440
ggttcaggga tgctggaaat actccccaag gaactggagc tctgctatcg aagccctgga    4500
gaagaccagc tgttctcgga gttctacgtt ggccacttgg gatcagggat caggctgcaa    4560
gtgaaagaca agaaagatga gactctggtg tgggaggcct tggtgaaacc aggagatctc    4620
atgcctgcaa ctactctgat ccctccagcc cgcatagccg taccttcacc tctggatgcc    4680
ccgcagttgc tgcactttgt ggaccagtat cgagagcagc tgatagcccg agtgacatcg    4740
gtggaggttg tcttggacaa actgcatgga caggtgctga gccaggagca gtacgagagg    4800
gtgctggctg agaacacgag gcccagccag atgcggaagc tgttcagctt gagccagtcc    4860
tgggaccgga agtgcaaaga tggactctac caagccctga aggagaccca tcctcacctc    4920
attatggaac tctgggagaa gggcagcaaa aagggactcc tgccactcag cagctgaagt    4980
atcaacacca gcccttgacc cttgagtcct ggctttggct gacccttctt tgggtctcag    5040
tttctttctc tgcaaacaag ttgccatctg gtttgccttc cagcactaaa gtaatggaac    5100
tttgatgatg cctttgctgg gcattatgtg tccatgccag gatgccaca gggggcccca    5160 gtccaggtgg cctaacagca tctcagggaa tgtccatctg gagctggcaa gaccctgca    5220 gacctcatag agcctcatct ggtggccaca gcagccaagc ctagagccct ccggatccca    5280
tccaggcgca aagaggaata ggagggacat ggaaccattt gcctctggct gtgtcacagg    5340
gtgagcccca aaattggggt tcagcgtggg aggccacgtg gattcttggc tttgtacagg    5400
aagatctaca agagcaagcc aacagagtaa agtggaagga agtttattca gaaaataaag    5460
gagtatcaca gctcttttag aatttgtcta gcaggctttc cagttttac cagaaaaccc    5520 ctataaatta aaaatttttt acttaaattt aagaattaaa aaaatacaaa aagaaaaaa    5580 tgaaaataaa ggaataagaa gttacctact ccaaaaaaaa aaa                      5623

<210> SEQ ID NO 13
<211> LENGTH: 5533
<212> TYPE: DNA
<213> ORGANISM: homo sapiens

<400> SEQUENCE: 13
cttgttgact aggcgctgtt cttgctggct ggtgccccag ggcctggaga ggtctgaaga      60
aacctgggag ccagcagccc ggggctccac tctgggttct gaaagcccat tcccgctct     120 gcggctcctc ccaccccacc tcttctcagc cttgcagctc aagggttgat ctcaggagtc    180
caggacccag gagagggaag aatctgagga acacagaaca gtgagcgttg cccacacccc    240
atctcccgtc accacatctc ccctcaccct caccctccct gcctggccct ggaccccatc    300
ccaggacctc cctatcagct gacttcttcc agtgtcttgc aggcccctct gggctcctcc    360
ctcccctggc ttttcctacc actccccctc tatcggcgtc tatctgtagg tgccctggga    420
tttataaaac tgggttccga atgctgaata agagacggta agagccaagg caaaggacag    480
cactgttctc tgcctgcctg ataccctcac cactgggaa catcccccag acaccctctt    540
aactccggga cagagatggc tggcggagcc tggggccgcc tggcctgtta cttggagttc    600
ctgaagaagg aggagctgaa ggagttccag cttctgctcg ccaataaagc gcactccagg    660
agctcttcgg gtgagacacc cgctcagcca gagaagacga gtggcatgga ggtggcctcg    720
tacctggtgg ctcagtatgg ggagcagcgg gcctgggacc tagccctcca tacctgggag    780
```

```
cagatggggc tgaggtcact gtgcgcccaa gcccaggaag gggcaggcca ctctccctca    840
ttcccctaca gcccaagtga accccacctg gggtctccca gccaacccac ctccaccgca    900
gtgctaatgc cctggatcca tgaattgccg gcggggtgca cccagggctc agagagaagg    960
gttttgagac agctgcctga cacatctgga cgccgctgga gagaaatctc tgcctcactc   1020
ctctaccaag ctcttccaag ctccccagac catgagtctc aagccagga gtcacccaac    1080
gcccccacat ccacagcagt gctggggagc tggggatccc cacctcagcc cagcctagca   1140
cccagagagc aggaggctcc tgggacccaa tggcctctgg atgaaacgtc aggaatttac   1200
tacacagaaa tcagagaaag agagagagag aaatcagaga aaggcaggcc ccatgggca    1260
gcggtggtag gaacgccccc acaggcgcac accagcctac agccccacca ccacccatgg   1320
gagccttctg tgagagagag cctctgttcc acatggccct ggaaaaatga ggattttaac   1380
caaaaattca cacagctgct acttctacaa agacctcacc ccagaagcca agatcccctg   1440
gtcaagagaa gctggcctga ttatgtggag gagaatcgag acatttaat tgagatcaga    1500
gacttatttg gcccaggcct ggatacccaa gaacctcgca tagtcatact gcaggggct    1560
gctggaattg ggaagtcaac actggccagg caggtgaagg aagcctgggg gagaggccag   1620
ctgtatgggg accgcttcca gcatgtcttc tacttcagct gcagagagct ggcccagtcc   1680
aaggtggtga gtctcgctga gctcatcgga aaagatggga cagccactcc ggctcccatt   1740
agacagatcc tgtctaggcc agagcggctg ctcttcatcc tcgatggtgt agatgagcca   1800
ggatgggtct gcaggagcc gagttctgag ctctgtctgc actggagcca gccacagccg    1860
gcggatgcac tgctgggcag tttgctgggg aaaactatac ttcccgaggc atccttcctg   1920
atcacggctc ggaccacagc tctgcagaac ctcattcctt ctttggagca ggcacgttgg   1980
gtagaggtcc tggggttctc tgagtccagc aggaaggaat atttctacag atatttcaca   2040
gatgaaaggc aagcaattag agcctttagg ttggtcaaat caaacaaaga gctctgggcc   2100
ctgtgtcttg tgccctgggt gtcctggctg gcctgcactt gcctgatgca gcagatgaag   2160
cggaaggaaa aactcacact gacttccaag accaccacaa ccctctgtct acattacctt   2220
gcccaggctc tccaagctca gccattggga ccccagctca gagacctctg ctctctggct   2280
gctgagggca tctggcaaaa aaagacccct ttcagtccag atgacctcag gaagcatggg   2340
ttagatgggg ccatcatctc caccttcttg aagatgggta ttcttcaaga gcaccccatc   2400
cctctgagct acagcttcat tcacctctgt ttccaagagt tctttgcagc aatgtcctat   2460
gtcttggagg atgagaaggg gagaggtaaa cattctaatt gcatcataga tttggaaaag   2520
acgctagaag catatggaat acatggcctg tttggggcat caaccacacg tttcctattg   2580
ggcctgttaa gtgatgaggg ggagagagag atggagaaca tctttcactg ccggctgtct   2640
caggggagga acctgatgca gtgggtcccg tccctgcagc tgctgctgca gccacactct   2700
ctggagtccc tccactgctt gtacgagact cggaacaaaa cgttcctgac acaagtgatg   2760
gcccatttcg aagaaatggg catgtgtgta gaaacagaca tggagctctt agtgtgcact   2820
ttctgcatta aattcagccg ccacgtgaag aagcttcagc tgattgaggg caggcagcac   2880
agatcaacat ggagccccac catggtagtc ctgttcaggt gggtcccagt cacagatgcc   2940
tattggcaga ttctcttctc cgtcctcaag gtcaccagaa acctgaagga gctggaccta   3000
agtggaaact cgctgagcca ctctgcagtg aagagtcttt gtaagaccct gagacgccct   3060
cgctgcctcc tggagaccct gcggttggct ggctgtggcc tcacagctga ggactgcaag   3120
```

| | |
|---|---|
| gaccttgcct ttgggctgag agccaaccag accctgaccg agctggacct gagcttcaat | 3180 |
| gtgctcacgg atgctggagc caaacacctt tgccagagac tgagacagcc gagctgcaag | 3240 |
| ctacagcgac tgcagctggt cagctgtggc ctcacgtctg actgctgcca ggacctggcc | 3300 |
| tctgtgctta gtgccagccc cagcctgaag gagctagacc tgcagcagaa caacctggat | 3360 |
| gacgttggcg tgcgactgct ctgtgagggg ctcaggcatc ctgcctgcaa actcatacgc | 3420 |
| ctggggaaac caagtgtgat gaccectact gagggcctgg atacgggaga gatgagtaat | 3480 |
| agcacatcct cactcaagcg gcagagactc ggatcagaga gggcggcttc ccatgttgct | 3540 |
| caggctaatc tcaaactcct ggacgtgagc aagatcttcc caattgctga gattgcagag | 3600 |
| gaaagctccc cagaggtagt accggtggaa ctcttgtgcg tgccttctcc tgcctctcaa | 3660 |
| ggggacctgc atacgaagcc tttggggact gacgatgact tctggggccc cacggggcct | 3720 |
| gtggctactg aggtagttga caaagaaaag aacttgtacc gagttcactt ccctgtagct | 3780 |
| ggctcctacc gctggcccaa cacgggtctc tgctttgtga tgagagaagc ggtgaccgtt | 3840 |
| gagattgaat tctgtgtgtg ggaccagttc ctggtgaga tcaacccaca gcacagctgg | 3900 |
| atggtggcag ggcctctgct ggacatcaag gctgagcctg agctgtgga agctgtgcac | 3960 |
| ctccctcact ttgtggctct ccaaggggge catgtggaca catccctgtt ccaaatggcc | 4020 |
| cactttaaag aggaggggat gctcctggag aagccagcca gggtggagct gcatcacata | 4080 |
| gttctgaaaa ccccagctt ctccccctig ggagtcctcc tgaaaatgat ccataatgcc | 4140 |
| ctgcgcttca ttcccgtcac ctctgtggtg ttgctttacc accgcgtcca tcctgaggaa | 4200 |
| gtcaccttcc acctctacct gatcccaagt gactgctcca ttcggaaggc catagatgat | 4260 |
| ctagaaatga aattccagtt tgtgcgaatc cacaagccac cccgctgac cccactttat | 4320 |
| atgggctgtc gttacactgt gtctgggtct ggttcaggga tgctggaaat actccccaag | 4380 |
| gaactggagc tctgctatcg aagccctgga gaagaccagc tgttctcgga gttctacgtt | 4440 |
| ggccacttgg gatcagggat caggctgcaa gtgaaagaca gaaagatga gactctggtg | 4500 |
| tgggaggcct tggtgaaacc aggagatctc atgcctgcaa ctactctgat ccctccagcc | 4560 |
| cgcatagccg taccttcacc tctggatgcc ccgcagttgc tgcactttgt ggaccagtat | 4620 |
| cgagagcagc tgatagcccg agtgacatcg gtggaggttg tcttggacaa actgcatgga | 4680 |
| caggtgctga gccaggagca gtacgagagg gtgctggctg agaacacgag gcccagccag | 4740 |
| atgcggaagc tgttcagctt gagccagtcc tgggaccgga agtgcaaaga tggactctac | 4800 |
| caagccctga aggagaccca tcctcacctc attatggaac tctgggagaa gggcagcaaa | 4860 |
| aagggactcc tgccactcag cagctgaagt atcaacacca gcccttgacc cttgagtcct | 4920 |
| ggctttggct gacccttctt tgggtctcag tttctttctc tgcaaacaag ttgccatctg | 4980 |
| gtttgccttc cagcactaaa gtaatggaac tttgatgatg cctttgctgg gcattatgtg | 5040 |
| tccatgccag ggatgccaca gggggcccca gtccaggtgg cctaacagca tctcagggaa | 5100 |
| tgtccatctg gagctggcaa gacccctgca gacctcatag agcctcatct ggtggccaca | 5160 |
| gcagccaagc ctagagccct ccggatccca tccaggcgca agaggaata ggagggacat | 5220 |
| ggaaccattt gcctctggct gtgtcacagg gtgagcccca aaattggggt tcagcgtggg | 5280 |
| aggccacgtg gattcttggc tttgtacagg aagatctaca agagcaagcc aacagagtaa | 5340 |
| agtggaagga agtttattca gaaaataaag gagtatcaca gctctttag aatttgtcta | 5400 |
| gcaggctttc cagttttac cagaaaaccc ctataaatta aaaatttttt acttaaattt | 5460 |
| aagaattaaa aaaatacaaa aagaaaaaa tgaaaataaa ggaataagaa gttacctact | 5520 |

```
ccaaaaaaaa aaa                                                    5533

<210> SEQ ID NO 14
<211> LENGTH: 5401
<212> TYPE: DNA
<213> ORGANISM: homo sapiens

<400> SEQUENCE: 14
cttgttgact aggcgctgtt cttgctggct ggtgccccag ggcctggaga ggtctgaaga      60
aacctgggag ccagcagccc ggggctccac tctgggttct gaaagcccat tccctgctct     120
gcggctcctc ccaccccacc tcttctcagc cttgcagctc aagggttgat ctcaggagtc     180
caggacccag gagagggaag aatctgagga acacagaaca gtgagcgttg cccacacccc     240
atctcccgtc accacatctc ccctcaccct caccctccct gcctggccct ggaccccatc     300
ccaggacctc cctatcagct gacttcttcc agtgtcttgc aggcccctct gggctcctcc     360
ctcccctggc ttttcctacc actcccctc tatcggcgtc tatctgtagg tgccctggga      420
tttataaaac tgggttccga atgctgaata agagacggta agagccaagg caaaggacag     480
cactgttctc tgcctgcctg ataccctcac cacctgggaa catcccccag acaccctctt     540
aactccggga cagagatggc tggcggagcc tggggccgcc tggcctgtta cttggagttc     600
ctgaagaagg aggagctgaa ggagttccag cttctgctcg ccaataaagc gcactccagg     660
agctcttcgg gtgagacacc cgctcagcca gagaagacga gtggcatgga ggtggcctcg     720
tacctggtgg ctcagtatgg ggagcagcgg gcctgggacc tagccctcca tacctgggag     780
cagatggggc tgaggtcact gtgcgcccaa gcccaggaag gggcaggcca ctctccctca     840
ttcccctaca gcccaagtga accccacctg gggtctccca gccaacccac ctccaccgca     900
gtgctaatgc cctggatcca tgaattgccg gcggggtgca cccagggctc agagagaagg     960
gttttgagac agctgcctga cacatctgga cgccgctgga gagaaatctc tgcctcactc    1020
ctctaccaag ctcttccaag ctccccagac catgagtctc caagccagga gtcacccaac    1080
gcccccacat ccacagcagt gctgggagc tgggatccc cacctcagcc cagcctagca     1140
cccagagagc aggaggctcc tgggacccaa tggcctctgg atgaaacgtc aggaatttac    1200
tacacagaaa tcagaaaag agagagagag aaatcagaga aaggcaggcc cccatgggca    1260
gcggtggtag aacgcccccc acaggcgcac accagcctac agcccaccca ccacccatgg    1320
gagccttctg tgagagagag cctctgttcc acatggccct ggaaaaatga ggattttaac    1380
caaaaattca cacagctgct acttctacaa agacctcacc ccagaagcca agatcccctg    1440
gtcaagagaa gctggcctga ttatgtggag gagaatcgag acatttaat tgagatcaga    1500
gacttatttg gccaggcct ggatacccaa gaacctcgca tagtcatact gcaggggct     1560
gctggaattg ggaagtcaac actggccagg caggtgaagg aagcctgggg gagaggccag    1620
ctgtatgggg accgcttcca gcatgtcttc tacttcagct gcagagagct ggcccagtcc    1680
aaggtggtga gtctcgctga gctcatcgga aaagatggga cagccactcc ggctcccatt    1740
agacagatcc tgtctaggcc agagcggctg ctcttcatcc tcgatggtgt agatgagcca    1800
ggatgggtct tgcaggagcc gagttctgag ctctgtctgc actggagcca gccacagccg    1860
gcggatgcac tgctgggcag tttgctgggg aaaactatac ttcccgaggc atccttcctg    1920
atcacgcctc ggaccacagc tctgcagaac ctcattcctt ctttggagca ggcacgttgg    1980
gtagaggtcc tggggttctc tgagtccagc aggaaggaat atttctacag atatttcaca    2040
```

```
gatgaaaggc aagcaattag agcctttagg ttggtcaaat caaacaaaga gctctgggcc    2100
ctgtgtcttg tgccctgggt gtcctggctg gcctgcactt gcctgatgca gcagatgaag    2160
cggaaggaaa aactcacact gacttccaag accaccacaa ccctctgtct acattacctt    2220
gcccaggctc tccaagctca gccattggga ccccagctca gagacctctg ctctctggct    2280
gctgagggca tctggcaaaa aaagacccct ttcagtccag atgacctcag gaagcatggg    2340
ttagatgggg ccatcatctc caccttcttg aagatgggta ttcttcaaga gcaccccatc    2400
cctctgagct acagcttcat tcacctctgt ttccaagagt tctttgcagc aatgtcctat    2460
gtcttggagg atgagaaggg gagaggtaaa cattctaatt gcatcataga tttggaaaag    2520
acgctagaag catatggaat acatggcctg tttggggcat caaccacacg tttcctattg    2580
ggcctgttaa gtgatgaggg ggagagagag atggagaaca tctttcactg ccggctgtct    2640
caggggagga acctgatgca gtgggtcccg tccctgcagc tgctgctgca gccacactct    2700
ctggagtccc tccactgctt gtacgagact cggaacaaaa cgttcctgac acaagtgatg    2760
gcccatttcg aagaaatggg catgtgtgta gaaacagaca tggagctctt agtgtgcact    2820
ttctgcatta aattcagccg ccacgtgaag aagcttcagc tgattgaggg caggcagcac    2880
agatcaacat ggagccccac catggtagtc ctgttcaggt gggtcccagt cacagatgcc    2940
tattggcaga ttctcttctc cgtcctcaag gtcaccagaa acctgaagga gctggaccta    3000 agtggaaaact cgctgagcca ctctgcagtg aagagtcttt gtaagaccct gagacgccct    3060
cgctgcctcc tggagaccct gcggttggct ggctgtggcc tcacagctga ggactgcaag    3120
gaccttgcct ttgggctgag agccaaccag accctgaccg agctggacct gagcttcaat    3180
gtgctcacgg atgctggagc caaacacctt gccagagac tgagacagcc gagctgcaag    3240
ctacagcgac tgcagctggt cagctgtggc ctcacgtctg actgctgcca ggacctggcc    3300
tctgtgctta gtgccagccc cagcctgaag gagctagacc tgcagcagaa caacctggat    3360
gacgttggcg tgcgactgct ctgtgagggg ctcaggcatc ctgcctgcaa actcatacgc    3420
ctggggaaac caagtgtgat gaccccctact gagggcctgg atacgggaga gatgagtaat    3480
agcacatcct cactcaagcg gcagagactc ggatcagaga gggcggcttc ccatgttgct    3540
caggctaatc tcaaactcct ggacgtgagc aagatcttcc caattgctga gattgcagag    3600
gaaagctccc cagaggtagt accggtggaa ctcttgtgcg tgccttctcc tgcctctcaa    3660
ggggacctgc atacgaagcc tttggggact gacgatgact tctggggccc cacggggcct    3720
gtggctactg aggtagttga caaagaaaag aacttgtacc gagttcactt ccctgtagct    3780
ggctcctacc gctggcccaa cacgggtctc tgctttgtga tgagagaagc ggtgaccgtt    3840
gagattgaat tctgtgtgtg ggaccagttc ctgggtgaga tcaacccaca gcacagctgg    3900
atggtggcag ggcctctgct ggacatcaag gctgagcctg gagctgtgga agctgtgcac    3960 ctcccctcact ttgtggctct ccaaggggggc catgtggaca catccctgtt ccaaatggcc    4020
cactttaaag aggagggat gctcctggag aagccagcca gggtggagct gcatcacata    4080
gttctggaaa accccagctt ctccccctg ggagtcctcc tgaaaatgat ccataatgcc    4140
ctgcgcttca ttcccgtcac ctctgtggtg ttgctttacc accgcgtcca tcctgaggaa    4200
gtcaccttcc acctctacct gatcccaagt gactgctcca ttcggaagga actggagctc    4260
tgctatcgaa gccctggaga agaccagctg ttctcggagt tctacgttgg ccacttggga    4320
tcagggatca ggctgcaagt gaaagacaag aaagatgaga ctctggtgtg ggaggccttg    4380
gtgaaaccag gagatctcat gcctgcaact actctgatcc ctccagcccg catagccgta    4440
```

```
ccttcacctc tggatgcccc gcagttgctg cactttgtgg accagtatcg agagcagctg    4500
atagcccgag tgacatcggt ggaggttgtc ttggacaaac tgcatggaca ggtgctgagc    4560
caggagcagt acgagagggt gctggctgag aacacgaggc ccagccagat gcggaagctg    4620
ttcagcttga gccagtcctg ggaccggaag tgcaaagatg gactctacca agccctgaag    4680
gagacccatc ctcacctcat tatggaactc tgggagaagg gcagcaaaaa gggactcctg    4740
ccactcagca gctgaagtat caacaccagc ccttgaccct tgagtcctgg ctttggctga    4800
cccttctttg ggtctcagtt tctttctctg caaacaagtt gccatctggt ttgccttcca    4860
gcactaaagt aatggaactt tgatgatgcc tttgctgggc attatgtgtc catgccaggg    4920
atgccacagg gggcccccagt ccaggtggcc taacagcatc tcagggaatg tccatctgga    4980
gctggcaaga cccctgcaga cctcatagag cctcatctgg tggccacagc agccaagcct    5040
agagccctcc ggatcccatc caggcgcaaa aaggaatagg agggacatgg aaccatttgc    5100
ctctggctgt gtcacagggt gagccccaaa attggggttc agcgtgggag ccacgtggaa    5160
ttcttggctt tgtacaggaa gatctacaag agcaagccaa cagagtaaag tggaaggaag    5220
tttattcaga aaataaagga gtatcacagc tcttttagaa tttgtctagc aggctttcca    5280 gttttttacca gaaaaccccct ataaattaaa aattttttac ttaaatttaa gaattaaaaa    5340
aatacaaaaa agaaaaaatg aaaataaagg aataagaagt tacctactcc aaaaaaaaaa    5400
a                                                                    5401

<210> SEQ ID NO 15
<211> LENGTH: 3538
<212> TYPE: DNA
<213> ORGANISM: homo sapiens

<400> SEQUENCE: 15
ggcaagacaa cgaggatttg cgtagggggc gagcctctga ggccacttgg ctcttacggc      60
cacgcagggc gccgcagatg cagccggagc ccgcttttcc ctctcaggac gaccctagg     120 ccgccagcag ttccctaccg acgaaggcga ctgtacagcg tccaccgcgt tcgtgcccac     180
ttacccgccg ccccactccg ggccgccggc tcgcagcagg accagcccgg ctgctacggc     240
cgcggataca cgccctcagg cccggcgctg cgcagcttgc ggaagctttc ccggacagac     300
tcgctgccag cggattggct gcgagcagcg ccaatctcac gttgccccccg ggcgaggcgg     360 gactcagtgc cgcgctctct gcacccgctc tgccgcgcgc gtgcgtgctg ggtgcgggtg     420
cgggtgcggg gttgggcctg cgcatcgggt gagacgctgg ctgcttgcgg ctagtggatg     480
gtaattgcct gcctcgcgct agcaggaagc tgctctgtta aaagcgaaaa tgaaacaatt     540
gcctgcggca acagttcgac tcctttcaag ttctcagatc atcacttcgg tggtcagtgt     600
tgtaaaagag cttattgaaa actccttgga tgctggtgcc acaagcgtag atgttaaact     660
ggagaactat ggatttgata aaattgaggt gcgagataac ggggagggta tcaaggctgt     720
tgatgcacct gtaatggcaa tgaagtacta cacctcaaaa ataaatagtc atgaagatct     780
tgaaaatttg acaacttacg gttttcgtgg agaagccttg gggtcaattt gttgtatagc     840
tgaggtttta attacaacaa gaacggctgc tgataatttt agcacccagt atgttttaga     900
tggcagtggc cacatacttt ctcagaaacc ttcacatctt ggtcaaggta caactgtaac     960
tgctttaaga ttatttaaga atctacctgt aagaaagcag ttttactcaa ctgcaaaaaa    1020
atgtaaagat gaaataaaaa agatccaaga tctcctcatg agctttggta tccttaaacc    1080
```

```
tgacttaagg attgtctttg tacataacaa ggcagttatt tggcagaaaa gcagagtatc   1140
agatcacaag atggctctca tgtcagttct ggggactgct gttatgaaca atatggaatc   1200
ctttcagtac cactctgaag aatctcagat ttatctcagt ggatttcttc caaagtgtga   1260
tgcagaccac tctttcacta gtctttcaac accagaaaga agtttcatct tcataaacag   1320
tcgaccagta catcaaaaag atatcttaaa gttaatccga catcattaca atctgaaatg   1380
cctaaaggaa tctactcgtt tgtatcctgt tttctttctg aaaatcgatg ttcctacagc   1440
tgatgttgat gtaaatttaa caccagataa aagccaagta ttattacaaa ataaggaatc   1500
tgttttaatt gctcttgaaa atctgatgac gacttgttat ggaccattac ctagtacaaa   1560
ttcttatgaa aataataaaa cagatgtttc cgcagctgac atcgttctta gtaaaacagc   1620
agaaacagat gtgcttttta ataaagtgga atcatctgga aagaattatt caaatgttga   1680
tacttcagtc attccattcc aaaatgatat gcataatgat gaatctggaa aaaacactga   1740
tgattgttta aatcaccaga taagtattgg tgactttggt tatggtcatt gtagtagtga   1800
aatttctaac attgataaaa acactaagaa tgcatttcag gacatttcaa tgagtaatgt   1860
atcatgggag aactctcaga cggaatatag taaaacttgt tttataagtt ccgttaagca   1920
cacccagtca gaaaatggca ataaagacca tatagatgag agtggggaaa atgaggaaga   1980
agcaggtctt gaaaactctt cggaaatttc tgcagatgag tggagcaggg gaaatatact   2040
taaaaattca gtgggagaga atattgaacc tgtgaaaatt ttagtgcctg aaaaaagttt   2100
accatgtaaa gtaagtaata ataattatcc aatccctgaa caaatgaatc ttaatgaaga   2160
ttcatgtaac aaaaaatcaa atgtaataga taataaatct ggaaaagtta cagcttatga   2220
tttacttagc aatcgagtaa tcaagaaacc catgtcagca agtgctcttt tgttcaaga   2280 tcatcgtcct cagtttctca tagaaaatcc taagactagt ttagaggatg caacactaca   2340
aattgaagaa ctgtggaaga cattgagtga agaggaaaaa ctgaaatatg aagagaaggc   2400
tactaaagac ttggaacgat acaatagtca atgaagaga gccattgaac aggagtcaca   2460
aatgtcacta aaagatggca gaaaaagat aaaacccacc agcgcatgga atttggccca   2520
gaagcacaag ttaaaaacct cattatctaa tcaaccaaaa cttgatgaac tccttcagtc   2580
ccaaattgaa aaagaagga gtcaaaatat taaaatggta cagatcccct tttctatgaa   2640
aaacttaaaa ataatttta agaaacaaaa caaagttgac ttagaagaga aggatgaacc   2700
ttgcttgatc cacaatctca ggtttcctga tgcatggcta atgacatcca aaacagaggt   2760
aatgttatta aatccatata gagtagaaga agccctgcta tttaaaagac ttcttgagaa   2820
tcataaactt cctgcagagc cactggaaaa gccaattatg ttaacagaga gtcttttta   2880 tggatctcat tatttagacg ttttatataa aatgacagca gatgaccaaa gatacagtgg   2940
atcaacttac ctgtctgatc ctcgtcttac agcgaatggt ttcaagataa aattgatacc   3000
aggagtttca attactgaaa attacttgga aatagaagga atggctaatt gtctcccatt   3060
ctatggagta gcagatttaa aagaaattct taatgctata ttaaacagaa atgcaaagga   3120
agtttatgaa tgtagacctc gcaaagtgat aagttattta gagggagaag cagtgcgtct   3180
atccagacaa ttacccatgt acttatcaaa agaggacatc caagcattta ctctacagaat   3240 gaagcaccag tttggaaatg aaattaaaga gtgtgttcat ggtcgcccat tttttcatca   3300
tttaacctat cttccagaaa ctacatgatt aaatatgttt aagaagatta gttaccattg   3360
aaattggttc tgtcataaaa cagcatgagt ctggttttaa attatctttg tattatgtgt   3420
cacatggtta ttttttaaat gaggattcac tgacttgttt ttatattgaa aaaagttcca   3480
```

```
cgtattgtag aaaacgtaaa taaactaata tagactattc aaaaaaaaaa aaaaaaaa    3538
```

<210> SEQ ID NO 16
<211> LENGTH: 3421
<212> TYPE: DNA
<213> ORGANISM: homo sapiens

<400> SEQUENCE: 16

```
ggcaagacaa cgaggatttg cgtaggggc gagcctctga ggccacttgg ctcttacggc      60
cacgcagggc gccgcagatg cagccggagc ccgcttttcc ctctcaggac gaccoctagg    120
ccgccagcag ttccctaccg acgaaggcga ctgtacagcg tccaccgcgt tcgtgcccac    180
ttacccgccg ccccactccg ggccgccggc tcgcagcagg accagcccgg ctgctacggc    240
cgcggataca cgccctcagg cccggcgctg cgcagcttgc ggaagctttc ccggacagac    300
tcgctgccag cggattggct gcgagcagcg ccaatctcac gttgccccg gcgaggcgg     360
gactcagtgc cgcgctctct gcacccgctc tgccgcgcgc gtgcgtgctg ggtgcgggtg    420
cgggtgcggg gttgggcctg cgcatcgggt gagacgctgg ctgcttgcgg ctagtggatg    480
gtaattgcct gcctcgcgct agcaggaagc tgctctgtta aaagcgaaaa tgaaacaatt    540
gcctgcggca acagttcgac tccttttcaag ttctcagatc atcacttcgg tggtcagtgt    600
tgtaaaagag cttattgaaa actccttgga tgctggtgcc acaagcgtag atgttaaact    660
ggagaactat ggatttgata aaattgaggt gcgagataac ggggagggta tcaaggctgt    720
tgatgcacct gtaatggcaa tgaagtacta cacctcaaaa ataaatagtc atgaagatct    780
tgaaaatttg acaacttacg gttttcgtgg agaagccttg gggtcaattt gttgtatagc    840
tgaggtttta attacaacaa gaacggctgc tgataatttt agcacccagt atgttttaga    900
tggcagtggc cacatacttt ctcagaaacc ttcacatctt ggtcaaggta caactgtaac    960
tgctttaaga ttattaaga atctaccgt aagaaagcag ttttactcaa ctgcaaaaaa    1020
atgtaaagat gaaataaaaa agatccaaga tctcctcatg agctttggta tccttaaacc    1080
tgacttaagg attgtctttg tacataacaa gatttatctc agtggatttc ttccaaagtg    1140
tgatgcagac cactctttca ctagtctttc aacaccagaa agaagtttca tcttcataaa    1200
cagtcgacca gtacatcaaa aagatatctt aaagttaatc cgacatcatt acaatctgaa    1260
atgcctaaag gaatctactc gtttgtatcc tgttttcttt ctgaaaatcg atgttcctac    1320
agctgatgtt gatgtaaatt taacaccaga taaaagccaa gtattattac aaaataagga    1380
atctgtttta attgctcttg aaaatctgat gacgacttgt tatggaccat acctagtac    1440
aaattcttat gaaaataata aaacagatgt ttccgcagct gacatcgttc ttagtaaaac    1500
agcagaaaca gatgtgcttt ttaataaagt ggaatcatct ggaaagaatt attcaaatgt    1560
tgatacttca gtcattccat tccaaaatga tatgcataat gatgaatctg aaaaaacac    1620
tgatgattgt ttaaatcacc agataagtat tggtgactt ggttatggtc attgtagtag    1680
tgaaatttct aacattgata aaaacactaa gaatgcattt caggacattt caatgagtaa    1740
tgtatcatgg gagaactctc agacggaata tagtaaaact tgttttataa gttccgttaa    1800
gcacacccag tcagaaaatg gcaataaaga ccatatagat gagagtgggg aaatgagga    1860
agaagcaggt cttgaaaact cttcggaaat ttctgcagat gagtggagca ggggaaatat    1920
acttaaaaat tcagtgggag agaatattga acctgtgaaa attttagtgc ctgaaaaag    1980
tttaccatgt aaagtaagta ataataatta tccaatccct gaacaaatga atcttaatga    2040
```

```
agattcatgt aacaaaaaat caaatgtaat agataataaa tctggaaaag ttacagctta    2100
tgatttactt agcaatcgag taatcaagaa acccatgtca gcaagtgctc tttttgttca    2160
agatcatcgt cctcagtttc tcatagaaaa tcctaagact agtttagagg atgcaacact    2220
acaaattgaa gaactgtgga agacattgag tgaagaggaa aaactgaaat atgaagagaa    2280
ggctactaaa gacttggaac gatacaatag tcaaatgaag agagccattg aacaggagtc    2340
acaaatgtca ctaaaagatg gcagaaaaaa gataaaaccc accagcgcat ggaatttggc    2400
ccagaagcac aagttaaaaa cctcattatc taatcaacca aaacttgatg aactccttca    2460
gtcccaaatt gaaaaagaa ggagtcaaaa tattaaaatg gtacagatcc ccttttctat    2520
gaaaaactta aaaataaatt ttaagaaaca aaacaaagtt gacttagaag agaaggatga    2580
accttgcttg atccacaatc tcaggtttcc tgatgcatgg ctaatgacat ccaaaacaga    2640
ggtaatgtta ttaaatccat atagagtaga agaagccctg ctatttaaaa gacttcttga    2700
gaatcataaa cttcctgcag agccactgga aaagccaatt atgttaacag agagtctttt    2760
taatggatct cattatttag acgttttata taaaatgaca gcagatgacc aaagatacag    2820
tggatcaact tacctgtctg atcctcgtct tacagcgaat ggtttcaaga taaaattgat    2880
accaggagtt tcaattactg aaaattactt ggaaatagaa ggaatggcta attgtctccc    2940
attctatgga gtagcagatt taaaagaaat tcttaatgct atattaaaca gaaatgcaaa    3000
ggaagtttat gaatgtagac ctcgcaaagt gataagttat ttagagggag aagcagtgcg    3060
tctatccaga caattaccca tgtacttatc aaaagaggac atccaagaca ttatctacag    3120
aatgaagcac cagtttggaa atgaaattaa agagtgtgtt catggtcgcc cattttttca    3180
tcatttaacc tatcttccag aaactacatg attaaatatg tttaagaaga ttagttacca    3240
ttgaaattgg ttctgtcata aaacagcatg agtctggttt taaattatct ttgtattatg    3300
tgtcacatgg ttattttta aatgaggatt cactgacttg tttttatatt gaaaaaagtt    3360
ccacgtattg tagaaaacgt aaataaacta atatagacta ttcaaaaaaa aaaaaaaaa    3420 a                                                                   3421

<210> SEQ ID NO 17
<211> LENGTH: 3052
<212> TYPE: DNA
<213> ORGANISM: homo sapiens

<400> SEQUENCE: 17
ggcaagacaa cgaggatttg cgtagggggc gagcctctga ggccacttgg ctcttacggc      60
cacgcagggc gccgcagatg cagccggagc ccgcttttcc ctctcaggac gacccctagg     120
ccgccagcag ttccctaccg acgaaggcga ctgtacagcg tccaccgcgt tcgtgcccac     180
ttacccgccg ccccactccg ggccgccggc tcgcagcagg accagcccgg ctgctacggc     240
cgcggataca cgcccctcag gcccggcgct gcgcagcttg cggaagcttt ccggacagac     300
tcgctgccag cggattggct gcgagcagcg ccaatctcac gttgccccg gggcgaggcgg      360 gactcagtgc cgcgctctct gcacccgctc tgccgcgcgc gtgcgtgctg ggtgcgggtg     420
cgggtgcggg gttgggcctg cgcatcgggt gagacgctgg ctgcttgcgg ctagtggatg     480
gtaattgcct gcctcgcgct agcaggaagc tgctctgtta aaagcgaaaa tgaaacaatt     540
gcctgcggca acagttcgac tccttttcaag ttctcagatc atcacttcgg tggtcagtgt    600
tgtaaaagag cttattgaaa actccttgga tgctggtgcc acaagcgtag atgttaaact    660
ggagaactat ggatttgata aaattgaggt gcgagataac ggggagggta tcaaggctgt    720
```

-continued

```
tgatgcacct gtaatggcaa tgaagtacta cacctcaaaa ataaatagtc atgaagatct    780
tgaaaatttg acaacttacg gttttcgtgg agaagccttg gggtcaattt gttgtatagc    840
tgaggtttta attacaacaa gaacggctgc tgataatttt agcacccagt atgttttaga    900
tggcagtggc cacatacttt ctcagaaacc ttcacatctt ggtcaaggta caactgtaac    960
tgctttaaga ttatttaaga atctacctgt aagaaagcag ttttactcaa ctgcaaaaaa   1020
atgtaaagat gaaataaaaa agatccaaga tctcctcatg agctttggta tccttaaacc   1080
tgacttaagg attgtctttg tacataacaa ggcagttatt tggcagaaaa gcagagtatc   1140
agatcacaag atggctctca tgtcagttct ggggactgct gttatgaaca atatggaatc   1200
ctttcagtac cactctgaag aatctcagat ttatctcagt ggatttcttc caaagtgtga   1260
tgcagaccac tctttcacta gtctttcaac accagaaaga agtttcatct tcataaacag   1320
tcgaccagta catcaaaaag atatcttaaa gttaatccga catcattaca atctgaaatg   1380
cctaaaggaa tctactcgtt tgtatcctgt tttctttctg aaaatcgatg ttcctacagc   1440
tgatgttgat gtaaatttaa caccagataa aagccaagta ttattacaaa ataaggaatc   1500
tgttttaatt gctcttgaaa atctgatgac gacttgttat ggaccattac ctagtacaaa   1560
ttcttatgaa aataataaaa cagatgtttc cgcagctgac atcgttctta gtaaaacagc   1620
agaaacagat gtgcttttta ataaagtgga atcatctgga aagaattatt caaatgttga   1680
tacttcagtc attccattcc aaaatgatat gcataatgat gaatctggaa aaaacactga   1740
tgattgttta aatcaccaga taagtattgg tgactttggt tatggtcatt gtagtagtga   1800
aatttctaac attgataaaa acactaagaa tgcatttcag gacatttcaa tgagtaatgt   1860
atcatgggag aactctcaga cggaatatag taaaacttgt tttataagtt ccgttaagca   1920
cacccagtca gaaaatggca ataaagacca tatagatgag agtggggaaa atgaggaaga   1980
agcaggtctt gaaaactctt cggaaatttc tgcagatgag tggagcaggg gaaatatact   2040
taaaaattca gtgggagaga atattgaacc tgtgaaaatt ttagtgcctg aaaaaagttt   2100
accatgtaaa gtaagtaata ataattatcc aatccctgaa caaatgaatc ttaatgaaga   2160
ttcatgtaac aaaaaatcaa atgtaataga taataaatct ggaaaagtta cagcttatga   2220
tttacttagc aatcgagtaa tcaagaaacc catgtcagca agtgctcttt tgttcaaga   2280 tcatcgtcct cagtttctca tagaaaatcc taagactagt ttagaggatg caacactaca   2340
aattgaagaa ctgtggaaga cattgagtga agaggaaaaa ctgaatcttt ttaatggatc   2400
tcattattta gacgttttat ataaaatgac agcagatgac caaagataca gtggatcaac   2460
ttacctgtct gatcctcgtc ttacagcgaa tggtttcaag ataaaattga taccaggagt   2520
ttcaattact gaaaattact tggaaataga aggaatggct aattgtctcc cattctatgg   2580
agtagcagat ttaaaagaaa ttcttaatgc tatattaaac agaaatgcaa aggaagttta   2640
tgaatgtaga cctcgcaaag tgataagtta tttagaggga gaagcagtgc gtctatccag   2700
acaattaccc atgtacttat caaaagagga catccaagac attatctaca gaatgaagca   2760
ccagtttgga aatgaaatta agagtgtgt tcatggtcgc ccattttttc atcatttaac   2820
ctatcttcca gaaactacat gattaaatat gtttaagaag attagttacc attgaaattg   2880
gttctgtcat aaaacagcat gagtctggtt ttaaattatc tttgtattat gtgtcacatg   2940
gttatttttt aaatgaggat tcactgactt gttttttatat tgaaaaagt tccacgtatt   3000 gtagaaaacg taaataaact aatatagact attcaaaaaa aaaaaaaaaa aa           3052
```

<210> SEQ ID NO 18
<211> LENGTH: 3830
<212> TYPE: DNA
<213> ORGANISM: homo sapiens

<400> SEQUENCE: 18

| | | | | | |
|---|---|---|---|---|---|
| ggtgtttata | agaatggaag | tgttgtttcc | ttgcccgatt | ccttcatgct | atatctcatg | 60 |
| aacctctgta | atcttggggg | agagactata | tttaatgatg | acaaacctgt | caccagtgta | 120 |
| gcaacaacag | tgtgaggaca | aaagcaaata | aaaattaaga | agcgttcaaa | tttatattca | 180 |
| acaaggaagt | catttcaatc | aacaacttct | gctgcattat | ttttccaaga | tgaaccgata | 240 |
| cacaaccatg | agacagttgg | gggacggcac | gtatgggagt | gtgcttatgg | gcaagagtaa | 300 |
| tgaatccggg | gagctggtgg | ccatcaaaag | gatgaagaga | aagttctatt | cttgggatga | 360 |
| atgcatgaac | ttgagagaag | ttaagtctct | gaagaaactt | aatcatgcca | atgttattaa | 420 |
| attgaaagaa | gttatcagag | aaaatgacca | tctttatttt | atatttgaat | atatgaaaga | 480 |
| aaacctctat | caattaatga | agacagaaaa | caagttgttc | cctgaatcag | tcatcagaaa | 540 |
| tattatgtat | caaatattgc | aagggctggc | ttttatccat | aaacatggct | ttttcatag | 600 |
| ggacatgaaa | ccagaaaact | tgctttgtat | gggtccagag | cttgtgaaaa | ttgctgattt | 660 |
| tggacttgca | agagaattaa | ggtcacagcc | accatacact | gattatgtat | ctaccagatg | 720 |
| gtatcgtgcc | cctgaagttt | tactgagatc | ttcagtttat | agttctccca | ttgatgtgtg | 780 |
| ggctgttgga | agtatcatgg | ctgaactcta | tatgttaagg | ccacttttcc | cagggacaag | 840 |
| tgaggtcgat | gaaatctta | aaatttgcca | agttttaggg | actcccaaaa | aaagtgactg | 900 |
| gccagaagga | taccagctgg | catcctctat | gaacttccgt | tttccccagt | gtgttcctat | 960 |
| aaacttaaaa | actcttattc | ccaatgccag | taatgaagct | attcagctca | tgaccgaaat | 1020 |
| gttgaattgg | gatccaaaga | acgaccgac | agcaagccag | gcattgaaac | acccatattt | 1080 |
| tcaagttggt | caggtattag | ccccttcgtc | aaatcatctg | gaatcaaaac | agtctttaaa | 1140 |
| taagcagctg | caaccattag | aatcaaagcc | atctttagtt | gaggtagagc | ctaagcctct | 1200 |
| gccggatata | atcgatcagg | ttgttggaca | accccagcca | aaaactagcc | agcagccact | 1260 |
| gcagcccatt | cagccgccac | agaacctgag | cgtccagcaa | cctccaaagc | aacagagtca | 1320 |
| ggagaaaccg | ccacaaacgc | tattcccgag | catcgtcaaa | acatgccaa | ctaagccaaa | 1380 |
| tggcacactg | agtcataaaa | gtggtaggag | gcgttgggt | cagactatct | tcaagtctgg | 1440 |
| agatagctgg | gaagagttgg | aggactatga | tttcggagcc | tcccattcca | agaagccaag | 1500 |
| catgggtgtt | tttaaagaaa | aaaggaaaaa | agattctcca | tttcggcttc | cagagccagt | 1560 |
| accctcaggc | tccaaccact | cgacagggga | aacaagagc | ttacctgctg | ttacttccct | 1620 |
| aaaatctgat | tccgaattgt | caactgctcc | aacctctaaa | cagtactact | tgaaacaatc | 1680 |
| aagatatctt | ccaggtgtga | atcccaagaa | ggtgtccttg | atagccagtg | aaaggaaat | 1740 |
| aaaccccac | acttggagca | accagttatt | ccccaagtca | ctgggacccg | ttgggggcaga | 1800 |
| acttgctttc | aaaaggagca | atgcaggaaa | tcttggaagt | tatgctactt | acaatcagtc | 1860 |
| aggatatatt | ccttccttc | tcaaaaaaga | agtgcagtca | gctggccaga | ggatccactt | 1920 |
| agcacctctc | aatgcaacgg | cttcagaata | tacctggaac | acaaaaactg | gtcgggggca | 1980 |
| gttttcagga | cgtacttata | atcctacagc | aaaaaaccta | aatattgtga | accgtgcaca | 2040 |
| gcccattccc | tcagtgcatg | ggaggacaga | ctgggtggcc | aagtatgagg | ccaccggta | 2100 |
| ggagtctatg | gtgtgaaacc | ctacagcatt | gctccgtaga | gtacgtgcaa | gttccttgac | 2160 |

```
cctgggaaat gtctacaaat gtctatttct actgagttct ggaagaaata tgcaaaagtg    2220
ggtacttgga agggcaaaaa tcatcccta ttttacttat ttccaagaaa tgcattttct     2280
tagcatcatt gcccacagtg ttgatatatg ggtaggatgt tacaaagtat tgaataaact    2340
atttgccaaa gtatgaagta tttgatctac aatttaataa atagtaaatc caataagaac    2400
ccttaaaaaa aaacaacttc cagaaaatgt ttagagtgtt ttagttttca tttgttgtat    2460
gtgcccaaat ggtttagtag ttcttcactt tgctgtggtt ggcttaagag gtttgtcttt    2520
tgtttttgta cagcagttgg gccaacctt gctggctgtc agctgtggtt cttatttgac     2580
taaggctctg cgctgccatt ttgtcaatga cagaaagatt gcaattattt gttttctac     2640
tttgaagcta tgggagcgat ggtaatttca atcttgagca ggatatcttt ttttttttt     2700
ttgaggcgat gtttcactct tgtgtccagg ctggagtgca gtggcactat cttggcttac    2760
tgcaacctcc acctcctggg ttcaagtgat tctcctgcct cagcctcccg agtagctggg    2820
attagaggcg tgtgccacca tgcctggcta attttgtag tattagtaga cagggttt       2880
caccatgttg gtcaggctca ggctggtctc aaactcctga cctcaggtga tccacctgcc    2940
tcggcctccc aaagtgcagg gcttacaggt gtgagccaca gtgcccagct ttttttttt     3000
tttttagaa ataaatttat cttaacata gagaatatca aagttatgcc acttgatttt      3060
agtggacggc ttgtgttttg atcttgacca gtacagttcc catgaattca aggtgacaat    3120
caagcccaat ggcttgatga cttcaatagt aaccaagtca aggttctctt ggctggacat    3180
cattaagaaa gttctggaaa ctgtgtttgt ttgatgctgg ttcattggac ttttcaaatt    3240
gttttgtttc tgtgtcccta ccagacacaa agatgaagtg tgccagctgg ttcccccaag    3300
ccagctcatg ctgctgacca ctgactcagc tctgaccttc acatttgctc tgaagcaagt    3360
gcgttcagct gctggggcag tgatatcaca tagtacatat attatttcct tagtttattt    3420
ccaaactggt attttaaata gacacttcga actttgggct actctgttta aatctgccac    3480
tttctggact ggaccttagt actgtaaatt ctttttaaag aataataatg ttaccaactg    3540
ctgagatttt tatgtatttt gtgactttgt aacaactgct attgtaataa gtgtcatctt    3600
gtgggcatta tacaaaggca tattataaaa taataatgat attttttgtat agaagagtca   3660
actgttcaga tgtaagatgt tgaaaaatgt taaaatctaa agagtaattt atcctagtgg    3720
taatggttat atgtatttgt acagtttaaa ttaatgtctc aaagctgtgc agtcttttgt    3780
tactgggaca cttttaaact ctgaataggc attaaaaaaa atatggctaa                3830
```

<210> SEQ ID NO 19
<211> LENGTH: 8025
<212> TYPE: DNA
<213> ORGANISM: homo sapiens

<400> SEQUENCE: 19

```
cggcgctgct ggaagatggc gagcggccgg gacgagcggc cgccttggcg gctagggcgg      60
ctcctgttgc tcatgtgcct gctgctgctg gggagctcgg cccgggcggc tcacatcaag     120
aaggcggagg cgactaccac aactacgagc gcgggcgccg aggcggccga gggccagttc     180
gaccgctact accacgaaga ggagttggag tcggcgctga gggaggcggc ggccgcgggc     240
ctccccggcc tggcccgcct ctttagcatc ggccgctcgg tggaaggccg gccgctgtgg     300
gtgcttcgcc tcaccgccgg cctggggtcg ctaatccctg agggcgacgc ggggcctgac     360
gctgccgggc ccgacgctgc ggggccgctg ctgcccggcc ggccccaggt gaagctggtg     420
```

-continued

```
ggcaacatgc atggcgacga gaccgtgtcg cgccaggtgt tgatctactt ggcccgcgag      480
ctggcggccg gctaccgccg cggggacccg cgcctggtcc gcctgctcaa caccaccgac      540
gtgtacctgc tgcccagcct caaccccgat ggcttcgagc gtgcccgcga gggcgactgt      600
ggcttcggcg acggcggccc gtccggggcc agcggccgcg acaatagtcg cggccgcgac      660
ctcaaccgaa gctttcccga ccagtttagc accggcgaac ccccgcccct ggacgaggtg      720
cccgaggtgc gcgccctcat cgagtggatc cgcaggaaca agtttgtgct ttctggaaat      780
ctgcatggtg gctcagtggt agcaagctat ccttttgatg attctccaga acataaggcc      840
actggaatct atagcaaaac ctcagatgat gaagtattta atacttggc aaaagcttat       900
gcttcaaacc accccataat gaaaactggt gagcctcatt gtccaggaga tgaagacgag      960
actttcaaag atggaatcac aaacggcgca cattggtatg atgtggaagg tggtatgcaa     1020
gattacaatt atgtgtgggc caactgtttt gagatcacat tagaactgtc ttgttgcaag     1080
tacccacctg cttcacagct tcgacaggaa tgggagaaca atcgtgagtc tttgatcaca     1140
ttgattgaaa aggttcacat tggagtgaaa ggatttgtta aagattccat aacaggatct     1200
gggttagaga atgcaaccat ctcagtggct ggtattaatc ataatatcac aacaggcaga     1260
tttggtgatt tctaccgatt acttgttcct ggaacttaca accttacagt agttttaact     1320
gggtatatgc cattgactgt tactaatgta gtggtgaaag aaggaccagc cacagaggtg     1380
gattttctc ttaggccaac tgtaacttca gtaatccctg acacgacaga ggctgtatca     1440
actgctagca cagttgctat acctaatatt ctttctggaa catcatcctc ctaccagcca     1500
attcagccaa aggactttca ccaccaccat ttccctgata tggaaatctt cttgagaagg     1560
tttgccaatg aatatcctaa cattacccgg ctttattcct tgggaaaatc agtagagtca     1620
agagaacttt atgtgatgga gatatctgat aatccgggtg tccatgaacc aggtgaacca     1680
gaatttaagt acattggaaa tatgcatgga aatgaagtgg ttggaagaga actgctgttg     1740
aacctcatag aataccttg taagaacttt ggaacagacc ctgaagtcac agatttggtt      1800
cataacacta gaattcacct tatgccatcc atgaatcctg atgggtatga aaagtcccag     1860
gaaggagatt caataagtgt aattggcaga acaacagca acaactttga cctgaaccga     1920
aatttcccag accagtttgt tcagatcaca gatcctacgc aaccagaaac tattgctgta     1980
atgagctgga tgaagtccta tccatttgta ctttcagcaa acctgcatgg aggttctttg     2040
gtggttaact ccccttttga tgatgatgaa caaggacttg ccacatatag taaatcacca     2100
gatgatgctg tgttccaaca aatagcactt tcttattcca aggaaaattc ccagatgttt     2160
caaggtagac cttgcaagaa tatgtatcct aatgaatatt ttcctcatgg aataacaaat     2220
ggagctagtt ggtataatgt gccaggagga atgcaggact ggaactattt acaaacaaat     2280
tgctttgaag tgactattga actaggttgt gtgaaatatc cacttgagaa agagctgcca     2340
aacttttggg aacagaatcg aagatcacta atccagttta tgaaacaggt tcatcagggc     2400
gtcagaggat ttgttctaga tgccacagat ggcagggta tattaaatgc caccattagt      2460
gttgctgaga ttaatcaccc agtgactact tacaaaactg agattactg cgtctcttg       2520
gttccaggaa cttataaaat cacagcatct gctcgagggt ataatccagt taccaagaat     2580
gtgactgtca agagtgaagg cgctattcag gtcaacttca cacttgttcg atcctcaaca     2640
gattcaaaca atgaatcaaa gaaggaaaa ggggctagca gcagcaccaa tgatgccagt      2700
gatccaacta ctaaagagtt tgaaacttta attaaagacc tttcagcgga gaatggtttg     2760
gaaagcctca tgttacgctc ctcctcaaat ctggctctgg ctctttatcg ataccattcc     2820
```

```
tacaaagact tatcagagtt tctgagagga cttgtaatga actatccaca tattacaaat    2880
cttaccaatt tgggacagag cactgaatat cgtcacattt ggtcccttga aatctccaat    2940
aagcccaatg tatctgagcc tgaagaacca aagattcgtt ttgttgctgg tatccatgga    3000
aatgcgccag ttggaactga actgcttttg gctctggcag aatttctctg cctgaactac    3060
aaaaagaacc cagctgttac ccaattggtt gacaggacta ggattgtgat tgtcccttct    3120
ctaaatccag atgggcgaga gagagctcaa gagaaagact gtacttcaaa ataggacaa     3180 acaaatgctc gtggcaaaga tttggataca gacttcacaa ataatgcctc ccaacctgag    3240
accaaagcca tcattgaaaa tttgattcaa aaacaggact ttagtctttc tgttgcctta    3300
gatggtggtt ccatgctggt cacatatcct tatgacaagc cagtacagac agtggaaaat    3360
aaagagactc tgaagcattt ggcatctctt tatgcaaata tcatccatc catgcacatg     3420 ggtcagccca gttgcccaaa taaatcagat gagaatattc caggaggagt aatgcgtgga    3480
gcagaatggc atagtcacct gggcagcatg aaggattata tgtcaccta tggccattgt     3540 ccggaaatca cagtatacac aagctgctgt tactttccta gtgctgcacg actcccttcc    3600
ttgtgggcag acaataagag atctcttctt agtatgttag tggaggttca caagggagtt    3660
catggatttg ttaaagataa gactggaaag ccaatctcta aagcagtcat tgtacttaat    3720
gaaggaataa aggtacaaac aaaagaggga ggttatttcc atgtactctt agcgccaggt    3780
gtccataaca ttattgccat cgctgatggg taccagcaac acattcaca ggtctttgtg      3840 catcatgatg cagctagttc tgtggtgata gtctttgaca cagataaccg gatatttggt    3900
ttgccaaggg agcttgtggt aactgtatca ggtgctacta tgtcggcatt gatcctaaca    3960
gcttgcatta tttggtgcat ctgctcaatc aagtctaata gacacaagga tggctttcat    4020
cggctcaggc agcatcatga tgagtatgaa gatgaaattc gcatgatgtc taccggctcc    4080
aagaagtccc tcctaagcca tgagttccag gatgaaacag acactgaaga ggaaacatta    4140
tattctagca acattgaaaa acacattttt gcatatctcc cagcataagt accaagcaaa    4200
attacagttc ctcttgggag aacactgcat taagaagaga gactctcttg cttcttcaaa    4260
gagctttggg aaattaaaatt gctaaatttg tattctctgt gaatttcact ggcagttttg   4320
aacttccctt ccttaaagta ctctaaacct ttaaaaaaaa atctgattta tgcagcagag    4380
atgggacagc cactttttct ttttaattta agatgagcta tttggagctt atgtaataat    4440
ggcataaagc caactagagg atgttgtatt ttgcacatca gatgtttact agtggcttta    4500 gtattttttct ttgttttaaa tggccaaaag aatccagaaa cattaaggca gggacagcag   4560
tcagaatcga cataaagctt taaaaactca aggttttttc aacctactga ggagtacttt    4620
tctctagttt taaatagct ggagtttttc ttattcaggt ttaatggagg ttgaattgat     4680
ttttaaacac ataatcagt aggaaatgaa taaatgggct tctgcatttg gctttctacc     4740
tgttccaagg ctagatcgga actggtagac tacgctgtaa gcaggatttc actacctctc    4800
ttaaggttta gcaaacttct aaatagccca ttttaaggga gaacttacta actttattgt    4860
gaaaggtcta aatgcccact tgaatgaagc tgagagagag atctagcaaa agctaaaact    4920
catgttgtct atctttgaac ttggtaaaaa cccacaggtg ctgctgctta tatctgtgaa    4980
gcactagctt attctaggaa tgcctgattc tttaatattg cctaaatcgg aacctttttc    5040
tatgttgcac acatggtttt cagatgaccc agccatctac aagatctgaa ttctactgaa    5100
aatatctaga aatgtggaag agacctactt gcacattctt aacctgtatt tgaacacaaa    5160
```

```
atatctatac ttcatgctcc agcccaagcc tataccctgt aatagcatac tattattgaa    5220
atcgcttgac cggtcttgtt cacataggcc tctgggagtg attttggttct ttgccctaat    5280 gtttcatttg acggtctctt tttgatcaac caattttttct aaaagttcag tcgaaagctt    5340
ttaagtatag cttcctccct tgaaaaaaaa tgtaaactat gactgctgag tgataaaaca    5400
ctgtggtgtg aaagtgtcat cttcactgcc aatcaggcaa agaccggaaa gatttgcatt    5460
ttattatgtc tgtcttatca tgcaatggaa atgatgcttt ttgtaagtat gcatcttacc    5520
aatgatgtaa cggtttaata cctttgaatg ttttaataac caagttgctg ctgaacttat    5580
actaaatcag gggaccaaaa aacttgctct tatcttctca aattgtattc tatatccatt    5640
aatgtatcag ttatcccaaa gccttcaggt ggaggggttt accaccttcc taggtcgttc    5700
aaccaggttt tgtgaggaat gcattcaaag tggctttata aaagaagatt ttctttagca    5760
agaataatga ggtcatgtca tttgttaata agtatctgtg ataaatccgt ggttcaaggt    5820
taagccattc tggtattctg gtattagcaa ctgtaaattc tgccacctca tacatggaac    5880
agagcttgtg ggatgctaat agttagtgaa gtatacatga tttaatttct aataatcttt    5940
atgttttctt taaggatggt ggtgtattgc tcttttcag ctttattttt aagagtacag    6000
tcaggaaacc aacaagggc ctaagagtgg ctgcccctgc ttgggacatt acagcaagtg    6060
aaacaaagtt aatgtgacaa gctttgcttt gttatcattg gtcttcacta gaggatacct    6120
tttacatgta cttctctctt ggatcaaata tgtcttaac tgtacatctc agtggctgga    6180
ggccatgcct ttaagcatg tgtaaaattt ttaaagaaat gaacatacac atagttattt    6240
tagtaatatt tcctgaaaga aaaccaaat tctgctataa gtcttgatct tcaatgaact    6300 tttaataat gcatttagct ggaaaacaag actttcccag cttgtattac ctagaagcgt    6360
gaatgtatag gatacctgac tactaagact atattctcag ccctgccctg tcttttattt    6420
gcgggtctaa tctaatatta gaatatatta accgcttaag gcattgaagc catatgggat    6480
ggggaatgca tttcttcagt gtttctccga gagactttcc atttccttgg agttatggcg    6540
gcaagtaagt atcatagtat taagaaattt gcctaaatct gagttgtgcc tttctttact    6600
cacaaggcat gggctttgtc ctggtgatca gtttgtaagc cttcttcctt cccagctcct    6660
taataaaagc aaagtgattg agtaggtaat gttcaaagtg tctgcctgtg tacatgtact    6720
tgtattgatt atgtagttca gtaagatgtg cccaagtcat ttcagaaaga aagacccttc    6780
agttttgatg cattttgctg aacacttggg tagtgagtgg gatcctatcc agttgaggaa    6840
tgcttgcaat gctcattgaa gggatttgct ttgggactttt gtcatcttcc agaaaggaaa    6900
catattgtat atttggccca gtgtgattga ttgctttatc tttggtaact tttacttgaa    6960
tgggatttgc tgaattaatg actattgaat ttaaaactaa ttatgagttg acaaataaat    7020
aaaaggtagt gtttatgtct gagcttattg tgtttgagct aacaccaggt tactcagtaa    7080
ccatgacctg ctcctccatt tccatttatt ctcaacatta aatagttta tcttgttgtt    7140 gccagaaatg cacttgtgcc aggtattgtc cctgctgtat gaaaagcttc ttggcaatga    7200
attctgtaat agtgccctac attatggttt tctggtggaa ttgttttaac agtgacaacc    7260
caggatttcc aatatatttt tgttttattg ttattaccaa aaattccact atgattgatg    7320
ttcagtgatt ttctatagca acttttttgg taactctttg ggtttctgat ttgttttagc    7380
taaaattttg gggatatgat ttgggtcttt gattaatgtc agctgaactt ggatttctag    7440
ttcatgaaga aatctctccc aatacccatt tatcctattt ttagcaataa ttcgttaatg    7500
attccacttg atttttcagaa tattgtcctg gttgatttg atttgacagc atacattatg    7560
```

```
aaatttgaaa gtaggttacc attttgaggc agttggatat aaattatgta aatatgtatg     7620
attatgattt ttataaatgg cataacatga gtgtactaac taccttctat gctggccatg     7680
ctacagattt tctggaggta tgacaatagt attttttat gctcagatta aaaatcagct      7740
tttcacctct ccagttttc caagtgatac tcccagttct agagcaatct acagctgttt     7800
atgtgaggtg cccaacaccc attcatctca agtgcttcag tctttggttt atttcatgca    7860
ctgtgccttc aaaatgaaat ttttaaaagg gactttaaat gaagttgaat agtagttttt    7920
aaaagtcaat ttgtaattta tgtgaaatct aactgtaatg aggtcctttc tgttttttat    7980
atgtaaacag atctactaat cctgtataaa agttatttta cgatg                    8025

<210> SEQ ID NO 20
<211> LENGTH: 928
<212> TYPE: DNA
<213> ORGANISM: homo sapiens

<400> SEQUENCE: 20
gctgtggccc tggcacctgc ccctgggctg ggacagccca ctgttccatg ctgcccaaga     60
aggctcagca caggcacaaa ccattgcccg gcactggccc gtgctgcctg agaaggattg    120
gcacgggcac agaccactgc ccccacctgc cctgcgccat ctacccaaga aggctcggca    180
cgggcaccaa ccactgcctc caactgcccc atgctgcctg agaaggcact gcacggccac    240
ccccaactgc cccgcactgt ccctacccgg gcagccatgc gagcggctgg aactctgctg    300
gccttctgct gcctggtctt gagcaccact gggggccctt ccccagatac ttgttcccag    360
gaccttaact cacgtgtgaa gccaggattt cctaaaacaa taaagaccaa tgacccagga    420
gtcctccaag cagccagata cagtgttgaa aagttcaaca actgcacgaa cgacatgttc    480
ttgttcaagg agtcccgcat cacaagggcc ctagttcaga tagtgaaagg cctgaaatat    540
atgctggagg tggaaattgg cagaactacc tgcaagaaaa accagcacct gcgtctggat    600
gactgtgact tccaaaccaa ccacaccttg aagcagactc tgagctgcta ctctgaagtc    660
tgggtcgtgc cctggctcca gcacttcgag gtgcctgttc tccgttgtca ctgaccccccg   720 cctcttcagc aagaccacag ccatgacaaa caccaggatg catgctcctt gtcccctccc    780
acccgcctca tgacccagcc tcacagaccc tctcaggcct ctgacgagtg agcgggtgaa    840
gtgccactgg gtcaccgcag ggcagctgga atggcagcat ggtagcacct cctaacagat    900
taaatagatc acatttgctt ctaaaatt                                        928

<210> SEQ ID NO 21
<211> LENGTH: 2545
<212> TYPE: DNA
<213> ORGANISM: homo sapiens

<400> SEQUENCE: 21
actcattcac ataaaacgct gcgcggccgg cggaatcccc ggcttctagg gcggcgagcg     60
gccgggctgg ctatcgagcg agcggggcgg gaacgcggag ttgcgccgcc gctcgggcgc    120
cgggctccgt cgcggccgca gccccgcggg tcgccctccc gtgcctcgcc cgcggacacc    180
ctggccgtgg acaccctggc cgtgggcacc cgcggggcgc gcggcgcggg gccgctggcc    240
ggcggcggcg gcggcatgaa ggtcacgtcg ctcgacgggc gccagctgcg caagatgctc    300
cgcaaggagg cggcggcgcg ctgcgtggtg ctcgactgcc ggccctatct ggccttcgct    360
gcctcgaacg tgcgcggctc gctcaacgtc aacctcaact cggtggtgct gcggcgggcc    420
```

```
cggggcggcg cggtgtcggc gcgctacgtg ctgcccgacg aggcggcgcg cgcgcggctc    480
ctgcaggagg cgcggcggcgg cgtcgcggcc gtggtggtgc tggaccaggg cagccgccac    540
tggcagaagc tgcgagagga gagcgccgcg cgtgtcgtcc tcacctcgct actcgcttgc    600
ctacccgccg gcccgcgggt ctacttcctc aaagggggat atgagacttt ctactcggaa    660
tatcctgagt gttgcgtgga tgtaaaaccc atttcacaag agaagattga gagtgagaga    720
gccctcatca gccagtgtgg aaaaccagtg gtaaatgtca gctacaggcc agcttatgac    780
cagggtggcc cagttgaaat ccttcccttc ctctaccttg gaagtgccta ccatgcatcc    840
aagtgcgagt tcctcgccaa cctgcacatc acagccctgc tgaatgtctc ccgacggacc    900
tccgaggcct gcgcgaccca cctacactac aaatggatcc ctgtggaaga cagccacacg    960
gctgacatta gctcccactt tcaagaagca atagacttca ttgactgtgt cagggaaaag   1020
ggaggcaagg tcctggtcca ctgtgaggct gggatctccc gttcacccac catctgcatg   1080
gcttacctta tgaagaccaa gcagttccgc ctgaaggagg ccttcgatta catcaagcag   1140
aggaggagca tggtctcgcc caactttggc ttcatgggcc agctcctgca gtacgaatct   1200
gagatcctgc cctccacgcc caaccccag cctccctcct gccaagggga ggcagcaggc   1260
tcttcactga taggccattt gcagacactg agccctgaca tgcagggtgc ctactgcaca   1320
ttccctgcct cggtgctggc accggtgcct acccactcaa cagtctcaga gctcagcaga   1380
agccctgtgg caacgccac atcctgctaa aactgggatg gaggaatcgg cccagcccca   1440
agagcaactg tgattttgt ttttaagact catggacatt tcatacctgt gcaatactga   1500
agacctcatt ctgtcatgct gccccagtga gatagtgagt ggtcaccagg cttgcaaatg   1560
aacttcagac ggacctcagg gtaggttctc gggactgaag gaaggccaag ccattacggg   1620
agcacagcat gtgctgacta ctgtacttcc agacccctgc cctcttggga ctgcccagtc   1680
cttgcacctc agagttcgcc ttttcatttc aagcataagg caataaatac ctgcagcaac   1740
gtgggagaaa gaagttgctg gaccaggaga aaaggcagtt atgaagccaa ttcattttga   1800
aggaagcaca atttccacct tatttttga actttggcag tttcaatgtc tgtctctgtt   1860
gcttcggggc ataagctgat caccgtctag ttgggaaagt aaccctacag ggttttgtagg   1920
gacatgatca gcatcctgat ttgaaccctg aaatgttgtg tagacaccct cttgggtcca   1980
atgaggtagt tggttgaagt agcaagatgt tggcttttct ggatttttt tgccatgggt   2040
tcttcactga ccttggactt tggcatgatt cttagtcata cttgaacttg tctcattcca   2100
cctcttctca gagcaactct tcctttggga aaagagttct tcagatcata gaccaaaaaa   2160
gtcataccctt cgaggtggta gcagtagatt ccaggaggag aagggtactt gctaggtatc   2220
ctgggtcagt ggcggtgcaa actggttttcc tcagctgcct gtccttctgt gtgcttatgt   2280
ctcttgtgac aattgttttc ctccctgccc ctggaggttg tcttcaagct gtggacttct   2340
gggatttgca gattttgcaa cgtggtacta cttttttttt cttttgtct gttagttatt   2400
tctccagggg aaaaggcaat aatttctaa gacccgtgtg aatgtgaaga aaagcagtat   2460
gttactggtt gttgttgttg ttcttgttttt ttatagtgta aataaaaat agtaaaagga   2520
gaaaagcaaa aaaaaaaaaa aaaaa                                         2545
```

<210> SEQ ID NO 22
<211> LENGTH: 6648
<212> TYPE: DNA
<213> ORGANISM: homo sapiens

<400> SEQUENCE: 22

```
acatgttact tcctgtatgg aggcatggcc agtttccagc cccgcgctct tcgttccttc    60
ccagcctgcg ccggagccac aactttcagg agcatggact gaaggcgccc tcgcccagc   120
gcccctctga gatcctttgt gttttcctcc gtttcctccg gccgtttcta ttttgggggg   180
ctctccgctc ccctgcctc tccctcccc ttccctctc gcaaacatgc ctccttcctt     240
cccggggccc tggaaggagc tgcctgcctg aagcccggag acgccgcgcc gcgctcagcc   300
ccgccgccgc ccgccggctc tcgggctgtg ctgcgctgcc gactcaagtt ggggatcctc   360
ggctgctcgc cgccgccgcc cgcggtccct gcctgcccca gcccggggc atcgccgccg    420
gccgccgact ccgcgccctg cccgatcggc tctctccttt ttaaacggaa agcagccttt   480
ctccgccgag aggatcgtcc ccagcgtggc tctgcgttcc cggtcacttt ttgagatttt   540
ccggggggcg ctcggcggct tcccggattc caaggggact cgggccgccg agcgcggggg   600
gcccgtggag cgggcgagcc ggggaagcgc cccggcttag cggaggctcg cacggaggca   660
agaacttatt caacaagttt acctccctgc tttcctcttt tcgatgtgcg ttttcggaca   720
tgcggaggtt actggaaccg tgttggtgga ttttgttcct gaaaatcacc agttccgtgc   780
tccattatgt cgtgtgcttc cccgcgttga cagaaggcta cgttggggcc ctgcacgaga   840
atagacacgg cagcgcagtg cagatccgca ggcgcaaggc ttcaggcgac ccgtactggg   900
cctactctgg tgcctatggt cctgagcact gggtcacgtc tagtgtcagc tgtggggcc    960
gtcaccagtc tcctattgac attttagacc agtatgcgcg tgttggggaa gaataccagg  1020
aactgcaact cgatggcttc gacaatgagt cttctaacaa aacctggatg aaaaacacag  1080
ggaaaacagt cgccatcctt ctgaaagacg actattttgt cagtggagct ggtctacctg  1140
gcagattcaa agctgagaag gtggaatttc actggggcca cagcaatggc tcagcgggct  1200
ctgaacacag catcaatggc aggaggtttc ctgttgagat gcagattttc ttttacaatc  1260
cagatgactt tgacagcttt caaaccgcaa tttctgagaa cagaataatc ggagccatgg  1320
ccatatttt tcaagtcagt ccgagggaca attctgcact ggatcctatt atccacgggt   1380
tgaagggtgt cgtacatcat gagaaggaga cctttctgga tcctttcgtc ctccgggacc  1440
tcctgcctgc atccctgggc agctattatc ggtacacagg ttccttgacc acaccaccgt  1500
gtagcgaaat agtggagtgg atagtcttcc ggagacccgt ccccatctct taccatcagc  1560
ttgaggcttt ttattccatc ttcaccacgg agcagcaaga ccatgtcaag tcggtggagt  1620
atctgagaaa taactttcga ccacagcagc gtctgcatga cagggtggtg tccaagtccg  1680
ccgtccgtga ctcctggaac cacgacatga cagacttctt agaaaaccca ctggggacag  1740
aagcctctaa agtttgcagc tctccacccca tccacatgaa ggtgcagcct ctgaaccaga  1800
cggcactgca ggtgtcctgg agccagccgg agactatcta ccacccaccc atcatgaact  1860
acatgatctc ctacagctgg accaagaatg aggacgagaa ggagaagacg tttacaaagg  1920
acagcgacaa agacttgaaa gccaccatta gccatgtctc acccgatagc ctttacctgt  1980
tccgagtcca ggccgtgtgt cggaacgaca tgcgcagcga ctttagccag acgatgctgt  2040
ttcaagctaa taccactcga atattccaag ggaccagaat agtgaaaaca ggagtgccca  2100
cagcgtctcc tgcctcttca gccgacatgg cccccatcag ctcggggtct tctacctgga  2160
cgtcctctgg catcccattc tcatttgttt ccatggcaac tgggatgggc cctcctcca   2220
gtggcagcca ggcacagtg gcctcggtgg tcaccagcac gctgctcgcc ggcctggggt   2280
tcggcggtgg tggcatctcc tctttccccca gcactgtgtg gcccacgcgc ctcccgacgg  2340
```

```
ccgcctcagc cagcaagcag gcggctaggc cagtcctagc caccacagag gccttggctt    2400
ctccagggcc cgatggtgat tcgtcaccaa ccaaggacgg cgagggcacc gaggaaggag    2460
agaaggatga gaaaagcgag agtgaggatg gggagcggga gcacgaggag gatggagaga    2520
aggactccga aaagaaggag aagagtgggg tgacccacgc tgccgaggag cggaatcaga    2580
cggagcccag ccccacaccc tcgtctccta acaggactgc cgagggaggg catcagacta    2640
tacctgggca tgagcaggat cacactgccg tccccacaga ccagcgggc ggaaggaggg    2700
atgccggccc aggcctggac cccgacatgg tcacctccac ccaagtgccc cccaccgcca    2760
cagaggagca gtatgcaggg agtgatccca agaggcccga aatgccatct aaaaagccta    2820
tgtcccgcgg ggaccgattt tctgaagaca gcagatttat cactgttaat ccagcggaaa    2880
aaaacacctc tggaatgata agccgccctg ctccagggag gatggagtgg atcatccctc    2940
tgattgtggt atcagccttg accttcgtgt gcctcatcct tctcattgct gtgctcgttt    3000
actggagagg gtgtaacaaa ataaagtcca agggctttcc cagacgtttc cgtgaagtgc    3060
cttcttctgg ggagagagga gagaagggga gcagaaaatg ttttcagact gctcatttct    3120
atgtggaaga cagcagttca cctcgagtgg tccctaatga agtatccct attattccta    3180
ttccggatga catggaagcc attcctgtca acagtttgt caaacacatc ggtgagctct    3240
attctaataa ccagcatggg ttctctgagg attttgagga agtccagcgc tgtactgctg    3300
atatgaacat cactgcagag cattccaatc atccagaaaa caagcacaaa aacagataca    3360
tcaacatttt agcatatgat cacagtaggg tgaagttaag acctttacca ggaaaagact    3420
ctaagcacag cgactacatt aatgcaaact atgttgatgg ttacaacaaa gcaaaagcct    3480
acattgccac ccaaggacct tgaagtctca catttgaaga tttctggagg atgatttggg    3540
aacaaaaac tggaatcatt gtgatgatta cgaaccttgt ggaaaaagga agacgaaaat    3600
gtgatcagta ttggccaaca gagaacagtg aggaatatgg aaacattatt gtcacgctga    3660
agagcacaaa aatacatgcc tgctacactg ttcgtcgttt ttcaatcaga aatacaaaag    3720
tgaaaaaggg tcagaaggga atcccaagg gtcgtcagaa tgaaagggta gtgatccagt    3780
atcactatac acagtggcct gacatgggag ttccccgagta tgcccttcca gtactgactt    3840
tcgtgaggag atcctcagca gctcggatgc cagaaacggg ccctgtgttg gtgcactgca    3900
gtgctggtgt gggcagaaca ggcacctata ttgtaataga cagcatgctg caacagataa    3960
aagacaaaag cacagttaac gtcctgggat tcctgaagca tatcaggaca cagcgtaact    4020
acctcgtcca gactgaggag cagtacacttt tcatccatga tgccttgttg aagccattc    4080
ttggaaagga gactgaagta tcttcaaatc agctgcacag ctatgttaac agcatcctta    4140
taccaggagt aggaggaaag acacgactgg aaaagcaatt caagctggtc acacagtgta    4200
atgcaaaata tgtggaatgt ttcagtgctc agaaagagtg taacaaagaa agaacagaa    4260
actcttcagt tgtgccatct gagcgtgctc gagtgggtct tgcaccattg cctggaatga    4320
aaggaacaga ttacattaat gcttcttata tcatgggcta ttataggagc aatgaattta    4380
ttataactca gcatcctctg ccacatacta cgaaagattt ctggcgaatg atttgggatc    4440
ataacgcaca gatcattgtc atgctgccag acaaccagag cttggcagaa gatgagtttg    4500
tgtactggcc aagtcgagaa gaatccatga actgtgaggc ctttaccgtc acccttatca    4560
gcaaagacag actgtgcctc tctaatgaag aacaaattat catccatgac tttatccttg    4620
aagctacaca ggatgactat gtcttagaag ttcggcactt tcagtgtccc aaatggccta    4680
acccagatgc ccccataagt agtaccttg aacttatcaa cgtcatcaag gaagaggcct    4740
```

```
taacaaggga tggtcccacc attgttcatg atgagtatgg agcagtttca gcaggaatgt      4800
tatgtgccct taccaccctg tcccagcaac tggagaatga aaatgctgtg gatgttttcc      4860
aggttgcaaa aatgatcaat cttatgaggc ctggagtatt cacagacatt gaacaatacc      4920
agttcatcta taaagcaatg cttagcttgg tcagcactaa agaaaatgga aatggtccca      4980
tgacagtaga caaaaatggt gctgttctta ttgcagatga atcagaccct gctgagagca      5040
tggagtccct agtgtgactg gaatcctgaa agggcactta atttgtaaac ttctgaagac      5100
tgagaacttt tttgaggcct tttttgccag actctaggtt atacaataac ccagttactt      5160
ttttacactg ataaaagttt tgatatttat tttttgccat tttatgtctt aatggtatcc      5220
tactgagcat ttgcacctct gttcatttca cacagtgaaa cgcaatttta cctagtttgc      5280
actatatgat cagtgttact gcctataatc ttatacaaca gcaaacctg atgtgacatt       5340 ccatgacgac atacatgcta cttttttta gttcaataca gtgaaggtct tgttatgac        5400 agtgaatatt gcttttatta ttattattgc tgaagtggtt gcattctact agcaggcaat      5460
gctgtacttt tcttcagtcc tcctctcctt tttattttag gcactgttca atactgtatg      5520
ccttctgtat tttaatggag tggatagcat tgttttcttt tacagactag caggctactg      5580
ggacctaaaa aggtctgtta atgtcatggc cttgaaacag ttccatttat gctggttaag      5640
agatccctta agaagttaga aggcttaaga actgcttcat gtgaacatcc cttattagtt      5700
acaaagttat attcacagtt ttttaaaaat gtgtcaaaat aaaggataac tctgtattac      5760
agctttcaca gtagctatgt ggacaatgtg ttatttccat tttgactctc taaaatagct      5820
acatcctaaa atcagggcta tctttaacaa tagcaagata gcaatattat atacaactca      5880
gttatgagac cctttagtta ttctccatta atgcttctta gtttgtaata ccatacctca      5940
cagtaggtag aagaatgaaa acttctgcag gtgtgtaatt ttgaaactag tcctctaaaa      6000
attccctatt actcctatag caatctaata aaaactacct acatagttac tgttttcttt      6060
ccttctttgc caaatgtttt ataataaatc tcttaattac atacatttttt ctacttaaga     6120 ttaaattgga aatactgtct tagcaaaagt cttgggacta tctaaactcc cacacataga      6180
taaatctgat ttggagagag aaatttaaaa tatttaatta aaggtgatac ccacattttc      6240 aagttttttaa aagagggaga tggctttgta tgcttttgtg tagtttagaa cagatacaca     6300
ttagtaaaag ataccaataa tcattagagc tcaaggaagt tattaggtgc agcctctgga     6360
gccatactca cgctgcagtg cataatggga aaattaggag cattaataag aaatttcagt      6420
agtgtttgta aggaaaataa gctacttact gagatctgtt tcttctattg catgtttgct      6480
tttgagggac agcttctgtc aaaagtgaaa tcatcaccag aactgggcct gttaggaaga      6540
atagggtttt atttactttt tatgtcaatt aacttcaaca aaaaggccac gctggctgct      6600
gtcatgccat ctgggtatgc attaaacatt aatgatgatc agcactga                  6648
```

<210> SEQ ID NO 23
<211> LENGTH: 4176
<212> TYPE: DNA
<213> ORGANISM: homo sapiens

<400> SEQUENCE: 23

```
ggcggtcccc tgttctcccc gctcaggtgc ggcgctgtgg caggaagcca ccccctcggt        60
cggccggtgc gcggggctgt tgcgccatcc gctccggctt tcgtaaccgc accctgggac      120
ggcccagaga cgctccagcg cgagttcctc aaatgttttc ctgcgttgcc aggaccgtcc      180
```

```
gccgctctga gtcatgtgcg agtgggaagt cgcactgaca ctgagccggg ccagagggag    240
aggagccgag cgcggcgcgg ggccgaggga ctcgcagtgt gtgtagagag ccgggctcct    300
gcggatgggg gctgcccccg gggcctgagc ccgcctgccc gccaccgcc ccgccccgcc    360 cctgccaccc ctgccgcccg gttcccatta gcctgtccgc ctctgcggga ccatggagtg    420
gtagccgagg aggaagcatg ctggccgtcg gctgcgcgct gctggctgcc ctgctggccg    480
cgccgggagc ggcgctggcc ccaaggcgct gccctgcgca ggaggtggcg agaggcgtgc    540
tgaccagtct gccaggagac agcgtgactc tgacctgccc gggggtagag ccggaagaca    600
atgccactgt tcactgggtg ctcaggaagc cggctgcagg ctcccacccc agcagatggg    660
ctggcatggg aaggaggctg ctgctgaggt cggtgcagct ccacgactct ggaaactatt    720
catgctaccg ggccggccgc ccagctggga ctgtgcactt gctggtggat gttcccccg     780 aggagcccca gctctcctgc ttccggaaga gccccctcag caatgttgtt tgtgagtggg    840
gtcctcggag cacccatcc ctgacgacaa aggctgtgct cttggtgagg aagtttcaga     900
acagtccggc cgaagacttc caggagccgt gccagtattc caggagtcc cagaagttct     960 cctgccagtt agcagtcccg gagggagaca gctctttcta catagtgtcc atgtgcgtcg    1020
ccagtagtgt cgggagcaag ttcagcaaaa ctcaaaccct tcagggttgt ggaatcttgc    1080
agcctgatcc gcctgccaac atcacagtca ctgccgtggc cagaaacccc gctggctca     1140 gtgtcacctg gcaagacccc cactcctgga actcatcttt ctacagacta cggtttgagc    1200
tcagatatcg ggctgaacgg tcaaagacat tcacaacatg gatggtcaag gacctccagc    1260
atcactgtgt catccacgac gcctgggcg gcctgaggca cgtggtgcag cttcgtgccc     1320
aggaggagtt cgggcaaggc gagtggagcg agtggagccc ggaggccatg gcacgccttt    1380
ggacagaatc caggagtcct ccagctgaga acgaggtgtc cacccccatg caggcactta    1440
ctactaataa agacgatgat aatattctct tcagagattc tgcaaatgcg acaagcctcc    1500
cagtgcaaga ttcttcttca gtaccactgc ccacattcct ggttgctgga gggagcctgg    1560
ccttcggaac gctcctctgc attgccattg ttctgaggtt caagaagacg tggaagctgc    1620
gggctctgaa ggaaggcaag acaagcatgc atccgccgta ctctttgggg cagctggtcc    1680
cggagaggcc tcgacccacc ccagtgcttg ttcctctcat ctccccaccg gtgtccccca    1740
gcagcctggg gtctgacaat acctcgagcc acaaccgacc agatgccagg acccacgga    1800 gcccttatga catcagcaat acagactact tcttccccag atagctggct gggtggcacc    1860
agcagcctgg accctgtgga tgataaaaca caaacgggct cagcaaaaga tgcttctcac    1920
tgccatgcca gcttatctca ggggtgtgcg gcctttggct tcacggaaga gccttgcgga    1980
aggttctacg ccaggggaaa atcagcctgc tccagctgtt cagctggttg aggttttcaaa    2040 cctccctttc caaatgccca gcttaaaggg gctagagtga acttgggcca ctgtgaagag    2100
aaccatatca agactctttg gacactcaca cggacactca aaagctgggc aggttggtgg    2160
gggcctcggt gtggagaagc ggctggcagc ccacccctca acacctctgc acaagctgca    2220
ccctcaggca ggtgggatgg atttccagcc aaagcctcct ccagccgcca tgctcctggc    2280
ccactgcatc gtttcatctt ccaactcaaa ctcttaaaac ccaagtgcct tagcaaattc    2340 tgttttcta ggcctgggga cggcttttac ttaaaccgcc aaggctgggg gaagaagctc     2400
tctcctccct ttcttcccta cagttgaaaa acagctgagg gtgagtgggt gaataataca    2460
gtatctcagg gcctggtcgt tttcaacaga attataatta gttcctcatt agcattttgc    2520
taaatgtgaa tgatgatcct aggcatttgc tgaatacaga ggcaactgca ttggctttgg    2580
```

```
gttgcaggac ctcaggtgag aagcagagga aggagaggag aggggcacag ggtctctacc    2640
atcccctgta gagtgggagc tgagtggggg atcacagcct ctgaaaacca atgttctctc    2700
ttctccacct cccacaaagg agagctagca gcagggaggg cttctgccat ttctgagatc    2760
aaaacggttt tactgcagct ttgtttgttg tcagctgaac ctgggtaact agggaagata    2820
atattaagga agacaatgtg aaaagaaaaa tgagcctggc aagaatgtgt ttaaacttgg    2880
tttttaaaaa actgctgact gttttctctt gagagggtgg aatatccaat attcgctgtg    2940
tcagcataga agtaacttac ttaggtgtgg gggaagcacc ataactttgt ttagcccaaa    3000
accaagtcaa gtgaaaaagg aggaagagaa aaaatatttt cctgccaggc atggtggccc    3060
acgcacttcg ggaggtcgag gcaggaggat cacttgagtc cagaagtttg agatcagcct    3120
gggcaatgtg ataaaacccc atctctacaa aaagcataaa aattagccaa gtgtggtaga    3180
gtgtgcctga agtcccagat acttgggggg ctgaggtggg aggatctctt gagcctggga    3240
ggtcaaggct gcagtgagcc gagattgcac cactgcactc cagcctgggt gacagagcaa    3300
gtgagaccct gtctcaaaaa agaaaaaga aaagaaaaa atattttccc tattagagaa    3360
gagattgtgg tttcattctg tatttgttt ttgtcttaaa aagtggaaaa atagcctgcc    3420
tcttctctac tctagggaaa aaccagcgtg tgactactcc cccaggtggt tatggagagg    3480
gtgtccggtc cctgtcccag tgccgagaag gaagcctccc acgactgccc ggcagggtcc    3540
tagaaattcc ccaccctgaa agccctgagc tttctgctat caaagaggtt ttaaaaaaat    3600
cccatttaaa aaaaatccct tacctcggtg ccttcctctt tttatttagt tccttgagtt    3660
gattcagctc tgcaagaatt gaagcaggac taaatgtcta gttgtaacac catgattaac    3720
cacttcagct gacttttctg tccgagcttt gaaaattcag tggtgttagt ggttacccag    3780
ttagctctca agttatcagg gtattccaga gtggggatat gatttaaatc agccgtgtaa    3840
ccatggaccc aatatttacc agaccacaaa acttttctaa tactctaccc tcttagaaaa    3900
accaccacca tcaccagaca ggtgcgaaag gatgaaagtg accatgtttt gtttacggtt    3960
ttccaggttt aagctgttac tgtcttcagt aagccgtgat tttcattgct gggcttgtct    4020 gtagattta gaccctattg ctgcttgagg caactcatct taggttggca aaaaggcagg    4080
atggccgggc gcggtggctc acgcctgtaa tcctagcact ttgggaggcc aaggtgggag    4140
gattgcttga gctcaggagt ttgagaccaa cctggg                              4176

<210> SEQ ID NO 24
<211> LENGTH: 4082
<212> TYPE: DNA
<213> ORGANISM: homo sapiens

<400> SEQUENCE: 24
ggcggtcccc tgttctcccc gctcaggtgc ggcgctgtgg caggaagcca cccctcggt       60 cggccggtgc gcggggctgt tgcgccatcc gctccggctt tcgtaaccgc acctgggac      120 ggcccagaga cgctccagcg cgagttcctc aaatgttttc ctgcgttgcc aggaccgtcc    180
gccgctctga gtcatgtgcg agtgggaagt cgcactgaca ctgagccggg ccagagggag    240
aggagccgag cgcggcgcgg ggccgaggga ctcgcagtgt gtgtagagag ccgggctcct    300
gcggatgggg gctgccccg gggcctgagc ccgcctgccc gcccaccgcc ccgccccgcc     360
cctgccaccc ctgccgcccg gttcccatta gcctgtccgc ctctgcggga ccatggagtg    420
gtagccgagg aggaagcatg ctggccgtcg gctgcgcgct gctggctgcc ctgctggccg    480
```

```
cgccgggagc ggcgctggcc ccaaggcgct gccctgcgca ggaggtggcg agaggcgtgc    540
tgaccagtct gccaggagac agcgtgactc tgacctgccc gggggtagag ccggaagaca    600
atgccactgt tcactgggtg ctcaggaagc cggctgcagg ctcccacccc agcagatggg    660
ctggcatggg aaggaggctg ctgctgaggt cggtgcagct ccacgactct ggaaactatt    720
catgctaccg ggccggccgc ccagctggga ctgtgcactt gctggtggat gttcccccg    780
aggagcccca gctctcctgc ttccggaaga gccccctcag caatgttgtt tgtgagtggg    840
gtcctcggag caccccatcc ctgacgacaa aggctgtgct cttggtgagg aagtttcaga    900
acagtccggc cgaagacttc caggagccgt gccagtattc caggagtcc cagaagttct    960
cctgccagtt agcagtcccg gagggagaca gctctttcta catagtgtcc atgtgcgtcg   1020
ccagtagtgt cggagcaag ttcagcaaaa ctcaaacctt tcagggttgt ggaatcttgc   1080
agcctgatcc gcctgccaac atcacagtca ctgccgtggc cagaaacccc cgctggctca   1140
gtgtcacctg gcaagacccc cactcctgga actcatcttt ctacagacta cggtttgagc   1200
tcagatatcg ggctgaacgg tcaaagacat tcacaacatg gatggtcaag gacctccagc   1260
atcactgtgt catccacgac gcctggagcg gcctgaggca cgtggtgcag cttcgtgccc   1320
aggaggagtt cgggcaaggc gagtggagcg agtggagccc ggaggccatg ggcacgcctt   1380
ggacagaatc caggagtcct ccagctgaga acgaggtgtc caccccccatg caggcactta   1440
ctactaataa agacgatgat aatattctct tcagagattc tgcaaatgcg acaagcctcc   1500
caggttcaag aagacgtgga agctgcgggc tctgaaggaa ggcaagacaa gcatgcatcc   1560
gccgtactct ttggggcagc tggtcccgga gaggcctcga cccacccag tgcttgttcc   1620
tctcatctcc ccaccggtgt cccccagcag cctgggtct gacaatacct cgagccacaa   1680
ccgaccagat gccagggacc cacggagccc ttatgacatc agcaatacag actacttctt   1740
ccccagatag ctggctgggt ggcaccagca gcctggaccc tgtggatgat aaaacacaaa   1800
cgggctcagc aaaagatgct tctcactgcc atgccagctt atctcagggg tgtgcggcct   1860
ttggcttcac ggaagagcct tgcggaaggt tctacgccag gggaaaatca gcctgctcca   1920
gctgttcagc tggttgaggt ttcaaacctc ccttttccaaa tgcccagctt aaaggggcta   1980
gagtgaactt gggccactgt gaagagaacc atatcaagac tctttggaca ctcacacgga   2040
cactcaaaag ctgggcaggt tggtgggggc ctcggtgtgg agaagcggct ggcagcccac   2100
ccctcaacac ctctgcacaa gctgcaccct caggcaggtg ggatggattt ccagccaaag   2160
cctcctccag ccgccatgct cctggcccac tgcatcgttt catcttccaa ctcaaactct   2220
taaaacccaa gtgccttagc aaattctgtt tttctaggcc tggggacggc ttttacttaa   2280
accgccaagg ctgggggaag aagctctctc ctcccttct tccctacagt tgaaaaacag   2340
ctgagggtga gtgggtgaat aatacagtat ctcagggcct ggtcgttttc aacagaatta   2400
taattagttc ctcattagca ttttgctaaa tgtgaatgat gatcctaggc atttgctgaa   2460
tacagaggca actgcattgg ctttgggttg caggacctca ggtgagaagc agaggaagga   2520
gaggagaggg gcacagggtc tctaccatcc cctgtagagt gggagctgag tggggatca   2580
cagcctctga aaccaatgt tctctcttct ccacctccca caaggagag ctagcagcag   2640
ggagggcttc tgccatttct gagatcaaaa cggttttact gcagctttgt tgttgtcag   2700
ctgaacctgg gtaactaggg aagataatat taaggaagac aatgtgaaaa gaaaaatgag   2760
cctggcaaga atgtgtttaa acttggtttt taaaaaactg ctgactgttt tctcttgaga   2820
gggtggaata tccaatattc gctgtgtcag catagaagta acttacttag gtgtggggga   2880
```

| | |
|---|---:|
| agcaccataa ctttgtttag cccaaaaccca agtcaagtga aaaggagga agagaaaaaa | 2940 |
| tattttcctg ccaggcatgg tggcccacgc acttcgggag gtcgaggcag gaggatcact | 3000 |
| tgagtccaga agtttgagat cagcctgggc aatgtgataa aaccccatct ctacaaaaag | 3060 |
| cataaaaatt agccaagtgt ggtagagtgt gcctgaagtc ccagatactt gggggctga | 3120 |
| ggtgggagga tctcttgagc ctgggaggtc aaggctgcag tgagccgaga ttgcaccact | 3180 |
| gcactccagc ctgggtgaca gagcaagtga gaccctgtct caaaaaaga aaagaaaaa | 3240 |
| gaaaaaatat tttccctatt agaagagaga ttgtggtttc attctgtatt ttgttttttgt | 3300 |
| cttaaaaagt ggaaaaatag cctgcctctt ctctactcta gggaaaaacc agcgtgtgac | 3360 |
| tactccccca ggtggttatg agagggtgt ccggtccctg tcccagtgcc gagaaggaag | 3420 |
| cctcccacga ctgcccggca gggtcctaga aattccccac cctgaaagcc ctgagctttc | 3480 |
| tgctatcaaa gaggttttaa aaaaatccca tttaaaaaaa atcccttacc tcggtgcctt | 3540 |
| cctctttta tttagttcct tgagttgatt cagctctgca agaattgaag caggactaaa | 3600 |
| tgtctagttg taacaccatg attaaccact tcagctgact tttctgtccg agctttgaaa | 3660 |
| attcagtggt gttagtggtt acccagttag ctctcaagtt atcagggtat tccagagtgg | 3720 |
| ggatatgatt taaatcagcc gtgtaaccat ggacccaata tttaccagac cacaaaactt | 3780 |
| ttctaatact ctaccctctt agaaaaacca ccaccatcac cagacaggtg cgaaaggatg | 3840 |
| aaagtgacca tgttttgttt acggttttcc aggtttaagc tgttactgtc ttcagtaagc | 3900 |
| cgtgattttc attgctgggc ttgtctgtag attttagacc ctattgctgc ttgaggcaac | 3960 |
| tcatcttagg ttggcaaaaa ggcaggatgg ccgggcgcgg tggctcacgc ctgtaatcct | 4020 |
| agcactttgg gaggccaagg tgggaggatt gcttgagctc aggagtttga gaccaacctg | 4080 |
| gg | 4082 |

<210> SEQ ID NO 25
<211> LENGTH: 4370
<212> TYPE: DNA
<213> ORGANISM: homo sapiens

<400> SEQUENCE: 25

| | |
|---|---:|
| ccgcgctctc tgatcagagg cgaagctcgg aggtcctaca ggtatggatc tctggcagct | 60 |
| gctgttgacc ttggcactgg caggatcaag tgatgctttt tctggaagtg aggccacagc | 120 |
| agctatcctt agcagagcac cctggagtct gcaaagtgtt aatccaggcc taaagacaaa | 180 |
| ttcttctaag gagcctaaat tcaccaagtg ccgttcacct gagcgagaga cttttttcatg | 240 |
| ccactggaca gatgaggttc atcatggtac aaagaaccta ggacccatac agctgttcta | 300 |
| taccagaagg aacactcaag aatggactca agaatggaaa gaatgccctg attatgtttc | 360 |
| tgctggggaa aacagctgtt actttaattc atcgtttacc tccatctgga taccttattg | 420 |
| tatcaagcta actagcaatg gtggtacagt ggatgaaaag tgtttctctg ttgatgaaat | 480 |
| agtgcaacca gatccaccca ttgccctcaa ctggacttta ctgaacgtca gtttaactgg | 540 |
| gattcatgca gatatccaag tgagatggga agcaccacgc aatgcagata ttcagaaagg | 600 |
| atggatggtt ctggagtatg aacttcaata caaagaagta aatgaaacta atgaaaat | 660 |
| gatggaccct atattgacaa catcagttcc agtgtactca ttgaaagtgg ataaggaata | 720 |
| tgaagtgcgt gtgagatcca acaacgaaa ctctggaaat tatggcgagt tcagtgaggt | 780 |
| gctctatgta acacttcctc agatgagcca atttacatgt gaagaagatt tctactttcc | 840 |

```
atggctctta attattatct ttggaatatt tgggctaaca gtgatgctat ttgtattctt    900
attttctaaa cagcaaagga ttaaaatgct gattctgccc ccagttccag ttccaaagat    960
taaaggaatc gatccagatc tcctcaagga aggaaaatta gaggaggtga acacaatctt   1020
agccattcat gatagctata aacccgaatt ccacagtgat gactcttggg ttgaatttat   1080
tgagctagat attgatgagc cagatgaaaa gactgaggaa tcagacacag acagacttct   1140
aagcagtgac catgagaaat cacatagtaa cctaggggtg aaggatggcg actctggacg   1200
taccagctgt tgtgaacctg acattctgga gactgatttc aatgccaatg acatacatga   1260
gggtacctca gaggttgctc agccacagag gttaaaaggg gaagcagatc tcttatgcct   1320
tgaccagaag aatcaaaata actcacctta tcatgatgct tgccctgcta ctcagcagcc   1380
cagtgttatc caagcagaga aaacaaacc acaaccactt cctactgaag agctgagtc    1440
aactcaccaa gctgcccata ttcagctaag caatccaagt tcactgtcaa acatcgactt   1500
ttatgcccag gtgagcgaca ttacaccagc aggtagtgtg gtcctttccc cgggccaaaa   1560
gaataaggca gggatgtccc aatgtgacat gcacccggaa atggtctcac tctgccaaga   1620
aaacttcctt atggacaatg cctacttctg tgaggcagat gccaaaaagt gcatccctgt   1680
ggctcctcac atcaaggttg aatcacacat acagccaagc ttaaaccaag aggacattta   1740
catcaccaca gaaagcctta ccactgctgc tgggaggcct gggacaggag aacatgttcc   1800
aggttctgag atgcctgtcc cagactatac ctccattcat atagtacagt ccccacaggg   1860
cctcatactc aatgcgactg ccttgccctt gcctgacaaa gagtttctct catcatgtgg   1920
ctatgtgagc acagaccaac tgaacaaaat catgccttag cctttctttg gtttcccaag   1980
agctacgtat ttaatagcaa agaattgact ggggcaataa cgtttaagcc aaaacaatgt   2040
ttaacccttt tttgggggag tgacaggatg gggtatggat tctaaaatgc cttttcccaa   2100
aatgttgaaa tatgatgtta aaaaaataag aagaatgctt aatcagatag atattcctat   2160
tgtgcaatgt aaatatttta aagaattgtg tcagactgtt tagtagcagt gattgtctta   2220
atattgtggg tgttaatttt tgatactaag cattgaatgg ctatgttttt aatgtatagt   2280
aaatcacgct ttttgaaaaa gcgaaaaaat caggtggctt ttgcggttca ggaaaattga   2340
atgcaaacca tagcacaggc taatttttg ttgtttctta aataagaaac ttttttattt   2400
aaaaaactaa aaactagagg tgagaaattt aaactataag caagaaggca aaaatagttt   2460
ggatatgtaa acatttatt ttgacataaa gttgataaag attttttaat aatttagact   2520
tcaagcatgg ctattttata ttacactaca cactgtgtac tgcagttggt atgacccctc   2580
taaggagtgt agcaactaca gtctaaagct ggtttaatgt tttggccaat gcacctaaag   2640
aaaaacaaac tcgtttttta caaagccctt ttatacctcc ccagactcct tcaacaattc   2700
taaaatgatt gtagtaatct gcattattgg aatataattg ttttatctga atttttaaac   2760
aagtatttgt taatttagaa aactttaaag cgtttgcaca gatcaactta ccaggcacca   2820
aaagaagtaa aagcaaaaaa gaaaaccctt tcttcaccaaa tcttggttga tgccaaaaaa   2880
aaatacatgc taagagaagt agaaatcata gctggttcac actgaccaag atacttaagt   2940
gctgcaattg cacgcggagt gagtttttta gtgcgtgcag atggtgagag ataagatcta   3000
tagcctctgc agcggaatct gttcacaccc aacttggttt tgctacataa ttatccagga   3060
agggaataag gtacaagaag cattttgtaa gttgaagcaa atcgaatgaa attaactggg   3120
taatgaaaca aagagttcaa gaaataagtt tttgtttcac agcctataac cagacacata   3180
ctcattttc atgataatga acagaacata gacagaagaa acaaggtttt cagtccccac   3240
```

```
agataactga aaattattta aaccgctaaa agaaactttc tttctcacta aatcttttat    3300
aggatttatt taaaatagca aaagaagaag tttcatcatt ttttacttcc tctctgagtg    3360
gactggcctc aaagcaagca ttcagaagaa aaagaagcaa cctcagtaat ttagaaatca    3420
ttttgcaatc ccttaatatc ctaaacatca ttcattttg ttgttgttgt tgttgttgag     3480
acagagtctc gctctgtcgc caggctagag tgcggtggcg cgatcttgac tcactgcaat    3540
ctccacctcc cacaggttca ggcgattccc gtgcctcagc ctcctgagta gctgggacta    3600
caggcacgca ccaccatgcc aggctaattt ttttgtattt tagcagagac ggggtttcac    3660
catgttggcc aggatggtct cgatctcctg acctcgtgat ccacccgact cggcctccca    3720
aagtgctggg attacaggtg taagccaccg tgcccagccc taaacatcat tcttgagagc    3780
attgggatat ctcctgaaaa ggtttatgaa aagaagaat ctcatctcag tgaagaatac     3840
ttctcatttt ttaaaaaagc ttaaaacttt gaagttagct ttaacttaaa tagtatttcc    3900
catttatcgc agacctttt taggaagcaa gcttaatggc tgataatttt aaattctctc     3960
tcttgcagga aggactatga aaagctagaa ttgagtgttt aaagttcaac atgttatttg    4020
taatagatgt ttgatagatt ttctgctact ttgctgctat ggttttctcc aagagctaca    4080
taatttagtt tcatataaag tatcatcagt gtagaaccta attcaattca aagctgtgtg    4140
tttggaagac tatcttacta tttcacaaca gcctgacaac atttctatag ccaaaaatag    4200
ctaaatacct caatcagtct cagaatgtca ttttggtact ttggtggcca cataagccat    4260
tattcactag tatgactagt tgtgtctggc agtttatatt taactctctt tatgtctgtg    4320 gatttttcc ttcaaagttt aataaattta ttttcttgga aaaaaaaaa                 4370

<210> SEQ ID NO 26
<211> LENGTH: 1518
<212> TYPE: DNA
<213> ORGANISM: homo sapiens

<400> SEQUENCE: 26
aaaacagccc ggagcctgca gcccagcccc acccagaccc atggctggac ctgccaccca      60
gagccccatg aagctgatgg ccctgcagct gctgctgtgg cacagtgcac tctggacagt     120
gcaggaagcc accccctgg gccctgccag ctccctgccc cagagcttcc tgctcaagtg     180
cttagagcaa gtgaggaaga tccagggcga tggcgcagcg ctccaggaga agctggtgag    240
tgagtgtgcc acctacaagc tgtgccaccc cgaggagctg gtgctgctcg acactctct    300 gggcatcccc tgggctcccc tgagcagctg ccccagccag gccctgcagc tggcaggctg    360
cttgagccaa ctccatagcg gccttttcct ctaccagggg ctcctgcagg ccctggaagg    420
gatctccccc gagttgggtc ccaccttgga cacactgcag ctggacgtcg ccgactttgc    480
caccaccatc tggcagcaga tggaagaact gggaatggcc cctgccctgc agcccaccca    540
gggtgccatg ccggccttcg cctctgcttt ccagcgccgg gcaggagggg tcctggttgc    600
ctcccatctg cagagcttcc tggaggtgtc gtaccgcgtt ctacgccacc ttgcccagcc    660
ctgagccaag ccctcccat cccatgtatt tatctctatt taatatttat gtctatttaa     720
gcctcatatt taaagacagg gaagagcaga acggagcccc aggcctctgt gtccttccct    780
gcatttctga gtttcattct cctgcctgta gcagtgagaa aaagctcctg tcctcccatc    840
ccctggactg ggaggtagat aggtaaatac caagtattta ttactatgac tgctccccag    900
ccctggctct gcaatgggca ctgggatgag ccgctgtgag cccctggtcc tgagggtccc    960
```

-continued

```
cacctgggac ccttgagagt atcaggtctc ccacgtggga gacaagaaat ccctgtttaa    1020
tatttaaaca gcagtgttcc ccatctgggt ccttgcaccc ctcactctgg cctcagccga    1080
ctgcacagcg gcccctgcat ccccttggct gtgaggcccc tggacaagca gaggtggcca    1140
gagctgggag gcatggccct ggggtcccac gaatttgctg gggaatctcg ttttcttct     1200 taagactttt gggacatggt ttgactcccg aacatcaccg acgtgtctcc tgttttctg     1260 ggtggcctcg ggacacctgc cctgccccca cgagggtcag gactgtgact ctttttaggg    1320
ccaggcaggt gcctggacat ttgccttgct ggacggggac tggggatgtg ggagggagca    1380
gacaggagga atcatgtcag gcctgtgtgt gaaaggaagc tccactgtca ccctccacct    1440
cttcaccccc cactcaccag tgtccctcc actgtcacat tgtaactgaa cttcaggata     1500
ataaagtgtt tgcctcca                                                  1518

<210> SEQ ID NO 27
<211> LENGTH: 1509
<212> TYPE: DNA
<213> ORGANISM: homo sapiens

<400> SEQUENCE: 27
aaaacagccc ggagcctgca gcccagcccc acccagaccc atggctggac ctgccaccca      60
gagccccatg aagctgatgg ccctgcagct gctgctgtgg cacagtgcac tctggacagt     120
gcaggaagcc accccctgg gcctgccag ctccctgccc cagagcttcc tgctcaagtg      180
cttagagcaa gtgaggaaga tccagggcga tggcgcagcg ctccaggaga agctgtgtgc    240
cacctacaag ctgtgccacc ccgaggagct ggtgctgctc ggacactctc tgggcatccc    300
ctgggctccc ctgagcagct gccccagcca ggccctgcag ctggcaggct gcttgagcca    360
actccatagc ggccttttcc tctaccaggg gctcctgcag gccctggaag ggatctcccc    420
cgagttgggt cccaccttgg acacactgca gctggacgtc gccgactttg ccaccaccat    480
ctggcagcag atggaagaac tgggaatggc ccctgccctg cagcccaccc agggtgccat    540
gccggccttc gcctctgctt ccagcgccg ggcaggaggg gtcctggttg cctcccatct    600
gcagagcttc ctggaggtgt cgtaccgcgt tctacgccac cttgcccagc cctgagccaa    660 gccctccca tcccatgtat ttatctctat ttaatattta tgtctattta agcctcatat      720
ttaaagacag ggaagagcag aacggagccc caggcctctg tgtccttccc tgcatttctg    780
agtttcattc tcctgcctgt agcagtgaga aaaagctcct gtcctcccat ccctggact     840 gggaggtaga taggtaaata ccaagtattt attactatga ctgctcccca gccctggctc    900
tgcaatgggc actgggatga ccgctgtga gcccctggtc ctgagggtcc ccacctggga    960
cccttgagag tatcaggtct cccacgtggg agacaagaaa tccctgttta atatttaaac    1020
agcagtgttc cccatctggg tccttgcacc cctcactctg gcctcagccg actgcacagc    1080
ggcccctgca tccccttggc tgtgaggccc ctggacaagc agaggtggcc agagctggga    1140
ggcatggccc tggggtccca cgaatttgct ggggaatctc gttttcttc ttaagactttt    1200 tgggacatgg tttgactccc gaacatcacc gacgtgtctc ctgttttct gggtggcctc    1260 gggacacctg cctgccccc acgagggtca ggactgtgac tcttttagg gccaggcagg    1320 tgcctggaca tttgccttgc tggacgggga ctggggatgt gggagggagc agacaggagg    1380
aatcatgtca ggcctgtgtg tgaaaggaag ctccactgtc acctccacc tcttccccc     1440 ccactcacca gtgtccctc cactgtcaca ttgtaactga acttcaggat aataaagtgt    1500
ttgcctcca                                                           1509
```

<210> SEQ ID NO 28
<211> LENGTH: 1703
<212> TYPE: DNA
<213> ORGANISM: homo sapiens

<400> SEQUENCE: 28

| | | | | | |
|---|---|---|---|---|---|
| aaaacagccc | ggagcctgca | gcccagcccc | acccagaccc | atggctggac | ctgccaccca | 60 |
| gagccccatg | aagctgatgg | gtgagtgtct | tggcccagga | tgggagagcc | gcctgccctg | 120 |
| gcatgggagg | gaggctggtg | tgacagaggg | gctggggatc | ccgttctgg | gaatggggat | 180 |
| taaaggcacc | cagtgtcccc | gagagggcct | caggtggtag | ggaacagcat | gtctcctgag | 240 |
| cccgctctgt | ccccagccct | gcagctgctg | ctgtggcaca | gtgcactctg | gacagtgcag | 300 |
| gaagccaccc | ccctgggccc | tgccagctcc | ctgccccaga | gcttcctgct | caagtgctta | 360 |
| gagcaagtga | ggaagatcca | gggcgatggc | gcagcgctcc | aggagaagct | gtgtgccacc | 420 |
| tacaagctgt | gccaccccga | ggagctggtg | ctgctcggac | actctctggg | catcccctgg | 480 |
| gctcccctga | gcagctgccc | cagccaggcc | ctgcagctgg | caggctgctt | gagccaactc | 540 |
| catagcggcc | ttttcctcta | ccaggggctc | ctgcaggccc | tggaagggat | ctcccccgag | 600 |
| ttgggtccca | ccttggacac | actgcagctg | gacgtcgccg | actttgccac | caccatctgg | 660 |
| cagcagatgg | aagaactggg | aatggcccct | gccctgcagc | ccacccaggg | tgccatgccg | 720 |
| gccttcgcct | ctgctttcca | gcgccgggca | ggaggggtcc | tggttgcctc | ccatctgcag | 780 |
| agcttcctgg | aggtgtcgta | ccgcgttcta | cgccaccttg | cccagccctg | agccaagccc | 840 |
| tccccatccc | atgtatttat | ctctatttaa | tatttatgtc | tatttaagcc | tcatatttaa | 900 |
| agacagggaa | gagcagaacg | gagccccagg | cctctgtgtc | cttccctgca | tttctgagtt | 960 |
| tcattctcct | gcctgtagca | gtgagaaaaa | gctcctgtcc | tcccatcccc | tggactggga | 1020 |
| ggtagatagg | taaataccaa | gtatttatta | ctatgactgc | tccccagccc | tggctctgca | 1080 |
| atgggcactg | ggatgagccg | ctgtgagccc | ctggtcctga | gggtccccac | ctgggaccct | 1140 |
| tgagagtatc | aggtctccca | cgtgggagac | aagaaatccc | tgtttaatat | ttaaacagca | 1200 |
| gtgttcccca | tctgggtcct | tgcacccctc | actctgccct | cagccgactg | cacagcggcc | 1260 |
| cctgcatccc | cttggctgtg | aggccctgg | acaagcagag | gtggccagag | ctgggaggca | 1320 |
| tggccctggg | gtcccacgaa | tttgctgggg | aatctcgttt | tcttcttaa | gacttttggg | 1380 |
| acatggtttg | actcccgaac | atcaccgacg | tgtctcctgt | ttttctgggt | ggcctcggga | 1440 |
| cacctgccct | gccccacga | gggtcaggac | tgtgactctt | tttagggcca | ggcaggtgcc | 1500 |
| tggacatttg | ccttgctgga | cggggactgg | ggatgtggga | gggagcagac | aggaggaatc | 1560 |
| atgtcaggcc | tgtgtgtgaa | aggaagctcc | actgtcaccc | tccacctctt | cacccccac | 1620 |
| tcaccagtgt | ccctccact | gtcacattgt | aactgaactt | caggataata | aagtgtttgc | 1680 |
| ctccaaaaaa | aaaaaaaaaa | aaa | | | | 1703 |

<210> SEQ ID NO 29
<211> LENGTH: 2165
<212> TYPE: DNA
<213> ORGANISM: homo sapiens

<400> SEQUENCE: 29

| | | | | | |
|---|---|---|---|---|---|
| ctgagcgaca | gcaagtgcag | cgggctccta | ccccgggtga | ggggtggcct | ccgcgtggga | 60 |
| tcgtgccctc | ttcagcccgc | tcctgtcccc | gacatcacgt | gtattccgca | cgtcccctcc | 120 |

```
gcgctgtgtg tctactgaga cggggaggcg tgacagggcc cgggtccctt ctcagtggtg      180
ctctgtgctt cagggcaagc tccccgtctc cgggcgcact tccctcgcct gtgttcggtc      240
catcctcctt tctccagcct cctccctcg caggtgggat cgtcggtggg accggagcgc      300
gggcgggcgc ggcccccgg gaccatggcc gggtccgaca ccgcgccctt cctcagccag      360
gcggatgacc cggacgacgg gccagtgcct ggcaccccgg ggttgccagg gtccacgggg      420
aacccgaagt ccgaggagcc cgaggtcccg gaccaggagg ggctgcagcg catcaccggc      480
ctgtctcccg gccgttcggc tctcatagtg gcggtgctgt gctacatcaa tctcctgaac      540
tacatggacc gcttcaccgt ggctggcgtc cttcccgaca tcgagcagtt cttcaacatc      600
ggggacagta gctctgggct catccagacc gtgttcatct ccagttacat ggtgttggca      660
cctgtgtttg gctacctggg tgacaggtac aatcggaagt atctcatgtg cgggggcatt      720
gccttctggt ccctggtgac actggggtca tccttcatcc ccggagagca tttctggctg      780
ctcctcctga cccggggcct ggtggggtc ggggaggcca gttattccac catccgcgcc      840
actctcattg ccgacctctt tgtggccgac agcggagcc ggatgctcag catcttctac      900
tttgccattc cggtgggcag tggtctgggc tacattgcag gctccaaagt gaaggatatg      960
gctggagact ggcactgggc tctgagggtg acaccgggtc taggagtggt ggccgttctg     1020
ctgctgttcc tggtagtgcg ggagccgcca aggggagccg tggagcgcca ctcagatttg     1080 ccaccectga accccacctc gtggtgggca gatctgaggg ctctggcaag aaatcctagt     1140
ttcgtcctgt cttccctggg cttcactgct gtggcctttg tcacgggctc cctggctctg     1200
tgggctccgg cattcctgct gcgttccgc gtggtccttg gggagacccc accctgcctt     1260
cccggagact cctgctcttc ctctgacagt ctcatctttg gactcatcac ctgcctgacc     1320
ggagtcctgg gtgtgggcct gggtgtggag atcagccgcc ggctccgcca ctccaacccc     1380
cgggctgatc ccctggtctg tgccactggc ctcctgggct ctgcacccTT cctcttcctg     1440
tcccttgcct gcgcccgtgg tagcatcgtg gccacttata ttttcatctt cattggagag     1500
accctcctgt ccatgaactg gggccatcgtg gccgacattc tgctgtacgt ggtgatccct     1560
acccgacgct ccaccgccga ggccttccag atcgtgctgt cccacctgct gggtgatgct     1620
gggagcccct acctcattgg cctgatctct gaccgcctgc gccggaactg gccccctcc     1680 ttcttgtccg agttccgggc tctgcagttc tcgctcatgc tctgcgcgtt tgttggggca     1740
ctgggcggcg cagccttcct gggcaccgcc atcttcattg aggccgaccg ccggcgggca     1800
cagctgcacg tgcagggcct gctgcacgaa gcagggtcca cagacgaccg gattgtggtg     1860
ccccagcggg gccgctccac ccgcgtgccc gtggccagtg tgctcatctg agaggctgcc     1920
gctcacctac ctgcacatct gccacagctg gccctgggcc cacccacga agggcctggg     1980 cctaacccct tggcctggcc cagcttccag agggaccctg ggccgtgtgc cagctcccag     2040
acactacatg ggtagctcag gggaggaggt ggggtccag gagggggatc cctctccaca     2100
ggggcagccc caagggctcg gtgctatttg taacggaata aaatttgtgc cagaaaaaaa     2160
aaaaa                                                                 2165
```

<210> SEQ ID NO 30
<211> LENGTH: 240
<212> TYPE: PRT
<213> ORGANISM: homo sapiens

<400> SEQUENCE: 30

Met Val Gly Gln Arg Val Leu Leu Leu Val Ala Phe Leu Leu Ser Gly

```
                1               5                  10                 15
            Val Leu Ser Glu Ala Ala Lys Ile Leu Thr Ile Ser Thr Leu Gly
                        20                  25                 30

Gly Ser His Tyr Leu Leu Asp Arg Val Ser Gln Ile Leu Gln Glu
                        35                  40                 45

His Gly His Asn Val Thr Met Leu His Gln Ser Gly Lys Phe Leu Ile
                50                  55                  60

Pro Asp Ile Lys Glu Glu Lys Ser Tyr Gln Val Ile Arg Trp Phe
            65                  70                  75                 80

Ser Pro Glu Asp His Gln Lys Arg Ile Lys Lys His Phe Asp Ser Tyr
                                85                  90                  95

Ile Glu Thr Ala Leu Asp Gly Arg Lys Glu Ser Glu Ala Leu Val Lys
                            100                 105                 110

Leu Met Glu Ile Phe Gly Thr Gln Cys Ser Tyr Leu Leu Ser Arg Lys
                            115                 120                 125

Asp Ile Met Asp Ser Leu Lys Asn Glu Asn Cys Asp Leu Val Phe Val
                    130                 135                 140

Glu Ala Phe Asp Phe Cys Ser Phe Leu Ile Ala Glu Lys Leu Val Lys
            145                 150                 155                 160

Pro Phe Val Ala Ile Leu Pro Thr Thr Phe Gly Ser Leu Asp Phe Gly
                                165                 170                 175

Leu Pro Ser Pro Leu Ser Tyr Val Pro Val Phe Pro Ser Leu Leu Thr
                            180                 185                 190

Asp His Met Asp Phe Trp Gly Arg Val Lys Asn Phe Leu Met Phe Phe
                        195                 200                 205

Ser Phe Ser Arg Ser Gln Trp Asp Met Gln Ser Thr Phe Asp Asn Thr
            210                 215                 220

Ile Lys Glu His Phe Pro Glu Gly Ser Arg Pro Val Leu Ser His Leu
            225                 230                 235                 240

<210> SEQ ID NO 31
<211> LENGTH: 523
<212> TYPE: PRT
<213> ORGANISM: homo sapiens

<400> SEQUENCE: 31

Met Ala Gly Gln Arg Val Leu Leu Val Gly Phe Leu Leu Pro Gly
            1               5                   10                  15

Val Leu Ser Glu Ala Ala Lys Ile Leu Thr Ile Ser Thr Val Gly
                        20                  25                  30

Gly Ser His Tyr Leu Leu Met Asp Arg Val Ser Gln Ile Leu Gln Asp
                        35                  40                  45

His Gly His Asn Val Thr Met Leu Asn His Lys Arg Gly Pro Phe Met
                50                  55                  60

Pro Asp Phe Lys Lys Glu Glu Lys Ser Tyr Gln Val Ile Ser Trp Leu
            65                  70                  75                  80

Ala Pro Glu Asp His Gln Arg Glu Phe Lys Lys Ser Phe Asp Phe Phe
                                85                  90                  95

Leu Glu Glu Thr Leu Gly Gly Arg Gly Lys Phe Glu Asn Leu Leu Asn
                            100                 105                 110

Val Leu Glu Tyr Leu Ala Leu Gln Cys Ser His Phe Leu Asn Arg Lys
                            115                 120                 125

Asp Ile Met Asp Ser Leu Lys Asn Glu Asn Phe Asp Met Val Ile Val
                    130                 135                 140
```

```
Glu Thr Phe Asp Tyr Cys Pro Phe Leu Ile Ala Glu Lys Leu Gly Lys
145                 150                 155                 160

Pro Phe Val Ala Ile Leu Ser Thr Ser Phe Gly Ser Leu Glu Phe Gly
                165                 170                 175

Leu Pro Ile Pro Leu Ser Tyr Val Pro Val Phe Arg Ser Leu Leu Thr
            180                 185                 190

Asp His Met Asp Phe Trp Gly Arg Val Lys Asn Phe Leu Met Phe Phe
        195                 200                 205

Ser Phe Cys Arg Arg Gln Gln His Met Gln Ser Thr Phe Asp Asn Thr
    210                 215                 220

Ile Lys Glu His Phe Thr Glu Gly Ser Arg Pro Val Leu Ser His Leu
225                 230                 235                 240

Leu Leu Lys Ala Glu Leu Trp Phe Ile Asn Ser Asp Phe Ala Phe Asp
                245                 250                 255

Phe Ala Arg Pro Leu Leu Pro Asn Thr Val Tyr Val Gly Gly Leu Met
            260                 265                 270

Glu Lys Pro Ile Lys Pro Val Pro Gln Asp Leu Glu Asn Phe Ile Ala
        275                 280                 285

Lys Phe Glu Asp Ser Gly Phe Val Leu Val Thr Leu Gly Ser Met Val
    290                 295                 300

Asn Thr Cys Gln Asn Pro Glu Ile Phe Lys Glu Met Asn Asn Ala Phe
305                 310                 315                 320

Ala His Leu Pro Gln Gly Val Ile Trp Lys Cys Gln Cys Ser His Trp
                325                 330                 335

Pro Lys Asp Val His Leu Ala Ala Asn Val Lys Ile Val Asp Trp Leu
            340                 345                 350

Pro Gln Ser Asp Leu Leu Ala His Pro Ser Ile Arg Leu Phe Val Thr
        355                 360                 365

His Gly Gly Gln Asn Ser Ile Met Glu Ala Ile Gln His Gly Val Pro
    370                 375                 380

Met Val Gly Ile Pro Leu Phe Gly Asp Gln Pro Glu Asn Met Val Arg
385                 390                 395                 400

Val Glu Ala Lys Lys Phe Gly Val Ser Ile Gln Leu Lys Lys Leu Lys
                405                 410                 415

Ala Glu Thr Leu Ala Leu Lys Met Lys Gln Ile Met Glu Asp Lys Arg
            420                 425                 430

Tyr Lys Ser Ala Ala Val Ala Ala Ser Val Ile Leu Arg Ser His Pro
        435                 440                 445

Leu Ser Pro Thr Gln Arg Leu Val Gly Trp Ile Asp His Val Leu Gln
    450                 455                 460

Thr Gly Gly Ala Thr His Leu Lys Pro Tyr Val Phe Gln Gln Pro Trp
465                 470                 475                 480

His Glu Gln Tyr Leu Leu Asp Val Phe Val Phe Leu Leu Gly Leu Thr
                485                 490                 495

Leu Gly Thr Leu Trp Leu Cys Gly Lys Leu Leu Gly Met Ala Val Trp
            500                 505                 510

Trp Leu Arg Gly Ala Arg Lys Val Lys Glu Thr
        515                 520

<210> SEQ ID NO 32
<211> LENGTH: 533
<212> TYPE: PRT
<213> ORGANISM: homo sapiens

<400> SEQUENCE: 32
```

-continued

```
Met Ala Phe Ala Asn Leu Arg Lys Val Leu Ile Ser Asp Ser Leu Asp
1               5                   10                  15

Pro Cys Cys Arg Lys Ile Leu Gln Asp Gly Leu Gln Val Val Glu
            20                  25                  30

Lys Gln Asn Leu Ser Lys Glu Glu Leu Ile Ala Glu Leu Gln Asp Cys
        35                  40                  45

Glu Gly Leu Ile Val Arg Ser Ala Thr Lys Val Thr Ala Asp Val Ile
    50                  55                  60

Asn Ala Ala Glu Lys Leu Gln Val Val Gly Arg Ala Gly Thr Gly Val
65                  70                  75                  80

Asp Asn Val Asp Leu Glu Ala Ala Thr Arg Lys Gly Ile Leu Val Met
            85                  90                  95

Asn Thr Pro Asn Gly Asn Ser Leu Ser Ala Ala Glu Leu Thr Cys Gly
            100                 105                 110

Met Ile Met Cys Leu Ala Arg Gln Ile Pro Gln Ala Thr Ala Ser Met
        115                 120                 125

Lys Asp Gly Lys Trp Glu Arg Lys Phe Met Gly Thr Glu Leu Asn
130                 135                 140

Gly Lys Thr Leu Gly Ile Leu Gly Leu Gly Arg Ile Gly Arg Glu Val
145                 150                 155                 160

Ala Thr Arg Met Gln Ser Phe Gly Met Lys Thr Ile Gly Tyr Asp Pro
                165                 170                 175

Ile Ile Ser Pro Glu Val Ser Ala Ser Phe Gly Val Gln Gln Leu Pro
            180                 185                 190

Leu Glu Glu Ile Trp Pro Leu Cys Asp Phe Ile Thr Val His Thr Pro
            195                 200                 205

Leu Leu Pro Ser Thr Thr Gly Leu Leu Asn Asp Asn Thr Phe Ala Gln
210                 215                 220

Cys Lys Lys Gly Val Arg Val Val Asn Cys Ala Arg Gly Gly Ile Val
225                 230                 235                 240

Asp Glu Gly Ala Leu Leu Arg Ala Leu Gln Ser Gly Gln Cys Ala Gly
            245                 250                 255

Ala Ala Leu Asp Val Phe Thr Glu Glu Pro Pro Arg Asp Arg Ala Leu
            260                 265                 270

Val Asp His Glu Asn Val Ile Ser Cys Pro His Leu Gly Ala Ser Thr
            275                 280                 285

Lys Glu Ala Gln Ser Arg Cys Gly Glu Glu Ile Ala Val Gln Phe Val
            290                 295                 300

Asp Met Val Lys Gly Lys Ser Leu Thr Gly Val Val Asn Ala Gln Ala
305                 310                 315                 320

Leu Thr Ser Ala Phe Ser Pro His Thr Lys Pro Trp Ile Gly Leu Ala
            325                 330                 335

Glu Ala Leu Gly Thr Leu Met Arg Ala Trp Ala Gly Ser Pro Lys Gly
            340                 345                 350

Thr Ile Gln Val Ile Thr Gln Gly Thr Ser Leu Lys Asn Ala Gly Asn
            355                 360                 365

Cys Leu Ser Pro Ala Val Ile Val Gly Leu Leu Lys Glu Ala Ser Lys
        370                 375                 380

Gln Ala Asp Val Asn Leu Val Asn Ala Lys Leu Leu Val Lys Glu Ala
385                 390                 395                 400

Gly Leu Asn Val Thr Thr Ser His Ser Pro Ala Ala Pro Gly Glu Gln
                405                 410                 415
```

-continued

```
Gly Phe Gly Glu Cys Leu Leu Ala Val Ala Leu Ala Gly Ala Pro Tyr
            420                 425                 430

Gln Ala Val Gly Leu Val Gln Gly Thr Thr Pro Val Leu Gln Gly Leu
        435                 440                 445

Asn Gly Ala Val Phe Arg Pro Glu Val Pro Leu Arg Arg Asp Leu Pro
450                 455                 460

Leu Leu Leu Phe Arg Thr Gln Thr Ser Asp Pro Ala Met Leu Pro Thr
465                 470                 475                 480

Met Ile Gly Leu Leu Ala Glu Ala Gly Val Arg Leu Leu Ser Tyr Gln
                485                 490                 495

Thr Ser Leu Val Ser Asp Gly Glu Thr Trp His Val Met Gly Ile Ser
            500                 505                 510

Ser Leu Leu Pro Ser Leu Glu Ala Trp Lys Gln His Val Thr Glu Ala
        515                 520                 525

Phe Gln Phe His Phe
        530

<210> SEQ ID NO 33
<211> LENGTH: 372
<212> TYPE: PRT
<213> ORGANISM: homo sapiens

<400> SEQUENCE: 33

Met Lys Tyr Leu Arg His Arg Arg Pro Asn Ala Thr Leu Ile Leu Ala
1               5                   10                  15

Ile Gly Ala Phe Thr Leu Leu Phe Ser Leu Leu Val Ser Pro Pro
            20                  25                  30

Thr Cys Lys Val Gln Glu Gln Pro Ala Ile Pro Glu Ala Leu Ala
        35                  40                  45

Trp Pro Thr Pro Thr Arg Pro Ala Pro Ala Pro Cys His Ala Asn
                50                  55                  60

Thr Ser Met Val Thr His Pro Asp Phe Ala Thr Gln Pro Gln His Val
65                  70                  75                  80

Gln Asn Phe Leu Leu Tyr Arg His Cys Arg His Phe Pro Leu Leu Gln
                85                  90                  95

Asp Val Pro Pro Ser Lys Cys Ala Gln Pro Val Phe Leu Leu Leu Val
            100                 105                 110

Ile Lys Ser Ser Pro Ser Asn Tyr Val Arg Arg Glu Leu Leu Arg Arg
        115                 120                 125

Thr Trp Gly Arg Glu Arg Lys Val Arg Gly Leu Gln Leu Arg Leu Leu
    130                 135                 140

Phe Leu Val Gly Thr Ala Ser Asn Pro His Glu Ala Arg Lys Val Asn
145                 150                 155                 160

Arg Leu Leu Glu Leu Glu Ala Gln Thr His Gly Asp Ile Leu Gln Trp
                165                 170                 175

Asp Phe His Asp Ser Phe Phe Asn Leu Thr Leu Lys Gln Val Leu Phe
            180                 185                 190

Leu Gln Trp Gln Glu Thr Arg Cys Ala Asn Ala Ser Phe Val Leu Asn
        195                 200                 205

Gly Asp Asp Asp Val Phe Ala His Thr Asp Asn Met Val Phe Tyr Leu
    210                 215                 220

Gln Asp His Asp Pro Gly Arg His Leu Phe Val Gly Gln Leu Ile Gln
225                 230                 235                 240

Asn Val Gly Pro Ile Arg Ala Phe Trp Ser Lys Tyr Tyr Val Pro Glu
                245                 250                 255
```

```
Val Val Thr Gln Asn Glu Arg Tyr Pro Pro Tyr Cys Gly Gly Gly
            260                 265                 270

Phe Leu Leu Ser Arg Phe Thr Ala Ala Leu Arg Arg Ala Ala His
            275                 280                 285

Val Leu Asp Ile Phe Pro Ile Asp Asp Val Phe Leu Gly Met Cys Leu
            290                 295                 300

Glu Leu Glu Gly Leu Lys Pro Ala Ser His Ser Gly Ile Arg Thr Ser
305                 310                 315                 320

Gly Val Arg Ala Pro Ser Gln Arg Leu Ser Ser Phe Asp Pro Cys Phe
                325                 330                 335

Tyr Arg Asp Leu Leu Val His Arg Phe Leu Pro Tyr Glu Met Leu
            340                 345                 350

Leu Met Trp Asp Ala Leu Asn Gln Pro Asn Leu Thr Cys Gly Asn Gln
            355                 360                 365

Thr Gln Ile Tyr
        370

<210> SEQ ID NO 34
<211> LENGTH: 177
<212> TYPE: PRT
<213> ORGANISM: homo sapiens

<400> SEQUENCE: 34

Met Ala Val Ala Asn Ser Ser Pro Val Asn Pro Val Phe Phe Asp
1               5                   10                  15

Val Ser Ile Gly Gly Gln Glu Val Gly Arg Met Lys Ile Glu Leu Phe
            20                  25                  30

Ala Asp Val Val Pro Lys Thr Ala Glu Asn Phe Arg Gln Phe Cys Thr
            35                  40                  45

Gly Glu Phe Arg Lys Asp Gly Val Pro Ile Gly Tyr Lys Gly Ser Thr
        50                  55                  60

Phe His Arg Val Ile Lys Asp Phe Met Ile Gln Gly Gly Asp Phe Val
65                  70                  75                  80

Asn Gly Asp Gly Thr Gly Val Ala Ser Ile Tyr Arg Gly Pro Phe Ala
                85                  90                  95

Asp Glu Asn Phe Lys Leu Arg His Ser Ala Pro Gly Leu Leu Ser Met
            100                 105                 110

Ala Asn Ser Gly Pro Ser Thr Asn Gly Cys Gln Phe Phe Ile Thr Cys
            115                 120                 125

Ser Lys Cys Asp Trp Leu Asp Gly Lys His Val Val Phe Gly Lys Ile
        130                 135                 140

Ile Asp Gly Leu Leu Val Met Arg Lys Ile Glu Asn Val Pro Thr Gly
145                 150                 155                 160

Pro Asn Asn Lys Pro Lys Leu Pro Val Val Ile Ser Gln Cys Gly Glu
                165                 170                 175

Met

<210> SEQ ID NO 35
<211> LENGTH: 3312
<212> TYPE: PRT
<213> ORGANISM: homo sapiens

<400> SEQUENCE: 35

Met Met Ala Arg Arg Pro Pro Trp Arg Gly Leu Gly Gly Arg Ser Thr
1               5                   10                  15
```

```
Pro Ile Leu Leu Leu Leu Leu Ser Leu Phe Pro Leu Ser Gln Glu
         20                  25                  30
Glu Leu Gly Gly Gly Gly His Gln Gly Trp Asp Pro Gly Leu Ala Ala
         35                  40                  45
Thr Thr Gly Pro Arg Ala His Ile Gly Gly Ala Leu Ala Leu Cys
     50                  55                  60
Pro Glu Ser Ser Gly Val Arg Glu Asp Gly Pro Gly Leu Gly Val
 65                  70                  75                  80
Arg Glu Pro Ile Phe Val Gly Leu Arg Gly Arg Gln Ser Ala Arg
                 85                  90                  95
Asn Ser Arg Gly Pro Pro Glu Gln Pro Asn Glu Glu Leu Gly Ile Glu
            100                 105                 110
His Gly Val Gln Pro Leu Gly Ser Arg Glu Arg Glu Thr Gly Gln Gly
        115                 120                 125
Pro Gly Ser Val Leu Tyr Trp Arg Pro Glu Val Ser Ser Cys Gly Arg
    130                 135                 140
Thr Gly Pro Leu Gln Arg Gly Ser Leu Ser Pro Gly Ala Leu Ser Ser
145                 150                 155                 160
Gly Val Pro Gly Ser Gly Asn Ser Ser Pro Leu Pro Ser Asp Phe Leu
                165                 170                 175
Ile Arg His His Gly Pro Lys Pro Val Ser Ser Gln Arg Asn Ala Gly
                180                 185                 190
Thr Gly Ser Arg Lys Arg Val Gly Thr Ala Arg Cys Cys Gly Glu Leu
        195                 200                 205
Trp Ala Thr Gly Ser Lys Gly Gln Gly Glu Arg Ala Thr Thr Ser Gly
210                 215                 220
Ala Glu Arg Thr Ala Pro Arg Arg Asn Cys Leu Pro Gly Ala Ser Gly
225                 230                 235                 240
Ser Gly Pro Glu Leu Asp Ser Ala Pro Arg Thr Ala Arg Thr Ala Pro
                245                 250                 255
Ala Ser Gly Ser Ala Pro Arg Glu Ser Arg Thr Ala Pro Glu Pro Ala
                260                 265                 270
Pro Lys Arg Met Arg Ser Arg Gly Leu Phe Arg Cys Arg Phe Leu Pro
            275                 280                 285
Gln Arg Pro Gly Pro Arg Pro Pro Gly Leu Pro Ala Arg Pro Glu Ala
        290                 295                 300
Arg Lys Val Thr Ser Ala Asn Arg Ala Arg Phe Arg Arg Ala Ala Asn
305                 310                 315                 320
Arg His Pro Gln Phe Pro Gln Tyr Asn Tyr Gln Thr Leu Val Pro Glu
                325                 330                 335
Asn Glu Ala Ala Gly Thr Ala Val Leu Arg Val Val Ala Gln Asp Pro
                340                 345                 350
Asp Ala Gly Glu Ala Gly Arg Leu Val Tyr Ser Leu Ala Ala Leu Met
            355                 360                 365
Asn Ser Arg Ser Leu Glu Leu Phe Ser Ile Asp Pro Gln Ser Gly Leu
    370                 375                 380
Ile Arg Thr Ala Ala Ala Leu Asp Arg Glu Ser Met Glu Arg His Tyr
385                 390                 395                 400
Leu Arg Val Thr Ala Gln Asp His Gly Ser Pro Arg Leu Ser Ala Thr
                405                 410                 415
Thr Met Val Ala Val Thr Val Ala Asp Arg Asn Asp His Ser Pro Val
            420                 425                 430
Phe Glu Gln Ala Gln Tyr Arg Glu Thr Leu Arg Glu Asn Val Glu Glu
```

```
                435                 440                 445
Gly Tyr Pro Ile Leu Gln Leu Arg Ala Thr Asp Gly Asp Ala Pro Pro
450                 455                 460

Asn Ala Asn Leu Arg Tyr Arg Phe Val Gly Pro Pro Ala Ala Arg Ala
465                 470                 475                 480

Ala Ala Ala Ala Ala Phe Glu Ile Asp Pro Arg Ser Gly Leu Ile Ser
                485                 490                 495

Thr Ser Gly Arg Val Asp Arg Glu His Met Glu Ser Tyr Glu Leu Val
            500                 505                 510

Val Glu Ala Ser Asp Gln Gly Gln Glu Pro Gly Pro Arg Ser Ala Thr
            515                 520                 525

Val Arg Val His Ile Thr Val Leu Asp Glu Asn Asp Asn Ala Pro Gln
530                 535                 540

Phe Ser Glu Lys Arg Tyr Val Ala Gln Val Arg Glu Asp Val Arg Pro
545                 550                 555                 560

His Thr Val Val Leu Arg Val Thr Ala Thr Asp Arg Asp Lys Asp Ala
                565                 570                 575

Asn Gly Leu Val His Tyr Asn Ile Ile Ser Gly Asn Ser Arg Gly His
            580                 585                 590

Phe Ala Ile Asp Ser Leu Thr Gly Glu Ile Gln Val Ala Pro Leu
595                 600                 605

Asp Phe Glu Ala Glu Arg Glu Tyr Ala Leu Arg Ile Arg Ala Gln Asp
610                 615                 620

Ala Gly Arg Pro Pro Leu Ser Asn Asn Thr Gly Leu Ala Ser Ile Gln
625                 630                 635                 640

Val Val Asp Ile Asn Asp His Ile Pro Ile Phe Val Ser Thr Pro Phe
                645                 650                 655

Gln Val Ser Val Leu Glu Asn Ala Pro Leu Gly His Ser Val Ile His
            660                 665                 670

Ile Gln Ala Val Asp Ala Asp His Gly Glu Asn Ala Arg Leu Glu Tyr
            675                 680                 685

Ser Leu Thr Gly Val Ala Pro Asp Thr Pro Phe Val Ile Asn Ser Ala
690                 695                 700

Thr Gly Trp Val Ser Val Ser Gly Pro Leu Asp Arg Glu Ser Val Glu
705                 710                 715                 720

His Tyr Phe Phe Gly Val Glu Ala Arg Asp His Gly Ser Pro Pro Leu
                725                 730                 735

Ser Ala Ser Ala Ser Val Thr Val Thr Val Leu Asp Val Asn Asp Asn
            740                 745                 750

Arg Pro Glu Phe Thr Met Lys Glu Tyr His Leu Arg Leu Asn Glu Asp
            755                 760                 765

Ala Ala Val Gly Thr Ser Val Val Ser Val Thr Ala Val Asp Arg Asp
770                 775                 780

Ala Asn Ser Ala Ile Ser Tyr Gln Ile Thr Gly Gly Asn Thr Arg Asn
785                 790                 795                 800

Arg Phe Ala Ile Ser Thr Gln Gly Gly Val Gly Leu Val Thr Leu Ala
                805                 810                 815

Leu Pro Leu Asp Tyr Lys Gln Glu Arg Tyr Phe Lys Leu Val Leu Thr
            820                 825                 830

Ala Ser Asp Arg Ala Leu His Asp His Cys Tyr Val His Ile Asn Ile
            835                 840                 845

Thr Asp Ala Asn Thr His Arg Pro Val Phe Gln Ser Ala His Tyr Ser
850                 855                 860
```

```
Val Ser Val Asn Glu Asp Arg Pro Met Gly Ser Thr Ile Val Ile
865                 870                 875                 880

Ser Ala Ser Asp Asp Val Gly Glu Asn Ala Arg Ile Thr Tyr Leu
            885                 890                 895

Leu Glu Asp Asn Leu Pro Gln Phe Arg Ile Asp Ala Asp Ser Gly Ala
                900                 905                 910

Ile Thr Leu Gln Ala Pro Leu Asp Tyr Glu Asp Gln Val Thr Tyr Thr
            915                 920                 925

Leu Ala Ile Thr Ala Arg Asp Asn Gly Ile Pro Gln Lys Ala Asp Thr
            930                 935                 940

Thr Tyr Val Glu Val Met Val Asn Asp Val Asn Asp Asn Ala Pro Gln
945                 950                 955                 960

Phe Val Ala Ser His Tyr Thr Gly Leu Val Ser Glu Asp Ala Pro Pro
                965                 970                 975

Phe Thr Ser Val Leu Gln Ile Ser Ala Thr Asp Arg Asp Ala His Ala
                980                 985                 990

Asn Gly Arg Val Gln Tyr Thr Phe Gln Asn Gly Glu Asp Gly Asp Gly
            995                 1000                1005

Asp Phe Thr Ile Glu Pro Thr Ser Gly Ile Val Arg Thr Val Arg
1010                1015                1020

Arg Leu Asp Arg Glu Ala Val Ser Val Tyr Glu Leu Thr Ala Tyr
1025                1030                1035

Ala Val Asp Arg Gly Val Pro Pro Leu Arg Thr Pro Val Ser Ile
1040                1045                1050

Gln Val Met Val Gln Asp Val Asn Asp Asn Ala Pro Val Phe Pro
1055                1060                1065

Ala Glu Glu Phe Glu Val Arg Val Lys Glu Asn Ser Ile Val Gly
1070                1075                1080

Ser Val Val Ala Gln Ile Thr Ala Val Asp Pro Asp Glu Gly Pro
1085                1090                1095

Asn Ala His Ile Met Tyr Gln Ile Val Glu Gly Asn Ile Pro Glu
1100                1105                1110

Leu Phe Gln Met Asp Ile Phe Ser Gly Glu Leu Thr Ala Leu Ile
1115                1120                1125

Asp Leu Asp Tyr Glu Ala Arg Gln Glu Tyr Val Ile Val Val Gln
1130                1135                1140

Ala Thr Ser Ala Pro Leu Val Ser Arg Ala Thr Val His Val Arg
1145                1150                1155

Leu Val Asp Gln Asn Asp Asn Ser Pro Val Leu Asn Asn Phe Gln
1160                1165                1170

Ile Leu Phe Asn Asn Tyr Val Ser Asn Arg Ser Asp Thr Phe Pro
1175                1180                1185

Ser Gly Ile Ile Gly Arg Ile Pro Ala Tyr Asp Pro Asp Val Ser
1190                1195                1200

Asp His Leu Phe Tyr Ser Phe Glu Arg Gly Asn Glu Leu Gln Leu
1205                1210                1215

Leu Val Val Asn Gln Thr Ser Gly Glu Leu Arg Leu Ser Arg Lys
1220                1225                1230

Leu Asp Asn Asn Arg Pro Leu Val Ala Ser Met Leu Val Thr Val
1235                1240                1245

Thr Asp Gly Leu His Ser Val Thr Ala Gln Cys Val Leu Arg Val
1250                1255                1260
```

```
Val Ile Ile Thr Glu Glu Leu Leu Ala Asn Ser Leu Thr Val Arg
    1265             1270                1275

Leu Glu Asn Met Trp Gln Glu Arg Phe Leu Ser Pro Leu Leu Gly
    1280             1285                1290

Arg Phe Leu Glu Gly Val Ala Ala Val Leu Ala Thr Pro Ala Glu
    1295             1300                1305

Asp Val Phe Ile Phe Asn Ile Gln Asn Asp Thr Asp Val Gly Gly
    1310             1315                1320

Thr Val Leu Asn Val Ser Phe Ser Ala Leu Ala Pro Arg Gly Ala
    1325             1330                1335

Gly Ala Gly Ala Ala Gly Pro Trp Phe Ser Ser Glu Glu Leu Gln
    1340             1345                1350

Glu Gln Leu Tyr Val Arg Arg Ala Ala Leu Ala Ala Arg Ser Leu
    1355             1360                1365

Leu Asp Val Leu Pro Phe Asp Asp Asn Val Cys Leu Arg Glu Pro
    1370             1375                1380

Cys Glu Asn Tyr Met Lys Cys Val Ser Val Leu Arg Phe Asp Ser
    1385             1390                1395

Ser Ala Pro Phe Leu Ala Ser Ala Ser Thr Leu Phe Arg Pro Ile
    1400             1405                1410

Gln Pro Ile Ala Gly Leu Arg Cys Arg Cys Pro Pro Gly Phe Thr
    1415             1420                1425

Gly Asp Phe Cys Glu Thr Glu Leu Asp Leu Cys Tyr Ser Asn Pro
    1430             1435                1440

Cys Arg Asn Gly Gly Ala Cys Ala Arg Arg Glu Gly Gly Tyr Thr
    1445             1450                1455

Cys Val Cys Arg Pro Arg Phe Thr Gly Glu Asp Cys Glu Leu Asp
    1460             1465                1470

Thr Glu Ala Gly Arg Cys Val Pro Gly Val Cys Arg Asn Gly Gly
    1475             1480                1485

Thr Cys Thr Asp Ala Pro Asn Gly Gly Phe Arg Cys Gln Cys Pro
    1490             1495                1500

Ala Gly Gly Ala Phe Glu Gly Pro Arg Cys Glu Val Ala Ala Arg
    1505             1510                1515

Ser Phe Pro Pro Ser Ser Phe Val Met Phe Arg Gly Leu Arg Gln
    1520             1525                1530

Arg Phe His Leu Thr Leu Ser Leu Ser Phe Ala Thr Val Gln Gln
    1535             1540                1545

Ser Gly Leu Leu Phe Tyr Asn Gly Arg Leu Asn Glu Lys His Asp
    1550             1555                1560

Phe Leu Ala Leu Glu Leu Val Ala Gly Gln Val Arg Leu Thr Tyr
    1565             1570                1575

Ser Thr Gly Glu Ser Asn Thr Val Val Ser Pro Thr Val Pro Gly
    1580             1585                1590

Gly Leu Ser Asp Gly Gln Trp His Thr Val His Leu Arg Tyr Tyr
    1595             1600                1605

Asn Lys Pro Arg Thr Asp Ala Leu Gly Gly Ala Gln Gly Pro Ser
    1610             1615                1620

Lys Asp Lys Val Ala Val Leu Ser Val Asp Asp Cys Asp Val Ala
    1625             1630                1635

Val Ala Leu Gln Phe Gly Ala Glu Ile Gly Asn Tyr Ser Cys Ala
    1640             1645                1650

Ala Ala Gly Val Gln Thr Ser Ser Lys Lys Ser Leu Asp Leu Thr
```

-continued

```
            1655                1660                1665
Gly Pro Leu Leu Leu Gly Gly Val Pro Asn Leu Pro Glu Asn Phe
        1670                1675                1680
Pro Val Ser His Lys Asp Phe Ile Gly Cys Met Arg Asp Leu His
        1685                1690                1695
Ile Asp Gly Arg Arg Val Asp Met Ala Ala Phe Val Ala Asn Asn
        1700                1705                1710
Gly Thr Met Ala Gly Cys Gln Ala Lys Leu His Phe Cys Asp Ser
        1715                1720                1725
Gly Pro Cys Lys Asn Ser Gly Phe Cys Ser Glu Arg Trp Gly Ser
        1730                1735                1740
Phe Ser Cys Asp Cys Pro Val Gly Phe Gly Gly Lys Asp Cys Gln
        1745                1750                1755
Leu Thr Met Ala His Pro His His Phe Arg Gly Asn Gly Thr Leu
        1760                1765                1770
Ser Trp Asn Phe Gly Ser Asp Met Ala Val Ser Val Pro Trp Tyr
        1775                1780                1785
Leu Gly Leu Ala Phe Arg Thr Arg Ala Thr Gln Gly Val Leu Met
        1790                1795                1800
Gln Val Gln Ala Gly Pro His Ser Thr Leu Leu Cys Gln Leu Asp
        1805                1810                1815
Arg Gly Leu Leu Ser Val Thr Val Thr Arg Gly Ser Gly Arg Ala
        1820                1825                1830
Ser His Leu Leu Leu Asp Gln Val Thr Val Ser Asp Gly Arg Trp
        1835                1840                1845
His Asp Leu Arg Leu Glu Leu Gln Glu Glu Pro Gly Gly Arg Arg
        1850                1855                1860
Gly His His Val Leu Met Val Ser Leu Asp Phe Ser Leu Phe Gln
        1865                1870                1875
Asp Thr Met Ala Val Gly Ser Glu Leu Gln Gly Leu Lys Val Lys
        1880                1885                1890
Gln Leu His Val Gly Gly Leu Pro Pro Gly Ser Ala Glu Glu Ala
        1895                1900                1905
Pro Gln Gly Leu Val Gly Cys Ile Gln Gly Val Trp Leu Gly Ser
        1910                1915                1920
Thr Pro Ser Gly Ser Pro Ala Leu Leu Pro Pro Ser His Arg Val
        1925                1930                1935
Asn Ala Glu Pro Gly Cys Val Val Thr Asn Ala Cys Ala Ser Gly
        1940                1945                1950
Pro Cys Pro Pro His Ala Asp Cys Arg Asp Leu Trp Gln Thr Phe
        1955                1960                1965
Ser Cys Thr Cys Gln Pro Gly Tyr Tyr Gly Pro Gly Cys Val Asp
        1970                1975                1980
Ala Cys Leu Leu Asn Pro Cys Gln Asn Gln Gly Ser Cys Arg His
        1985                1990                1995
Leu Pro Gly Ala Pro His Gly Tyr Thr Cys Asp Cys Val Gly Gly
        2000                2005                2010
Tyr Phe Gly His His Cys Glu His Arg Met Asp Gln Gln Cys Pro
        2015                2020                2025
Arg Gly Trp Trp Gly Ser Pro Thr Cys Gly Pro Cys Asn Cys Asp
        2030                2035                2040
Val His Lys Gly Phe Asp Pro Asn Cys Asn Lys Thr Asn Gly Gln
        2045                2050                2055
```

```
Cys His Cys Lys Glu Phe His Tyr Arg Pro Arg Gly Ser Asp Ser
2060                 2065                 2070

Cys Leu Pro Cys Asp Cys Tyr Pro Val Gly Ser Thr Ser Arg Ser
2075                 2080                 2085

Cys Ala Pro His Ser Gly Gln Cys Pro Cys Arg Pro Gly Ala Leu
2090                 2095                 2100

Gly Arg Gln Cys Asn Ser Cys Asp Ser Pro Phe Ala Glu Val Thr
2105                 2110                 2115

Ala Ser Gly Cys Arg Val Leu Tyr Asp Ala Cys Pro Lys Ser Leu
2120                 2125                 2130

Arg Ser Gly Val Trp Trp Pro Gln Thr Lys Phe Gly Val Leu Ala
2135                 2140                 2145

Thr Val Pro Cys Pro Arg Gly Ala Leu Gly Ala Ala Val Arg Leu
2150                 2155                 2160

Cys Asp Glu Ala Gln Gly Trp Leu Glu Pro Asp Leu Phe Asn Cys
2165                 2170                 2175

Thr Ser Pro Ala Phe Arg Glu Leu Ser Leu Leu Leu Asp Gly Leu
2180                 2185                 2190

Glu Leu Asn Lys Thr Ala Leu Asp Thr Met Glu Ala Lys Lys Leu
2195                 2200                 2205

Ala Gln Arg Leu Arg Glu Val Thr Gly His Thr Asp His Tyr Phe
2210                 2215                 2220

Ser Gln Asp Val Arg Val Thr Ala Arg Leu Leu Ala His Leu Leu
2225                 2230                 2235

Ala Phe Glu Ser His Gln Gln Gly Phe Gly Leu Thr Ala Thr Gln
2240                 2245                 2250

Asp Ala His Phe Asn Glu Asn Leu Leu Trp Ala Gly Ser Ala Leu
2255                 2260                 2265

Leu Ala Pro Glu Thr Gly Asp Leu Trp Ala Ala Leu Gly Gln Arg
2270                 2275                 2280

Ala Pro Gly Gly Ser Pro Gly Ser Ala Gly Leu Val Arg His Leu
2285                 2290                 2295

Glu Glu Tyr Ala Ala Thr Leu Ala Arg Asn Met Glu Leu Thr Tyr
2300                 2305                 2310

Leu Asn Pro Met Gly Leu Val Thr Pro Asn Ile Met Leu Ser Ile
2315                 2320                 2325

Asp Arg Met Glu His Pro Ser Ser Pro Arg Gly Ala Arg Arg Tyr
2330                 2335                 2340

Pro Arg Tyr His Ser Asn Leu Phe Arg Gly Gln Asp Ala Trp Asp
2345                 2350                 2355

Pro His Thr His Val Leu Leu Pro Ser Gln Ser Pro Arg Pro Ser
2360                 2365                 2370

Pro Ser Glu Val Leu Pro Thr Ser Ser Ser Ile Glu Asn Ser Thr
2375                 2380                 2385

Thr Ser Ser Val Val Pro Pro Ala Pro Pro Glu Pro Glu Pro
2390                 2395                 2400

Gly Ile Ser Ile Ile Ile Leu Leu Val Tyr Arg Thr Leu Gly Gly
2405                 2410                 2415

Leu Leu Pro Ala Gln Phe Gln Ala Glu Arg Arg Gly Ala Arg Leu
2420                 2425                 2430

Pro Gln Asn Pro Val Met Asn Ser Pro Val Val Ser Val Ala Val
2435                 2440                 2445
```

```
Phe His Gly Arg Asn Phe Leu Arg Gly Ile Leu Glu Ser Pro Ile
2450                2455                2460

Ser Leu Glu Phe Arg Leu Leu Gln Thr Ala Asn Arg Ser Lys Ala
2465                2470                2475

Ile Cys Val Gln Trp Asp Pro Pro Gly Leu Ala Glu Gln His Gly
2480                2485                2490

Val Trp Thr Ala Arg Asp Cys Glu Leu Val His Arg Asn Gly Ser
2495                2500                2505

His Ala Arg Cys Arg Cys Ser Arg Thr Gly Thr Phe Gly Val Leu
2510                2515                2520

Met Asp Ala Ser Pro Arg Glu Arg Leu Glu Gly Asp Leu Glu Leu
2525                2530                2535

Leu Ala Val Phe Thr His Val Val Ala Val Ser Val Ala Ala
2540                2545                2550

Leu Val Leu Thr Ala Ala Ile Leu Leu Ser Leu Arg Ser Leu Lys
2555                2560                2565

Ser Asn Val Arg Gly Ile His Ala Asn Val Ala Ala Ala Leu Gly
2570                2575                2580

Val Ala Glu Leu Leu Phe Leu Leu Gly Ile His Arg Thr His Asn
2585                2590                2595

Gln Leu Val Cys Thr Ala Val Ala Ile Leu Leu His Tyr Phe Phe
2600                2605                2610

Leu Ser Thr Phe Ala Trp Leu Phe Val Gln Gly Leu His Leu Tyr
2615                2620                2625

Arg Met Gln Val Glu Pro Arg Asn Val Asp Arg Gly Ala Met Arg
2630                2635                2640

Phe Tyr His Ala Leu Gly Trp Gly Val Pro Ala Val Leu Leu Gly
2645                2650                2655

Leu Ala Val Gly Leu Asp Pro Glu Gly Tyr Gly Asn Pro Asp Phe
2660                2665                2670

Cys Trp Ile Ser Val His Glu Pro Leu Ile Trp Ser Phe Ala Gly
2675                2680                2685

Pro Val Val Leu Val Ile Val Met Asn Gly Thr Met Phe Leu Leu
2690                2695                2700

Ala Ala Arg Thr Ser Cys Ser Thr Gly Gln Arg Glu Ala Lys Lys
2705                2710                2715

Thr Ser Ala Leu Thr Leu Arg Ser Ser Phe Leu Leu Leu Leu Leu
2720                2725                2730

Val Ser Ala Ser Trp Leu Phe Gly Leu Leu Ala Val Asn His Ser
2735                2740                2745

Ile Leu Ala Phe His Tyr Leu His Ala Gly Leu Cys Gly Leu Gln
2750                2755                2760

Gly Leu Ala Val Leu Leu Leu Phe Cys Val Leu Asn Ala Asp Ala
2765                2770                2775

Arg Ala Ala Trp Met Pro Ala Cys Leu Gly Arg Lys Ala Ala Pro
2780                2785                2790

Glu Glu Ala Arg Pro Ala Pro Gly Leu Gly Pro Gly Ala Tyr Asn
2795                2800                2805

Asn Thr Ala Leu Phe Glu Glu Ser Gly Leu Ile Arg Ile Thr Leu
2810                2815                2820

Gly Ala Ser Thr Val Ser Ser Val Ser Ser Ala Arg Ser Gly Arg
2825                2830                2835

Thr Gln Asp Gln Asp Ser Gln Arg Gly Arg Ser Tyr Leu Arg Asp
```

```
                2840                2845                2850
Asn Val Leu Val Arg His Gly Ser Ala Ala Asp His Thr Asp His
    2855                2860                2865
Ser Leu Gln Ala His Ala Gly Pro Thr Asp Leu Asp Val Ala Met
    2870                2875                2880
Phe His Arg Asp Ala Gly Ala Asp Ser Asp Ser Asp Ser Asp Leu
    2885                2890                2895
Ser Leu Glu Glu Glu Arg Ser Leu Ser Ile Pro Ser Ser Glu Ser
    2900                2905                2910
Glu Asp Asn Gly Arg Thr Arg Gly Arg Phe Gln Arg Pro Leu Cys
    2915                2920                2925
Arg Ala Ala Gln Ser Glu Arg Leu Leu Thr His Pro Lys Asp Val
    2930                2935                2940
Asp Gly Asn Asp Leu Leu Ser Tyr Trp Pro Ala Leu Gly Glu Cys
    2945                2950                2955
Glu Ala Ala Pro Cys Ala Leu Gln Thr Trp Gly Ser Glu Arg Arg
    2960                2965                2970
Leu Gly Leu Asp Thr Ser Lys Asp Ala Ala Asn Asn Asn Gln Pro
    2975                2980                2985
Asp Pro Ala Leu Thr Ser Gly Asp Glu Thr Ser Leu Gly Arg Ala
    2990                2995                3000
Gln Arg Gln Arg Lys Gly Ile Leu Lys Asn Arg Leu Gln Tyr Pro
    3005                3010                3015
Leu Val Pro Gln Thr Arg Gly Ala Pro Glu Leu Ser Trp Cys Arg
    3020                3025                3030
Ala Ala Thr Leu Gly His Arg Ala Val Pro Ala Ala Ser Tyr Gly
    3035                3040                3045
Arg Ile Tyr Ala Gly Gly Gly Thr Gly Ser Leu Ser Gln Pro Ala
    3050                3055                3060
Ser Arg Tyr Ser Ser Arg Glu Gln Leu Asp Leu Leu Arg Arg
    3065                3070                3075
Gln Leu Ser Arg Glu Arg Leu Glu Glu Ala Pro Ala Pro Val Leu
    3080                3085                3090
Arg Pro Leu Ser Arg Pro Gly Ser Gln Glu Cys Met Asp Ala Ala
    3095                3100                3105
Pro Gly Arg Leu Glu Pro Lys Asp Arg Gly Ser Thr Leu Pro Arg
    3110                3115                3120
Arg Gln Pro Pro Arg Asp Tyr Pro Gly Ala Met Ala Gly Arg Phe
    3125                3130                3135
Gly Ser Arg Asp Ala Leu Asp Leu Gly Ala Pro Arg Glu Trp Leu
    3140                3145                3150
Ser Thr Leu Pro Pro Pro Arg Arg Thr Arg Asp Leu Asp Pro Gln
    3155                3160                3165
Pro Pro Pro Leu Pro Leu Ser Pro Gln Arg Gln Leu Ser Arg Asp
    3170                3175                3180
Pro Leu Leu Pro Ser Arg Pro Leu Asp Ser Leu Ser Arg Ser Ser
    3185                3190                3195
Asn Ser Arg Glu Gln Leu Asp Gln Val Pro Ser Arg His Pro Ser
    3200                3205                3210
Arg Glu Ala Leu Gly Pro Leu Pro Gln Leu Leu Arg Ala Arg Glu
    3215                3220                3225
Asp Ser Val Ser Gly Pro Ser His Gly Pro Ser Thr Glu Gln Leu
    3230                3235                3240
```

```
Asp Ile Leu Ser Ser Ile Leu Ala Ser Phe Asn Ser Ser Ala Leu
    3245                3250                3255

Ser Ser Val Gln Ser Ser Ser Thr Pro Leu Gly Pro His Thr Thr
    3260                3265                3270

Ala Thr Pro Ser Ala Thr Ala Ser Val Leu Gly Pro Ser Thr Pro
    3275                3280                3285

Arg Ser Ala Thr Ser His Ser Ile Ser Glu Leu Ser Pro Asp Ser
    3290                3295                3300

Glu Val Pro Arg Ser Glu Gly His Ser
    3305                3310

<210> SEQ ID NO 36
<211> LENGTH: 297
<212> TYPE: PRT
<213> ORGANISM: homo sapiens

<400> SEQUENCE: 36

Met Lys His Ile Ile Asn Ser Tyr Glu Asn Ile Asn Asn Thr Ala Arg
1               5                   10                  15

Asn Asn Ser Asp Cys Pro Arg Val Val Leu Pro Glu Glu Ile Phe Phe
            20                  25                  30

Thr Ile Ser Ile Val Gly Val Leu Glu Asn Leu Ile Val Leu Leu Ala
        35                  40                  45

Val Phe Lys Asn Lys Asn Leu Gln Ala Pro Met Tyr Phe Phe Ile Cys
    50                  55                  60

Ser Leu Ala Ile Ser Asp Met Leu Gly Ser Leu Tyr Lys Ile Leu Glu
65                  70                  75                  80

Asn Ile Leu Ile Ile Leu Arg Asn Met Gly Tyr Leu Lys Pro Arg Gly
                85                  90                  95

Ser Phe Glu Thr Thr Ala Asp Asp Ile Ile Asp Ser Leu Phe Val Leu
            100                 105                 110

Ser Leu Leu Gly Ser Ile Phe Ser Leu Ser Val Ile Ala Ala Asp Arg
        115                 120                 125

Tyr Ile Thr Ile Phe His Ala Leu Arg Tyr His Ser Ile Val Thr Met
    130                 135                 140

Arg Arg Thr Val Val Val Leu Thr Val Ile Trp Thr Phe Cys Thr Gly
145                 150                 155                 160

Thr Gly Ile Thr Met Val Ile Phe Ser His His Val Pro Thr Val Ile
                165                 170                 175

Thr Phe Thr Ser Leu Phe Pro Leu Met Leu Val Phe Ile Leu Cys Leu
            180                 185                 190

Tyr Val His Met Phe Leu Leu Ala Arg Ser His Thr Arg Lys Ile Ser
        195                 200                 205

Thr Leu Pro Arg Ala Asn Met Lys Gly Ala Ile Thr Leu Thr Ile Leu
    210                 215                 220

Leu Gly Val Phe Ile Phe Cys Trp Ala Pro Phe Val Leu His Val Leu
225                 230                 235                 240

Leu Met Thr Phe Cys Pro Ser Asn Pro Tyr Cys Ala Cys Tyr Met Ser
                245                 250                 255

Leu Phe Gln Val Asn Gly Met Leu Ile Met Cys Asn Ala Val Ile Asp
            260                 265                 270

Pro Phe Ile Tyr Ala Phe Arg Ser Pro Glu Leu Arg Asp Ala Phe Lys
        275                 280                 285

Lys Met Ile Phe Cys Ser Arg Tyr Trp
```

290                 295

<210> SEQ ID NO 37
<211> LENGTH: 378
<212> TYPE: PRT
<213> ORGANISM: homo sapiens

<400> SEQUENCE: 37

Met Val Trp Gly Lys Ile Cys Trp Phe Ser Gln Arg Ala Gly Trp Thr
1               5                   10                  15

Val Phe Ala Glu Ser Gln Ile Ser Leu Ser Cys Ser Leu Cys Leu His
            20                  25                  30

Ser Gly Asp Gln Glu Ala Gln Asn Pro Asn Leu Val Ser Gln Leu Cys
        35                  40                  45

Gly Val Phe Leu Gln Asn Glu Thr Asn Glu Thr Ile His Met Gln Met
    50                  55                  60

Ser Met Ala Val Gly Gln Gln Ala Leu Pro Leu Asn Ile Ile Ala Pro
65                  70                  75                  80

Lys Ala Val Leu Val Ser Leu Cys Gly Val Leu Leu Asn Gly Thr Val
                85                  90                  95

Phe Trp Leu Leu Cys Cys Gly Ala Thr Asn Pro Tyr Met Val Tyr Ile
            100                 105                 110

Leu His Leu Val Ala Ala Asp Val Ile Tyr Leu Cys Cys Ser Ala Val
        115                 120                 125

Gly Phe Leu Gln Val Thr Leu Thr Tyr His Gly Val Val Phe Phe
    130                 135                 140

Ile Pro Asp Phe Leu Ala Ile Leu Ser Pro Phe Ser Phe Glu Val Cys
145                 150                 155                 160

Leu Cys Leu Leu Val Ala Ile Ser Thr Glu Arg Cys Val Cys Val Leu
                165                 170                 175

Phe Pro Ile Trp Tyr Arg Cys His Arg Pro Lys Tyr Thr Ser Asn Val
            180                 185                 190

Val Cys Thr Leu Ile Trp Gly Leu Pro Phe Cys Ile Asn Ile Val Lys
        195                 200                 205

Ser Leu Phe Leu Thr Tyr Trp Lys His Val Lys Ala Cys Val Ile Phe
    210                 215                 220

Leu Lys Leu Ser Gly Leu Phe His Ala Ile Leu Ser Leu Val Met Cys
225                 230                 235                 240

Val Ser Ser Leu Thr Leu Leu Ile Arg Phe Leu Cys Cys Ser Gln Gln
                245                 250                 255

Gln Lys Ala Thr Arg Val Tyr Ala Val Val Gln Ile Ser Ala Pro Met
            260                 265                 270

Phe Leu Leu Trp Ala Leu Pro Leu Ser Val Ala Pro Leu Ile Thr Asp
        275                 280                 285

Phe Lys Met Phe Val Thr Thr Ser Tyr Leu Ile Ser Leu Phe Leu Ile
    290                 295                 300

Ile Asn Ser Ser Ala Asn Pro Ile Ile Tyr Phe Phe Val Gly Ser Leu
305                 310                 315                 320

Arg Lys Lys Arg Leu Lys Glu Ser Leu Arg Val Ile Leu Gln Arg Ala
                325                 330                 335

Leu Ala Asp Lys Pro Glu Val Gly Arg Asn Lys Lys Ala Ala Gly Ile
            340                 345                 350

Asp Pro Met Glu Gln Pro His Ser Thr Gln His Val Glu Asn Leu Leu
        355                 360                 365

Pro Arg Glu His Arg Val Asp Val Glu Thr
    370                 375

<210> SEQ ID NO 38
<211> LENGTH: 2527
<212> TYPE: PRT
<213> ORGANISM: homo sapiens

<400> SEQUENCE: 38

Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
        35                  40                  45

Glu His Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
    130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
        195                 200                 205

Leu Ser Ala Leu Thr Asn Phe Lys Asp Glu Glu Glu Ile Val Leu His
    210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
            260                 265                 270

Leu Leu His Arg Leu Thr Leu Gly Asn Phe Phe Asn Ile Leu Val Leu
        275                 280                 285

Asn Glu Val His Glu Phe Val Val Lys Ala Val Gln Gln Tyr Pro Glu
    290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Glu Asp Lys Leu Phe Trp Leu Glu Ala
            340                 345                 350

Cys Tyr Lys Ala Leu Thr Trp His Arg Lys Asn Lys His Val Gln Glu
        355                 360                 365

```
Ala Ala Cys Trp Ala Leu Asn Asn Leu Leu Met Tyr Gln Asn Ser Leu
    370                 375                 380
His Glu Lys Ile Gly Asp Glu Asp Gly His Phe Pro Ala His Arg Glu
385                 390                 395                 400
Val Met Leu Ser Met Leu Met His Ser Ser Lys Glu Val Phe Gln
            405                 410                 415
Ala Ser Ala Asn Ala Leu Ser Thr Leu Leu Glu Gln Asn Val Asn Phe
            420                 425                 430
Arg Lys Ile Leu Leu Ser Lys Gly Ile His Leu Asn Val Leu Glu Leu
        435                 440                 445
Met Gln Lys His Ile His Ser Pro Glu Val Ala Glu Ser Gly Cys Lys
    450                 455                 460
Met Leu Asn His Leu Phe Glu Gly Ser Asn Thr Ser Leu Asp Ile Met
465                 470                 475                 480
Ala Ala Val Val Pro Lys Ile Leu Thr Val Met Lys Arg His Glu Thr
            485                 490                 495
Ser Leu Pro Val Gln Leu Glu Ala Leu Arg Ala Ile Leu His Phe Ile
            500                 505                 510
Val Pro Gly Met Pro Glu Glu Ser Arg Glu Asp Thr Glu Phe His His
        515                 520                 525
Lys Leu Asn Met Val Lys Lys Gln Cys Phe Lys Asn Asp Ile His Lys
    530                 535                 540
Leu Val Leu Ala Ala Leu Asn Arg Phe Ile Gly Asn Pro Gly Ile Gln
545                 550                 555                 560
Lys Cys Gly Leu Lys Val Ile Ser Ser Ile Val His Phe Pro Asp Ala
            565                 570                 575
Leu Glu Met Leu Ser Leu Glu Gly Ala Met Asp Ser Val Leu His Thr
            580                 585                 590
Leu Gln Met Tyr Pro Asp Asp Gln Glu Ile Gln Cys Leu Gly Leu Ser
        595                 600                 605
Leu Ile Gly Tyr Leu Ile Thr Lys Lys Asn Val Phe Ile Gly Thr Gly
    610                 615                 620
His Leu Leu Ala Lys Ile Leu Val Ser Ser Leu Tyr Arg Phe Lys Asp
625                 630                 635                 640
Val Ala Glu Ile Gln Thr Lys Gly Phe Gln Thr Ile Leu Ala Ile Leu
            645                 650                 655
Lys Leu Ser Ala Ser Phe Ser Lys Leu Leu Val His His Ser Phe Asp
            660                 665                 670
Leu Val Ile Phe His Gln Met Ser Ser Asn Ile Met Glu Gln Lys Asp
        675                 680                 685
Gln Gln Phe Leu Asn Leu Cys Cys Lys Cys Phe Ala Lys Val Ala Met
    690                 695                 700
Asp Asp Tyr Leu Lys Asn Val Met Leu Glu Arg Ala Cys Asp Gln Asn
705                 710                 715                 720
Asn Ser Ile Met Val Glu Cys Leu Leu Leu Gly Ala Asp Ala Asn
            725                 730                 735
Gln Ala Lys Glu Gly Ser Ser Leu Ile Cys Gln Val Cys Glu Lys Glu
            740                 745                 750
Ser Ser Pro Lys Leu Val Glu Leu Leu Leu Asn Ser Gly Ser Arg Glu
        755                 760                 765
Gln Asp Val Arg Lys Ala Leu Thr Ile Ser Ile Gly Lys Gly Asp Ser
    770                 775                 780
```

```
Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
            805                 810                 815

Trp Leu Gly Pro Leu Phe Pro Asp Lys Thr Ser Asn Leu Arg Lys Gln
        820                 825                 830

Thr Asn Ile Ala Ser Thr Leu Ala Arg Met Val Ile Arg Tyr Gln Met
            835                 840                 845

Lys Ser Ala Val Glu Glu Gly Thr Ala Ser Gly Ser Asp Gly Asn Phe
        850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
            885                 890                 895

Gly Ser Glu Gly Ser Phe Leu Val Lys Lys Ser Asn Ser Ile Ser
        900                 905                 910

Val Gly Glu Phe Tyr Arg Asp Ala Val Leu Gln Arg Cys Ser Pro Asn
        915                 920                 925

Leu Gln Arg His Ser Asn Ser Leu Gly Pro Ile Phe Asp His Glu Asp
    930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
            965                 970                 975

Leu Ala Ser Glu Arg Glu Tyr Ile Thr Ser Leu Asp Leu Ser Ala Asn
        980                 985                 990

Glu Leu Arg Asp Ile Asp Ala Leu  Ser Gln Lys Cys Cys  Ile Ser Val
        995                 1000                 1005

His Leu  Glu His Leu Glu Lys  Leu Glu Leu His Gln  Asn Ala Leu
    1010                 1015                 1020

Thr Ser  Phe Pro Gln Gln Leu  Cys Glu Thr Leu Lys  Ser Leu Thr
    1025                 1030                 1035

His Leu  Asp Leu His Ser Asn  Lys Phe Thr Ser Phe  Pro Ser Tyr
    1040                 1045                 1050

Leu Leu  Lys Met Ser Cys Ile  Ala Asn Leu Asp Val  Ser Arg Asn
    1055                 1060                 1065

Asp Ile  Gly Pro Ser Val Val  Leu Asp Pro Thr Val  Lys Cys Pro
    1070                 1075                 1080

Thr Leu  Lys Gln Phe Asn Leu  Ser Tyr Asn Gln Leu  Ser Phe Val
    1085                 1090                 1095

Pro Glu  Asn Leu Thr Asp Val  Val Glu Lys Leu Glu  Gln Leu Ile
    1100                 1105                 1110

Leu Glu  Gly Asn Lys Ile Ser  Gly Ile Cys Ser Pro  Leu Arg Leu
    1115                 1120                 1125

Lys Glu  Leu Lys Ile Leu Asn  Leu Ser Lys Asn His  Ile Ser Ser
    1130                 1135                 1140

Leu Ser  Glu Asn Phe Leu Glu  Ala Cys Pro Lys Val  Glu Ser Phe
    1145                 1150                 1155

Ser Ala  Arg Met Asn Phe Leu  Ala Ala Met Pro Phe  Leu Pro Pro
    1160                 1165                 1170

Ser Met  Thr Ile Leu Lys Leu  Ser Gln Asn Lys Phe  Ser Cys Ile
    1175                 1180                 1185

Pro Glu  Ala Ile Leu Asn Leu  Pro His Leu Arg Ser  Leu Asp Met
```

```
              1190                1195                1200

Ser  Ser  Asn  Asp  Ile  Gln  Tyr  Leu  Pro  Gly  Pro  Ala  His  Trp  Lys
    1205                1210                1215

Ser  Leu  Asn  Leu  Arg  Glu  Leu  Leu  Phe  Ser  His  Asn  Gln  Ile  Ser
    1220                1225                1230

Ile  Leu  Asp  Leu  Ser  Glu  Lys  Ala  Tyr  Leu  Trp  Ser  Arg  Val  Glu
    1235                1240                1245

Lys  Leu  His  Leu  Ser  His  Asn  Lys  Leu  Lys  Glu  Ile  Pro  Pro  Glu
    1250                1255                1260

Ile  Gly  Cys  Leu  Glu  Asn  Leu  Thr  Ser  Leu  Asp  Val  Ser  Tyr  Asn
    1265                1270                1275

Leu  Glu  Leu  Arg  Ser  Phe  Pro  Asn  Glu  Met  Gly  Lys  Leu  Ser  Lys
    1280                1285                1290

Ile  Trp  Asp  Leu  Pro  Leu  Asp  Glu  Leu  His  Leu  Asn  Phe  Asp  Phe
    1295                1300                1305

Lys  His  Ile  Gly  Cys  Lys  Ala  Lys  Asp  Ile  Ile  Arg  Phe  Leu  Gln
    1310                1315                1320

Gln  Arg  Leu  Lys  Lys  Ala  Val  Pro  Tyr  Asn  Arg  Met  Lys  Leu  Met
    1325                1330                1335

Ile  Val  Gly  Asn  Thr  Gly  Ser  Gly  Lys  Thr  Thr  Leu  Leu  Gln  Gln
    1340                1345                1350

Leu  Met  Lys  Thr  Lys  Lys  Ser  Asp  Leu  Gly  Met  Gln  Ser  Ala  Thr
    1355                1360                1365

Val  Gly  Ile  Asp  Val  Lys  Asp  Trp  Pro  Ile  Gln  Ile  Arg  Asp  Lys
    1370                1375                1380

Arg  Lys  Arg  Asp  Leu  Val  Leu  Asn  Val  Trp  Asp  Phe  Ala  Gly  Arg
    1385                1390                1395

Glu  Glu  Phe  Tyr  Ser  Thr  His  Pro  His  Phe  Met  Thr  Gln  Arg  Ala
    1400                1405                1410

Leu  Tyr  Leu  Ala  Val  Tyr  Asp  Leu  Ser  Lys  Gly  Gln  Ala  Glu  Val
    1415                1420                1425

Asp  Ala  Met  Lys  Pro  Trp  Leu  Phe  Asn  Ile  Lys  Ala  Arg  Ala  Ser
    1430                1435                1440

Ser  Ser  Pro  Val  Ile  Leu  Val  Gly  Thr  His  Leu  Asp  Val  Ser  Asp
    1445                1450                1455

Glu  Lys  Gln  Arg  Lys  Ala  Cys  Met  Ser  Lys  Ile  Thr  Lys  Glu  Leu
    1460                1465                1470

Leu  Asn  Lys  Arg  Gly  Phe  Pro  Ala  Ile  Arg  Asp  Tyr  His  Phe  Val
    1475                1480                1485

Asn  Ala  Thr  Glu  Glu  Ser  Asp  Ala  Leu  Ala  Lys  Leu  Arg  Lys  Thr
    1490                1495                1500

Ile  Ile  Asn  Glu  Ser  Leu  Asn  Phe  Lys  Ile  Arg  Asp  Gln  Leu  Val
    1505                1510                1515

Val  Gly  Gln  Leu  Ile  Pro  Asp  Cys  Tyr  Val  Glu  Leu  Glu  Lys  Ile
    1520                1525                1530

Ile  Leu  Ser  Glu  Arg  Lys  Asn  Val  Pro  Ile  Glu  Phe  Pro  Val  Ile
    1535                1540                1545

Asp  Arg  Lys  Arg  Leu  Leu  Gln  Leu  Val  Arg  Glu  Asn  Gln  Leu  Gln
    1550                1555                1560

Leu  Asp  Glu  Asn  Glu  Leu  Pro  His  Ala  Val  His  Phe  Leu  Asn  Glu
    1565                1570                1575

Ser  Gly  Val  Leu  Leu  His  Phe  Gln  Asp  Pro  Ala  Leu  Gln  Leu  Ser
    1580                1585                1590
```

```
Asp Leu Tyr Phe Val Glu Pro Lys Trp Leu Cys Lys Ile Met Ala
    1595            1600                1605

Gln Ile Leu Thr Val Lys Val Glu Gly Cys Pro Lys His Pro Lys
    1610            1615                1620

Gly Ile Ile Ser Arg Arg Asp Val Glu Lys Phe Leu Ser Lys Lys
    1625            1630                1635

Arg Lys Phe Pro Lys Asn Tyr Met Ser Gln Tyr Phe Lys Leu Leu
    1640            1645                1650

Glu Lys Phe Gln Ile Ala Leu Pro Ile Gly Glu Glu Tyr Leu Leu
    1655            1660                1665

Val Pro Ser Ser Leu Ser Asp His Arg Pro Val Ile Glu Leu Pro
    1670            1675                1680

His Cys Glu Asn Ser Glu Ile Ile Ile Arg Leu Tyr Glu Met Pro
    1685            1690                1695

Tyr Phe Pro Met Gly Phe Trp Ser Arg Leu Ile Asn Arg Leu Leu
    1700            1705                1710

Glu Ile Ser Pro Tyr Met Leu Ser Gly Arg Glu Arg Ala Leu Arg
    1715            1720                1725

Pro Asn Arg Met Tyr Trp Arg Gln Gly Ile Tyr Leu Asn Trp Ser
    1730            1735                1740

Pro Glu Ala Tyr Cys Leu Val Gly Ser Glu Val Leu Asp Asn His
    1745            1750                1755

Pro Glu Ser Phe Leu Lys Ile Thr Val Pro Ser Cys Arg Lys Gly
    1760            1765                1770

Cys Ile Leu Leu Gly Gln Val Val Asp His Ile Asp Ser Leu Met
    1775            1780                1785

Glu Glu Trp Phe Pro Gly Leu Leu Glu Ile Asp Ile Cys Gly Glu
    1790            1795                1800

Gly Glu Thr Leu Leu Lys Lys Trp Ala Leu Tyr Ser Phe Asn Asp
    1805            1810                1815

Gly Glu Glu His Gln Lys Ile Leu Leu Asp Asp Leu Met Lys Lys
    1820            1825                1830

Ala Glu Glu Gly Asp Leu Leu Val Asn Pro Asp Gln Pro Arg Leu
    1835            1840                1845

Thr Ile Pro Ile Ser Gln Ile Ala Pro Asp Leu Ile Leu Ala Asp
    1850            1855                1860

Leu Pro Arg Asn Ile Met Leu Asn Asn Asp Glu Leu Glu Phe Glu
    1865            1870                1875

Gln Ala Pro Glu Phe Leu Leu Gly Asp Gly Ser Phe Gly Ser Val
    1880            1885                1890

Tyr Arg Ala Ala Tyr Glu Gly Glu Glu Val Ala Val Lys Ile Phe
    1895            1900                1905

Asn Lys His Thr Ser Leu Arg Leu Leu Arg Gln Glu Leu Val Val
    1910            1915                1920

Leu Cys His Leu His His Pro Ser Leu Ile Ser Leu Leu Ala Ala
    1925            1930                1935

Gly Ile Arg Pro Arg Met Leu Val Met Glu Leu Ala Ser Lys Gly
    1940            1945                1950

Ser Leu Asp Arg Leu Leu Gln Gln Asp Lys Ala Ser Leu Thr Arg
    1955            1960                1965

Thr Leu Gln His Arg Ile Ala Leu His Val Ala Asp Gly Leu Arg
    1970            1975                1980
```

```
Tyr Leu His Ser Ala Met Ile Ile Tyr Arg Asp Leu Lys Pro His
    1985            1990            1995

Asn Val Leu Leu Phe Thr Leu Tyr Pro Asn Ala Ala Ile Ile Ala
    2000            2005            2010

Lys Ile Ala Asp Tyr Gly Ile Ala Gln Tyr Cys Cys Arg Met Gly
    2015            2020            2025

Ile Lys Thr Ser Glu Gly Thr Pro Gly Phe Arg Ala Pro Glu Val
    2030            2035            2040

Ala Arg Gly Asn Val Ile Tyr Asn Gln Gln Ala Asp Val Tyr Ser
    2045            2050            2055

Phe Gly Leu Leu Leu Tyr Asp Ile Leu Thr Thr Gly Gly Arg Ile
    2060            2065            2070

Val Glu Gly Leu Lys Phe Pro Asn Glu Phe Asp Glu Leu Glu Ile
    2075            2080            2085

Gln Gly Lys Leu Pro Asp Pro Val Lys Glu Tyr Gly Cys Ala Pro
    2090            2095            2100

Trp Pro Met Val Glu Lys Leu Ile Lys Gln Cys Leu Lys Glu Asn
    2105            2110            2115

Pro Gln Glu Arg Pro Thr Ser Ala Gln Val Phe Asp Ile Leu Asn
    2120            2125            2130

Ser Ala Glu Leu Val Cys Leu Thr Arg Arg Ile Leu Leu Pro Lys
    2135            2140            2145

Asn Val Ile Val Glu Cys Met Val Ala Thr His His Asn Ser Arg
    2150            2155            2160

Asn Ala Ser Ile Trp Leu Gly Cys Gly His Thr Asp Arg Gly Gln
    2165            2170            2175

Leu Ser Phe Leu Asp Leu Asn Thr Glu Gly Tyr Thr Ser Glu Glu
    2180            2185            2190

Val Ala Asp Ser Arg Ile Leu Cys Leu Ala Leu Val His Leu Pro
    2195            2200            2205

Val Glu Lys Glu Ser Trp Ile Val Ser Gly Thr Gln Ser Gly Thr
    2210            2215            2220

Leu Leu Val Ile Asn Thr Glu Asp Gly Lys Lys Arg His Thr Leu
    2225            2230            2235

Glu Lys Met Thr Asp Ser Val Thr Cys Leu Tyr Cys Asn Ser Phe
    2240            2245            2250

Ser Lys Gln Ser Lys Gln Lys Asn Phe Leu Leu Val Gly Thr Ala
    2255            2260            2265

Asp Gly Lys Leu Ala Ile Phe Glu Asp Lys Thr Val Lys Leu Lys
    2270            2275            2280

Gly Ala Ala Pro Leu Lys Ile Leu Asn Ile Gly Asn Val Ser Thr
    2285            2290            2295

Pro Leu Met Cys Leu Ser Glu Ser Thr Asn Ser Thr Glu Arg Asn
    2300            2305            2310

Val Met Trp Gly Gly Cys Gly Thr Lys Ile Phe Ser Phe Ser Asn
    2315            2320            2325

Asp Phe Thr Ile Gln Lys Leu Ile Glu Thr Arg Thr Ser Gln Leu
    2330            2335            2340

Phe Ser Tyr Ala Ala Phe Ser Asp Ser Asn Ile Ile Thr Val Val
    2345            2350            2355

Val Asp Thr Ala Leu Tyr Ile Ala Lys Gln Asn Ser Pro Val Val
    2360            2365            2370

Glu Val Trp Asp Lys Lys Thr Glu Lys Leu Cys Gly Leu Ile Asp
```

```
              2375                2380                2385

Cys Val His Phe Leu Arg Glu Val Met Val Lys Glu Asn Lys Glu
        2390                2395                2400

Ser Lys His Lys Met Ser Tyr Ser Gly Arg Val Lys Thr Leu Cys
        2405                2410                2415

Leu Gln Lys Asn Thr Ala Leu Trp Ile Gly Thr Gly Gly Gly His
        2420                2425                2430

Ile Leu Leu Leu Asp Leu Ser Thr Arg Arg Leu Ile Arg Val Ile
        2435                2440                2445

Tyr Asn Phe Cys Asn Ser Val Arg Val Met Met Thr Ala Gln Leu
        2450                2455                2460

Gly Ser Leu Lys Asn Val Met Leu Val Leu Gly Tyr Asn Arg Lys
        2465                2470                2475

Asn Thr Glu Gly Thr Gln Lys Gln Lys Glu Ile Gln Ser Cys Leu
        2480                2485                2490

Thr Val Trp Asp Ile Asn Leu Pro His Glu Val Gln Asn Leu Glu
        2495                2500                2505

Lys His Ile Glu Val Arg Lys Glu Leu Ala Glu Lys Met Arg Arg
        2510                2515                2520

Thr Ser Val Glu
        2525

<210> SEQ ID NO 39
<211> LENGTH: 1375
<212> TYPE: PRT
<213> ORGANISM: homo sapiens

<400> SEQUENCE: 39

Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Leu Ala Asn Lys Ala
            20                  25                  30

His Ser Arg Ser Ser Ser Gly Glu Thr Pro Ala Gln Pro Glu Lys Thr
        35                  40                  45

Ser Gly Met Glu Val Ala Ser Tyr Leu Val Ala Gln Tyr Gly Glu Gln
    50                  55                  60

Arg Ala Trp Asp Leu Ala Leu His Thr Trp Glu Gln Met Gly Leu Arg
65                  70                  75                  80

Ser Leu Cys Ala Gln Ala Gln Glu Gly Ala Gly His Ser Pro Ser Phe
                85                  90                  95

Pro Tyr Ser Pro Ser Glu Pro His Leu Gly Ser Pro Ser Gln Pro Thr
            100                 105                 110

Ser Thr Ala Val Leu Met Pro Trp Ile His Glu Leu Pro Ala Gly Cys
        115                 120                 125

Thr Gln Gly Ser Glu Arg Arg Val Leu Arg Gln Leu Pro Asp Thr Ser
    130                 135                 140

Gly Arg Arg Trp Arg Glu Ile Ser Ala Ser Leu Leu Tyr Gln Ala Leu
145                 150                 155                 160

Pro Ser Ser Pro Asp His Glu Ser Pro Ser Gln Glu Ser Pro Asn Ala
                165                 170                 175

Pro Thr Ser Thr Ala Val Leu Gly Ser Trp Gly Ser Pro Pro Gln Pro
            180                 185                 190

Ser Leu Ala Pro Arg Glu Gln Glu Ala Pro Gly Thr Gln Trp Pro Leu
        195                 200                 205
```

-continued

```
Asp Glu Thr Ser Gly Ile Tyr Tyr Thr Glu Ile Arg Glu Arg Glu Arg
    210                 215                 220
Glu Lys Ser Glu Lys Gly Arg Pro Pro Trp Ala Ala Val Val Gly Thr
225                 230                 235                 240
Pro Pro Gln Ala His Thr Ser Leu Gln Pro His His His Pro Trp Glu
                245                 250                 255
Pro Ser Val Arg Glu Ser Leu Cys Ser Thr Trp Pro Trp Lys Asn Glu
            260                 265                 270
Asp Phe Asn Gln Lys Phe Thr Gln Leu Leu Leu Gln Arg Pro His
        275                 280                 285
Pro Arg Ser Gln Asp Pro Leu Val Lys Arg Ser Trp Pro Asp Tyr Val
290                 295                 300
Glu Glu Asn Arg Gly His Leu Ile Glu Ile Arg Asp Leu Phe Gly Pro
305                 310                 315                 320
Gly Leu Asp Thr Gln Glu Pro Arg Ile Val Ile Leu Gln Gly Ala Ala
                325                 330                 335
Gly Ile Gly Lys Ser Thr Leu Ala Arg Gln Val Lys Glu Ala Trp Gly
            340                 345                 350
Arg Gly Gln Leu Tyr Gly Asp Arg Phe Gln His Val Phe Tyr Phe Ser
        355                 360                 365
Cys Arg Glu Leu Ala Gln Ser Lys Val Val Ser Leu Ala Glu Leu Ile
    370                 375                 380
Gly Lys Asp Gly Thr Ala Thr Pro Ala Pro Ile Arg Gln Ile Leu Ser
385                 390                 395                 400
Arg Pro Glu Arg Leu Leu Phe Ile Leu Asp Gly Val Asp Glu Pro Gly
                405                 410                 415
Trp Val Leu Gln Glu Pro Ser Ser Glu Leu Cys Leu His Trp Ser Gln
            420                 425                 430
Pro Gln Pro Ala Asp Ala Leu Leu Gly Ser Leu Leu Gly Lys Thr Ile
        435                 440                 445
Leu Pro Glu Ala Ser Phe Leu Ile Thr Ala Arg Thr Thr Ala Leu Gln
    450                 455                 460
Asn Leu Ile Pro Ser Leu Glu Gln Ala Arg Trp Val Glu Val Leu Gly
465                 470                 475                 480
Phe Ser Glu Ser Ser Arg Lys Glu Tyr Phe Tyr Arg Tyr Phe Thr Asp
                485                 490                 495
Glu Arg Gln Ala Ile Arg Ala Phe Arg Leu Val Lys Ser Asn Lys Glu
            500                 505                 510
Leu Trp Ala Leu Cys Leu Val Pro Trp Val Ser Trp Leu Ala Cys Thr
        515                 520                 525
Cys Leu Met Gln Gln Met Lys Arg Lys Glu Lys Leu Thr Leu Thr Ser
    530                 535                 540
Lys Thr Thr Thr Thr Leu Cys Leu His Tyr Leu Ala Gln Ala Leu Gln
545                 550                 555                 560
Ala Gln Pro Leu Gly Pro Gln Leu Arg Asp Leu Cys Ser Leu Ala Ala
                565                 570                 575
Glu Gly Ile Trp Gln Lys Lys Thr Leu Phe Ser Pro Asp Asp Leu Arg
            580                 585                 590
Lys His Gly Leu Asp Gly Ala Ile Ile Ser Thr Phe Leu Lys Met Gly
        595                 600                 605
Ile Leu Gln Glu His Pro Ile Pro Leu Ser Tyr Ser Phe Ile His Leu
    610                 615                 620
Cys Phe Gln Glu Phe Phe Ala Ala Met Ser Tyr Val Leu Glu Asp Glu
```

-continued

```
              625                 630                 635                 640
Lys Gly Arg Gly Lys His Ser Asn Cys Ile Ile Asp Leu Glu Lys Thr
                    645                 650                 655

Leu Glu Ala Tyr Gly Ile His Gly Leu Phe Gly Ala Ser Thr Thr Arg
                    660                 665                 670

Phe Leu Leu Gly Leu Leu Ser Asp Glu Gly Glu Arg Glu Met Glu Asn
                    675                 680                 685

Ile Phe His Cys Arg Leu Ser Gln Gly Arg Asn Leu Met Gln Trp Val
        690                 695                 700

Pro Ser Leu Gln Leu Leu Gln Pro His Ser Leu Glu Ser Leu His
705                 710                 715                 720

Cys Leu Tyr Glu Thr Arg Asn Lys Thr Phe Leu Thr Gln Val Met Ala
                    725                 730                 735

His Phe Glu Glu Met Gly Met Cys Val Glu Thr Asp Met Glu Leu Leu
                    740                 745                 750

Val Cys Thr Phe Cys Ile Lys Phe Ser Arg His Val Lys Lys Leu Gln
                    755                 760                 765

Leu Ile Glu Gly Arg Gln His Arg Ser Thr Trp Ser Pro Thr Met Val
        770                 775                 780

Val Leu Phe Arg Trp Val Pro Val Thr Asp Ala Tyr Trp Gln Ile Leu
785                 790                 795                 800

Phe Ser Val Leu Lys Val Thr Arg Asn Leu Lys Glu Leu Asp Leu Ser
                    805                 810                 815

Gly Asn Ser Leu Ser His Ser Ala Val Lys Ser Leu Cys Lys Thr Leu
                    820                 825                 830

Arg Arg Pro Arg Cys Leu Leu Glu Thr Leu Arg Leu Ala Gly Cys Gly
                    835                 840                 845

Leu Thr Ala Glu Asp Cys Lys Asp Leu Ala Phe Gly Leu Arg Ala Asn
        850                 855                 860

Gln Thr Leu Thr Glu Leu Asp Leu Ser Phe Asn Val Leu Thr Asp Ala
865                 870                 875                 880

Gly Ala Lys His Leu Cys Gln Arg Leu Arg Gln Pro Ser Cys Lys Leu
                    885                 890                 895

Gln Arg Leu Gln Leu Val Ser Cys Gly Leu Thr Ser Asp Cys Cys Gln
                    900                 905                 910

Asp Leu Ala Ser Val Leu Ser Ala Ser Pro Ser Leu Lys Glu Leu Asp
        915                 920                 925

Leu Gln Gln Asn Asn Leu Asp Asp Val Gly Val Arg Leu Leu Cys Glu
        930                 935                 940

Gly Leu Arg His Pro Ala Cys Lys Leu Ile Arg Leu Gly Leu Asp Gln
945                 950                 955                 960

Thr Thr Leu Ser Asp Glu Met Arg Gln Glu Leu Arg Ala Leu Glu Gln
                    965                 970                 975

Glu Lys Pro Gln Leu Leu Ile Phe Ser Arg Arg Lys Pro Ser Val Met
                    980                 985                 990

Thr Pro Thr Glu Gly Leu Asp Thr Gly Glu Met Ser Asn Ser Thr Ser
            995                 1000                1005

Ser Leu Lys Arg Gln Arg Leu Gly Ser Glu Arg Ala Ala Ser His
    1010                1015                1020

Val Ala Gln Ala Asn Leu Lys Leu Leu Asp Val Ser Lys Ile Phe
    1025                1030                1035

Pro Ile Ala Glu Ile Ala Gly Lys Ser His Glu Glu Ser Ser Pro
    1040                1045                1050
```

```
Glu Val Val Pro Val Glu Leu Leu Cys Val Pro Ser Pro Ala Ser
    1055                1060                1065

Gln Gly Asp Leu His Thr Lys Pro Leu Gly Thr Asp Asp Phe
    1070                1075                1080

Trp Gly Pro Thr Gly Pro Val Ala Thr Glu Val Val Asp Lys Glu
    1085                1090                1095

Lys Asn Leu Tyr Arg Val His Phe Pro Val Ala Gly Ser Tyr Arg
    1100                1105                1110

Trp Pro Asn Thr Gly Leu Cys Phe Val Met Arg Glu Ala Val Thr
    1115                1120                1125

Val Glu Ile Glu Phe Cys Val Trp Asp Gln Phe Leu Gly Glu Ile
    1130                1135                1140

Asn Pro Gln His Ser Trp Met Val Ala Gly Pro Leu Leu Asp Ile
    1145                1150                1155

Lys Ala Glu Pro Gly Ala Val Glu Ala Val His Leu Pro His Phe
    1160                1165                1170

Val Ala Leu Gln Gly Gly His Val Asp Thr Ser Leu Phe Gln Met
    1175                1180                1185

Ala His Phe Lys Glu Glu Gly Met Leu Leu Glu Lys Pro Ala Arg
    1190                1195                1200

Val Glu Leu His His Ile Val Leu Glu Asn Pro Ser Phe Ser Pro
    1205                1210                1215

Leu Gly Val Leu Leu Lys Met Ile His Asn Ala Leu Arg Phe Ile
    1220                1225                1230

Pro Val Thr Ser Val Val Leu Tyr His Arg Val His Pro Glu
    1235                1240                1245

Glu Val Thr Phe His Leu Tyr Leu Ile Pro Ser Asp Cys Ser Ile
    1250                1255                1260

Arg Lys Ala Ile Asp Asp Leu Glu Met Lys Phe Gln Phe Val Arg
    1265                1270                1275

Ile His Lys Pro Pro Pro Leu Thr Pro Leu Tyr Met Gly Cys Arg
    1280                1285                1290

Tyr Thr Val Ser Gly Ser Gly Ser Gly Met Leu Glu Ile Leu Pro
    1295                1300                1305

Lys Glu Leu Glu Leu Cys Tyr Arg Ser Pro Gly Glu Asp Gln Leu
    1310                1315                1320

Phe Ser Glu Phe Tyr Val Gly His Leu Gly Ser Gly Ile Arg Leu
    1325                1330                1335

Gln Val Lys Asp Lys Lys Asp Glu Thr Leu Val Trp Glu Ala Leu
    1340                1345                1350

Val Lys Pro Gly Arg Asn Thr Ser Gln Pro Trp Asn Leu Arg Cys
    1355                1360                1365

Asn Arg Asp Ala Arg Arg Tyr
    1370            1375

<210> SEQ ID NO 40
<211> LENGTH: 1429
<212> TYPE: PRT
<213> ORGANISM: homo sapiens

<400> SEQUENCE: 40

Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Leu Ala Asn Lys Ala
```

-continued

```
                 20                  25                  30
His Ser Arg Ser Ser Ser Gly Glu Thr Pro Ala Gln Pro Glu Lys Thr
             35                  40                  45

Ser Gly Met Glu Val Ala Ser Tyr Leu Val Ala Gln Tyr Gly Glu Gln
 50                  55                  60

Arg Ala Trp Asp Leu Ala Leu His Thr Trp Glu Gln Met Gly Leu Arg
 65                  70                  75                  80

Ser Leu Cys Ala Gln Ala Gln Glu Gly Ala Gly His Ser Pro Ser Phe
             85                  90                  95

Pro Tyr Ser Pro Ser Glu Pro His Leu Gly Ser Pro Ser Gln Pro Thr
            100                 105                 110

Ser Thr Ala Val Leu Met Pro Trp Ile His Glu Leu Pro Ala Gly Cys
            115                 120                 125

Thr Gln Gly Ser Glu Arg Arg Val Leu Arg Gln Leu Pro Asp Thr Ser
            130                 135                 140

Gly Arg Arg Trp Arg Glu Ile Ser Ala Ser Leu Leu Tyr Gln Ala Leu
145                 150                 155                 160

Pro Ser Ser Pro Asp His Glu Ser Pro Ser Gln Glu Ser Pro Asn Ala
                165                 170                 175

Pro Thr Ser Thr Ala Val Leu Gly Ser Trp Gly Ser Pro Pro Gln Pro
            180                 185                 190

Ser Leu Ala Pro Arg Glu Gln Glu Ala Pro Gly Thr Gln Trp Pro Leu
            195                 200                 205

Asp Glu Thr Ser Gly Ile Tyr Tyr Thr Glu Ile Arg Glu Arg Glu Arg
            210                 215                 220

Glu Lys Ser Glu Lys Gly Arg Pro Pro Trp Ala Ala Val Val Gly Thr
225                 230                 235                 240

Pro Pro Gln Ala His Thr Ser Leu Gln Pro His His His Pro Trp Glu
                245                 250                 255

Pro Ser Val Arg Glu Ser Leu Cys Ser Thr Trp Pro Trp Lys Asn Glu
                260                 265                 270

Asp Phe Asn Gln Lys Phe Thr Gln Leu Leu Leu Leu Gln Arg Pro His
                275                 280                 285

Pro Arg Ser Gln Asp Pro Leu Val Lys Arg Ser Trp Pro Asp Tyr Val
            290                 295                 300

Glu Glu Asn Arg Gly His Leu Ile Glu Ile Arg Asp Leu Phe Gly Pro
305                 310                 315                 320

Gly Leu Asp Thr Gln Glu Pro Arg Ile Val Ile Leu Gln Gly Ala Ala
                325                 330                 335

Gly Ile Gly Lys Ser Thr Leu Ala Arg Gln Val Lys Glu Ala Trp Gly
                340                 345                 350

Arg Gly Gln Leu Tyr Gly Asp Arg Phe Gln His Val Phe Tyr Phe Ser
            355                 360                 365

Cys Arg Glu Leu Ala Gln Ser Lys Val Val Ser Leu Ala Glu Leu Ile
            370                 375                 380

Gly Lys Asp Gly Thr Ala Thr Pro Ala Pro Ile Arg Gln Ile Leu Ser
385                 390                 395                 400

Arg Pro Glu Arg Leu Leu Phe Ile Leu Asp Gly Val Asp Glu Pro Gly
                405                 410                 415

Trp Val Leu Gln Glu Pro Ser Ser Glu Leu Cys Leu His Trp Ser Gln
            420                 425                 430

Pro Gln Pro Ala Asp Ala Leu Leu Gly Ser Leu Leu Gly Lys Thr Ile
            435                 440                 445
```

```
Leu Pro Glu Ala Ser Phe Leu Ile Thr Ala Arg Thr Ala Leu Gln
    450                 455                 460

Asn Leu Ile Pro Ser Leu Glu Gln Ala Arg Trp Val Glu Val Leu Gly
465                 470                 475                 480

Phe Ser Glu Ser Ser Arg Lys Glu Tyr Phe Tyr Arg Tyr Phe Thr Asp
                485                 490                 495

Glu Arg Gln Ala Ile Arg Ala Phe Arg Leu Val Lys Ser Asn Lys Glu
            500                 505                 510

Leu Trp Ala Leu Cys Leu Val Pro Trp Val Ser Trp Leu Ala Cys Thr
            515                 520                 525

Cys Leu Met Gln Gln Met Lys Arg Lys Glu Lys Leu Thr Leu Thr Ser
530                 535                 540

Lys Thr Thr Thr Thr Leu Cys Leu His Tyr Leu Ala Gln Ala Leu Gln
545                 550                 555                 560

Ala Gln Pro Leu Gly Pro Gln Leu Arg Asp Leu Cys Ser Leu Ala Ala
                565                 570                 575

Glu Gly Ile Trp Gln Lys Lys Thr Leu Phe Ser Pro Asp Asp Leu Arg
            580                 585                 590

Lys His Gly Leu Asp Gly Ala Ile Ile Ser Thr Phe Leu Lys Met Gly
    595                 600                 605

Ile Leu Gln Glu His Pro Ile Pro Leu Ser Tyr Ser Phe Ile His Leu
    610                 615                 620

Cys Phe Gln Glu Phe Phe Ala Ala Met Ser Tyr Val Leu Glu Asp Glu
625                 630                 635                 640

Lys Gly Arg Gly Lys His Ser Asn Cys Ile Ile Asp Leu Glu Lys Thr
                645                 650                 655

Leu Glu Ala Tyr Gly Ile His Gly Leu Phe Gly Ala Ser Thr Thr Arg
            660                 665                 670

Phe Leu Leu Gly Leu Leu Ser Asp Glu Gly Glu Arg Glu Met Glu Asn
            675                 680                 685

Ile Phe His Cys Arg Leu Ser Gln Gly Arg Asn Leu Met Gln Trp Val
    690                 695                 700

Pro Ser Leu Gln Leu Leu Leu Gln Pro His Ser Leu Glu Ser Leu His
705                 710                 715                 720

Cys Leu Tyr Glu Thr Arg Asn Lys Thr Phe Leu Thr Gln Val Met Ala
                725                 730                 735

His Phe Glu Glu Met Gly Met Cys Val Glu Thr Asp Met Glu Leu Leu
            740                 745                 750

Val Cys Thr Phe Cys Ile Lys Phe Ser Arg His Val Lys Lys Leu Gln
            755                 760                 765

Leu Ile Glu Gly Arg Gln His Arg Ser Thr Trp Ser Pro Thr Met Val
770                 775                 780

Val Leu Phe Arg Trp Val Pro Val Thr Asp Ala Tyr Trp Gln Ile Leu
785                 790                 795                 800

Phe Ser Val Leu Lys Val Thr Arg Asn Leu Lys Glu Leu Asp Leu Ser
                805                 810                 815

Gly Asn Ser Leu Ser His Ser Ala Val Lys Ser Leu Cys Lys Thr Leu
            820                 825                 830

Arg Arg Pro Arg Cys Leu Leu Glu Thr Leu Arg Leu Ala Gly Cys Gly
            835                 840                 845

Leu Thr Ala Glu Asp Cys Lys Asp Leu Ala Phe Gly Leu Arg Ala Asn
    850                 855                 860
```

```
Gln Thr Leu Thr Glu Leu Asp Leu Ser Phe Asn Val Leu Thr Asp Ala
865                 870                 875                 880

Gly Ala Lys His Leu Cys Gln Arg Leu Arg Gln Pro Ser Cys Lys Leu
            885                 890                 895

Gln Arg Leu Gln Leu Val Ser Cys Gly Leu Thr Ser Asp Cys Cys Gln
            900                 905                 910

Asp Leu Ala Ser Val Leu Ser Ala Ser Pro Ser Leu Lys Glu Leu Asp
            915                 920                 925

Leu Gln Gln Asn Asn Leu Asp Asp Val Gly Val Arg Leu Leu Cys Glu
    930                 935                 940

Gly Leu Arg His Pro Ala Cys Lys Leu Ile Arg Leu Gly Leu Asp Gln
945                 950                 955                 960

Thr Thr Leu Ser Asp Glu Met Arg Gln Glu Leu Arg Ala Leu Glu Gln
                965                 970                 975

Glu Lys Pro Gln Leu Leu Ile Phe Ser Arg Arg Lys Pro Ser Val Met
            980                 985                 990

Thr Pro Thr Glu Gly Leu Asp Thr Gly Glu Met Ser Asn Ser Thr Ser
            995                 1000                1005

Ser Leu Lys Arg Gln Arg Leu Gly Ser Glu Arg Ala Ala Ser His
    1010                1015                1020

Val Ala Gln Ala Asn Leu Lys Leu Leu Asp Val Ser Lys Ile Phe
    1025                1030                1035

Pro Ile Ala Glu Ile Ala Glu Glu Ser Ser Pro Glu Val Val Pro
    1040                1045                1050

Val Glu Leu Leu Cys Val Pro Ser Pro Ala Ser Gln Gly Asp Leu
    1055                1060                1065

His Thr Lys Pro Leu Gly Thr Asp Asp Asp Phe Trp Gly Pro Thr
    1070                1075                1080

Gly Pro Val Ala Thr Glu Val Val Asp Lys Glu Lys Asn Leu Tyr
    1085                1090                1095

Arg Val His Phe Pro Val Ala Gly Ser Tyr Arg Trp Pro Asn Thr
    1100                1105                1110

Gly Leu Cys Phe Val Met Arg Glu Ala Val Thr Val Glu Ile Glu
    1115                1120                1125

Phe Cys Val Trp Asp Gln Phe Leu Gly Glu Ile Asn Pro Gln His
    1130                1135                1140

Ser Trp Met Val Ala Gly Pro Leu Leu Asp Ile Lys Ala Glu Pro
    1145                1150                1155

Gly Ala Val Glu Ala Val His Leu Pro His Phe Val Ala Leu Gln
    1160                1165                1170

Gly Gly His Val Asp Thr Ser Leu Phe Gln Met Ala His Phe Lys
    1175                1180                1185

Glu Glu Gly Met Leu Leu Glu Lys Pro Ala Arg Val Glu Leu His
    1190                1195                1200

His Ile Val Leu Glu Asn Pro Ser Phe Ser Pro Leu Gly Val Leu
    1205                1210                1215

Leu Lys Met Ile His Asn Ala Leu Arg Phe Ile Pro Val Thr Ser
    1220                1225                1230

Val Val Leu Leu Tyr His Arg Val His Pro Glu Glu Val Thr Phe
    1235                1240                1245

His Leu Tyr Leu Ile Pro Ser Asp Cys Ser Ile Arg Lys Glu Leu
    1250                1255                1260

Glu Leu Cys Tyr Arg Ser Pro Gly Glu Asp Gln Leu Phe Ser Glu
```

-continued

```
                1265                1270                1275
Phe Tyr Val Gly His Leu Gly Ser Gly Ile Arg Leu Gln Val Lys
            1280                1285                1290
Asp Lys Lys Asp Glu Thr Leu Val Trp Glu Ala Leu Val Lys Pro
        1295                1300                1305
Gly Asp Leu Met Pro Ala Thr Thr Leu Ile Pro Pro Ala Arg Ile
    1310                1315                1320
Ala Val Pro Ser Pro Leu Asp Ala Pro Gln Leu Leu His Phe Val
1325                1330                1335
Asp Gln Tyr Arg Glu Gln Leu Ile Ala Arg Val Thr Ser Val Glu
    1340                1345                1350
Val Val Leu Asp Lys Leu His Gly Gln Val Leu Ser Gln Glu Gln
1355                1360                1365
Tyr Glu Arg Val Leu Ala Glu Asn Thr Arg Pro Ser Gln Met Arg
        1370                1375                1380
Lys Leu Phe Ser Leu Ser Gln Ser Trp Asp Arg Lys Cys Lys Asp
    1385                1390                1395
Gly Leu Tyr Gln Ala Leu Lys Glu Thr His Pro His Leu Ile Met
1400                1405                1410
Glu Leu Trp Glu Lys Gly Ser Lys Lys Gly Leu Leu Pro Leu Ser
        1415                1420                1425
Ser
```

<210> SEQ ID NO 41
<211> LENGTH: 1473
<212> TYPE: PRT
<213> ORGANISM: homo sapiens

<400> SEQUENCE: 41

```
Met Ala Gly Gly Ala Trp Gly Arg Leu Ala Cys Tyr Leu Glu Phe Leu
1               5                   10                  15
Lys Lys Glu Glu Leu Lys Glu Phe Gln Leu Leu Leu Ala Asn Lys Ala
            20                  25                  30
His Ser Arg Ser Ser Ser Gly Glu Thr Pro Ala Gln Pro Glu Lys Thr
        35                  40                  45
Ser Gly Met Glu Val Ala Ser Tyr Leu Val Ala Gln Tyr Gly Glu Gln
    50                  55                  60
Arg Ala Trp Asp Leu Ala Leu His Thr Trp Glu Gln Met Gly Leu Arg
65                  70                  75                  80
Ser Leu Cys Ala Gln Ala Gln Glu Gly Ala Gly His Ser Pro Ser Phe
                85                  90                  95
Pro Tyr Ser Pro Ser Glu Pro His Leu Gly Ser Pro Ser Gln Pro Thr
            100                 105                 110
Ser Thr Ala Val Leu Met Pro Trp Ile His Glu Leu Pro Ala Gly Cys
        115                 120                 125
Thr Gln Gly Ser Glu Arg Arg Val Leu Arg Gln Leu Pro Asp Thr Ser
    130                 135                 140
Gly Arg Arg Trp Arg Glu Ile Ser Ala Ser Leu Leu Tyr Gln Ala Leu
145                 150                 155                 160
Pro Ser Ser Pro Asp His Glu Ser Pro Gln Glu Ser Pro Asn Ala
                165                 170                 175
Pro Thr Ser Thr Ala Val Leu Gly Ser Trp Gly Ser Pro Pro Gln Pro
            180                 185                 190
Ser Leu Ala Pro Arg Glu Gln Glu Ala Pro Gly Thr Gln Trp Pro Leu
```

```
            195                 200                 205
Asp Glu Thr Ser Gly Ile Tyr Tyr Thr Glu Ile Arg Glu Arg Glu Arg
210                 215                 220
Glu Lys Ser Glu Lys Gly Arg Pro Pro Trp Ala Ala Val Val Gly Thr
225                 230                 235                 240
Pro Pro Gln Ala His Thr Ser Leu Gln Pro His His His Pro Trp Glu
                245                 250                 255
Pro Ser Val Arg Glu Ser Leu Cys Ser Thr Trp Pro Trp Lys Asn Glu
                260                 265                 270
Asp Phe Asn Gln Lys Phe Thr Gln Leu Leu Leu Gln Arg Pro His
                275                 280                 285
Pro Arg Ser Gln Asp Pro Leu Val Lys Arg Ser Trp Pro Asp Tyr Val
290                 295                 300
Glu Glu Asn Arg Gly His Leu Ile Glu Ile Arg Asp Leu Phe Gly Pro
305                 310                 315                 320
Gly Leu Asp Thr Gln Glu Pro Arg Ile Val Ile Leu Gln Gly Ala Ala
                325                 330                 335
Gly Ile Gly Lys Ser Thr Leu Ala Arg Gln Val Lys Glu Ala Trp Gly
                340                 345                 350
Arg Gly Gln Leu Tyr Gly Asp Arg Phe Gln His Val Phe Tyr Phe Ser
                355                 360                 365
Cys Arg Glu Leu Ala Gln Ser Lys Val Val Ser Leu Ala Glu Leu Ile
370                 375                 380
Gly Lys Asp Gly Thr Ala Thr Pro Ala Pro Ile Arg Gln Ile Leu Ser
385                 390                 395                 400
Arg Pro Glu Arg Leu Leu Phe Ile Leu Asp Gly Val Asp Glu Pro Gly
                405                 410                 415
Trp Val Leu Gln Glu Pro Ser Ser Glu Leu Cys Leu His Trp Ser Gln
                420                 425                 430
Pro Gln Pro Ala Asp Ala Leu Leu Gly Ser Leu Leu Gly Lys Thr Ile
                435                 440                 445
Leu Pro Glu Ala Ser Phe Leu Ile Thr Ala Arg Thr Thr Ala Leu Gln
450                 455                 460
Asn Leu Ile Pro Ser Leu Glu Gln Ala Arg Trp Val Glu Val Leu Gly
465                 470                 475                 480
Phe Ser Glu Ser Ser Arg Lys Glu Tyr Phe Tyr Arg Tyr Phe Thr Asp
                485                 490                 495
Glu Arg Gln Ala Ile Arg Ala Phe Arg Leu Val Lys Ser Asn Lys Glu
                500                 505                 510
Leu Trp Ala Leu Cys Leu Val Pro Trp Val Ser Trp Leu Ala Cys Thr
                515                 520                 525
Cys Leu Met Gln Gln Met Lys Arg Lys Glu Lys Leu Thr Leu Thr Ser
                530                 535                 540
Lys Thr Thr Thr Thr Leu Cys Leu His Tyr Leu Ala Gln Ala Leu Gln
545                 550                 555                 560
Ala Gln Pro Leu Gly Pro Gln Leu Arg Asp Leu Cys Ser Leu Ala Ala
                565                 570                 575
Glu Gly Ile Trp Gln Lys Lys Thr Leu Phe Ser Pro Asp Asp Leu Arg
                580                 585                 590
Lys His Gly Leu Asp Gly Ala Ile Ile Ser Thr Phe Leu Lys Met Gly
                595                 600                 605
Ile Leu Gln Glu His Pro Ile Pro Leu Ser Tyr Ser Phe Ile His Leu
                610                 615                 620
```

-continued

```
Cys Phe Gln Glu Phe Phe Ala Ala Met Ser Tyr Val Leu Glu Asp Glu
625                 630                 635                 640

Lys Gly Arg Gly Lys His Ser Asn Cys Ile Ile Asp Leu Glu Lys Thr
            645                 650                 655

Leu Glu Ala Tyr Gly Ile His Gly Leu Phe Gly Ala Ser Thr Thr Arg
            660                 665                 670

Phe Leu Leu Gly Leu Leu Ser Asp Glu Gly Glu Arg Glu Met Glu Asn
            675                 680                 685

Ile Phe His Cys Arg Leu Ser Gln Gly Arg Asn Leu Met Gln Trp Val
690                 695                 700

Pro Ser Leu Gln Leu Leu Gln Pro His Ser Leu Glu Ser Leu His
705                 710                 715                 720

Cys Leu Tyr Glu Thr Arg Asn Lys Thr Phe Leu Thr Gln Val Met Ala
            725                 730                 735

His Phe Glu Glu Met Gly Met Cys Val Glu Thr Asp Met Glu Leu Leu
            740                 745                 750

Val Cys Thr Phe Cys Ile Lys Phe Ser Arg His Val Lys Lys Leu Gln
            755                 760                 765

Leu Ile Glu Gly Arg Gln His Arg Ser Thr Trp Ser Pro Thr Met Val
770                 775                 780

Val Leu Phe Arg Trp Val Pro Val Thr Asp Ala Tyr Trp Gln Ile Leu
785                 790                 795                 800

Phe Ser Val Leu Lys Val Thr Arg Asn Leu Lys Glu Leu Asp Leu Ser
            805                 810                 815

Gly Asn Ser Leu Ser His Ser Ala Val Lys Ser Leu Cys Lys Thr Leu
            820                 825                 830

Arg Arg Pro Arg Cys Leu Leu Glu Thr Leu Arg Leu Ala Gly Cys Gly
            835                 840                 845

Leu Thr Ala Glu Asp Cys Lys Asp Leu Ala Phe Gly Leu Arg Ala Asn
850                 855                 860

Gln Thr Leu Thr Glu Leu Asp Leu Ser Phe Asn Val Leu Thr Asp Ala
865                 870                 875                 880

Gly Ala Lys His Leu Cys Gln Arg Leu Arg Gln Pro Ser Cys Lys Leu
            885                 890                 895

Gln Arg Leu Gln Leu Val Ser Cys Gly Leu Thr Ser Asp Cys Cys Gln
            900                 905                 910

Asp Leu Ala Ser Val Leu Ser Ala Ser Pro Ser Leu Lys Glu Leu Asp
            915                 920                 925

Leu Gln Gln Asn Asn Leu Asp Asp Val Gly Val Arg Leu Leu Cys Glu
            930                 935                 940

Gly Leu Arg His Pro Ala Cys Lys Leu Ile Arg Leu Gly Leu Asp Gln
945                 950                 955                 960

Thr Thr Leu Ser Asp Glu Met Arg Gln Glu Leu Arg Ala Leu Glu Gln
            965                 970                 975

Glu Lys Pro Gln Leu Leu Ile Phe Ser Arg Arg Lys Pro Ser Val Met
            980                 985                 990

Thr Pro Thr Glu Gly Leu Asp Thr Gly Glu Met Ser Asn Ser Thr Ser
            995                 1000                1005

Ser Leu Lys Arg Gln Arg Leu Gly Ser Glu Arg Ala Ala Ser His
        1010                1015                1020

Val Ala Gln Ala Asn Leu Lys Leu Leu Asp Val Ser Lys Ile Phe
        1025                1030                1035
```

```
Pro Ile Ala Glu Ile Ala Glu Glu Ser Ser Pro Glu Val Val Pro
    1040                1045                1050

Val Glu Leu Leu Cys Val Pro Ser Pro Ala Ser Gln Gly Asp Leu
    1055                1060                1065

His Thr Lys Pro Leu Gly Thr Asp Asp Asp Phe Trp Gly Pro Thr
    1070                1075                1080

Gly Pro Val Ala Thr Glu Val Val Asp Lys Glu Lys Asn Leu Tyr
    1085                1090                1095

Arg Val His Phe Pro Val Ala Gly Ser Tyr Arg Trp Pro Asn Thr
    1100                1105                1110

Gly Leu Cys Phe Val Met Arg Glu Ala Val Thr Val Glu Ile Glu
    1115                1120                1125

Phe Cys Val Trp Asp Gln Phe Leu Gly Glu Ile Asn Pro Gln His
    1130                1135                1140

Ser Trp Met Val Ala Gly Pro Leu Leu Asp Ile Lys Ala Glu Pro
    1145                1150                1155

Gly Ala Val Glu Ala Val His Leu Pro His Phe Val Ala Leu Gln
    1160                1165                1170

Gly Gly His Val Asp Thr Ser Leu Phe Gln Met Ala His Phe Lys
    1175                1180                1185

Glu Glu Gly Met Leu Leu Glu Lys Pro Ala Arg Val Glu Leu His
    1190                1195                1200

His Ile Val Leu Glu Asn Pro Ser Phe Ser Pro Leu Gly Val Leu
    1205                1210                1215

Leu Lys Met Ile His Asn Ala Leu Arg Phe Ile Pro Val Thr Ser
    1220                1225                1230

Val Val Leu Leu Tyr His Arg Val His Pro Glu Glu Val Thr Phe
    1235                1240                1245

His Leu Tyr Leu Ile Pro Ser Asp Cys Ser Ile Arg Lys Ala Ile
    1250                1255                1260

Asp Asp Leu Glu Met Lys Phe Gln Phe Val Arg Ile His Lys Pro
    1265                1270                1275

Pro Pro Leu Thr Pro Leu Tyr Met Gly Cys Arg Tyr Thr Val Ser
    1280                1285                1290

Gly Ser Gly Ser Gly Met Leu Glu Ile Leu Pro Lys Glu Leu Glu
    1295                1300                1305

Leu Cys Tyr Arg Ser Pro Gly Glu Asp Gln Leu Phe Ser Glu Phe
    1310                1315                1320

Tyr Val Gly His Leu Gly Ser Gly Ile Arg Leu Gln Val Lys Asp
    1325                1330                1335

Lys Lys Asp Glu Thr Leu Val Trp Glu Ala Leu Val Lys Pro Gly
    1340                1345                1350

Asp Leu Met Pro Ala Thr Thr Leu Ile Pro Pro Ala Arg Ile Ala
    1355                1360                1365

Val Pro Ser Pro Leu Asp Ala Pro Gln Leu Leu His Phe Val Asp
    1370                1375                1380

Gln Tyr Arg Glu Gln Leu Ile Ala Arg Val Thr Ser Val Glu Val
    1385                1390                1395

Val Leu Asp Lys Leu His Gly Gln Val Leu Ser Gln Glu Gln Tyr
    1400                1405                1410

Glu Arg Val Leu Ala Glu Asn Thr Arg Pro Ser Gln Met Arg Lys
    1415                1420                1425

Leu Phe Ser Leu Ser Gln Ser Trp Asp Arg Lys Cys Lys Asp Gly
```

```
                1430              1435              1440
Leu Tyr Gln Ala Leu Lys Glu Thr His Pro His Leu Ile Met Glu
        1445              1450              1455
Leu Trp Glu Lys Gly Ser Lys Lys Gly Leu Leu Pro Leu Ser Ser
        1460              1465              1470

<210> SEQ ID NO 42
<211> LENGTH: 1443
<212> TYPE: PRT
<213> ORGANISM: homo sapiens

<400> SEQUENCE: 42

Met Ala Gly Gly Ala Trp Gly Arg Leu Ala Cys Tyr Leu Glu Phe Leu
1                5                  10                  15
Lys Lys Glu Glu Leu Lys Glu Phe Gln Leu Leu Leu Ala Asn Lys Ala
            20                  25                  30
His Ser Arg Ser Ser Ser Gly Glu Thr Pro Ala Gln Pro Glu Lys Thr
        35                  40                  45
Ser Gly Met Glu Val Ala Ser Tyr Leu Val Ala Gln Tyr Gly Glu Gln
    50                  55                  60
Arg Ala Trp Asp Leu Ala Leu His Thr Trp Glu Gln Met Gly Leu Arg
65                  70                  75                  80
Ser Leu Cys Ala Gln Ala Gln Glu Gly Ala Gly His Ser Pro Ser Phe
                85                  90                  95
Pro Tyr Ser Pro Ser Glu Pro His Leu Gly Ser Pro Ser Gln Pro Thr
            100                 105                 110
Ser Thr Ala Val Leu Met Pro Trp Ile His Glu Leu Pro Ala Gly Cys
        115                 120                 125
Thr Gln Gly Ser Glu Arg Arg Val Leu Arg Gln Leu Pro Asp Thr Ser
    130                 135                 140
Gly Arg Arg Trp Arg Glu Ile Ser Ala Ser Leu Leu Tyr Gln Ala Leu
145                 150                 155                 160
Pro Ser Ser Pro Asp His Glu Ser Pro Ser Gln Glu Ser Pro Asn Ala
                165                 170                 175
Pro Thr Ser Thr Ala Val Leu Gly Ser Trp Gly Ser Pro Pro Gln Pro
            180                 185                 190
Ser Leu Ala Pro Arg Glu Gln Glu Ala Pro Gly Thr Gln Trp Pro Leu
        195                 200                 205
Asp Glu Thr Ser Gly Ile Tyr Tyr Thr Glu Ile Arg Glu Arg Glu Arg
    210                 215                 220
Glu Lys Ser Glu Lys Gly Arg Pro Pro Trp Ala Ala Val Val Gly Thr
225                 230                 235                 240
Pro Pro Gln Ala His Thr Ser Leu Gln Pro His His His Pro Trp Glu
                245                 250                 255
Pro Ser Val Arg Glu Ser Leu Cys Ser Thr Trp Pro Trp Lys Asn Glu
            260                 265                 270
Asp Phe Asn Gln Lys Phe Thr Gln Leu Leu Leu Leu Gln Arg Pro His
        275                 280                 285
Pro Arg Ser Gln Asp Pro Leu Val Lys Arg Ser Trp Pro Asp Tyr Val
    290                 295                 300
Glu Glu Asn Arg Gly His Leu Ile Glu Ile Arg Asp Leu Phe Gly Pro
305                 310                 315                 320
Gly Leu Asp Thr Gln Glu Pro Arg Ile Val Ile Leu Gln Gly Ala Ala
                325                 330                 335
```

-continued

```
Gly Ile Gly Lys Ser Thr Leu Ala Arg Gln Val Lys Glu Ala Trp Gly
            340                 345                 350
Arg Gly Gln Leu Tyr Gly Asp Arg Phe Gln His Val Phe Tyr Phe Ser
        355                 360                 365
Cys Arg Glu Leu Ala Gln Ser Lys Val Val Ser Leu Ala Glu Leu Ile
    370                 375                 380
Gly Lys Asp Gly Thr Ala Thr Pro Ala Pro Ile Arg Gln Ile Leu Ser
385                 390                 395                 400
Arg Pro Glu Arg Leu Phe Ile Leu Asp Gly Val Asp Glu Pro Gly
            405                 410                 415
Trp Val Leu Gln Glu Pro Ser Ser Glu Leu Cys Leu His Trp Ser Gln
        420                 425                 430
Pro Gln Pro Ala Asp Ala Leu Leu Gly Ser Leu Leu Gly Lys Thr Ile
    435                 440                 445
Leu Pro Glu Ala Ser Phe Leu Ile Thr Ala Arg Thr Thr Ala Leu Gln
450                 455                 460
Asn Leu Ile Pro Ser Leu Glu Gln Ala Arg Trp Val Glu Val Leu Gly
465                 470                 475                 480
Phe Ser Glu Ser Ser Arg Lys Glu Tyr Phe Tyr Arg Tyr Phe Thr Asp
            485                 490                 495
Glu Arg Gln Ala Ile Arg Ala Phe Arg Leu Val Lys Ser Asn Lys Glu
        500                 505                 510
Leu Trp Ala Leu Cys Leu Val Pro Trp Val Ser Trp Leu Ala Cys Thr
    515                 520                 525
Cys Leu Met Gln Gln Met Lys Arg Lys Glu Lys Leu Thr Leu Thr Ser
545                 550                 555                 560
Lys Thr Thr Thr Thr Leu Cys Leu His Tyr Leu Ala Gln Ala Leu Gln
545                 550                 555                 560
Ala Gln Pro Leu Gly Pro Gln Leu Arg Asp Leu Cys Ser Leu Ala Ala
            565                 570                 575
Glu Gly Ile Trp Gln Lys Lys Thr Leu Phe Ser Pro Asp Asp Leu Arg
        580                 585                 590
Lys His Gly Leu Asp Gly Ala Ile Ile Ser Thr Phe Leu Lys Met Gly
    595                 600                 605
Ile Leu Gln Glu His Pro Ile Pro Leu Ser Tyr Ser Phe Ile His Leu
610                 615                 620
Cys Phe Gln Glu Phe Phe Ala Ala Met Ser Tyr Val Leu Glu Asp Glu
625                 630                 635                 640
Lys Gly Arg Gly Lys His Ser Asn Cys Ile Ile Asp Leu Glu Lys Thr
            645                 650                 655
Leu Glu Ala Tyr Gly Ile His Gly Leu Phe Gly Ala Ser Thr Thr Arg
        660                 665                 670
Phe Leu Leu Gly Leu Leu Ser Asp Glu Gly Glu Arg Glu Met Glu Asn
    675                 680                 685
Ile Phe His Cys Arg Leu Ser Gln Gly Arg Asn Leu Met Gln Trp Val
690                 695                 700
Pro Ser Leu Gln Leu Leu Leu Gln Pro His Ser Leu Glu Ser Leu His
705                 710                 715                 720
Cys Leu Tyr Glu Thr Arg Asn Lys Thr Phe Leu Thr Gln Val Met Ala
            725                 730                 735
His Phe Glu Glu Met Gly Met Cys Val Glu Thr Asp Met Glu Leu Leu
        740                 745                 750
Val Cys Thr Phe Cys Ile Lys Phe Ser Arg His Val Lys Lys Leu Gln
```

-continued

```
            755                 760                 765
Leu Ile Glu Gly Arg Gln His Arg Ser Thr Trp Ser Pro Thr Met Val
770                 775                 780
Val Leu Phe Arg Trp Val Pro Val Thr Asp Ala Tyr Trp Gln Ile Leu
785                 790                 795                 800
Phe Ser Val Leu Lys Val Thr Arg Asn Leu Lys Glu Leu Asp Leu Ser
                805                 810                 815
Gly Asn Ser Leu Ser His Ser Ala Val Lys Ser Leu Cys Lys Thr Leu
                820                 825                 830
Arg Arg Pro Arg Cys Leu Leu Glu Thr Leu Arg Leu Ala Gly Cys Gly
                835                 840                 845
Leu Thr Ala Glu Asp Cys Lys Asp Leu Ala Phe Gly Leu Arg Ala Asn
850                 855                 860
Gln Thr Leu Thr Glu Leu Asp Leu Ser Phe Asn Val Leu Thr Asp Ala
865                 870                 875                 880
Gly Ala Lys His Leu Cys Gln Arg Leu Arg Gln Pro Ser Cys Lys Leu
                885                 890                 895
Gln Arg Leu Gln Leu Val Ser Cys Gly Leu Thr Ser Asp Cys Cys Gln
                900                 905                 910
Asp Leu Ala Ser Val Leu Ser Ala Ser Pro Ser Leu Lys Glu Leu Asp
                915                 920                 925
Leu Gln Gln Asn Asn Leu Asp Asp Val Gly Val Arg Leu Leu Cys Glu
                930                 935                 940
Gly Leu Arg His Pro Ala Cys Lys Leu Ile Arg Leu Gly Lys Pro Ser
945                 950                 955                 960
Val Met Thr Pro Thr Glu Gly Leu Asp Thr Gly Glu Met Ser Asn Ser
                965                 970                 975
Thr Ser Ser Leu Lys Arg Gln Arg Leu Gly Ser Glu Arg Ala Ala Ser
                980                 985                 990
His Val Ala Gln Ala Asn Leu Lys  Leu Leu Asp Val Ser  Lys Ile Phe
                995                 1000                1005
Pro Ile  Ala Glu Ile  Ala Glu  Glu Ser Ser Pro Glu  Val Val Pro
        1010                1015                1020
Val Glu  Leu Leu Cys Val Pro  Ser Pro Ala Ser Gln  Gly Asp Leu
        1025                1030                1035
His Thr  Lys Pro Leu Gly Thr  Asp Asp Asp Phe Trp  Gly Pro Thr
        1040                1045                1050
Gly Pro  Val Ala Thr Glu Val  Val Asp Lys Glu Lys  Asn Leu Tyr
        1055                1060                1065
Arg Val  His Phe Pro Val Ala  Gly Ser Tyr Arg Trp  Pro Asn Thr
        1070                1075                1080
Gly Leu  Cys Phe Val Met Arg  Glu Ala Val Thr Val  Glu Ile Glu
        1085                1090                1095
Phe Cys  Val Trp Asp Gln Phe  Leu Gly Glu Ile Asn  Pro Gln His
        1100                1105                1110
Ser Trp  Met Val Ala Gly Pro  Leu Leu Asp Ile Lys  Ala Glu Pro
        1115                1120                1125
Gly Ala  Val Glu Ala Val His  Leu Pro His Phe Val  Ala Leu Gln
        1130                1135                1140
Gly Gly  His Val Asp Thr Ser  Leu Phe Gln Met Ala  His Phe Lys
        1145                1150                1155
Glu Glu  Gly Met Leu Leu Glu  Lys Pro Ala Arg Val  Glu Leu His
        1160                1165                1170
```

His Ile Val Leu Glu Asn Pro Ser Phe Ser Pro Leu Gly Val Leu
    1175                1180                1185

Leu Lys Met Ile His Asn Ala Leu Arg Phe Ile Pro Val Thr Ser
    1190                1195                1200

Val Val Leu Leu Tyr His Arg Val His Pro Glu Glu Val Thr Phe
    1205                1210                1215

His Leu Tyr Leu Ile Pro Ser Asp Cys Ser Ile Arg Lys Ala Ile
    1220                1225                1230

Asp Asp Leu Glu Met Lys Phe Gln Phe Val Arg Ile His Lys Pro
    1235                1240                1245

Pro Pro Leu Thr Pro Leu Tyr Met Gly Cys Arg Tyr Thr Val Ser
    1250                1255                1260

Gly Ser Gly Ser Gly Met Leu Glu Ile Leu Pro Lys Glu Leu Glu
    1265                1270                1275

Leu Cys Tyr Arg Ser Pro Gly Glu Asp Gln Leu Phe Ser Glu Phe
    1280                1285                1290

Tyr Val Gly His Leu Gly Ser Gly Ile Arg Leu Gln Val Lys Asp
    1295                1300                1305

Lys Lys Asp Glu Thr Leu Val Trp Glu Ala Leu Val Lys Pro Gly
    1310                1315                1320

Asp Leu Met Pro Ala Thr Thr Leu Ile Pro Pro Ala Arg Ile Ala
    1325                1330                1335

Val Pro Ser Pro Leu Asp Ala Pro Gln Leu Leu His Phe Val Asp
    1340                1345                1350

Gln Tyr Arg Glu Gln Leu Ile Ala Arg Val Thr Ser Val Glu Val
    1355                1360                1365

Val Leu Asp Lys Leu His Gly Gln Val Leu Ser Gln Glu Gln Tyr
    1370                1375                1380

Glu Arg Val Leu Ala Glu Asn Thr Arg Pro Ser Gln Met Arg Lys
    1385                1390                1395

Leu Phe Ser Leu Ser Gln Ser Trp Asp Arg Lys Cys Lys Asp Gly
    1400                1405                1410

Leu Tyr Gln Ala Leu Lys Glu Thr His Pro His Leu Ile Met Glu
    1415                1420                1425

Leu Trp Glu Lys Gly Ser Lys Lys Gly Leu Leu Pro Leu Ser Ser
    1430                1435                1440

<210> SEQ ID NO 43
<211> LENGTH: 932
<212> TYPE: PRT
<213> ORGANISM: homo sapiens

<400> SEQUENCE: 43

Met Lys Gln Leu Pro Ala Ala Thr Val Arg Leu Leu Ser Ser Ser Gln
1               5                   10                  15

Ile Ile Thr Ser Val Val Ser Val Lys Glu Leu Ile Glu Asn Ser
            20                  25                  30

Leu Asp Ala Gly Ala Thr Ser Val Asp Val Lys Leu Glu Asn Tyr Gly
        35                  40                  45

Phe Asp Lys Ile Glu Val Arg Asp Asn Gly Glu Gly Ile Lys Ala Val
    50                  55                  60

Asp Ala Pro Val Met Ala Met Lys Tyr Tyr Thr Ser Lys Ile Asn Ser
65                  70                  75                  80

His Glu Asp Leu Glu Asn Leu Thr Thr Tyr Gly Phe Arg Gly Glu Ala

-continued

```
                    85                  90                  95
Leu Gly Ser Ile Cys Cys Ile Ala Glu Val Leu Ile Thr Thr Arg Thr
                100                 105                 110

Ala Ala Asp Asn Phe Ser Thr Gln Tyr Val Leu Asp Gly Ser Gly His
                115                 120                 125

Ile Leu Ser Gln Lys Pro Ser His Leu Gly Gln Gly Thr Thr Val Thr
            130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
                165                 170                 175

Met Ser Phe Gly Ile Leu Lys Pro Asp Leu Arg Ile Val Phe Val His
                180                 185                 190

Asn Lys Ala Val Ile Trp Gln Lys Ser Arg Val Ser Asp His Lys Met
            195                 200                 205

Ala Leu Met Ser Val Leu Gly Thr Ala Val Met Asn Asn Met Glu Ser
                210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                245                 250                 255

Arg Ser Phe Ile Phe Ile Asn Ser Arg Pro Val His Gln Lys Asp Ile
                260                 265                 270

Leu Lys Leu Ile Arg His His Tyr Asn Leu Lys Cys Leu Lys Glu Ser
            275                 280                 285

Thr Arg Leu Tyr Pro Val Phe Phe Leu Lys Ile Asp Val Pro Thr Ala
290                 295                 300

Asp Val Asp Val Asn Leu Thr Pro Asp Lys Ser Gln Val Leu Leu Gln
305                 310                 315                 320

Asn Lys Glu Ser Val Leu Ile Ala Leu Glu Asn Leu Met Thr Thr Cys
                325                 330                 335

Tyr Gly Pro Leu Pro Ser Thr Asn Ser Tyr Glu Asn Asn Lys Thr Asp
                340                 345                 350

Val Ser Ala Ala Asp Ile Val Leu Ser Lys Thr Ala Glu Thr Asp Val
            355                 360                 365

Leu Phe Asn Lys Val Glu Ser Ser Gly Lys Asn Tyr Ser Asn Val Asp
            370                 375                 380

Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
                405                 410                 415

Gly Tyr Gly His Cys Ser Ser Glu Ile Ser Asn Ile Asp Lys Asn Thr
            420                 425                 430

Lys Asn Ala Phe Gln Asp Ile Ser Met Ser Asn Val Ser Trp Glu Asn
            435                 440                 445

Ser Gln Thr Glu Tyr Ser Lys Thr Cys Phe Ile Ser Ser Val Lys His
        450                 455                 460

Thr Gln Ser Glu Asn Gly Asn Lys Asp His Ile Asp Glu Ser Gly Glu
465                 470                 475                 480

Asn Glu Glu Glu Ala Gly Leu Glu Asn Ser Ser Glu Ile Ser Ala Asp
                485                 490                 495

Glu Trp Ser Arg Gly Asn Ile Leu Lys Asn Ser Val Gly Glu Asn Ile
            500                 505                 510
```

```
Glu Pro Val Lys Ile Leu Val Pro Glu Lys Ser Leu Pro Cys Lys Val
            515                 520                 525

Ser Asn Asn Asn Tyr Pro Ile Pro Glu Gln Met Asn Leu Asn Glu Asp
    530                 535                 540

Ser Cys Asn Lys Lys Ser Asn Val Ile Asp Asn Lys Ser Gly Lys Val
545                 550                 555                 560

Thr Ala Tyr Asp Leu Leu Ser Asn Arg Val Ile Lys Lys Pro Met Ser
                565                 570                 575

Ala Ser Ala Leu Phe Val Gln Asp His Arg Pro Gln Phe Leu Ile Glu
            580                 585                 590

Asn Pro Lys Thr Ser Leu Glu Asp Ala Thr Leu Gln Ile Glu Glu Leu
            595                 600                 605

Trp Lys Thr Leu Ser Glu Glu Lys Leu Lys Tyr Glu Glu Lys Ala
            610                 615                 620

Thr Lys Asp Leu Glu Arg Tyr Asn Ser Gln Met Lys Arg Ala Ile Glu
625                 630                 635                 640

Gln Glu Ser Gln Met Ser Leu Lys Asp Gly Arg Lys Lys Ile Lys Pro
                645                 650                 655

Thr Ser Ala Trp Asn Leu Ala Gln Lys His Lys Leu Lys Thr Ser Leu
            660                 665                 670

Ser Asn Gln Pro Lys Leu Asp Glu Leu Leu Gln Ser Gln Ile Glu Lys
            675                 680                 685

Arg Arg Ser Gln Asn Ile Lys Met Val Gln Ile Pro Phe Ser Met Lys
            690                 695                 700

Asn Leu Lys Ile Asn Phe Lys Lys Gln Asn Lys Val Asp Leu Glu Glu
705                 710                 715                 720

Lys Asp Glu Pro Cys Leu Ile His Asn Leu Arg Phe Pro Asp Ala Trp
                725                 730                 735

Leu Met Thr Ser Lys Thr Glu Val Met Leu Leu Asn Pro Tyr Arg Val
                740                 745                 750

Glu Glu Ala Leu Leu Phe Lys Arg Leu Leu Glu Asn His Lys Leu Pro
            755                 760                 765

Ala Glu Pro Leu Glu Lys Pro Ile Met Leu Thr Glu Ser Leu Phe Asn
            770                 775                 780

Gly Ser His Tyr Leu Asp Val Leu Tyr Lys Met Thr Ala Asp Asp Gln
785                 790                 795                 800

Arg Tyr Ser Gly Ser Thr Tyr Leu Ser Asp Pro Arg Leu Thr Ala Asn
                805                 810                 815

Gly Phe Lys Ile Lys Leu Ile Pro Gly Val Ser Ile Thr Glu Asn Tyr
                820                 825                 830

Leu Glu Ile Glu Gly Met Ala Asn Cys Leu Pro Phe Tyr Gly Val Ala
            835                 840                 845

Asp Leu Lys Glu Ile Leu Asn Ala Ile Leu Asn Arg Asn Ala Lys Glu
850                 855                 860

Val Tyr Glu Cys Arg Pro Arg Lys Val Ile Ser Tyr Leu Glu Gly Glu
865                 870                 875                 880

Ala Val Arg Leu Ser Arg Gln Leu Pro Met Tyr Leu Ser Lys Glu Asp
                885                 890                 895

Ile Gln Asp Ile Ile Tyr Arg Met Lys His Gln Phe Gly Asn Glu Ile
            900                 905                 910

Lys Glu Cys Val His Gly Arg Pro Phe Phe His Leu Thr Tyr Leu
            915                 920                 925
```

Pro Glu Thr Thr
    930

<210> SEQ ID NO 44
<211> LENGTH: 623
<212> TYPE: PRT
<213> ORGANISM: homo sapiens

<400> SEQUENCE: 44

Met Asn Arg Tyr Thr Thr Met Arg Gln Leu Gly Asp Gly Thr Tyr Gly
1               5                   10                  15

Ser Val Leu Met Gly Lys Ser Asn Glu Ser Gly Glu Leu Val Ala Ile
            20                  25                  30

Lys Arg Met Lys Arg Lys Phe Tyr Ser Trp Asp Glu Cys Met Asn Leu
        35                  40                  45

Arg Glu Val Lys Ser Leu Lys Lys Leu Asn His Ala Asn Val Ile Lys
    50                  55                  60

Leu Lys Glu Val Ile Arg Glu Asn Asp His Leu Tyr Phe Ile Phe Glu
65                  70                  75                  80

Tyr Met Lys Glu Asn Leu Tyr Gln Leu Met Lys Asp Arg Asn Lys Leu
                85                  90                  95

Phe Pro Glu Ser Val Ile Arg Asn Ile Met Tyr Gln Ile Leu Gln Gly
            100                 105                 110

Leu Ala Phe Ile His Lys His Gly Phe Phe His Arg Asp Met Lys Pro
        115                 120                 125

Glu Asn Leu Leu Cys Met Gly Pro Glu Leu Val Lys Ile Ala Asp Phe
    130                 135                 140

Gly Leu Ala Arg Glu Leu Arg Ser Gln Pro Pro Tyr Thr Asp Tyr Val
145                 150                 155                 160

Ser Thr Arg Trp Tyr Arg Ala Pro Glu Val Leu Leu Arg Ser Ser Val
                165                 170                 175

Tyr Ser Ser Pro Ile Asp Val Trp Ala Val Gly Ser Ile Met Ala Glu
            180                 185                 190

Leu Tyr Met Leu Arg Pro Leu Phe Pro Gly Thr Ser Glu Val Asp Glu
        195                 200                 205

Ile Phe Lys Ile Cys Gln Val Leu Gly Thr Pro Lys Lys Ser Asp Trp
    210                 215                 220

Pro Glu Gly Tyr Gln Leu Ala Ser Ser Met Asn Phe Arg Phe Pro Gln
225                 230                 235                 240

Cys Val Pro Ile Asn Leu Lys Thr Leu Ile Pro Asn Ala Ser Asn Glu
                245                 250                 255

Ala Ile Gln Leu Met Thr Glu Met Leu Asn Trp Asp Pro Lys Lys Arg
            260                 265                 270

Pro Thr Ala Ser Gln Ala Leu Lys His Pro Tyr Phe Gln Val Gly Gln
        275                 280                 285

Val Leu Gly Pro Ser Ser Asn His Leu Glu Ser Lys Gln Ser Leu Asn
    290                 295                 300

Lys Gln Leu Gln Pro Leu Glu Ser Lys Pro Ser Leu Val Glu Val Glu
305                 310                 315                 320

Pro Lys Pro Leu Pro Asp Ile Ile Asp Gln Val Val Gly Gln Pro Gln
                325                 330                 335

Pro Lys Thr Ser Gln Gln Pro Leu Gln Pro Ile Gln Pro Pro Gln Asn
            340                 345                 350

Leu Ser Val Gln Gln Pro Pro Lys Gln Gln Ser Gln Glu Lys Pro Pro
        355                 360                 365

```
Gln Thr Leu Phe Pro Ser Ile Val Lys Asn Met Pro Thr Lys Pro Asn
    370                 375                 380

Gly Thr Leu Ser His Lys Ser Gly Arg Arg Trp Gly Gln Thr Ile
385                 390                 395                 400

Phe Lys Ser Gly Asp Ser Trp Glu Glu Leu Glu Asp Tyr Asp Phe Gly
                405                 410                 415

Ala Ser His Ser Lys Lys Pro Ser Met Gly Val Phe Lys Glu Lys Arg
            420                 425                 430

Lys Lys Asp Ser Pro Phe Arg Leu Pro Glu Pro Val Pro Ser Gly Ser
        435                 440                 445

Asn His Ser Thr Gly Glu Asn Lys Ser Leu Pro Ala Val Thr Ser Leu
    450                 455                 460

Lys Ser Asp Ser Glu Leu Ser Thr Ala Pro Thr Ser Lys Gln Tyr Tyr
465                 470                 475                 480

Leu Lys Gln Ser Arg Tyr Leu Pro Gly Val Asn Pro Lys Lys Val Ser
                485                 490                 495

Leu Ile Ala Ser Gly Lys Glu Ile Asn Pro His Thr Trp Ser Asn Gln
            500                 505                 510

Leu Phe Pro Lys Ser Leu Gly Pro Val Gly Ala Glu Leu Ala Phe Lys
        515                 520                 525

Arg Ser Asn Ala Gly Asn Leu Gly Ser Tyr Ala Thr Tyr Asn Gln Ser
    530                 535                 540

Gly Tyr Ile Pro Ser Phe Leu Lys Lys Glu Val Gln Ser Ala Gly Gln
545                 550                 555                 560

Arg Ile His Leu Ala Pro Leu Asn Ala Thr Ala Ser Glu Tyr Thr Trp
                565                 570                 575

Asn Thr Lys Thr Gly Arg Gly Gln Phe Ser Gly Arg Thr Tyr Asn Pro
            580                 585                 590

Thr Ala Lys Asn Leu Asn Ile Val Asn Arg Ala Gln Pro Ile Pro Ser
        595                 600                 605

Val His Gly Arg Thr Asp Trp Val Ala Lys Tyr Gly His Arg
    610                 615                 620

<210> SEQ ID NO 45
<211> LENGTH: 1380
<212> TYPE: PRT
<213> ORGANISM: homo sapiens

<400> SEQUENCE: 45

Met Ala Ser Gly Arg Asp Glu Arg Pro Pro Trp Arg Leu Gly Arg Leu
1               5                   10                  15

Leu Leu Leu Met Cys Leu Leu Leu Gly Ser Ser Ala Arg Ala Ala
            20                  25                  30

His Ile Lys Lys Ala Glu Ala Thr Thr Thr Thr Ser Ala Gly Ala
        35                  40                  45

Glu Ala Ala Glu Gly Gln Phe Asp Arg Tyr Tyr His Glu Glu Leu
    50                  55                  60

Glu Ser Ala Leu Arg Glu Ala Ala Ala Gly Leu Pro Gly Leu Ala
65                  70                  75                  80

Arg Leu Phe Ser Ile Gly Arg Ser Val Glu Gly Arg Pro Leu Trp Val
                85                  90                  95

Leu Arg Leu Thr Ala Gly Leu Gly Ser Leu Ile Pro Glu Gly Asp Ala
            100                 105                 110

Gly Pro Asp Ala Ala Gly Pro Asp Ala Ala Gly Pro Leu Leu Pro Gly
```

```
            115                 120                 125
Arg Pro Gln Val Lys Leu Val Gly Asn Met His Gly Asp Glu Thr Val
130                 135                 140

Ser Arg Gln Val Leu Ile Tyr Leu Ala Arg Glu Leu Ala Ala Gly Tyr
145                 150                 155                 160

Arg Arg Gly Asp Pro Arg Leu Val Arg Leu Leu Asn Thr Thr Asp Val
                165                 170                 175

Tyr Leu Leu Pro Ser Leu Asn Pro Asp Gly Phe Glu Arg Ala Arg Glu
            180                 185                 190

Gly Asp Cys Gly Phe Gly Asp Gly Pro Ser Gly Ala Ser Gly Arg
            195                 200                 205

Asp Asn Ser Arg Gly Arg Asp Leu Asn Arg Ser Phe Pro Asp Gln Phe
        210                 215                 220

Ser Thr Gly Glu Pro Pro Ala Leu Asp Glu Val Pro Glu Val Arg Ala
225                 230                 235                 240

Leu Ile Glu Trp Ile Arg Arg Asn Lys Phe Val Leu Ser Gly Asn Leu
                245                 250                 255

His Gly Gly Ser Val Val Ala Ser Tyr Pro Phe Asp Asp Ser Pro Glu
            260                 265                 270

His Lys Ala Thr Gly Ile Tyr Ser Lys Thr Ser Asp Asp Glu Val Phe
        275                 280                 285

Lys Tyr Leu Ala Lys Ala Tyr Ala Ser Asn His Pro Ile Met Lys Thr
290                 295                 300

Gly Glu Pro His Cys Pro Gly Asp Glu Asp Thr Phe Lys Asp Gly
305                 310                 315                 320

Ile Thr Asn Gly Ala His Trp Tyr Asp Val Glu Gly Gly Met Gln Asp
                325                 330                 335

Tyr Asn Tyr Val Trp Ala Asn Cys Phe Glu Ile Thr Leu Glu Leu Ser
            340                 345                 350

Cys Cys Lys Tyr Pro Pro Ala Ser Gln Leu Arg Gln Glu Trp Glu Asn
        355                 360                 365

Asn Arg Glu Ser Leu Ile Thr Leu Ile Glu Lys Val His Ile Gly Val
        370                 375                 380

Lys Gly Phe Val Lys Asp Ser Ile Thr Gly Ser Gly Leu Glu Asn Ala
385                 390                 395                 400

Thr Ile Ser Val Ala Gly Ile Asn His Asn Ile Thr Thr Gly Arg Phe
                405                 410                 415

Gly Asp Phe Tyr Arg Leu Leu Val Pro Gly Thr Tyr Asn Leu Thr Val
            420                 425                 430

Val Leu Thr Gly Tyr Met Pro Leu Thr Val Thr Asn Val Val Val Lys
        435                 440                 445

Glu Gly Pro Ala Thr Glu Val Asp Phe Ser Leu Arg Pro Thr Val Thr
        450                 455                 460

Ser Val Ile Pro Asp Thr Thr Glu Ala Val Ser Thr Ala Ser Thr Val
465                 470                 475                 480

Ala Ile Pro Asn Ile Leu Ser Gly Thr Ser Ser Ser Tyr Gln Pro Ile
                485                 490                 495

Gln Pro Lys Asp Phe His His His Phe Pro Asp Met Glu Ile Phe
            500                 505                 510

Leu Arg Arg Phe Ala Asn Glu Tyr Pro Asn Ile Thr Arg Leu Tyr Ser
        515                 520                 525

Leu Gly Lys Ser Val Glu Ser Arg Glu Leu Tyr Val Met Glu Ile Ser
530                 535                 540
```

-continued

```
Asp Asn Pro Gly Val His Glu Pro Gly Glu Pro Glu Phe Lys Tyr Ile
545                 550                 555                 560

Gly Asn Met His Gly Asn Glu Val Val Gly Arg Glu Leu Leu Leu Asn
            565                 570                 575

Leu Ile Glu Tyr Leu Cys Lys Asn Phe Gly Thr Asp Pro Glu Val Thr
        580                 585                 590

Asp Leu Val His Asn Thr Arg Ile His Leu Met Pro Ser Met Asn Pro
    595                 600                 605

Asp Gly Tyr Glu Lys Ser Gln Glu Gly Asp Ser Ile Ser Val Ile Gly
610                 615                 620

Arg Asn Asn Ser Asn Asn Phe Asp Leu Asn Arg Asn Phe Pro Asp Gln
625                 630                 635                 640

Phe Val Gln Ile Thr Asp Pro Thr Gln Pro Glu Thr Ile Ala Val Met
            645                 650                 655

Ser Trp Met Lys Ser Tyr Pro Phe Val Leu Ser Ala Asn Leu His Gly
        660                 665                 670

Gly Ser Leu Val Val Asn Tyr Pro Phe Asp Asp Glu Gln Gly Leu
    675                 680                 685

Ala Thr Tyr Ser Lys Ser Pro Asp Asp Ala Val Phe Gln Gln Ile Ala
690                 695                 700

Leu Ser Tyr Ser Lys Glu Asn Ser Gln Met Phe Gln Gly Arg Pro Cys
705                 710                 715                 720

Lys Asn Met Tyr Pro Asn Glu Tyr Phe Pro His Gly Ile Thr Asn Gly
            725                 730                 735

Ala Ser Trp Tyr Asn Val Pro Gly Gly Met Gln Asp Trp Asn Tyr Leu
        740                 745                 750

Gln Thr Asn Cys Phe Glu Val Thr Ile Glu Leu Gly Cys Val Lys Tyr
    755                 760                 765

Pro Leu Glu Lys Glu Leu Pro Asn Phe Trp Glu Gln Asn Arg Arg Ser
770                 775                 780

Leu Ile Gln Phe Met Lys Gln Val His Gln Gly Val Arg Gly Phe Val
785                 790                 795                 800

Leu Asp Ala Thr Asp Gly Arg Gly Ile Leu Asn Ala Thr Ile Ser Val
            805                 810                 815

Ala Glu Ile Asn His Pro Val Thr Thr Tyr Lys Thr Gly Asp Tyr Trp
        820                 825                 830

Arg Leu Leu Val Pro Gly Thr Tyr Lys Ile Thr Ala Ser Ala Arg Gly
    835                 840                 845

Tyr Asn Pro Val Thr Lys Asn Val Thr Val Lys Ser Glu Gly Ala Ile
850                 855                 860

Gln Val Asn Phe Thr Leu Val Arg Ser Ser Thr Asp Ser Asn Asn Glu
865                 870                 875                 880

Ser Lys Lys Gly Lys Gly Ala Ser Ser Thr Asn Asp Ala Ser Asp
            885                 890                 895

Pro Thr Thr Lys Glu Phe Glu Thr Leu Ile Lys Asp Leu Ser Ala Glu
        900                 905                 910

Asn Gly Leu Glu Ser Leu Met Leu Arg Ser Ser Asn Leu Ala Leu
    915                 920                 925

Ala Leu Tyr Arg Tyr His Ser Tyr Lys Asp Leu Ser Glu Phe Leu Arg
930                 935                 940

Gly Leu Val Met Asn Tyr Pro His Ile Thr Asn Leu Thr Asn Leu Gly
945                 950                 955                 960
```

```
Gln Ser Thr Glu Tyr Arg His Ile Trp Ser Leu Glu Ile Ser Asn Lys
            965                 970                 975
Pro Asn Val Ser Glu Pro Glu Pro Lys Ile Arg Phe Val Ala Gly
            980                 985                 990
Ile His Gly Asn Ala Pro Val Gly Thr Glu Leu Leu Leu Ala Leu Ala
            995                 1000                1005
Glu Phe Leu Cys Leu Asn Tyr Lys Lys Asn Pro Ala Val Thr Gln
        1010                1015                1020
Leu Val Asp Arg Thr Arg Ile Val Ile Val Pro Ser Leu Asn Pro
        1025                1030                1035
Asp Gly Arg Glu Arg Ala Gln Glu Lys Asp Cys Thr Ser Lys Ile
        1040                1045                1050
Gly Gln Thr Asn Ala Arg Gly Lys Asp Leu Asp Thr Asp Phe Thr
        1055                1060                1065
Asn Asn Ala Ser Gln Pro Glu Thr Lys Ala Ile Ile Glu Asn Leu
        1070                1075                1080
Ile Gln Lys Gln Asp Phe Ser Leu Ser Val Ala Leu Asp Gly Gly
        1085                1090                1095
Ser Met Leu Val Thr Tyr Pro Tyr Asp Lys Pro Val Gln Thr Val
        1100                1105                1110
Glu Asn Lys Glu Thr Leu Lys His Leu Ala Ser Leu Tyr Ala Asn
        1115                1120                1125
Asn His Pro Ser Met His Met Gly Gln Pro Ser Cys Pro Asn Lys
        1130                1135                1140
Ser Asp Glu Asn Ile Pro Gly Gly Val Met Arg Gly Ala Glu Trp
        1145                1150                1155
His Ser His Leu Gly Ser Met Lys Asp Tyr Ser Val Thr Tyr Gly
        1160                1165                1170
His Cys Pro Glu Ile Thr Val Tyr Thr Ser Cys Cys Tyr Phe Pro
        1175                1180                1185
Ser Ala Ala Arg Leu Pro Ser Leu Trp Ala Asp Asn Lys Arg Ser
        1190                1195                1200
Leu Leu Ser Met Leu Val Glu Val His Lys Gly Val His Gly Phe
        1205                1210                1215
Val Lys Asp Lys Thr Gly Lys Pro Ile Ser Lys Ala Val Ile Val
        1220                1225                1230
Leu Asn Glu Gly Ile Lys Val Gln Thr Lys Glu Gly Gly Tyr Phe
        1235                1240                1245
His Val Leu Leu Ala Pro Gly Val His Asn Ile Ala Ile Ala
        1250                1255                1260
Asp Gly Tyr Gln Gln Gln His Ser Gln Val Phe Val His His Asp
        1265                1270                1275
Ala Ala Ser Ser Val Val Ile Val Phe Asp Thr Asp Asn Arg Ile
        1280                1285                1290
Phe Gly Leu Pro Arg Glu Leu Val Val Thr Val Ser Gly Ala Thr
        1295                1300                1305
Met Ser Ala Leu Ile Leu Thr Ala Cys Ile Ile Trp Cys Ile Cys
        1310                1315                1320
Ser Ile Lys Ser Asn Arg His Lys Asp Gly Phe His Arg Leu Arg
        1325                1330                1335
Gln His His Asp Glu Tyr Glu Asp Glu Ile Arg Met Met Ser Thr
        1340                1345                1350
Gly Ser Lys Lys Ser Leu Leu Ser His Glu Phe Gln Asp Glu Thr
```

```
             1355                1360                1365
Asp Thr Glu Glu Glu Thr Leu Tyr Ser Ser Lys His
        1370                1375                1380

<210> SEQ ID NO 46
<211> LENGTH: 167
<212> TYPE: PRT
<213> ORGANISM: homo sapiens

<400> SEQUENCE: 46

Met Leu Pro Glu Lys Ala Leu His Gly His Pro Gln Leu Pro Arg Thr
1               5                   10                  15

Val Pro Thr Arg Ala Ala Met Arg Ala Ala Gly Thr Leu Leu Ala Phe
            20                  25                  30

Cys Cys Leu Val Leu Ser Thr Thr Gly Gly Pro Ser Pro Asp Thr Cys
        35                  40                  45

Ser Gln Asp Leu Asn Ser Arg Val Lys Pro Gly Phe Pro Lys Thr Ile
50                  55                  60

Lys Thr Asn Asp Pro Gly Val Leu Gln Ala Ala Arg Tyr Ser Val Glu
65                  70                  75                  80

Lys Phe Asn Asn Cys Thr Asn Asp Met Phe Leu Phe Lys Glu Ser Arg
                85                  90                  95

Ile Thr Arg Ala Leu Val Gln Ile Val Lys Gly Leu Lys Tyr Met Leu
            100                 105                 110

Glu Val Glu Ile Gly Arg Thr Thr Cys Lys Lys Asn Gln His Leu Arg
        115                 120                 125

Leu Asp Asp Cys Asp Phe Gln Thr Asn His Thr Leu Lys Gln Thr Leu
130                 135                 140

Ser Cys Tyr Ser Glu Val Trp Val Val Pro Trp Leu Gln His Phe Glu
145                 150                 155                 160

Val Pro Val Leu Arg Cys His
                165

<210> SEQ ID NO 47
<211> LENGTH: 384
<212> TYPE: PRT
<213> ORGANISM: homo sapiens

<400> SEQUENCE: 47

Met Lys Val Thr Ser Leu Asp Gly Arg Gln Leu Arg Lys Met Leu Arg
1               5                   10                  15

Lys Glu Ala Ala Arg Cys Val Val Leu Asp Cys Arg Pro Tyr Leu
            20                  25                  30

Ala Phe Ala Ala Ser Asn Val Arg Gly Ser Leu Asn Val Asn Leu Asn
        35                  40                  45

Ser Val Val Leu Arg Arg Ala Arg Gly Gly Ala Val Ser Ala Arg Tyr
50                  55                  60

Val Leu Pro Asp Glu Ala Ala Arg Leu Leu Gln Glu Gly Gly
65                  70                  75                  80

Gly Gly Val Ala Ala Val Val Leu Asp Gln Gly Ser Arg His Trp
            85                  90                  95

Gln Lys Leu Arg Glu Glu Ser Ala Ala Arg Val Val Leu Thr Ser Leu
            100                 105                 110

Leu Ala Cys Leu Pro Ala Gly Pro Arg Val Tyr Phe Leu Lys Gly Gly
        115                 120                 125

Tyr Glu Thr Phe Tyr Ser Glu Tyr Pro Glu Cys Cys Val Asp Val Lys
```

```
            130                 135                 140
Pro Ile Ser Gln Glu Lys Ile Glu Ser Glu Arg Ala Leu Ile Ser Gln
145                 150                 155                 160

Cys Gly Lys Pro Val Val Asn Val Ser Tyr Arg Pro Ala Tyr Asp Gln
                165                 170                 175

Gly Gly Pro Val Glu Ile Leu Pro Phe Leu Tyr Leu Gly Ser Ala Tyr
            180                 185                 190

His Ala Ser Lys Cys Glu Phe Leu Ala Asn Leu His Ile Thr Ala Leu
        195                 200                 205

Leu Asn Val Ser Arg Arg Thr Ser Glu Ala Cys Ala Thr His Leu His
    210                 215                 220

Tyr Lys Trp Ile Pro Val Glu Asp Ser His Thr Ala Asp Ile Ser Ser
225                 230                 235                 240

His Phe Gln Glu Ala Ile Asp Phe Ile Asp Cys Val Arg Glu Lys Gly
                245                 250                 255

Gly Lys Val Leu Val His Cys Glu Ala Gly Ile Ser Arg Ser Pro Thr
            260                 265                 270

Ile Cys Met Ala Tyr Leu Met Lys Thr Lys Gln Phe Arg Leu Lys Glu
        275                 280                 285

Ala Phe Asp Tyr Ile Lys Gln Arg Arg Ser Met Val Ser Pro Asn Phe
    290                 295                 300

Gly Phe Met Gly Gln Leu Leu Gln Tyr Glu Ser Glu Ile Leu Pro Ser
305                 310                 315                 320

Thr Pro Asn Pro Gln Pro Pro Ser Cys Gln Gly Glu Ala Ala Gly Ser
                325                 330                 335

Ser Leu Ile Gly His Leu Gln Thr Leu Ser Pro Asp Met Gln Gly Ala
            340                 345                 350

Tyr Cys Thr Phe Pro Ala Ser Val Leu Ala Pro Val Pro Thr His Ser
        355                 360                 365

Thr Val Ser Glu Leu Ser Arg Ser Pro Val Ala Thr Ala Thr Ser Cys
    370                 375                 380

<210> SEQ ID NO 48
<211> LENGTH: 1445
<212> TYPE: PRT
<213> ORGANISM: homo sapiens

<400> SEQUENCE: 48

Met Arg Arg Leu Leu Glu Pro Cys Trp Trp Ile Leu Phe Leu Lys Ile
1               5                   10                  15

Thr Ser Ser Val Leu His Tyr Val Val Cys Phe Pro Ala Leu Thr Glu
                20                  25                  30

Gly Tyr Val Gly Ala Leu His Glu Asn Arg His Gly Ser Ala Val Gln
            35                  40                  45

Ile Arg Arg Arg Lys Ala Ser Gly Asp Pro Tyr Trp Ala Tyr Ser Gly
        50                  55                  60

Ala Tyr Gly Pro Glu His Trp Val Thr Ser Val Ser Cys Gly Gly
65                  70                  75                  80

Arg His Gln Ser Pro Ile Asp Ile Leu Asp Gln Tyr Ala Arg Val Gly
                85                  90                  95

Glu Glu Tyr Gln Glu Leu Gln Leu Asp Gly Phe Asp Asn Glu Ser Ser
            100                 105                 110

Asn Lys Thr Trp Met Lys Asn Thr Gly Lys Thr Val Ala Ile Leu Leu
        115                 120                 125
```

```
Lys Asp Asp Tyr Phe Val Ser Gly Ala Gly Leu Pro Gly Arg Phe Lys
130                 135                 140

Ala Glu Lys Val Glu Phe His Trp Gly His Ser Asn Gly Ser Ala Gly
145                 150                 155                 160

Ser Glu His Ser Ile Asn Gly Arg Arg Phe Pro Val Glu Met Gln Ile
                165                 170                 175

Phe Phe Tyr Asn Pro Asp Asp Phe Asp Ser Phe Gln Thr Ala Ile Ser
            180                 185                 190

Glu Asn Arg Ile Ile Gly Ala Met Ala Ile Phe Phe Gln Val Ser Pro
        195                 200                 205

Arg Asp Asn Ser Ala Leu Asp Pro Ile Ile His Gly Leu Lys Gly Val
210                 215                 220

Val His His Glu Lys Glu Thr Phe Leu Asp Pro Phe Val Leu Arg Asp
225                 230                 235                 240

Leu Leu Pro Ala Ser Leu Gly Ser Tyr Tyr Arg Tyr Thr Gly Ser Leu
                245                 250                 255

Thr Thr Pro Pro Cys Ser Glu Ile Val Glu Trp Ile Val Phe Arg Arg
            260                 265                 270

Pro Val Pro Ile Ser Tyr His Gln Leu Glu Ala Phe Tyr Ser Ile Phe
        275                 280                 285

Thr Thr Glu Gln Gln Asp His Val Lys Ser Val Glu Tyr Leu Arg Asn
290                 295                 300

Asn Phe Arg Pro Gln Gln Arg Leu His Asp Arg Val Val Ser Lys Ser
305                 310                 315                 320

Ala Val Arg Asp Ser Trp Asn His Asp Met Thr Asp Phe Leu Glu Asn
                325                 330                 335

Pro Leu Gly Thr Glu Ala Ser Lys Val Cys Ser Ser Pro Ile His
            340                 345                 350

Met Lys Val Gln Pro Leu Asn Gln Thr Ala Leu Gln Val Ser Trp Ser
            355                 360                 365

Gln Pro Glu Thr Ile Tyr His Pro Pro Ile Met Asn Tyr Met Ile Ser
370                 375                 380

Tyr Ser Trp Thr Lys Asn Glu Asp Glu Lys Glu Lys Thr Phe Thr Lys
385                 390                 395                 400

Asp Ser Asp Lys Asp Leu Lys Ala Thr Ile Ser His Val Ser Pro Asp
                405                 410                 415

Ser Leu Tyr Leu Phe Arg Val Gln Ala Val Cys Arg Asn Asp Met Arg
            420                 425                 430

Ser Asp Phe Ser Gln Thr Met Leu Phe Gln Ala Asn Thr Thr Arg Ile
            435                 440                 445

Phe Gln Gly Thr Arg Ile Val Lys Thr Gly Val Pro Thr Ala Ser Pro
450                 455                 460

Ala Ser Ser Ala Asp Met Ala Pro Ile Ser Ser Gly Ser Ser Thr Trp
465                 470                 475                 480

Thr Ser Ser Gly Ile Pro Phe Ser Phe Val Ser Met Ala Thr Gly Met
                485                 490                 495

Gly Pro Ser Ser Gly Ser Gln Ala Thr Val Ala Ser Val Val Thr
            500                 505                 510

Ser Thr Leu Leu Ala Gly Leu Gly Phe Gly Gly Gly Ile Ser Ser
            515                 520                 525

Phe Pro Ser Thr Val Trp Pro Thr Arg Leu Pro Thr Ala Ala Ser Ala
530                 535                 540

Ser Lys Gln Ala Ala Arg Pro Val Leu Ala Thr Thr Glu Ala Leu Ala
```

```
            545                 550                 555                 560
Ser Pro Gly Pro Asp Gly Asp Ser Ser Pro Thr Lys Asp Gly Glu Gly
                565                 570                 575

Thr Glu Glu Gly Glu Lys Asp Glu Lys Ser Glu Ser Glu Asp Gly Glu
                580                 585                 590

Arg Glu His Glu Glu Asp Gly Glu Lys Asp Ser Glu Lys Glu Lys
                595                 600                 605

Ser Gly Val Thr His Ala Ala Glu Glu Arg Asn Gln Thr Glu Pro Ser
        610                 615                 620

Pro Thr Pro Ser Ser Pro Asn Arg Thr Ala Glu Gly Gly His Gln Thr
625                 630                 635                 640

Ile Pro Gly His Glu Gln Asp His Thr Ala Val Pro Thr Asp Gln Thr
                645                 650                 655

Gly Gly Arg Arg Asp Ala Gly Pro Gly Leu Asp Pro Asp Met Val Thr
                660                 665                 670

Ser Thr Gln Val Pro Pro Thr Ala Thr Glu Glu Gln Tyr Ala Gly Ser
            675                 680                 685

Asp Pro Lys Arg Pro Glu Met Pro Ser Lys Lys Pro Met Ser Arg Gly
        690                 695                 700

Asp Arg Phe Ser Glu Asp Ser Arg Phe Ile Thr Val Asn Pro Ala Glu
705                 710                 715                 720

Lys Asn Thr Ser Gly Met Ile Ser Arg Ala Pro Gly Arg Met Glu
                725                 730                 735

Trp Ile Ile Pro Leu Ile Val Val Ser Ala Leu Thr Phe Val Cys Leu
                740                 745                 750

Ile Leu Leu Ile Ala Val Leu Val Tyr Trp Arg Gly Cys Asn Lys Ile
            755                 760                 765

Lys Ser Lys Gly Phe Pro Arg Arg Phe Arg Glu Val Pro Ser Ser Gly
        770                 775                 780

Glu Arg Gly Glu Lys Gly Ser Arg Lys Cys Phe Gln Thr Ala His Phe
785                 790                 795                 800

Tyr Val Glu Asp Ser Ser Ser Pro Arg Val Val Pro Asn Glu Ser Ile
                805                 810                 815

Pro Ile Ile Pro Ile Pro Asp Asp Met Glu Ala Ile Pro Val Lys Gln
                820                 825                 830

Phe Val Lys His Ile Gly Glu Leu Tyr Ser Asn Asn Gln His Gly Phe
            835                 840                 845

Ser Glu Asp Phe Glu Glu Val Gln Arg Cys Thr Ala Asp Met Asn Ile
        850                 855                 860

Thr Ala Glu His Ser Asn His Pro Glu Asn Lys His Lys Asn Arg Tyr
865                 870                 875                 880

Ile Asn Ile Leu Ala Tyr Asp His Ser Arg Val Lys Leu Arg Pro Leu
                885                 890                 895

Pro Gly Lys Asp Ser Lys His Ser Asp Tyr Ile Asn Ala Asn Tyr Val
                900                 905                 910

Asp Gly Tyr Asn Lys Ala Lys Ala Tyr Ile Ala Thr Gln Gly Pro Leu
            915                 920                 925

Lys Ser Thr Phe Glu Asp Phe Trp Arg Met Ile Trp Glu Gln Asn Thr
        930                 935                 940

Gly Ile Ile Val Met Ile Thr Asn Leu Val Glu Lys Gly Arg Arg Lys
945                 950                 955                 960

Cys Asp Gln Tyr Trp Pro Thr Glu Asn Ser Glu Glu Tyr Gly Asn Ile
                965                 970                 975
```

```
Ile Val Thr Leu Lys Ser Thr Lys Ile His Ala Cys Tyr Thr Val Arg
            980                 985                 990

Arg Phe Ser Ile Arg Asn Thr Lys  Val Lys Lys Gly Gln  Lys Gly Asn
            995                 1000                1005

Pro Lys Gly Arg Gln Asn Glu  Arg Val Val Ile Gln  Tyr His Tyr
        1010                1015                1020

Thr Gln Trp Pro Asp Met Gly  Val Pro Glu Tyr Ala  Leu Pro Val
        1025                1030                1035

Leu Thr Phe Val Arg Arg Ser  Ser Ala Ala Arg Met  Pro Glu Thr
        1040                1045                1050

Gly Pro Val Leu Val His Cys  Ser Ala Gly Val Gly  Arg Thr Gly
        1055                1060                1065

Thr Tyr Ile Val Ile Asp Ser  Met Leu Gln Gln Ile  Lys Asp Lys
        1070                1075                1080

Ser Thr Val Asn Val Leu Gly  Phe Leu Lys His Ile  Arg Thr Gln
        1085                1090                1095

Arg Asn Tyr Leu Val Gln Thr  Glu Glu Gln Tyr Ile  Phe Ile His
        1100                1105                1110

Asp Ala Leu Leu Glu Ala Ile  Leu Gly Lys Glu Thr  Glu Val Ser
        1115                1120                1125

Ser Asn Gln Leu His Ser Tyr  Val Asn Ser Ile Leu  Ile Pro Gly
        1130                1135                1140

Val Gly Gly Lys Thr Arg Leu  Glu Lys Gln Phe Lys  Leu Val Thr
        1145                1150                1155

Gln Cys Asn Ala Lys Tyr Val  Glu Cys Phe Ser Ala  Gln Lys Glu
        1160                1165                1170

Cys Asn Lys Glu Lys Asn Arg  Asn Ser Ser Val Val  Pro Ser Glu
        1175                1180                1185

Arg Ala Arg Val Gly Leu Ala  Pro Leu Pro Gly Met  Lys Gly Thr
        1190                1195                1200

Asp Tyr Ile Asn Ala Ser Tyr  Ile Met Gly Tyr Tyr  Arg Ser Asn
        1205                1210                1215

Glu Phe Ile Ile Thr Gln His  Pro Leu Pro His Thr  Thr Lys Asp
        1220                1225                1230

Phe Trp Arg Met Ile Trp Asp  His Asn Ala Gln Ile  Ile Val Met
        1235                1240                1245

Leu Pro Asp Asn Gln Ser Leu  Ala Glu Asp Glu Phe  Val Tyr Trp
        1250                1255                1260

Pro Ser Arg Glu Glu Ser Met  Asn Cys Glu Ala Phe  Thr Val Thr
        1265                1270                1275

Leu Ile Ser Lys Asp Arg Leu  Cys Leu Ser Asn Glu  Glu Gln Ile
        1280                1285                1290

Ile Ile His Asp Phe Ile Leu  Glu Ala Thr Gln Asp  Asp Tyr Val
        1295                1300                1305

Leu Glu Val Arg His Phe Gln  Cys Pro Lys Trp Pro  Asn Pro Asp
        1310                1315                1320

Ala Pro Ile Ser Ser Thr Phe  Glu Leu Ile Asn Val  Ile Lys Glu
        1325                1330                1335

Glu Ala Leu Thr Arg Asp Gly  Pro Thr Ile Val His  Asp Glu Tyr
        1340                1345                1350

Gly Ala Val Ser Ala Gly Met  Leu Cys Ala Leu Thr  Thr Leu Ser
        1355                1360                1365
```

```
Gln Gln Leu Glu Asn Glu Asn Ala Val Asp Val Phe Gln Val Ala
    1370                1375                1380

Lys Met Ile Asn Leu Met Arg Pro Gly Val Phe Thr Asp Ile Glu
    1385                1390                1395

Gln Tyr Gln Phe Ile Tyr Lys Ala Met Leu Ser Leu Val Ser Thr
    1400                1405                1410

Lys Glu Asn Gly Asn Gly Pro Met Thr Val Asp Lys Asn Gly Ala
    1415                1420                1425

Val Leu Ile Ala Asp Glu Ser Asp Pro Ala Glu Ser Met Glu Ser
    1430                1435                1440

Leu Val
    1445

<210> SEQ ID NO 49
<211> LENGTH: 468
<212> TYPE: PRT
<213> ORGANISM: homo sapiens

<400> SEQUENCE: 49

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
                20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285
```

```
Val Val Gln Leu Arg Ala Gln Glu Phe Gly Gln Gly Glu Trp Ser
    290                 295                 300
Glu Trp Ser Pro Glu Ala Met Gly Thr Pro Trp Thr Glu Ser Arg Ser
305                 310                 315                 320
Pro Pro Ala Glu Asn Glu Val Ser Thr Pro Met Gln Ala Leu Thr Thr
                325                 330                 335
Asn Lys Asp Asp Asp Asn Ile Leu Phe Arg Asp Ser Ala Asn Ala Thr
            340                 345                 350
Ser Leu Pro Val Gln Asp Ser Ser Val Pro Leu Pro Thr Phe Leu
        355                 360                 365
Val Ala Gly Gly Ser Leu Ala Phe Gly Thr Leu Leu Cys Ile Ala Ile
    370                 375                 380
Val Leu Arg Phe Lys Lys Thr Trp Lys Leu Arg Ala Leu Lys Glu Gly
385                 390                 395                 400
Lys Thr Ser Met His Pro Pro Tyr Ser Leu Gly Gln Leu Val Pro Glu
                405                 410                 415
Arg Pro Arg Pro Thr Pro Val Leu Val Pro Leu Ile Ser Pro Pro Val
            420                 425                 430
Ser Pro Ser Ser Leu Gly Ser Asp Asn Thr Ser Ser His Asn Arg Pro
        435                 440                 445
Asp Ala Arg Asp Pro Arg Ser Pro Tyr Asp Ile Ser Asn Thr Asp Tyr
    450                 455                 460
Phe Phe Pro Arg
465

<210> SEQ ID NO 50
<211> LENGTH: 365
<212> TYPE: PRT
<213> ORGANISM: homo sapiens

<400> SEQUENCE: 50

Met Leu Ala Val Gly Cys Ala Leu Leu Ala Ala Leu Leu Ala Ala Pro
1               5                   10                  15
Gly Ala Ala Leu Ala Pro Arg Arg Cys Pro Ala Gln Glu Val Ala Arg
            20                  25                  30
Gly Val Leu Thr Ser Leu Pro Gly Asp Ser Val Thr Leu Thr Cys Pro
        35                  40                  45
Gly Val Glu Pro Glu Asp Asn Ala Thr Val His Trp Val Leu Arg Lys
    50                  55                  60
Pro Ala Ala Gly Ser His Pro Ser Arg Trp Ala Gly Met Gly Arg Arg
65                  70                  75                  80
Leu Leu Leu Arg Ser Val Gln Leu His Asp Ser Gly Asn Tyr Ser Cys
                85                  90                  95
Tyr Arg Ala Gly Arg Pro Ala Gly Thr Val His Leu Leu Val Asp Val
            100                 105                 110
Pro Pro Glu Glu Pro Gln Leu Ser Cys Phe Arg Lys Ser Pro Leu Ser
        115                 120                 125
Asn Val Val Cys Glu Trp Gly Pro Arg Ser Thr Pro Ser Leu Thr Thr
    130                 135                 140
Lys Ala Val Leu Leu Val Arg Lys Phe Gln Asn Ser Pro Ala Glu Asp
145                 150                 155                 160
Phe Gln Glu Pro Cys Gln Tyr Ser Gln Glu Ser Gln Lys Phe Ser Cys
                165                 170                 175
Gln Leu Ala Val Pro Glu Gly Asp Ser Ser Phe Tyr Ile Val Ser Met
```

```
                180             185              190
Cys Val Ala Ser Ser Val Gly Ser Lys Phe Ser Lys Thr Gln Thr Phe
            195                 200             205

Gln Gly Cys Gly Ile Leu Gln Pro Asp Pro Ala Asn Ile Thr Val
        210                 215             220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
        290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asn Ile Leu Phe Arg Asp Ser Ala Asn Ala Thr
                340                 345                 350

Ser Leu Pro Gly Ser Arg Arg Arg Gly Ser Cys Gly Leu
                355                 360             365

<210> SEQ ID NO 51
<211> LENGTH: 638
<212> TYPE: PRT
<213> ORGANISM: homo sapiens

<400> SEQUENCE: 51

Met Asp Leu Trp Gln Leu Leu Leu Thr Leu Ala Leu Ala Gly Ser Ser
1               5                   10                  15

Asp Ala Phe Ser Gly Ser Glu Ala Thr Ala Ala Ile Leu Ser Arg Ala
                20                  25                  30

Pro Trp Ser Leu Gln Ser Val Asn Pro Gly Leu Lys Thr Asn Ser Ser
            35                  40                  45

Lys Glu Pro Lys Phe Thr Lys Cys Arg Ser Pro Glu Arg Glu Thr Phe
        50                  55                  60

Ser Cys His Trp Thr Asp Glu Val His His Gly Thr Lys Asn Leu Gly
65                  70                  75                  80

Pro Ile Gln Leu Phe Tyr Thr Arg Arg Asn Thr Gln Glu Trp Thr Gln
                85                  90                  95

Glu Trp Lys Glu Cys Pro Asp Tyr Val Ser Ala Gly Glu Asn Ser Cys
            100                 105                 110

Tyr Phe Asn Ser Ser Phe Thr Ser Ile Trp Ile Pro Tyr Cys Ile Lys
        115                 120                 125

Leu Thr Ser Asn Gly Gly Thr Val Asp Glu Lys Cys Phe Ser Val Asp
130                 135                 140

Glu Ile Val Gln Pro Asp Pro Pro Ile Ala Leu Asn Trp Thr Leu Leu
145                 150                 155                 160

Asn Val Ser Leu Thr Gly Ile His Ala Asp Ile Gln Val Arg Trp Glu
                165                 170                 175

Ala Pro Arg Asn Ala Asp Ile Gln Lys Gly Trp Met Val Leu Glu Tyr
            180                 185                 190
```

```
Glu Leu Gln Tyr Lys Glu Val Asn Glu Thr Lys Trp Lys Met Met Asp
            195                 200                 205

Pro Ile Leu Thr Thr Ser Val Pro Val Tyr Ser Leu Lys Val Asp Lys
        210                 215                 220

Glu Tyr Glu Val Arg Val Arg Ser Lys Gln Arg Asn Ser Gly Asn Tyr
225                 230                 235                 240

Gly Glu Phe Ser Glu Val Leu Tyr Val Thr Leu Pro Gln Met Ser Gln
                245                 250                 255

Phe Thr Cys Glu Glu Asp Phe Tyr Pro Trp Leu Leu Ile Ile Ile
            260                 265                 270

Phe Gly Ile Phe Gly Leu Thr Val Met Leu Phe Val Phe Leu Phe Ser
        275                 280                 285

Lys Gln Gln Arg Ile Lys Met Leu Ile Leu Pro Pro Val Pro Val Pro
    290                 295                 300

Lys Ile Lys Gly Ile Asp Pro Asp Leu Leu Lys Glu Gly Lys Leu Glu
305                 310                 315                 320

Glu Val Asn Thr Ile Leu Ala Ile His Asp Ser Tyr Lys Pro Glu Phe
                325                 330                 335

His Ser Asp Asp Ser Trp Val Glu Phe Ile Glu Leu Asp Ile Asp Glu
            340                 345                 350

Pro Asp Glu Lys Thr Glu Glu Ser Asp Thr Asp Arg Leu Leu Ser Ser
        355                 360                 365

Asp His Glu Lys Ser His Ser Asn Leu Gly Val Lys Asp Gly Asp Ser
    370                 375                 380

Gly Arg Thr Ser Cys Cys Glu Pro Asp Ile Leu Glu Thr Asp Phe Asn
385                 390                 395                 400

Ala Asn Asp Ile His Glu Gly Thr Ser Glu Val Ala Gln Pro Gln Arg
                405                 410                 415

Leu Lys Gly Glu Ala Asp Leu Leu Cys Leu Asp Gln Lys Asn Gln Asn
            420                 425                 430

Asn Ser Pro Tyr His Asp Ala Cys Pro Ala Thr Gln Gln Pro Ser Val
        435                 440                 445

Ile Gln Ala Glu Lys Asn Lys Pro Gln Pro Leu Pro Thr Glu Gly Ala
    450                 455                 460

Glu Ser Thr His Gln Ala Ala His Ile Gln Leu Ser Asn Pro Ser Ser
465                 470                 475                 480

Leu Ser Asn Ile Asp Phe Tyr Ala Gln Val Ser Asp Ile Thr Pro Ala
                485                 490                 495

Gly Ser Val Val Leu Ser Pro Gly Gln Lys Asn Lys Ala Gly Met Ser
            500                 505                 510

Gln Cys Asp Met His Pro Glu Met Val Ser Leu Cys Gln Glu Asn Phe
        515                 520                 525

Leu Met Asp Asn Ala Tyr Phe Cys Glu Ala Asp Ala Lys Lys Cys Ile
    530                 535                 540

Pro Val Ala Pro His Ile Lys Val Glu Ser His Ile Gln Pro Ser Leu
545                 550                 555                 560

Asn Gln Glu Asp Ile Tyr Ile Thr Thr Glu Ser Leu Thr Thr Ala Ala
                565                 570                 575

Gly Arg Pro Gly Thr Gly Glu His Val Pro Gly Ser Glu Met Pro Val
            580                 585                 590

Pro Asp Tyr Thr Ser Ile His Ile Val Gln Ser Pro Gln Gly Leu Ile
        595                 600                 605

Leu Asn Ala Thr Ala Leu Pro Leu Pro Asp Lys Glu Phe Leu Ser Ser
```

```
                610                 615                 620
Cys Gly Tyr Val Ser Thr Asp Gln Leu Asn Lys Ile Met Pro
625                 630                 635

<210> SEQ ID NO 52
<211> LENGTH: 207
<212> TYPE: PRT
<213> ORGANISM: homo sapiens

<400> SEQUENCE: 52

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205

<210> SEQ ID NO 53
<211> LENGTH: 204
<212> TYPE: PRT
<213> ORGANISM: homo sapiens

<400> SEQUENCE: 53

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
```

```
            100                 105                 110
Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
            195                 200

<210> SEQ ID NO 54
<211> LENGTH: 200
<212> TYPE: PRT
<213> ORGANISM: homo sapiens

<400> SEQUENCE: 54

Met Ser Pro Glu Pro Ala Leu Ser Pro Ala Leu Gln Leu Leu Leu Trp
1               5                   10                  15

His Ser Ala Leu Trp Thr Val Gln Glu Ala Thr Pro Leu Gly Pro Ala
            20                  25                  30

Ser Ser Leu Pro Gln Ser Phe Leu Leu Lys Cys Leu Glu Gln Val Arg
        35                  40                  45

Lys Ile Gln Gly Asp Gly Ala Ala Leu Gln Glu Lys Leu Cys Ala Thr
    50                  55                  60

Tyr Lys Leu Cys His Pro Glu Glu Leu Val Leu Leu Gly His Ser Leu
65                  70                  75                  80

Gly Ile Pro Trp Ala Pro Leu Ser Ser Cys Pro Ser Gln Ala Leu Gln
                85                  90                  95

Leu Ala Gly Cys Leu Ser Gln Leu His Ser Gly Leu Phe Leu Tyr Gln
            100                 105                 110

Gly Leu Leu Gln Ala Leu Glu Gly Ile Ser Pro Glu Leu Gly Pro Thr
        115                 120                 125

Leu Asp Thr Leu Gln Leu Asp Val Ala Asp Phe Ala Thr Thr Ile Trp
    130                 135                 140

Gln Gln Met Glu Glu Leu Gly Met Ala Pro Ala Leu Gln Pro Thr Gln
145                 150                 155                 160

Gly Ala Met Pro Ala Phe Ala Ser Ala Phe Gln Arg Arg Ala Gly Gly
                165                 170                 175

Val Leu Val Ala Ser His Leu Gln Ser Phe Leu Glu Val Ser Tyr Arg
            180                 185                 190

Val Leu Arg His Leu Ala Gln Pro
        195                 200

<210> SEQ ID NO 55
<211> LENGTH: 528
<212> TYPE: PRT
<213> ORGANISM: homo sapiens

<400> SEQUENCE: 55

Met Ala Gly Ser Asp Thr Ala Pro Phe Leu Ser Gln Ala Asp Asp Pro
1               5                   10                  15

Asp Asp Gly Pro Val Pro Gly Thr Pro Gly Leu Pro Gly Ser Thr Gly
```

-continued

```
                20                  25                  30
Asn Pro Lys Ser Glu Glu Pro Glu Val Pro Asp Gln Glu Gly Leu Gln
            35                  40                  45
Arg Ile Thr Gly Leu Ser Pro Gly Arg Ser Ala Leu Ile Val Ala Val
        50                  55                  60
Leu Cys Tyr Ile Asn Leu Leu Asn Tyr Met Asp Arg Phe Thr Val Ala
65                  70                  75                  80
Gly Val Leu Pro Asp Ile Glu Gln Phe Phe Asn Ile Gly Asp Ser Ser
                85                  90                  95
Ser Gly Leu Ile Gln Thr Val Phe Ile Ser Ser Tyr Met Val Leu Ala
            100                 105                 110
Pro Val Phe Gly Tyr Leu Gly Asp Arg Tyr Asn Arg Lys Tyr Leu Met
        115                 120                 125
Cys Gly Gly Ile Ala Phe Trp Ser Leu Val Thr Leu Gly Ser Ser Phe
    130                 135                 140
Ile Pro Gly Glu His Phe Trp Leu Leu Leu Thr Arg Gly Leu Val
145                 150                 155                 160
Gly Val Gly Glu Ala Ser Tyr Ser Thr Ile Ala Pro Thr Leu Ile Ala
                165                 170                 175
Asp Leu Phe Val Ala Asp Gln Arg Ser Arg Met Leu Ser Ile Phe Tyr
            180                 185                 190
Phe Ala Ile Pro Val Gly Ser Gly Leu Gly Tyr Ile Ala Gly Ser Lys
        195                 200                 205
Val Lys Asp Met Ala Gly Asp Trp His Trp Ala Leu Arg Val Thr Pro
    210                 215                 220
Gly Leu Gly Val Val Ala Val Leu Leu Leu Phe Leu Val Val Arg Glu
225                 230                 235                 240
Pro Pro Arg Gly Ala Val Glu Arg His Ser Asp Leu Pro Pro Leu Asn
                245                 250                 255
Pro Thr Ser Trp Trp Ala Asp Leu Arg Ala Leu Ala Arg Asn Pro Ser
            260                 265                 270
Phe Val Leu Ser Ser Leu Gly Phe Thr Ala Val Ala Phe Val Thr Gly
        275                 280                 285
Ser Leu Ala Leu Trp Ala Pro Ala Phe Leu Leu Arg Ser Arg Val Val
    290                 295                 300
Leu Gly Glu Thr Pro Pro Cys Leu Pro Gly Asp Ser Cys Ser Ser Ser
305                 310                 315                 320
Asp Ser Leu Ile Phe Gly Leu Ile Thr Cys Leu Thr Gly Val Leu Gly
                325                 330                 335
Val Gly Leu Gly Val Glu Ile Ser Arg Arg Leu Arg His Ser Asn Pro
            340                 345                 350
Arg Ala Asp Pro Leu Val Cys Ala Thr Gly Leu Leu Gly Ser Ala Pro
        355                 360                 365
Phe Leu Phe Leu Ser Leu Ala Cys Ala Arg Gly Ser Ile Val Ala Thr
    370                 375                 380
Tyr Ile Phe Ile Phe Ile Gly Glu Thr Leu Leu Ser Met Asn Trp Ala
385                 390                 395                 400
Ile Val Ala Asp Ile Leu Leu Tyr Val Val Ile Pro Thr Arg Arg Ser
                405                 410                 415
Thr Ala Glu Ala Phe Gln Ile Val Leu Ser His Leu Leu Gly Asp Ala
            420                 425                 430
Gly Ser Pro Tyr Leu Ile Gly Leu Ile Ser Asp Arg Leu Arg Arg Asn
        435                 440                 445
```

```
Trp Pro Pro Ser Phe Leu Ser Glu Phe Arg Ala Leu Gln Phe Ser Leu
    450                 455                 460

Met Leu Cys Ala Phe Val Gly Ala Leu Gly Gly Ala Ala Phe Leu Gly
465                 470                 475                 480

Thr Ala Ile Phe Ile Glu Ala Asp Arg Arg Ala Gln Leu His Val
                485                 490                 495

Gln Gly Leu Leu His Glu Ala Gly Ser Thr Asp Asp Arg Ile Val Val
                500                 505                 510

Pro Gln Arg Gly Arg Ser Thr Arg Val Pro Val Ala Ser Val Leu Ile
            515                 520                 525
```

<210> SEQ ID NO 56
<211> LENGTH: 19
<212> TYPE: DNA
<213> ORGANISM: Homo sapiens

<400> SEQUENCE: 56
cgcacctcaa gccctatgt                                                19

<210> SEQ ID NO 57
<211> LENGTH: 19
<212> TYPE: DNA
<213> ORGANISM: Homo sapiens

<400> SEQUENCE: 57
aacatggtcc gagtagaag                                                19

<210> SEQ ID NO 58
<211> LENGTH: 19
<212> TYPE: DNA
<213> ORGANISM: Homo sapiens

<400> SEQUENCE: 58
agaggagctg atagcggag                                                19

<210> SEQ ID NO 59
<211> LENGTH: 19
<212> TYPE: DNA
<213> ORGANISM: Homo sapiens

<400> SEQUENCE: 59
aatgggagcg gaagaagtt                                                19

<210> SEQ ID NO 60
<211> LENGTH: 19
<212> TYPE: DNA
<213> ORGANISM: Homo sapiens

<400> SEQUENCE: 60
catcctgcag tgggacttc                                                19

<210> SEQ ID NO 61
<211> LENGTH: 19
<212> TYPE: DNA
<213> ORGANISM: Homo sapiens

<400> SEQUENCE: 61
caacatggtc ttctacctg                                                19

<210> SEQ ID NO 62
<211> LENGTH: 19

```
<212> TYPE: DNA
<213> ORGANISM: Homo sapiens

<400> SEQUENCE: 62
gtacaaatgg ctgtcagtt                                              19

<210> SEQ ID NO 63
<211> LENGTH: 19
<212> TYPE: DNA
<213> ORGANISM: Homo sapiens

<400> SEQUENCE: 63
ttgagaatgt tcccacagg                                              19

<210> SEQ ID NO 64
<211> LENGTH: 19
<212> TYPE: DNA
<213> ORGANISM: Homo sapiens

<400> SEQUENCE: 64
atggagatgg tactggagt                                              19

<210> SEQ ID NO 65
<211> LENGTH: 19
<212> TYPE: DNA
<213> ORGANISM: Homo sapiens

<400> SEQUENCE: 65
aggatgcagc taacaacaa                                              19

<210> SEQ ID NO 66
<211> LENGTH: 19
<212> TYPE: DNA
<213> ORGANISM: Homo sapiens

<400> SEQUENCE: 66
actgtgcgcg tacacataa                                              19

<210> SEQ ID NO 67
<211> LENGTH: 19
<212> TYPE: DNA
<213> ORGANISM: Homo sapiens

<400> SEQUENCE: 67
atgctccaca atttgtggc                                              19

<210> SEQ ID NO 68
<211> LENGTH: 19
<212> TYPE: DNA
<213> ORGANISM: Homo sapiens

<400> SEQUENCE: 68
catgggctat ctcaagcca                                              19

<210> SEQ ID NO 69
<211> LENGTH: 19
<212> TYPE: DNA
<213> ORGANISM: Homo sapiens

<400> SEQUENCE: 69
aacatgggct atctcaagc                                              19

<210> SEQ ID NO 70
```

```
<211> LENGTH: 19
<212> TYPE: DNA
<213> ORGANISM: Homo sapiens

<400> SEQUENCE: 70
cagaacccaa acctggtat                                                19

<210> SEQ ID NO 71
<211> LENGTH: 19
<212> TYPE: DNA
<213> ORGANISM: Homo sapiens

<400> SEQUENCE: 71
gccatattgt ctcccttct                                                19

<210> SEQ ID NO 72
<211> LENGTH: 19
<212> TYPE: DNA
<213> ORGANISM: Homo sapiens

<400> SEQUENCE: 72
acagcagcgc caaccctat                                                19

<210> SEQ ID NO 73
<211> LENGTH: 19
<212> TYPE: DNA
<213> ORGANISM: Homo sapiens

<400> SEQUENCE: 73
aaggctcgcg cttcttctt                                                19

<210> SEQ ID NO 74
<211> LENGTH: 19
<212> TYPE: DNA
<213> ORGANISM: Homo sapiens

<400> SEQUENCE: 74
cattgagaca agaacaagc                                                19

<210> SEQ ID NO 75
<211> LENGTH: 19
<212> TYPE: DNA
<213> ORGANISM: Homo sapiens

<400> SEQUENCE: 75
agatggactc taccaagcc                                                19

<210> SEQ ID NO 76
<211> LENGTH: 19
<212> TYPE: DNA
<213> ORGANISM: Homo sapiens

<400> SEQUENCE: 76
attgggaagt caacactgg                                                19

<210> SEQ ID NO 77
<211> LENGTH: 19
<212> TYPE: DNA
<213> ORGANISM: Homo sapiens

<400> SEQUENCE: 77
cagatgtttc cgcagctga                                                19
```

```
<210> SEQ ID NO 78
<211> LENGTH: 19
<212> TYPE: DNA
<213> ORGANISM: Homo sapiens

<400> SEQUENCE: 78
ccagacaatt acccatgta                                              19

<210> SEQ ID NO 79
<211> LENGTH: 19
<212> TYPE: DNA
<213> ORGANISM: Homo sapiens

<400> SEQUENCE: 79
acctccaaag caacagagt                                              19

<210> SEQ ID NO 80
<211> LENGTH: 19
<212> TYPE: DNA
<213> ORGANISM: Homo sapiens

<400> SEQUENCE: 80
agttgttccc tgaatcagt                                              19

<210> SEQ ID NO 81
<211> LENGTH: 19
<212> TYPE: DNA
<213> ORGANISM: Homo sapiens

<400> SEQUENCE: 81
aagtcccagg aaggagatt                                              19

<210> SEQ ID NO 82
<211> LENGTH: 19
<212> TYPE: DNA
<213> ORGANISM: Homo sapiens

<400> SEQUENCE: 82
acattcacag gtctttgtg                                              19

<210> SEQ ID NO 83
<211> LENGTH: 19
<212> TYPE: DNA
<213> ORGANISM: Homo sapiens

<400> SEQUENCE: 83
cgaacgacat gttcttgtt                                              19

<210> SEQ ID NO 84
<211> LENGTH: 19
<212> TYPE: DNA
<213> ORGANISM: Homo sapiens

<400> SEQUENCE: 84
cttgttccca ggaccttaa                                              19

<210> SEQ ID NO 85
<211> LENGTH: 19
<212> TYPE: DNA
<213> ORGANISM: Homo sapiens

<400> SEQUENCE: 85
tgacattagc tcccactttt                                             19
```

-continued

```
<210> SEQ ID NO 86
<211> LENGTH: 19
<212> TYPE: DNA
<213> ORGANISM: Homo sapiens

<400> SEQUENCE: 86
actgggatgg aggaatcgg                                                  19

<210> SEQ ID NO 87
<211> LENGTH: 19
<212> TYPE: DNA
<213> ORGANISM: Homo sapiens

<400> SEQUENCE: 87
ccaggagtag gaggaaaga                                                  19

<210> SEQ ID NO 88
<211> LENGTH: 19
<212> TYPE: DNA
<213> ORGANISM: Homo sapiens

<400> SEQUENCE: 88
cggagcagca agaccatgt                                                  19

<210> SEQ ID NO 89
<211> LENGTH: 19
<212> TYPE: DNA
<213> ORGANISM: Homo sapiens

<400> SEQUENCE: 89
acagtccggc cgaagactt                                                  19

<210> SEQ ID NO 90
<211> LENGTH: 19
<212> TYPE: DNA
<213> ORGANISM: Homo sapiens

<400> SEQUENCE: 90
actattcatg ctaccgggc                                                  19

<210> SEQ ID NO 91
<211> LENGTH: 19
<212> TYPE: DNA
<213> ORGANISM: Homo sapiens

<400> SEQUENCE: 91
caacatggat ggtcaagga                                                  19

<210> SEQ ID NO 92
<211> LENGTH: 19
<212> TYPE: DNA
<213> ORGANISM: Homo sapiens

<400> SEQUENCE: 92
agtgagatgg gaagcacca                                                  19

<210> SEQ ID NO 93
<211> LENGTH: 19
<212> TYPE: DNA
<213> ORGANISM: Homo sapiens

<400> SEQUENCE: 93
atgacataca tgagggtac                                                  19
```

<210> SEQ ID NO 94
<211> LENGTH: 19
<212> TYPE: DNA
<213> ORGANISM: Homo sapiens

<400> SEQUENCE: 94
tggaagaact gggaatggc                                                   19

<210> SEQ ID NO 95
<211> LENGTH: 19
<212> TYPE: DNA
<213> ORGANISM: Homo sapiens

<400> SEQUENCE: 95
ctttgccacc accatctgg                                                   19

<210> SEQ ID NO 96
<211> LENGTH: 19
<212> TYPE: DNA
<213> ORGANISM: Homo sapiens

<400> SEQUENCE: 96
aagctcctgt cctcccatc                                                   19

<210> SEQ ID NO 97
<211> LENGTH: 19
<212> TYPE: DNA
<213> ORGANISM: Homo sapiens

<400> SEQUENCE: 97
ccgccatctt cattgaggc                                                   19

<210> SEQ ID NO 98
<211> LENGTH: 19
<212> TYPE: DNA
<213> ORGANISM: Homo sapiens

<400> SEQUENCE: 98
atcttctact ttgccattc                                                   19

<210> SEQ ID NO 99
<211> LENGTH: 19
<212> TYPE: DNA
<213> ORGANISM: homo sapiens

<400> SEQUENCE: 99
actacatgga ccgcttcac                                                   19

<210> SEQ ID NO 100
<211> LENGTH: 12
<212> TYPE: RNA
<213> ORGANISM: Artificial
<220> FEATURE:
<223> OTHER INFORMATION: Loop sequence

<400> SEQUENCE: 100
guuugcuaua ac                                                          12

<210> SEQ ID NO 101
<211> LENGTH: 6132
<212> TYPE: DNA
<213> ORGANISM: Homo sapiens

<400> SEQUENCE: 101

```
aattggaagc aaatgacatc acagcaggtc agagaaaaag ggttgagcgg caggcaccca      60
gagtagtagg tctttggcat taggagcttg agcccagacg gccctagcag ggaccccagc     120
gcccgagaga ccatgcagag gtcgcctctg gaaaaggcca gcgttgtctc caaacttttt     180
ttcagctgga ccagaccaat tttgaggaaa ggatacagac agcgcctgga attgtcagac     240
atataccaaa tcccttctgt tgattctgct gacaatctat ctgaaaaatt ggaaagagaa     300
tgggatagag agctggcttc aaagaaaaat cctaaactca ttaatgccct tcggcgatgt     360
ttttctgga gatttatgtt ctatggaatc ttttatatt taggggaagt caccaaagca      420
gtacagcctc tcttactggg aagaatcata gcttcctatg acccggataa caaggaggaa     480
cgctctatcg cgatttatct aggcatagggc ttatgccttc tctttattgt gaggacactg    540
ctcctacacc cagccatttt tggccttcat cacattggaa tgcagatgag aatagctatg     600
tttagtttga tttataagaa gactttaaag ctgtcaagcc gtgttctaga taaataagt      660
attggacaac ttgttagtct ccttccaac aacctgaaca aatttgatga aggacttgca      720
ttggcacatt tcgtgtggat cgctcctttg caagtggcac tcctcatggg gctaatctgg     780
gagttgttac aggcgtctgc cttctgtgga cttggtttcc tgatagtcct tgcccttttt     840
caggctgggc tagggagaat gatgatgaag tacagagatc agagagctgg gaagatcagt     900
gaaagacttg tgattacctc agaaatgatt gaaaatatcc aatctgttaa ggcatactgc     960
tgggaagaag caatggaaaa aatgattgaa aacttaagac aaacagaact gaaactgact    1020
cggaaggcag cctatgtgag atacttcaat agctcagcct tcttcttctc agggttcttt    1080
gtggtgtttt tatctgtgct tccctatgca ctaatcaaag gaatcatcct ccggaaaata    1140
ttcaccacca tctcattctg cattgttctg cgcatggcgg tcactcggca atttccctgg    1200
gctgtacaaa catggtatga ctctcttgga gcaataaaca aaatacagga tttcttacaa    1260
aagcaagaat ataagacatt ggaatataac ttaacgacta cagaagtagt gatggagaat    1320
gtaacagcct tctgggagga gggatttggg gaattatttg agaaagcaaa acaaaacaat    1380
aacaatagaa aaacttctaa tggtgatgac agcctcttct tcagtaattt ctcacttctt    1440
ggtactcctg tcctgaaaga tattaatttc aagatagaaa gaggacagtt gttggcggtt    1500
gctggatcca ctggagcagg caagacttca cttctaatgg tgattatggg agaactggag    1560
ccttcagagg gtaaaattaa gcacagtgga agaatttcat tctgttctca gttttcctgg    1620
attatgcctg gcaccattaa agaaaatatc atctttggtg tttcctatga tgaatataga    1680
tacagaagcg tcatcaaagc atgccaacta gaagaggaca tctccaagtt tgcagagaaa    1740
gacaatatag ttcttggaga aggtggaatc acactgagtg gaggtcaacg agcaagaatt    1800
tctttagcaa gagcagtata caaagatgct gatttgtatt tattagactc tccttttgga    1860
tacctagatt ttttaacaga aaaagaaata tttgaaagct gtgtctgtaa actgatggct    1920
aacaaaacta ggattttggt cacttctaaa atggaacatt taaagaaagc tgacaaaata    1980
ttaattttgc atgaaggtag cagctatttt tatgggacat tttcagaact ccaaaatcta    2040
cagccagact ttagctcaaa actcatggga tgtgattctt tcgaccaatt tagtgcagaa    2100
agaagaaatt caatcctaac tgagaccta caccgtttct cattagaagg agatgctcct    2160
gtctcctgga cagaaacaaa aaaacaatct tttaaacaga ctggagagtt tgggaaaaa     2220
aggaagaatt ctattctcaa tccaatcaac tctatacgaa aatttccat tgtgcaaaag    2280
actccccttac aaatgaatgg catcgaagag gattctgatg agcctttaga gagaaggctg    2340
```

```
tccttagtac cagattctga gcagggagag gcgatactgc ctcgcatcag cgtgatcagc    2400
actggcccca cgcttcaggc acgaaggagg cagtctgtcc tgaacctgat gacacactca    2460
gttaaccaag gtcagaacat tcaccgaaag acaacagcat ccacacgaaa agtgtcactg    2520
gcccctcagg caaacttgac tgaactggat atatattcaa gaaggttatc tcaagaaact    2580
ggcttggaaa taagtgaaga aattaacgaa gaagacttaa aggagtgctt ttttgatgat    2640
atggagagca taccagcagt gactacatgg aacacatacc ttcgatatat tactgtccac    2700
aagagcttaa ttttgtgct aatttggtgc ttagtaattt ttctggcaga ggtggctgct    2760
tctttggttg tgctgtggct ccttggaaac actcctcttc aagacaaagg gaatagtact    2820
catagtagaa ataacagcta tgcagtgatt atcaccagca ccagttcgta ttatgtgttt    2880
tacatttacg tgggagtagc cgacactttg cttgctatgg gattcttcag aggtctacca    2940
ctggtgcata ctctaatcac agtgtcgaaa attttacacc acaaaatgtt acattctgtt    3000
cttcaagcac ctatgtcaac cctcaacacg ttgaaagcag gtgggattct taatagattc    3060
tccaaagata tagcaatttt ggatgacctt ctgcctctta ccatatttga cttcatccag    3120
ttgttattaa ttgtgattgg agctatagca gttgtcgcag ttttacaacc ctacatcttt    3180
gttgcaacag tgccagtgat agtggctttt attatgttga gagcatattt cctccaaacc    3240
tcacagcaac tcaaacaact ggaatctgaa ggcaggagtc caattttcac tcatcttgtt    3300
acaagcttaa aaggactatg gacacttcgt gccttcggac ggcagcctta ctttgaaact    3360
ctgttccaca aagctctgaa tttacatact gccaactggt tcttgtacct gtcaacactg    3420
cgctggttcc aaatgagaat agaaatgatt tttgtcatct tcttcattgc tgttaccttc    3480
atttccattt taacaacagg agaaggagaa ggaagagttg gtattatcct gactttagcc    3540
atgaatatca tgagtacatt gcagtgggct gtaaactcca gcatagatgt ggatagcttg    3600
atgcgatctg tgagccgagt ctttaagttc attgacatgc caacagaagg taaacctacc    3660
aagtcaacca aaccatacaa gaatggccaa ctctcgaaag ttatgattat tgagaattca    3720
cacgtgaaga aagatgacat ctggccctca gggggccaaa tgactgtcaa agatctcaca    3780
gcaaaataca cagaaggtgg aaatgccata ttagagaaca tttccttctc aataagtcct    3840
ggccagaggg tgggcctctt gggaagaact ggatcaggga agagtacttt gttatcagct    3900
tttttgagac tactgaacac tgaaggagaa atccagatcg atggtgtgtc ttgggattca    3960
ataactttgc aacagtggag gaaagccttt ggagtgatac cacagaaagt atttatttt    4020 tctgaacat ttagaaaaaa cttggatccc tatgaacagt ggagtgatca agaaatatgg    4080
aaagttgcag atgaggttgg gctcagatct gtgatagaac agtttcctgg gaagcttgac    4140
tttgtccttg tggatggggg ctgtgtccta agccatggcc acaagcagtt gatgtgcttg    4200
gctagatctg ttctcagtaa ggcgaagatc ttgctgcttg atgaacccag tgctcatttg    4260
gatccagtaa cataccaaat aattagaaga actctaaaac aagcatttgc tgattgcaca    4320
gtaattctct gtgaacacag gatagaagca atgctggaat gccaacaatt tttggtcata    4380
gaagagaaca aagtgcggca gtacgattcc atccagaaac tgctgaacga gaggagcctc    4440
ttccggcaag ccatcagccc ctccgacagg gtgaagctct tccccaccg gaactcaagc    4500 aagtgcaagt ctaagcccca gattgctgct ctgaaagagg agacagaaga gaggtgcaa    4560 gatcaaggc tttagagagc agcataaatg ttgacatggg acatttgctc atggaattgg    4620
agctcgtggg acagtcacct catggaattg gagctcgtgg aacagttacc tctgcctcag    4680
```

```
aaaacaagga tgaattaagt ttttttttaa aaaagaaaca tttggtaagg ggaattgagg    4740
acactgatat gggtcttgat aaatggcttc ctggcaatag tcaaattgtg tgaaaggtac    4800
ttcaaatcct tgaagattta ccacttgtgt tttgcaagcc agattttcct gaaaacccctt   4860 gccatgtgct agtaattgga aaggcagctc taaatgtcaa tcagcctagt tgatcagctt    4920
attgtctagt gaaactcgtt aatttgtagt gttggagaag aactgaaatc atacttctta   4980
gggttatgat taagtaatga taactggaaa cttcagcggt ttatataagc ttgtattcct    5040
ttttctctcc tctccccatg atgtttagaa acacaactat attgtttgct aagcattcca    5100
actatctcat ttccaagcaa gtattagaat accacaggaa ccacaagact gcacatcaaa    5160
atatgcccca ttcaacatct agtgagcagt caggaaagag aacttccaga tcctggaaat    5220
cagggttagt attgtccagg tctaccaaaa atctcaatat ttcagataat cacaatacat    5280
cccttacctg ggaaagggct gttataatct ttcacagggg acaggatggt tcccttgatg    5340
aagaagttga tatgcctttt cccaactcca gaaagtgaca agctcacaga cctttgaact    5400
agagtttagc tggaaaagta tgttagtgca aattgtcaca ggacagccct tctttccaca    5460
gaagctccag gtagagggtg tgtaagtaga taggccatgg gcactgtggg tagacacaca    5520
tgaagtccaa gcatttagat gtataggttg atggtggtat gttttcaggc tagatgtatg    5580
tacttcatgc tgtctacact aagagagaat gagagacaca ctgaagaagc accaatcatg    5640
aattagtttt atatgcttct gttttataat tttgtgaagc aaaatttttt ctctaggaaa    5700
tatttatttt aataatgttt caaacatata taacaatgct gtattttaaa agaatgatta    5760
tgaattacat ttgtataaaa taattttat atttgaaata ttgacttttt atggcactag     5820
tatttctatg aaatattatg ttaaaactgg gacaggggag aacctagggt gatattaacc    5880
aggggccatg aatcaccttt tggtctggag ggaagccttg gggctgatgc agttgttgcc    5940
cacagctgta tgattcccag ccagcacagc ctcttagatg cagttctgaa gaagatggta    6000
ccaccagtct gactgtttcc atcaagggta cactgccttc tcaactccaa actgactctt    6060
aagaagactg cattatattt attactgtaa gaaaatatca cttgtcaata aaatccatac    6120
atttgtgtga aa                                                        6132

<210> SEQ ID NO 102
<211> LENGTH: 21
<212> TYPE: DNA
<213> ORGANISM: artificial
<220> FEATURE:
<223> OTHER INFORMATION: Primer

<400> SEQUENCE: 102
ccgtttacgt ggagactcgc c                                               21

<210> SEQ ID NO 103
<211> LENGTH: 25
<212> TYPE: DNA
<213> ORGANISM: Artificial
<220> FEATURE:
<223> OTHER INFORMATION: Primer

<400> SEQUENCE: 103
cccccacctt atatatattc tttcc                                           25
```

METHODS FOR IDENTIFYING AND COMPOUNDS USEFUL FOR INCREASING THE FUNCTIONAL ACTIVITY AND CELL SURFACE EXPRESSION OF CF-ASSOCIATED MUTANT CYSTIC FIBROSIS TRANSMEMBRANE CONDUCTANCE REGULATOR

CROSS REFERENCE TO RELATED APPLICATIONS

The present application is a National Stage Application claiming the priority of co-pending PCT Application No. PCT/EP2009/061732 filed Sep. 10, 2009, which in turn, claims priority from U.S. Provisional Application Ser. No. 61/191,809, filed Sep. 11, 2008. Applicants claim the benefits of 35 U.S.C. §120 as to the PCT application and priority under 35 U.S.C. §119 as to the said U.S. provisional application, and the entire disclosures of both applications are incorporated herein by reference in their entireties.

BACKGROUND OF THE INVENTION

The present invention relates to agents, and methods for identifying compounds, which agents and compounds result in the increased functional activity of CF-associated mutant Cystic Fibrosis Transmembrane Conductance Regulator (CFTR). In addition, the invention relates to compositions and methods for the use thereof in treating conditions that are characterized by a decrease in function of CF-associated mutant CFTR including cystic fibrosis (CF), and other protein misfolding diseases.

Cystic Fibrosis Transmembrane Conductance Regulator, a member of the ATP-binding cassette (ABC) transporter family, is believed to regulate the chloride channel responsible for cAMP-mediated chloride secretion in epithelial cells. For reviews on cystic fibrosis we refer to Guggino and Stanton, 2006) and Rowe et al., 2005. By its chloride channel function, CFTR plays a key role in chloride secretion and water balance in epithelia throughout the body. CFTR has been identified and sequenced (Riordan et al., 1989). Defects in this gene causing diminished activity and/or expression of CFTR lead to cystic fibrosis. CF is the most common fatal genetic disease in humans affecting approximately one in every 2,500 infants born in the United States of America. In patients with CF, expression of the CF-associated gene in epithelial cells leads to reduced cellular apical chloride conductance, causing an imbalance in ion and fluid transport. It is widely believed that this leads to the abnormal mucus secretion in pancreatic ductules and in the airways that ultimately results in the pulmonary infections and epithelial cell damage typically associated with disease progression in CF. In addition to respiratory problems, CF patients typically suffer from gastrointestinal problems, and pancreatic insufficiency. Males are almost uniformly infertile and fertility is decreased in females.

Sequence analysis of the CFTR gene of CF chromosomes has revealed a variety of disease-causing mutations. At present, more than 1000 mutations in the CF gene have been identified (http://www.genet.sickkids.on.ca/cftr/ or http://www.ncbi.nlm.nih.gov/entrez/dispomim.cgi?id=602421), but population studies have indicated that the most common CF mutation, a deletion of the 3 nucleotides that encode phenylalanine at position 508 of the CFTR amino acid sequence, is associated with approximately 70% of the cases of cystic fibrosis. The mutated CFTR protein is referred to as ΔF508.

It is believed that the deletion of residue 508 in ΔF508-CFTR prevents the nascent protein from folding correctly, resulting in the inability of this mutant protein to exit the endoplasmic reticulum (ER), and traffic to the plasma membrane. As a result, insufficient amounts of the mature protein are present at the plasma membrane and chloride transport within epithelial tissues is significantly reduced (Quinton, 1990). Studies have shown, however, that ΔF508-CFTR, when presented at the plasma membrane is functional as a cAMP-responsive Cl$^-$ channel (Denning et al., 1992). Correcting ΔF508-CFTR maturation, allowing exit of ΔF508-CFTR from the ER, or enhancing the activity of ΔF508-CFTR would constitute a mode of action of a novel drug to treat CF.

In fact, the cellular phenomenon of defective ER processing of ABC transporters, or other proteins, by the ER machinery has been shown to be the underlying basis not only for CF disease, but for a wide range of other isolated and inherited diseases (Ulloa-Aguirre et al., 2004). This means that drugs found for CF treatment may also be effective in the treatment of other diseases.

No therapy currently exists that restores the function of mutant CFTR. Restoring mutant CFTR function is expected to decrease CF-associated complications, and improve quality of life and expected life-span of CF patients.

Therefore, there is a clear need for molecules that facilitate the folding, processing and/or migration of the ΔF508-CFTR to the plasma membrane, thereby increasing the density of ΔF508-CFTR in the membrane, and rescuing the function of ΔF508-CFTR (correctors). These correctors may be an inhibitory agent, particularly small molecule drug compounds or biologic drugs, which target a protein regulating the processing of ΔF508-CFTR through the ER. To enable the development of such a drug, there is a need to identify target proteins, that, when antagonized, increase the density and functional performance of ΔF508-CFTR in the plasma membrane.

An example of such a protein target is syntaxin-8 (STX8), which is involved in trafficking of vesicles and has been shown to bind to the wild-type CFTR (Antonin et al., 2000; Bilan et al., 2004; Thoreau et al., 1999). It has been shown that syntaxin-8 can function as a drug target by correcting CF-associated mutant CFTR function (Fischer et al., 2006). Another positive control is BCAP31 (Lambert et al., 2001). It has been previously demonstrated that down-regulation of BCAP31 by Ad-siRNA allows functional restoration of ΔF508-CFTR (Fischer et al., 2006).

Therefore, there remains a need to identify further targets which may be of use in the diagnosis, prevention and or treatment of disorders involving ER-associated protein misfolding and in particular diseases characterized by abnormal trafficking of a disease-associated protein. Exemplary conditions include, but are not limited to, Cystic Fibrosis, Parkinson's disease, Gaucher's disease, nephrogenic diabetes insipidus, emphysema and liver disease, Maple syrup urine disease, Fabry's disease, hypogonadotropic hypogonadism, hyperinsulinemic hypoglycemia, beta-galactosidosis, Wilson's disease, long QT syndrome and retinitis pimentosa, transthyretin-linked amyloidosis, Alzheimer's disease, prion disease, and inclusion body myositis. In particular the disease is Cystic Fibrosis. As many of the clinical symptoms (e.g. airway obstruction, chronic inflammation, mucus overproduction, enhanced cytokine production) of CF overlap with those of asthma and COPD (Chronic Obstructive Pulmonary Disease), these targets may also be of use in the diagnosis, prevention and or treatment of asthma and COPD.

SUMMARY OF THE INVENTION

The present invention is based on the discovery that agents which inhibit the expression and/or activity of the TARGETS disclosed herein are able to result in the increased functional activity of CF-associated mutant Cystic Fibrosis Transmembrane Conductance Regulator (CFTR) in human airway bronchial epithelial cells. The present invention therefore provides TARGETS which are involved in the pathway involved in cellular trafficking/protein trafficking and/or folding, methods for screening for agents capable of modulating the expression and/or activity of TARGETS and uses of these agents in the prevention and/or treatment of ER-associated protein misfolding diseases, in particular Cystic Fibrosis.

The present invention relates to a method for identifying compounds that increase the functional activity of CF-associated mutant CFTR, comprising contacting the compound with the identified TARGETS or their protein domain fragments (SEQ ID. NO 30-55) under conditions that allow said TARGETS or their protein domain fragments to bind to the compound, and measuring a compound-polypeptide property related to the increased functional activity of CF-associated mutant CFTR.

In particular the present invention provides TARGETS which are involved in the pathway involved in cellular trafficking, particularly of CFTR, methods for screening for agents capable of modulating the expression and/or activity of TARGETS and uses of these agents in the prevention and/or treatment of CF. The present invention provides TARGETS which are involved in or otherwise associated with airway epithelial cell function. The present invention provides TARGETS which are involved in inflammation and the inflammatory response, particularly associated with CF and/or in airway epithelial cells. The invention provides uses of agents directed against these targets in CF and other airway diseases involving an inflammatory aspect or component, including asthma and COPD.

Aspects of the present method include the in vitro assay of compounds using identified TARGETS, and cellular assays wherein identified TARGET inhibition is followed by observing indicators of efficacy, including chloride channel activity. Another aspect of the invention is a method of treatment or prevention of a condition involving a decrease in functional activity of CF-associated mutant CFTR, in a subject suffering or susceptible thereto, by administering a pharmaceutical composition comprising an effective corrector for enhancing the functional activity of CF-associated mutant CFTR.

The present invention relates to a method for identifying compounds that inhibit the TARGET(s), comprising contacting the compound with the identified TARGETS (SEQ ID NO: 30-55) or their protein domain fragments under conditions wherein the compounds may interact with or influence the TARGET(s), measuring the expression or activity of a protein which is misfolded in an ER-associated protein misfolding disease, and selecting compounds which increase the expression or activity of the protein which is misfolded in the ER-associated protein misfolding disease. In one such method the expression or activity of ΔF508 CFTR, misfolded in the disease CF, is measured. In exemplary further such methods, the expression or activity of fibrillin, misfolded in Marfan syndrome, or of alpha galactosidase, misfolded in Fabry's disease, or of rhodopsin, misfolded in retinitis pigmentosa, or beta-amyloid protein, misfolded in Alzheimer's disease, is/are measured, and compounds which increase the proper expression or activity thereof are selected.

The present invention relates to a method for identifying compounds that are able to modulate protein folding and trafficking, and particularly ER-associated protein folding and cellular trafficking, comprising contacting a compound with a polypeptide comprising an amino acid sequence selected from the group consisting of SEQ ID NO: 30-55 (hereinafter "TARGETS") and fragments thereof, under conditions that allow said polypeptide to bind to said compound, and measuring a compound-polypeptide property related to cellular trafficking of proteins. In a specific embodiment, the present invention relates to a method for identifying compounds that are able to modulate the protein folding, trafficking or activity of the mutant CFTR protein in airway epithelial cells, comprising contacting a compound with a polypeptide comprising an amino acid sequence selected from the group consisting of SEQ ID NO: 30-55 (hereinafter "TARGETS") and fragments thereof, under conditions that allow said polypeptide to bind to said compound, and measuring a compound-polypeptide property related to CFTR expression or activity. In a specific embodiment the compound-polypeptide property measured is CFTR-mediated halide flux. In a specific embodiment, the property measured is CFTR expression on the cell surface.

Aspects of the present method include the in vitro assay of compounds using polypeptide of a TARGET, or fragments thereof, such fragments including the amino acid sequences described by SEQ ID NO: 30-55 and cellular assays wherein TARGET inhibition is followed by observing indicators of efficacy including, for example, TARGET expression levels, TARGET enzymatic activity, CFTR protein levels, CFTR activity, CFTR-mediated halide flux, and/or other assessments of protein folding/trafficking or inflammation and inflammatory response.

The present invention also relates to
(1) expression inhibitory agents comprising a polynucleotide selected from the group of an antisense polynucleotide, a ribozyme, and a small interfering RNA (siRNA), wherein said polynucleotide comprises a nucleic acid sequence complementary to, or engineered from, a naturally occurring polynucleotide sequence encoding a TARGET polypeptide said polynucleotide sequence comprising a sequence selected from the group consisting of SEQ ID NO: 1-29 and
(2) pharmaceutical compositions comprising said agent(s), useful in the treatment, or prevention, of a disease characterized by ER-associated protein misfolding, including in particular Cystic Fibrosis.

Another aspect of the invention is a method of treatment, or prevention of a condition related to a disease characterized by ER-associated protein misfolding, in particular Cystic Fibrosis, in a subject suffering or susceptible thereto, by administering a pharmaceutical composition comprising an effective TARGET-expression inhibiting amount of a expression-inhibitory agent or an effective TARGET activity inhibiting amount of a activity-inhibitory agent.

A further aspect of the present invention is a method for diagnosis of a disease characterized by ER-associated protein misfolding comprising measurement of indicators of levels of TARGET expression in a subject. In particular the present invention relates to a method for the diagnosis of Cystic Fibrosis.

Another aspect of this invention relates to the use of agents which inhibit a TARGET as disclosed herein in a therapeutic method, a pharmaceutical composition, and the manufacture of such composition, useful for the treatment of a disease involving protein misfolding. In particular, the present method relates to the use of the agents which inhibit a TARGET in the treatment of a disease characterized by ER-associated protein misfolding, and in particular, a disease characterized by abnormal trafficking of a disease-associated protein. Suitable conditions include, but are not limited to, Cystic Fibrosis, Parkinson's disease, Gaucher's disease, nephrogenic diabetes insipidus, emphysema and liver disease (alpha-1-antitrypsin deficiency), Maple syrup urine disease, Fabry's disease, hypogonadotropic hypogonadism, hyperinsulinemic hypoglycemia, beta-galactosidosis, Wilson's disease, long QT syndrome, retinitis pigmentosa, transthyretin-linked amyloidosis, Alzheimer's disease, prion disease, and inclusion body myositis. In particular the disease is Cystic Fibrosis.

Other objects and advantages will become apparent from a consideration of the ensuing description taken in conjunction with the following illustrative drawings.

BRIEF DESCRIPTION OF THE FIGURES

FIGS. 1A and 1B: Expression of halide-sensitive fluorescent protein YFP

DETAILED DESCRIPTION OF THE INVENTION

Figure 1B:
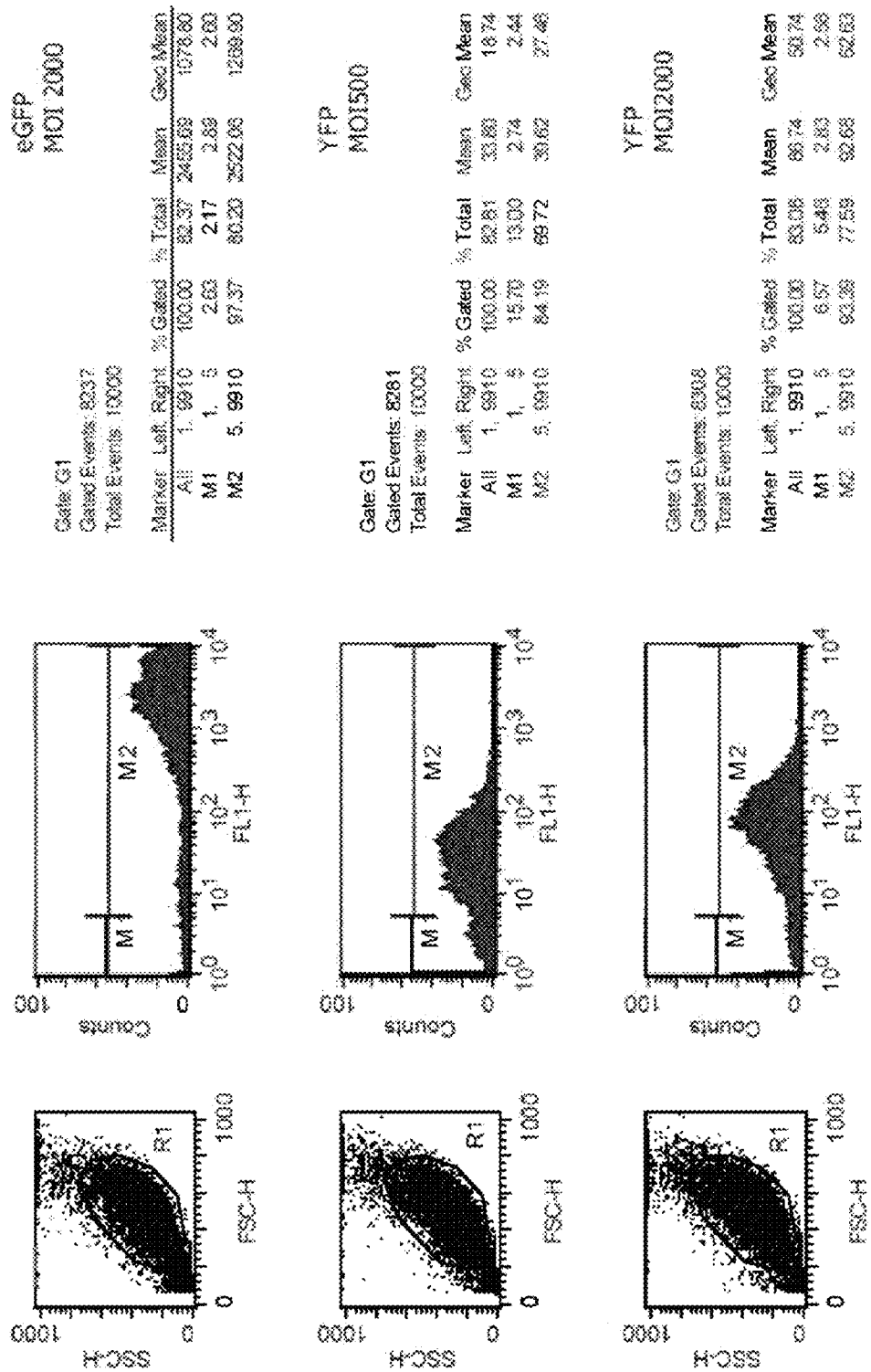

The following terms are intended to have the meanings presented therewith below and are useful in understanding the description and intended scope of the present invention.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense.

The term 'assay' means any process used to measure a specific property of a compound. A 'screening assay' means a process used to characterize or select compounds based upon their activity from a collection of compounds.

The term 'binding affinity' is a property that describes how strongly two or more compounds associate with each other in a non-covalent relationship. Binding affinities can be characterized qualitatively, (such as 'strong', 'weak', 'high', or 'low') or quantitatively (such as measuring the $K_D$).

The term 'carrier' means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

The term 'complex' means the entity created when two or more compounds bind to, contact, or associate with each other.

The term 'compound' is used herein in the context of a 'test compound' or a 'drug candidate compound' described in connection with the assays of the present invention. As such, these compounds comprise organic or inorganic compounds, derived synthetically, recombinantly, or from natural sources.

The compounds include inorganic or organic compounds such as polynucleotides, lipids or hormone analogs. Other biopolymeric organic test compounds include peptides comprising from about 2 to about 40 amino acids and larger polypeptides comprising from about 40 to about 500 amino acids, including polypeptide ligands, enzymes, receptors, channels, antibodies or antibody conjugates.

The term 'condition' or 'disease' means the overt presentation of symptoms (i.e., illness) or the manifestation of abnormal clinical indicators (for example, biochemical indicators or diagnostic indicators). Alternatively, the term 'disease' refers to a genetic or environmental risk of or propensity for developing such symptoms or abnormal clinical indicators.

The term 'contact' or 'contacting' means bringing at least two moieties together, whether in an in vitro system or an in vivo system.

The term 'derivatives of a polypeptide' relates to those peptides, oligopeptides, polypeptides, proteins and enzymes that comprise a stretch of contiguous amino acid residues of the polypeptide and that retain a biological activity of the protein, for example, polypeptides that have amino acid mutations compared to the amino acid sequence of a naturally-occurring form of the polypeptide. A derivative may further comprise additional naturally occurring, altered, glycosylated, acylated or non-naturally occurring amino acid residues compared to the amino acid sequence of a naturally occurring form of the polypeptide. It may also contain one or more non-amino acid substituents, or heterologous amino acid substituents, compared to the amino acid sequence of a naturally occurring form of the polypeptide, for example a reporter molecule or other ligand, covalently or non-covalently bound to the amino acid sequence.

The term 'derivatives of a polynucleotide' relates to DNA-molecules, RNA-molecules, and oligonucleotides that comprise a stretch of nucleic acid residues of the polynucleotide, for example, polynucleotides that may have nucleic acid mutations as compared to the nucleic acid sequence of a naturally occurring form of the polynucleotide. A derivative may further comprise nucleic acids with modified backbones such as PNA, polysiloxane, and 2'-O-(2-methoxy) ethyl-phosphorothioate, non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection.

The term 'endogenous' shall mean a material that a cell or mammal (as the context dictates) naturally produces. Endogenous in reference to the term 'protease', 'kinase', or G-Protein Coupled Receptor ('GPCR') shall mean that which is naturally produced by a cell, for example a mammalian cell (for example, not limitation a human cell), or by a mammal (for example, and not limitation, a human). In contrast, the term non-endogenous in this context shall mean that which is not naturally produced by a cell, in particular by a mammalian cell, (for example, not limitation a human cell), or that is not naturally produced by a mammal (for example, and not limitation, a human). Both terms can be utilized to describe both in vivo and in vitro systems. For example, and without limitation, in a screening approach, the endogenous or non-endogenous TARGET may be in reference to an in vitro screening system. As a further example and not limitation, where the genome of a mammal has been manipulated to include a non-endogenous TARGET, screening of a candidate compound by means of an in vivo system is viable.

The term 'expressible nucleic acid' means a nucleic acid coding for a proteinaceous molecule, an RNA molecule, or a DNA molecule.

The term 'expression' comprises both endogenous expression and overexpression by transduction.

The term 'expression inhibitory agent' means a polynucleotide designed to interfere selectively with the transcription, translation and/or expression of a specific polypeptide or protein normally expressed within a cell. More particularly, 'expression inhibitory agent' comprises a DNA or RNA molecule that contains a nucleotide sequence identical to or complementary to at least about 15-30, particularly at least 17, sequential nucleotides within the polyribonucleotide sequence coding for a specific polypeptide or protein. Exemplary expression inhibitory molecules include ribozymes, double stranded siRNA molecules, self-complementary single-stranded siRNA molecules, genetic antisense constructs, and synthetic RNA antisense molecules with modified stabilized backbones.

The term 'fragment of a polynucleotide' relates to oligonucleotides that comprise a stretch of contiguous nucleic acid residues that exhibit substantially a similar, but not necessarily identical, activity as the complete sequence. In a particular aspect, 'fragment' may refer to a oligonucleotide comprising a nucleic acid sequence of at least 5 nucleic acid residues (preferably, at least 10 nucleic acid residues, at least 15 nucleic acid residues, at least 20 nucleic acid residues, at least 25 nucleic acid residues, at least 40 nucleic acid residues, at least 50 nucleic acid residues, at least 60 nucleic acid residues, at least 70 nucleic acid residues, at least 80 nucleic acid residues, at least 90 nucleic acid residues, at least 100 nucleic acid residues, at least 125 nucleic acid residues, at least 150 nucleic acid residues, at least 175 nucleic acid residues, at least 200 nucleic acid residues, or at least 250 nucleic acid residues) of the nucleic acid sequence of said complete sequence.

The term 'fragment of a polypeptide' relates to peptides, oligopeptides, polypeptides, proteins, monomers, subunits and enzymes that comprise a stretch of contiguous amino acid residues, and exhibit substantially a similar, but not necessarily identical, functional or expression activity as the complete sequence. In a particular aspect, 'fragment' may refer to a peptide or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of said complete sequence.

The term 'hybridization' means any process by which a strand of nucleic acid binds with a complementary strand through base pairing. The term 'hybridization complex' refers to a complex formed between two nucleic acid sequences by virtue of the formation of hydrogen bonds between complementary bases. A hybridization complex may be formed in solution (for example, $C_{0t}$ or $R_{0t}$ analysis) or formed between one nucleic acid sequence present in solution and another nucleic acid sequence immobilized on a solid support (for example, paper, membranes, filters, chips, pins or glass slides, or any other appropriate substrate to which cells or their nucleic acids have been fixed). The term "stringent conditions" refers to conditions that permit hybridization between polynucleotides and the claimed polynucleotides. Stringent conditions can be defined by salt concentration, the concentration of organic solvent, for example, formamide, temperature, and other conditions well known in the art. In particular, reducing the concentration of salt, increasing the concentration of formamide, or raising the hybridization temperature can increase stringency. The term 'standard hybridization conditions' refers to salt and temperature conditions substantially equivalent to 5×SSC and 65° C. for both hybridization and wash. However, one skilled in the art will appreciate that such 'standard hybridization conditions' are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20$^{\circ}$C below the predicted or determined $T_m$ with washes of higher stringency, if desired.

The term 'inhibit' or 'inhibiting', in relationship to the term 'response' means that a response is decreased or prevented in the presence of a compound as opposed to in the absence of the compound.

The term 'inhibition' refers to the reduction, down regulation of a process or the elimination of a stimulus for a process, which results in the absence or minimization of the expression or activity of a protein or polypeptide.

The term 'induction' refers to the inducing, up-regulation, or stimulation of a process, which results in the expression or activity of a protein or polypeptide.

The term 'ligand' means an endogenous, naturally occurring molecule specific for an endogenous, naturally occurring receptor.

The term 'pharmaceutically acceptable salts' refers to the non-toxic, inorganic and organic acid addition salts, and base addition salts, of compounds which inhibit the expression or activity of TARGETS as disclosed herein. These salts can be prepared in situ during the final isolation and purification of compounds useful in the present invention.

The term 'polypeptide' relates to proteins (such as TARGETS), proteinaceous molecules, fragments of proteins, monomers, subunits or portions of polymeric proteins, peptides, oligopeptides and enzymes (such as kinases, proteases, GPCR's etc.).

The term 'polynucleotide' means a polynucleic acid, in single or double stranded form, and in the sense or antisense orientation, complementary polynucleic acids that hybridize to a particular polynucleic acid under stringent conditions, and polynucleotides that are homologous in at least about 60 percent of its base pairs, and more particularly 70 percent of its base pairs are in common, most particularly 90 percent, and in a particular embodiment, 100 percent of its base pairs. The polynucleotides include polyribonucleic acids, polydeoxyribonucleic acids, and synthetic analogues thereof. It also includes nucleic acids with modified backbones such as peptide nucleic acid (PNA), polysiloxane, and 2'-O-(2- methoxy)ethylphosphorothioate. The polynucleotides are described by sequences that vary in length, that range from about 10 to about 5000 bases, particularly about 100 to about 4000 bases, more particularly about 250 to about 2500 bases. One polynucleotide embodiment comprises from about 10 to about 30 bases in length. A particular embodiment of polynucleotide is the polyribonucleotide of from about 17 to about 22 nucleotides, more commonly described as small interfering RNAs (siRNAs). Another particular embodiment are nucleic acids with modified backbones such as peptide nucleic acid (PNA), polysiloxane, and 2'-O-(2-methoxy)ethylphosphorothioate, or including non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection. Polynucleotides herein are selected to be 'substantially' complementary to different strands of a particular target DNA sequence. This means that the polynucleotides must be sufficiently complementary to hybridize with their respective strands. Therefore, the polynucleotide sequence need not reflect the exact sequence of the target sequence. For example, a non-complementary nucleotide fragment may be attached to the 5' end of the polynucleotide, with the remainder of the polynucleotide sequence being complementary to the strand. Alternatively, non-complementary bases or longer sequences can be interspersed into the polynucleotide, provided that the polynucleotide sequence has sufficient complementarity with the sequence of the strand to hybridize therewith under stringent conditions or to form the template for the synthesis of an extension product.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term 'solvate' means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

The term 'subject' includes humans and other mammals.

'Therapeutically effective amount' means that amount of a drug, compound, expression inhibitory agent, or pharmaceutical agent that will elicit the biological or medical response of a subject that is being sought by a medical doctor or other clinician. In particular, with regard to increasing the functional activity of CF-associated mutant CFTR, the term "effective amount" is intended to include an effective amount of a compound or agent that will bring about a biologically meaningful increase in CFTR-dependent halide flux.

The term 'treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, 'treating' or 'treatment' relates to slowing the progression of the disease.

The term 'vectors' also relates to plasmids as well as to viral vectors, such as recombinant viruses, or the nucleic acid encoding the recombinant virus.

The term 'vertebrate cells' means cells derived from animals having vertebral structure, including fish, avian, reptilian, amphibian, marsupial, and mammalian species. Preferred cells are derived from mammalian species, and most preferred cells are human cells. Mammalian cells include feline, canine, bovine, equine, caprine, ovine, porcine and murine, such as mice and rats, and rabbits.

The term 'TARGET' or 'TARGETS' means the protein(s) identified in accordance with the assays described herein and determined to be involved in the modulation of a Cystic Fibrosis phenotype. The term TARGET or TARGETS includes and contemplates alternative species forms, isoforms, and variants, such as allelic variants, including as a result of allelic or natural variation in the amino acid sequence, and splice variants, alternate in frame exons, and alternative or premature termination or start sites, including known or recognized isoforms or variants thereof such as indicated in Table 1.

The term 'disease characterized by ER-associated protein misfolding' refers to a disease which involves, results at least in part from, or includes a protein misfolding aspect, particularly wherein a protein is not processed and/or sorted by or through the endoplasmic reticulum (ER) in a proper, efficient, or effective manner, such that it is misprocessed, poorly processed, degraded, or misfolded, resulting in such instances in less protein processed to the cell membrane or other protein location destination, or in processed protein having reduced or altered activity. The term includes, but is not limited to, exemplary diseases selected from Cystic Fibrosis, Parkinson's disease, Gaucher's disease, nephrogenic diabetes insipidus, emphysema and liver disease (alpha-1 antitrypsin deficiency), Maple syrup urine disease, Fabry's disease, hypogonadotropic hypogonadism, hyperinsulinemic hypoglycemia, beta-galactosidosis, Wilson's disease, long QT syndrome retinitis pigmentosa, transthyretin-linked amyloidosis, Alzheimer's disease, prion disease, and inclusion body myositis. Such diseases can be associated with misfolding of proteins, or alternatively folded proteins, including misfolded CFTR (Cystic Fibrosis), misfolded fibrillin (Marfan syndrome), misfolded alpha gatactosidase (Fabry's disease), misfolded beta glucocerebrosidase (Gaucher's disease), misfolded hERG receptor (long QT syndrome), misfolded rhodopsin (retinitis pigmentosa), misfolded or alternatively folded beta amyloid protein (Alzheimer's disease), and misfolded or alternatively folded prion protein (Prion Disease).

Targets

The present invention is based on the present inventors' discovery that the TARGETS are factors in the translocation of ΔF508 CFTR to the plasma membrane, whereby inhibition of the TARGETS results in an increase in CFTR-mediated halide flux. The TARGETS are factors or protein molecules involved in protein trafficking and/or folding such that their inhibition results in an increased amount of ΔF508 CFTR being trafficked to, expressed, and/or active at the plasma membrane. The TARGETS may also serve a role in inflammation and/or the inflammatory response, particularly in pulmonary epithelial cells. In the present application, the effect of down-regulation of syntaxin-8, which is involved in trafficking of vesicles and has been shown to bind to the wild type CFTR (Antonin et al. 2000; Bilan et al., 2004; Thoreau et al., 1999), or BCAP31, for which down-regulation by Ad-siRNA allows functional restoration of ΔF508 CFTR (Fischer et al., 2006), is used as a positive control in a screen of 11,330 Ad-siRNAs to identify novel TARGETS.

CFTR is an ion channel. Ion channels are membrane protein complexes and their function is to facilitate the diffusion of ions across biological membranes. Membranes, or phospholipid bilayers, build a hydrophobic, low dielectric barrier to hydrophilic and charged molecules. Ion channels provide a high conducting, hydrophilic pathway across the hydrophobic interior of the membrane. The activity of an ion channel can be measured using classical patch clamping. High-throughput fluorescence-based or tracer-based assays are also widely available to measure ion channel activity. These fluorescent-based assays screen compounds on the basis of their ability to either open or close an ion channel thereby changing the concentration of specific fluorescent dyes across a membrane. In the case of the tracer based assay, the changes in concentration of the tracer within and outside the cell are measured by radioactivity measurement or gas absorption spectrometry.

The TARGETS listed in Table 1 below were identified herein as involved in the modulation of the migration of ΔF508-CFTR to the plasma membrane, therefore, inhibitors of these TARGETS are able to increase the density of ΔF508-CFTR in the membrane, and rescue the function of ΔF508-CFTR. These TARGETS are proposed to have a general role in modulating the folding of proteins within the ER and their subsequent trafficking to the cell membrane. Therefore these TARGETS are involved in diseases characterized by ER-associated protein misfolding, in particular Cystic Fibrosis.

Therefore, in one aspect, the present invention relates to a method for assaying for drug candidate compounds that modulate trafficking of a disease-associated protein comprising contacting the compound with a polypeptide comprising an amino acid sequence of SEQ ID NO: 30-55, or fragment thereof, under conditions that allow said polypeptide to bind to the compound, and detecting the formation of a complex between the polypeptide and the compound. In particular said method is used to identify an agent that increases the functional activity of CF-associated mutant CFTR said method. In particular said method may be used to identify drug candidate compounds that promote migration of ΔF508-CFTR to the plasma membrane. One particular means of measuring the complex formation is to determine the binding affinity of said compound to said polypeptide.

More particularly, the invention relates to a method for identifying an agent or compound that increases the functional activity of CF-associated mutant CFTR said method comprising:
(a) contacting a population of mammalian cells with one or more compound that exhibits binding affinity for a TARGET polypeptide, or fragment thereof, and
(b) measuring a compound-polypeptide property related to ΔF508-CFTR activity or expression.

In a further aspect of the present invention said method is used to identify a compound that increases the activity or expression of CF-associated mutant CFTR by promoting migration or trafficking of ΔF508-CFTR to the plasma membrane.

In a further aspect, the present invention relates to a method for assaying for drug candidate compounds that modulate trafficking of a disease-associated protein comprising contacting the compound with a polypeptide comprising an amino acid sequence of SEQ ID NO: 30-55, or fragment thereof, under conditions that allow said compound to modulate the activity or expression of the polypeptide, and determining the activity or expression of the polypeptide. In particular said method may be used to identify drug candidate compounds capable of promoting the migration of ΔF508-CFTR to the plasma membrane. One particular means of measuring the activity or expression of the polypeptide is to determine the amount of said polypeptide using a polypeptide binding agent, such as an antibody, or to determine the activity of said polypeptide in a biological or biochemical measure, for instance the amount of phosphorylation of a target of a kinase polypeptide.

The compound-polypeptide property referred to above is related to the expression and/or activity of the TARGET, and is a measurable phenomenon chosen by the person of ordinary skill in the art. The measurable property may be, for example, the binding affinity of said compound for a peptide domain of the polypeptide TARGET, a property related to the folding or activity of the disease-related protein or the level of any one of a number of biochemical marker levels of CF-associated mutant CFTR activity. In a preferred method, CF-associated mutant CFTR activity is measured by measuring CFTR-dependent halide flux, which can be monitored by using a reporter protein, halide-sensitive fluorescent protein YFP. It has been reported that cells expressing this reporter protein show enhanced fluorescence quenching of YFP by extracellular isomolar iodide solutions in the presence of activated CFTR (Galietta et al., 2001b). Fluorescence quenching is a measure of halide transport—as halide ions cross the plasma membrane, the halide ions interact with halide-sensitive fluorescent protein YFP, and quench the fluorescence of YFP. Fluorescence quenching is measured on a fluorescence plate reader.

In an additional aspect, the present invention relates to a method for assaying for drug candidate compounds that modulate trafficking of a disease-associated protein, comprising contacting the compound with a nucleic acid encoding a TARGET polypeptide, including a nucleic acid sequence selected from SEQ ID NO: 1-29, or fragment/portion thereof, under conditions that allow said nucleic acid to bind to or otherwise associate with the compound, and detecting the formation of a complex between the nucleic acid and the compound. In particular, said method may be used to identify drug candidate compounds able to promote migration of ΔF508-CFTR to the plasma membrane. One particular means of measuring the complex formation is to determine the binding affinity of said compound to said nucleic acid or the presence of a complex by virtue of resistance to nucleases or by gel mobility assays. Alternatively, complex formation may be determined by inhibition of nucleic acid transcription or translation.

In a particular embodiment of the invention, the TARGET polypeptide comprises an amino acid sequence selected from the group consisting of SEQ ID No: 30-55 as listed in Table 1. In an embodiment of the invention, the nucleic acid capable of encoding the TARGET polypeptide comprises a nucleic acid sequence selected from the group consisting of SEQ ID NO:

1-29 as listed in Table 1. Table 1 provides TARGET exemplary human nucleic acid and protein sequence, including recognized variants or isoforms where more than one accession number and SEQ ID NO: is indicated. Isoforms or variants of the TARGET(S) include nucleic acid or proteins with or utilizing alternate in frame exons, alternative splicing or splice variants, and alternative or premature termination variants.

TABLE 1

TARGETS

| TARGET Gene Symbol | GenBank nucleic acid Acc#: | SEQ ID NO: DNA | GenBank protein Acc#: | SEQ ID NO: Protein | Class |
|---|---|---|---|---|---|
| UGT3A1 | NM_152404 | 1 | NP_689617 | 30 | enzyme |
| UGT3A2 | NM_174914 | 2 | NP_777574 | 31 | enzyme |
| PHGDH | NM_006623 | 3 | NP_006614 | 32 | enzyme |
| B3GNT3 | NM_014256 | 4 | NP_055071 | 33 | enzyme |
| PPIH | NM_006347 | 5 | NP_006338 | 34 | enzyme/chaperone |
| CELSR3 | NM_001407 | 6 | NP_001398 | 35 | GPCR |
| MC2R | NM_000529 | 7 | NP_000520 | 36 | GPCR |
| MAS1L | NM_052967 | 8 | NP_443199 | 37 | GPCR |
| LRRK2 | NM_198578 | 9 | NP_940980 | 38 | kinase/nucleotide binding |
| NLRP1 | NM_001033053 | 10 | NP_001028225 | 39 | kinase/nucleotide binding |
|  | NM_014922 | 11 | NP_055737 | 40 | binding |
|  | NM_033004 | 12 | NP_127497 | 41 |  |
|  | NM_033006 | 13 | NP_127499 | 42 |  |
|  | NM_033007 | 14 |  |  |  |
| PMS1 | NM_000534 | 15 | NP_000525 | 43 | kinase/nucleotide binding |
|  | NM_001128143 | 16 |  |  |  |
|  | NM_001128144 | 17 |  |  |  |
| MAK | NM_005906 | 18 | NP_005897 | 44 | kinase/nucleotide binding |
| CPD | NM_001304 | 19 | NP_001295 | 45 | peptidase/peptidase inhibitor |
| CST7 | NM_003650 | 20 | NP_003641 | 46 | peptidase/peptidase inhibitor |
| DUSP5 | NM_004419 | 21 | NP_004410 | 47 | phosphatase |
| PTPRG | NM_002841 | 22 | NP_002832 | 48 | phosphatase/receptor |
| IL6R | NM_000565 | 23 | NP_000556 | 49 | receptor |
|  | NM_181359 | 24 | NP_852004 | 50 |  |
| GHR | NM_000163 | 25 | NP_000154 | 51 | receptor |
| CSF3 | NM_000759 | 26 | NP_000750 | 52 | secreted |
|  | NM_172219 | 27 | NP_757373 | 53 |  |
|  | NM_172220 | 28 | NP_757374 | 54 |  |
| SPNS1 | NM_032038 | 29 | NP_114427 | 55 | transporter |

Depending on the choice of the skilled artisan, the present assay method may be designed to function as a series of measurements, each of which is designed to determine whether the drug candidate compound is indeed acting on the TARGET to thereby increase the functional activity of CF-associated mutant CFTR. For example, an assay designed to determine the binding affinity of a compound to the TARGET, or fragment thereof, may be necessary, but not sufficient, to ascertain whether the test compound would be useful for increasing the functional activity of CF-associated mutant CFTR when administered to a subject. Nonetheless, such binding information would be useful in identifying a set of test compounds for use in an assay that would measure a different property, further down the biochemical pathway, such as halide flux, assayed by measuring the quenching of a halide-sensitive fluorescent protein. Such additional assay(s) may be designed to confirm that the test compound, having binding affinity for the TARGET, actually increases the functional activity of CF-associated mutant CFTR.

Suitable controls should always be in place to insure against false positive readings. In a particular embodiment of the present invention the screening method comprises the additional step of comparing the compound to a suitable control. In one embodiment, the control may be a cell or a sample that has not been in contact with the test compound. In an alternative embodiment, the control may be a cell that does not express the TARGET; for example in one aspect of such an embodiment the test cell may naturally express the TARGET and the control cell may have been contacted with an agent, e.g. an siRNA, which inhibits or prevents expression of the TARGET. Alternatively, in another aspect of such an embodiment, the cell in its native state does not express the TARGET and the test cell has been engineered so as to express the TARGET, so that in this embodiment, the control could be the untransformed native cell. Whilst exemplary controls are described herein, this should not be taken as limiting; it is within the scope of a person of skill in the art to select appropriate controls for the experimental conditions being used.

The order of taking these measurements is not believed to be critical to the practice of the present invention, which may be practiced in any order. For example, one may first perform a screening assay of a set of compounds for which no information is known respecting the compounds' binding affinity for the TARGET. Alternatively, one may screen a set of compounds identified as having binding affinity for a TARGET protein domain, or a class of compounds identified as being an inhibitor of the TARGET. However, for the present assay to be meaningful to the ultimate use of the drug candidate compounds in diseases characterized by ER-associated protein misfolding a measurement of functional activity or appropriate expression of the relevant protein is necessary. In a specific embodiment the disease is cystic fibrosis and the protein is CF-associated mutant CFTR. In alternative embodiments, the disease is Marfan syndrome and the protein is fibrillin, or the disease is Fabry's disease and the protein is alpha gatactosidase, or the disease is Gaucher's disease and the protein is beta glucocerebrosidase, or the disease is long QT syndrome and the protein is misfolded hERG receptor, or the disease is retinitis pigmentosa and the protein is rhodopsin, or the disease is Alzheimer's disease and the protein is beta-amyloid or the disease is prion disease and the protein is prion protein. Validation studies, including controls, and measurements of binding affinity to the polypeptides of the invention are nonetheless useful in identifying a compound useful in any therapeutic or diagnostic application.

Analogous approaches based on art-recognized methods and assays may be applicable with respect to the TARGETS and compounds in any of various disease(s) characterized by ER-associated protein misfolding or inflammatory diseases, including airway epithelial cell diseases, asthma, COPD. An assay or assays may be designed to confirm that the test compound, having binding affinity for the TARGET, increases the functional activity and/or alters the protein misfolding or protein trafficking of a protein associated with misfolding disease. In one such method the expression or activity of ΔF508 CFTR, misfolded in the disease CF, is measured. In the case of CF, and in lieu of animal models, chambers with primary human airway epithelial cells (Li et al, 2004) may be utilized in further assessing the TARGETS and/or compounds. In exemplary further such methods, the expression or activity of fibrillin, misfolded in Marfan syndrome, or of alpha galactosidase, misfolded in Fabry disease, or of rhodopsin, misfolded ion retinitis pigmentosa, or beta amyloid protein, misfolded in Alzheimer's disease, is/are measured, and compounds which increase the proper expression or activity thereof are selected. Protein trafficking may be assessed or monitored in art-recognized methods, including in vitro, ex vivo, and animal systems.

The present assay method may be practiced in vitro, using one or more of the TARGET proteins, or fragments thereof, including monomers, portions or subunits of polymeric proteins, peptides, oligopeptides and enzymatically active portions thereof.

The binding affinity of the compound with the TARGET or a fragment thereof can be measured by methods known in the art, such as using surface plasmon resonance biosensors (Biacore), by saturation binding analysis with a labeled compound (e.g. Scatchard and Lindmo analysis), by differential UV spectrophotometer, fluorescence polarization assay, Fluorometric Imaging Plate Reader (FLIPR®) system, Fluorescence resonance energy transfer, and Bioluminescence resonance energy transfer. The binding affinity of compounds can also be expressed in dissociation constant (Kd) or as $IC_{50}$ or $EC_{50}$. The $IC_{50}$ represents the concentration of a compound that is required for 50% inhibition of binding of another ligand to the polypeptide. The $EC_{50}$ represents the concentration required for obtaining 50% of the maximum effect in any assay that measures the TARGET function. The dissociation constant, Kd, is a measure of how well a ligand binds to the polypeptide, it is equivalent to the ligand concentration required to saturate exactly half of the binding-sites on the polypeptide. Compounds with a high affinity binding have low Kd, $IC_{50}$ and $EC_{50}$ values, i.e. in the range of 100 nM to 1 pM; a moderate to low affinity binding relates to a high Kd, $IC_{50}$ and $EC_{50}$ values, i.e. in the micromolar range.

The present assay method may also be practiced in a cellular assay. A host cell expressing the TARGET can be a cell with endogenous expression or a cell over-expressing the TARGET e.g. by transduction. When the endogenous expression of the polypeptide is not sufficient to determine a baseline that can easily be measured, one may use host cells that over-express the TARGET. Over-expression has the advantage that the level of the TARGET substrate end products is higher than the activity level by endogenous expression. Accordingly, measuring such levels using presently available techniques is easier. In one such cellular assay, the biological activity of the TARGET may be measured by measuring the functional activity of for instance CF-associated mutant CFTR.

One embodiment of the present method for identifying a compound that increases CFTR expression and/or activity comprises culturing a population of mammalian cells expressing a TARGET polypeptide, or a functional fragment or derivative thereof; determining a first level of CFTR or ΔF508-CFTR expression at the cell membrane and/or activity of CFTR or ΔF508-CFTR in said population of cells; eventually activating the population of cells; exposing said population of cells to a compound, or a mixture of compounds; determining a second level of CFTR or ΔF508-CFTR expression and/or activity in said population of cells during or after exposure of said population of cells to said compound, or the mixture of said compounds; and identifying the compound(s) that induce ΔF508-CFTR migration to the cell membrane and/or CFTR or ΔF508-CFTR activity.

As noted above, promotion of disease-related protein trafficking may be determined by measuring the expression and/or activity of the TARGET polypeptide and/or CFTR or ΔF508-CFTR.

The expression and/or activity of CFTR or ΔF508-CFTR can be determined by methods known in the art such as immunohistochemistry using specific antibodies, or an activity assay as described herein.

The present inventors identified TARGET genes involved in disease-related protein trafficking by using a 'knock-down' library. This type of library is a screen in which siRNA molecules are transduced into cells by recombinant adenoviruses, which siRNA molecules inhibit or repress the expression of a specific gene as well as expression and activity of the corresponding gene product in a cell. Each siRNA in a viral vector corresponds to a specific natural gene. By identifying a siRNA that promotes migration of ΔF508-CFTR to the cell membrane, a direct correlation can be drawn between the specific gene expression and the pathway for rescuing mutant CFTR receptors. The TARGET genes identified using the knock-down library (the protein expression products thereof herein referred to as "TARGET" polypeptides) are then used in the present inventive method for identifying compounds that can be used to correct mutant CFTR expression and/or activity. Indeed, shRNA compounds comprising the sequences listed in Table 2 (SEQ ID NOs: 56-99) inhibit the expression and/or activity of these TARGET genes and promote migration of ΔF508-CFTR in cells, confirming the role of the TARGETS in the protein-trafficking pathway.

TABLE 2

KD TARGET sequences useful in the practice of the present expression-inhibitory agent invention

| TARGET Gene Symbol | SEQ ID NO: DNA | Sequences | SEQ ID NO: Knock-Down |
|---|---|---|---|
| UGT3A1 or UTG3A2 | 1, 2 | CGCACCTCAAGCCCTATGT; | 56 |

TABLE 2-continued

KD TARGET sequences useful in the practice of the present expression-inhibitory agent invention

| TARGET Gene Symbol | SEQ ID NO: DNA | Sequences | SEQ ID NO: Knock-Down |
|---|---|---|---|
| UGT3A2 | 2 | AACATGGTCCGAGTAGAAG | 57 |
| PHGDH | 3 | AGAGGAGCTGATAGCGGAG; | 58 |
|  |  | AATGGGAGCGGAAGAAGTT | 59 |
| B3GNT3 | 4 | CATCCTGCAGTGGGACTTC; | 60 |
|  |  | CAACATGGTCTTCTACCTG | 61 |
| PPIH | 5 | GTACAAATGGCTGTCAGTT; | 62 |
|  |  | TTGAGAATGTTCCCACAGG; | 63 |
|  |  | ATGGAGATGGTACTGGAGT | 64 |
| CELSR3 | 6 | AGGATGCAGCTAACAACAA; | 65 |
|  |  | ACTGTGCGCGTACACATAA; | 66 |
|  |  | ATGCTCCACAATTTGTGGC | 67 |
| MC2R | 7 | CATGGGCTATCTCAAGCCA; | 68 |
|  |  | AACATGGGCTATCTCAAGC | 69 |
| MAS1L | 8 | CAGAACCCAAACCTGGTAT; | 70 |
|  |  | GCCATATTGTCTCCCTTCT; | 71 |
|  |  | ACAGCAGCGCCAACCCTAT | 72 |
| LRRK2 | 9 | AAGGCTCGCGCTTCTTCTT; | 73 |
|  |  | CATTGAGACAAGAACAAGC | 74 |
| NLRP1 | 10, 11, 12, 13, 14 | AGATGGACTCTACCAAGCC; | 75 |
|  |  | ATTGGGAAGTCAACACTGG | 76 |
| PMS1 | 15, 16, 17 | CAGATGTTTCCGCAGCTGA; | 77 |
|  |  | CCAGACAATTACCCATGTA | 78 |
| MAK | 18 | ACCTCCAAAGCAACAGAGT; | 79 |
|  |  | AGTTGTTCCCTGAATCAGT | 80 |
| CPD | 19 | AAGTCCCAGGAAGGAGATT; | 81 |
|  |  | ACATTCACAGGTCTTTGTG | 82 |
| CST7 | 20 | CGAACGACATGTTCTTGTT; | 83 |
|  |  | CTTGTTCCCAGGACCTTAA | 84 |
| DUSP5 | 21 | TGACATTAGCTCCCACTTT; | 85 |
|  |  | ACTGGGATGGAGGAATCGG | 86 |
| PTPRG | 22 | CCAGGAGTAGGAGGAAAGA; | 87 |
|  |  | CGGAGCAGCAAGACCATGT | 88 |
| IL6R | 23, 24 | ACAGTCCGGCCGAAGACTT; | 89 |
|  |  | ACTATTCATGCTACCGGGC; | 90 |
|  |  | CAACATGGATGGTCAAGGA | 91 |
| GHR | 25 | AGTGAGATGGGAAGCACCA; | 92 |
|  |  | ATGACATACATGAGGGTAC | 93 |
| CSF3 | 26, 27, 28 | TGGAAGAACTGGGAATGGC; | 94 |
|  |  | CTTTGCCACCACCATCTGG; | 95 |
|  |  | AAGCTCCTGTCCTCCCATC | 96 |
| SPNS1 | 29 | CCGCCATCTTCATTGAGGC; | 97 |
|  |  | ATCTTCTACTTTGCCATTC; | 98 |
|  |  | ACTACATGGACCGCTTCAC | 99 |

The present invention further relates to a method for identifying a compound that increases the functional activity of CF-associated mutant CFTR, comprising:
(a) contacting a compound with a polypeptide comprising an amino acid sequence selected from the group consisting of SEQ ID NO: 30-55;
(b) determining the binding affinity of the compound to the polypeptide;
(c) contacting a population of mammalian cells expressing said polypeptide with the compound that exhibits at least a moderate binding affinity; and
(d) identifying the compound that increases the functional activity of CF-associated mutant CFTR.

In one aspect, the assay method involves contacting a compound with a polypeptide comprising a fragment of an amino acid sequence selected from the group consisting of SEQ ID NO: 30-55. In one aspect, the assay method includes contacting cells expressing said polypeptide or fragment with the compound that exhibits a binding affinity in the micromolar range. In an aspect, the binding affinity exhibited is at least 10 micromolar. In one aspect, the binding affinity is at least 1 micromolar. In one aspect, the binding affinity is at least 500 nanomolar.

The assay method may be based on the particular expression or activity of the TARGET polypeptide, including but not limited to an enzyme activity. Thus, assays for the enzyme TARGETs identified as SEQ ID NOs: 30-34 may be based on enzymatic activity or enzyme expression. Assays for the peptidase/protease or peptidase inhibitor/protease inhibitor TARGETs identified as SEQ ID NOs: 45-46 may be based on protease activity or expression. Assays for the kinase TARGETs identified as SEQ ID NOs: 38-44 may be based on kinase activity or expression, including but not limited to phosphorylation of a kinase target. Assays for the phosphatase TARGETs identified as SEQ ID NOs: 47-48 may be based on phosphatase activity or expression, including but not limited to dephosphorylation of a phosphatase target. Assays for the GPCR and receptor TARGETs identified as SEQ ID NO: 35-37, 48-51 may be based on GPCR activity or expression, including downstream mediators or activators. Assays for the secreted TARGETs identified as SEQ ID NOs: 52-54 may utilize activity or expression in soluble culture media or secreted activity. Assays for the transporter TARGET identified as SEQ ID NOs: 55 may use techniques well known to those of skill in the art including classical patch clamping, high-throughput fluorescence based or tracer based assays which measure the ability of a compound to open or close an ion channel thereby changing the concentration of fluorescent dyes or tracers across a membrane or within a cell. The measurable phenomenon, activity or property may be selected or chosen by the skilled artisan. The person of ordinary skill in the art may select from any of a number of assay formats, systems or design one using his knowledge and expertise in the art.

Table 1 lists the TARGETS identified using applicants' knock-down library in the CFTR assay described below, including the class of polypeptides identified. TARGETS have been identified in polypeptide classes including kinase, protease, enzyme, GPCR, phosphodiesterase and phosphatase, for instance. Specific methods to determine the activity of a kinase by measuring the phosphorylation of a substrate by the kinase, which measurements are performed in the presence or absence of a compound, are well known in the art.

Specific methods to determine the inhibition by a compound by measuring the cleavage of the substrate by the polypeptide, which is a protease, are well known in the art. Classically, substrates are used in which a fluorescent group is linked to a quencher through a peptide sequence that is a substrate that can be cleaved by the target protease. Cleavage of the linker separates the fluorescent group and quencher, giving rise to an increase in fluorescence.

G-protein coupled receptors (GPCR) are capable of activating an effector protein, resulting in changes in second messenger levels in the cell. The activity of a GPCR can be measured by measuring the activity level of such second messengers. Two important and useful second messengers in the cell are cyclic AMP (cAMP) and $Ca^{2+}$. The activity levels can be measured by methods known to persons skilled in the art, either directly by ELISA or radioactive technologies or by using substrates that generate a fluorescent or luminescent signal when contacted with $Ca^{2+}$ or indirectly by reporter gene analysis. The activity level of the one or more secondary messengers may typically be determined with a reporter gene controlled by a promoter, wherein the promoter is responsive to the second messenger. Promoters known and used in the art for such purposes are the cyclic-AMP responsive promoter that is responsive for the cyclic-AMP levels in the cell, and the NF-AT responsive promoter that is sensitive to cytoplasmic $Ca^{2+}$-levels in the cell. The reporter gene typically has a gene product that is easily detectable. The reporter gene can either be stably infected or transiently transfected in the host cell. Useful reporter genes are alkaline phosphatase, enhanced green fluorescent protein, destabilized green fluorescent protein, luciferase and β-galactosidase.

It should be understood that the cells expressing the polypeptides, may be cells naturally expressing the polypeptides, or the cells may be transfected to express the polypeptides, as described above. Also, the cells may be transduced to overexpress the polypeptide, or may be transfected to express a non-endogenous form of the polypeptide, which can be differentially assayed or assessed.

In one particular embodiment the methods of the present invention further comprise the step of contacting the population of cells with an agonist of the polypeptide. This is useful in methods wherein the expression of the polypeptide in a certain chosen population of cells is too low for a proper detection of its activity. By using an agonist the polypeptide may be triggered, enabling a proper read-out if the compound inhibits the polypeptide. Similar considerations apply to the measurement of the activity of CFTR. In a particular embodiment, the cells used in the present method are mammalian lung epithelial cells. The lung epithelial cells, in the assay contemplated, may be activated (e.g. by cytokines).

A method for identifying a compound that modulates trafficking of a disease-associated protein, comprising:
(a) contacting a compound with a polypeptide comprising an amino acid sequence selected from the group consisting of SEQ ID NO: 30-55, and fragments thereof; and
(b) measuring a compound-polypeptide property related to protein trafficking.

In one embodiment of the present invention the method relates to identifying a compound that promotes migration of ΔF508-CFTR to the plasma membrane.

In one embodiment of the present invention the compound-polypeptide property related to protein trafficking is binding affinity.

In one embodiment of the present invention the compound-polypeptide property related to protein trafficking is increased activity of ΔF508-CFTR or CFTR.

In one embodiment of the present invention the compound-polypeptide property related to protein trafficking is the activity of said polypeptide. In particular, in one embodiment the compound inhibits the activity of said polypeptide.

In one embodiment of the present invention the compound-polypeptide property related to protein trafficking is the expression of said polypeptide. In particular, in one embodiment the compound inhibits the expression of said polypeptide.

The present invention further relates to a method for identifying a compound that modulates trafficking of a protein misfolding disease-related protein, wherein said compound exhibits at least a moderate binding affinity to an amino acid selected from the group of SEQ ID NOS: 30-55, said method comprising:
a) contacting a compound with a population of mammalian cells expressing a polypeptide comprising an amino acid sequence selected from the group consisting of SEQ ID NOS: 30-55, wherein the cells also express the protein misfolding disease-related protein;
b) determining the activity or expression of the protein misfolding disease-related protein; and
d) identifying the compound that modulates protein trafficking as the compound which alters the activity or expression of the protein misfolding disease-related protein.

In one such method, the compound exhibits a binding affinity to an amino acid selected from the group of SEQ ID NOS: 30-55 of at least 10 micromolar. In one aspect, the binding affinity is at least 1 micromolar. In one aspect, the binding affinity is at least 500 nanomolar.

The present invention further relates to a method for identifying a compound that modulates trafficking of a disease-related protein, said method comprising:
a) contacting a compound with a polypeptide comprising an amino acid sequence selected from the group consisting of SEQ ID NO: 30-55;
b) determining the binding affinity of the compound to the polypeptide;
c) contacting a population of mammalian cells expressing said polypeptide with the compound that exhibits a binding affinity of at least 10 micromolar; and
d) identifying the compound that modulates protein trafficking.

The present invention further relates to a method for identifying a compound that modulates trafficking of a disease-related protein said method comprising:
  a) contacting a compound with a polypeptide comprising an amino acid sequence selected from the group consisting of SEQ ID NO: 30-55;
  b) determining the ability of the compound inhibit the expression or activity of the polypeptide;
  c) contacting a population of mammalian cells expressing said polypeptide with the compound that significantly inhibits the expression or activity of the polypeptide; and
  d) identifying the compound that modulates protein trafficking.

In a particular aspect of the present invention the methods described above include the additional step of comparing the compound to be tested to a control, where the control is a population of cells that have not been contacted with the test compound.

In a particular aspect of the present invention the methods described above include the additional step of comparing the compound to be tested to a control, where the control is a population of cells that do not express said polypeptide.

For high-throughput purposes, libraries of compounds may be used such as antibody fragment libraries, peptide phage display libraries, peptide libraries (e.g. LOPAP™, Sigma Aldrich), lipid libraries (BioMol), synthetic compound libraries (e.g. LOPAC™, Sigma Aldrich, BioFocus DPI) or natural compound libraries (Specs, TimTec, BioFocus DPI).

Preferred drug candidate compounds are low molecular weight compounds. Low molecular weight compounds, i.e. with a molecular weight of 500 Dalton or less, are likely to have good absorption and permeation in biological systems and are consequently more likely to be successful drug candidates than compounds with a molecular weight above 500 Dalton (Lipinski et al. (1997)). Peptides comprise another preferred class of drug candidate compounds. Peptides may be excellent drug candidates and there are multiple examples of commercially valuable peptides such as fertility hormones and platelet aggregation inhibitors. Natural compounds are another preferred class of drug candidate compound. Such compounds are found in and extracted from natural sources, and which may thereafter be synthesized. The lipids are another preferred class of drug candidate compound.

Another preferred class of drug candidate compounds is an antibody. The present invention also provides antibodies directed against the TARGETS. These antibodies may be endogenously produced to bind to the TARGETS within the cell, or added to the tissue to bind to the TARGET polypeptide present outside the cell. These antibodies may be monoclonal antibodies or polyclonal antibodies. The present invention includes chimeric, single chain, and humanized antibodies, as well as FAb fragments and the products of a FAb expression library, and Fv fragments and the products of an Fv expression library.

In certain embodiments, polyclonal antibodies may be used in the practice of the invention. The skilled artisan knows methods of preparing polyclonal antibodies. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. Antibodies may also be generated against the intact TARGET protein or polypeptide, or against a fragment, derivatives including conjugates, or other epitope of the TARGET protein or polypeptide, such as the TARGET embedded in a cellular membrane, or a library of antibody variable regions, such as a phage display library.

It may be useful to conjugate the immunizing agent to a protein known to be immunogenic in the mammal being immunized Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). One skilled in the art without undue experimentation may select the immunization protocol.

In some embodiments, the antibodies may be monoclonal antibodies. Monoclonal antibodies may be prepared using methods known in the art. The monoclonal antibodies of the present invention may be "humanized" to prevent the host from mounting an immune response to the antibodies. A "humanized antibody" is one in which the complementarity determining regions (CDRs) and/or other portions of the light and/or heavy variable domain framework are derived from a non-human immunoglobulin, but the remaining portions of the molecule are derived from one or more human immunoglobulins. Humanized antibodies also include antibodies characterized by a humanized heavy chain associated with a donor or acceptor unmodified light chain or a chimeric light chain, or vice versa. The humanization of antibodies may be accomplished by methods known in the art (see, e.g. Mark and Padlan, (1994) "Chapter 4. Humanization of Monoclonal Antibodies", The Handbook of Experimental Pharmacology Vol. 113, Springer-Verlag, New York). Transgenic animals may be used to express humanized antibodies.

Human antibodies can also be produced using various techniques known in the art, including phage display libraries (Hoogenboom and Winter, (1991) J. Mol. Biol. 227:381-8; Marks et al. (1991) J. Mol. Biol. 222:581-97). The techniques of Cole, et al. and Boerner, et al. are also available for the preparation of human monoclonal antibodies (Cole, et al. (1985) Monoclonal Antibodies and Cancer Therapy, Alan R. Liss, p. 77; Boerner, et al (1991) J. Immunol., 147(1):86-95).

Techniques known in the art for the production of single chain antibodies can be adapted to produce single chain antibodies to the TARGETS. The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

Bispecific antibodies are monoclonal, preferably human or humanized, antibodies that have binding specificities for at least two different antigens and preferably for a cell-surface protein or receptor or receptor subunit. In the present case, one of the binding specificities is for one domain of the TARGET; the other one is for another domain of the TARGET.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello (1983) Nature 305:537-9). Because of the random assortment of immunoglobulin heavy and light chains, these hybridomas (quadromas) produce a potential mixture of ten different antibody molecules, of which only one has the correct bispecific structure. Affinity chromatography steps usually accomplish the purification of the correct molecule. Similar procedures are disclosed in Trauneeker, et al. (1991) EMBO J. 10:3655-9.

According to another preferred embodiment, the assay method uses a drug candidate compound identified as having a binding affinity for the TARGET, and/or has already been identified as having down-regulating activity such as antagonist activity for the TARGET.

The present invention further relates to a method for increasing functional activity of CF-associated mutant CFTR comprising contacting said cells with an expression inhibitory agent comprising a polynucleotide sequence that complements at least about 15 to about 30, particularly at least 17 to about 30, most particularly at least 17 to about 25 contiguous nucleotides of a nucleotide sequence encoding a polypeptide TARGET or portion thereof including the nucleotide sequences selected from the group consisting of SEQ ID NO: 1-29.

Another aspect of the present invention relates to a method for increasing the functional activity of CF-associated mutant CFTR, comprising by contacting said cell with an expression-inhibiting agent that inhibits the translation in the cell of a polyribonucleotide encoding the TARGET. A particular embodiment relates to a composition comprising a polynucleotide including at least one antisense strand that functions to pair the agent with the TARGET mRNA, and thereby down-regulate or block the expression of the TARGET. The inhibitory agent preferably comprises antisense polynucleotide, a ribozyme, and a small interfering RNA (siRNA), wherein said agent comprises a nucleic acid sequence complementary to, or engineered from, a naturally-occurring polynucleotide sequence encoding a portion of a polypeptide comprising the amino acid sequence SEQ ID NO: 30-55. In a preferred embodiment the expression-inhibiting agent is complementary to a polynucleotide sequence consisting of SEQ ID NO: 1-29. In a preferred embodiment, the nucleotide sequence is complementary to a polynucleotide comprising a sequence selected from the group SEQ ID NO: 56-99. In another preferred embodiment the expression-inhibiting agent is complementary to a polynucleotide sequence selected from the group consisting of SEQ ID NO: 56-99.

An embodiment of the present invention relates to a method wherein the expression-inhibiting agent is selected from the group consisting of antisense RNA, antisense oligodeoxynucleotide (ODN), a ribozyme that cleaves the polyribonucleotide coding for SEQ ID NO: 30-55, a small interfering RNA (siRNA, preferably shRNA) that is sufficiently complementary to a portion of the polyribonucleotide coding for SEQ ID NO: 30-55, such that the siRNA, preferably shRNA, interferes with the translation of the TARGET polyribonucleotide to the TARGET polypeptide. Preferably the expression-inhibiting agent is an antisense RNA, ribozyme, antisense oligodeoxynucleotide, or siRNA, preferably shRNA, complementary to a nucleotide sequence selected from the group consisting of SEQ ID NO: 1-29. In a preferred embodiment, the nucleotide sequence is complementary to a polynucleotide comprising a sequence selected from the group SEQ ID NO: 56-99. In another preferred embodiment, the nucleotide sequence is complementary to a polynucleotide selected from the group consisting of SEQ ID NO: 56-99.

The down regulation of gene expression using antisense nucleic acids can be achieved at the translational or transcriptional level. Antisense nucleic acids of the invention are preferably nucleic acid fragments capable of specifically hybridizing with all or part of a nucleic acid encoding the TARGET or the corresponding messenger RNA. In addition, antisense nucleic acids may be designed which decrease expression of the nucleic acid sequence capable of encoding the TARGET by inhibiting splicing of its primary transcript. Any length of antisense sequence is suitable for practice of the invention so long as it is capable of down-regulating or blocking expression of a nucleic acid coding for the TARGETS. Preferably, the antisense sequence is at least about 17 nucleotides in length. The preparation and use of antisense nucleic acids, DNA encoding antisense RNAs and the use of oligo and genetic antisense is known in the art.

One embodiment of expression-inhibitory agent is a nucleic acid that is antisense to a nucleic acid selected from the group consisting of SEQ ID NO: 1-29. For example, an antisense nucleic acid (e.g. DNA) may be introduced into cells in vitro, or administered to a subject in vivo, as gene therapy to inhibit cellular expression of a nucleic acid selected from the group consisting of SEQ ID NO: 1-29. Antisense oligonucleotides preferably comprise a sequence containing from about 15 to about 100 nucleotides and more preferably the antisense oligonucleotides comprise from about 17 to about 30, most particularly at least 17 to about 25. Antisense nucleic acids may be prepared from about 10 to about 30 contiguous nucleotides complementary to a nucleic acid sequence selected from the sequences of SEQ ID NO: 1-29.

The skilled artisan can readily utilize any of several strategies to facilitate and simplify the selection process for antisense nucleic acids and oligonucleotides effective in inhibition of TARGET OPG expression. Predictions of the binding energy or calculation of thermodynamic indices between an oligonucleotide and a complementary sequence in an mRNA molecule may be utilized (Chiang et al. (1991) J. Biol. Chem. 266:18162-18171; Stull et al. (1992) Nucl. Acids Res. 20:3501-3508). Antisense oligonucleotides may be selected on the basis of secondary structure (Wickstrom et al (1991) in Prospects for Antisense Nucleic Acid Therapy of Cancer and AIDS, Wickstrom, ed., Wiley-Liss, Inc., New York, pp. 7-24; Lima et al. (1992) Biochem. 31:12055-12061). Schmidt and Thompson (U.S. Pat. No. 6,416,951) describe a method for identifying a functional antisense agent comprising hybridizing an RNA with an oligonucleotide and measuring in real time the kinetics of hybridization by hybridizing in the presence of an intercalation dye or incorporating a label and measuring the spectroscopic properties of the dye or the label's signal in the presence of unlabelled oligonucleotide. In addition, any of a variety of computer programs may be utilized which predict suitable antisense oligonucleotide sequences or antisense targets utilizing various criteria recognized by the skilled artisan, including for example the absence of self-complementarity, the absence hairpin loops, the absence of stable homodimer and duplex formation (stability being assessed by predicted energy in kcal/mol). Examples of such computer programs are readily available and known to the skilled artisan and include the OLIGO 4 or OLIGO 6 program (Molecular Biology Insights, Inc., Cascade, Colo.) and the Oligo Tech program (Oligo Therapeutics Inc., Wilsonville, Oreg.). In addition, antisense oligonucleotides suitable in the present invention may be identified by screening an oligonucleotide library, or a library of nucleic acid molecules, under hybridization conditions and selecting for those which hybridize to the target RNA or nucleic acid (see for example U.S. Pat. No. 6,500,615). Mishra and Toulme have also developed a selection procedure based on selective amplification of oligonucleotides that bind target (Mishra et al (1994) Life Sciences 317:977-982). Oligonucleotides may also be selected by their ability to mediate cleavage of target RNA by RNAse H, by selection and characterization of the cleavage fragments (Ho et al (1996) Nucl Acids Res 24:1901-1907; Ho et al (1998) Nature Biotechnology 16:59-630). Generation and targeting of oligonucleotides to GGGA motifs of RNA molecules has also been described (U.S. Pat. No. 6,277,981).

The antisense nucleic acids are preferably oligonucleotides and may consist entirely of deoxyribo-nucleotides, modified deoxyribonucleotides, or some combination of both. The antisense nucleic acids can be synthetic oligonucleotides. The oligonucleotides may be chemically modified, if desired, to improve stability and/or selectivity. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its target site, the RNA-DNA duplex activates the endogenous enzyme ribonuclease (RNase) H, which cleaves the mRNA component of the hybrid molecule. Oligonucleotides may also contain one or more substituted sugar moieties. Particular oligonucleotides comprise one of the following at the 2' position: OH, SH, $SCH_3$, F, OCN, heterocloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. Similar modifications may also be made at other positions on the oligonucleotide, particularly the 3' position of the sugar on the 3' terminal nucleotide and the 5' position of 5' terminal nucleotide.

In addition, antisense oligonucleotides with phosphoramidite and polyamide (peptide) linkages can be synthesized. These molecules should be very resistant to nuclease degradation. Furthermore, chemical groups can be added to the 2' carbon of the sugar moiety and the 5 carbon (C-5) of pyrimidines to enhance stability and facilitate the binding of the antisense oligonucleotide to its target site. Modifications may include 2'-deoxy, O-pentoxy, O-propoxy, O-methoxy, fluoro, methoxyethoxy phosphorothioates, modified bases, as well as other modifications known to those of skill in the art.

Another type of expression-inhibitory agent that can reduce the level of the TARGETS is the ribozyme. Ribozymes are catalytic RNA molecules (RNA enzymes) that have separate catalytic and substrate binding domains. The substrate binding sequence combines by nucleotide complementarity and, possibly, non-hydrogen bond interactions with its target sequence. The catalytic portion cleaves the target RNA at a specific site. The substrate domain of a ribozyme can be engineered to direct it to a specified mRNA sequence. The ribozyme recognizes and then binds a target mRNA through complementary base pairing. Once it is bound to the correct target site, the ribozyme acts enzymatically to cut the target mRNA. Cleavage of the mRNA by a ribozyme destroys its ability to direct synthesis of the corresponding polypeptide. Once the ribozyme has cleaved its target sequence, it is released and can repeatedly bind and cleave at other mRNAs.

Ribozyme forms include a hammerhead motif, a hairpin motif, a hepatitis delta virus, group I intron or RNaseP RNA (in association with an RNA guide sequence) motif or Neurospora VS RNA motif. Ribozymes possessing a hammerhead or hairpin structure are readily prepared since these catalytic RNA molecules can be expressed within cells from eukaryotic promoters (Chen, et al. (1992) Nucleic Acids Res. 20:4581-9). A ribozyme of the present invention can be expressed in eukaryotic cells from the appropriate DNA vector. If desired, the activity of the ribozyme may be augmented by its release from the primary transcript by a second ribozyme (Ventura, et al. (1993) Nucleic Acids Res. 21:3249-55).

Ribozymes may be chemically synthesized by combining an oligodeoxyribonucleotide with a ribozyme catalytic domain (20 nucleotides) flanked by sequences that hybridize to the target mRNA after transcription. The oligodeoxyribonucleotide is amplified by using the substrate binding sequences as primers. The amplification product is cloned into a eukaryotic expression vector.

Ribozymes are expressed from transcription units inserted into DNA, RNA, or viral vectors. Transcription of the ribozyme sequences are driven from a promoter for eukaryotic RNA polymerase I (pol (I), RNA polymerase II (pol II), or RNA polymerase III (pol III). Transcripts from pol II or pol III promoters will be expressed at high levels in all cells; the levels of a given pol II promoter in a given cell type will depend on nearby gene regulatory sequences. Prokaryotic RNA polymerase promoters are also used, providing that the prokaryotic RNA polymerase enzyme is expressed in the appropriate cells (Gao and Huang, (1993) Nucleic Acids Res. 21:2867-72). It has been demonstrated that ribozymes expressed from these promoters can function in mammalian cells (Kashani-Sabet, et al. (1992) Antisense Res. Dev. 2:3-15).

A particularly preferred inhibitory agent is a small interfering RNA (siRNA, preferably shRNA). siRNA, preferably shRNA, mediate the post-transcriptional process of gene silencing by double stranded RNA (dsRNA) that is homologous in sequence to the silenced RNA. siRNA according to the present invention comprises a sense strand of 15-30, particularly 17-30, most particularly 17-25 nucleotides complementary or homologous to a contiguous 17-25 nucleotide sequence of a sequence selected from the group consisting of SEQ ID NO: 1-29, and an antisense strand of 17-23 nucleotides complementary to the sense strand. Exemplary sequences are described as sequences complementary to SEQ ID NO: 56-99. The most preferred siRNA comprises sense and anti-sense strands that are 100 percent complementary to each other and the target polynucleotide sequence. Preferably the siRNA further comprises a loop region linking the sense and the antisense strand.

A self-complementing single stranded siRNA molecule polynucleotide according to the present invention comprises a sense portion and an antisense portion connected by a loop region linker. Preferably, the loop region sequence is 4-30 nucleotides long, more preferably 5-15 nucleotides long and most preferably 12 nucleotides long. In a most particular embodiment the linker sequence is UUGCUAUA or GUUUGCUAUAAC (SEQ ID NO: 100). Self-complementary single stranded siRNAs form hairpin loops and are more stable than ordinary dsRNA. In addition, they are more easily produced from vectors.

Analogous to antisense RNA, the siRNA can be modified to confirm resistance to nucleolytic degradation, or to enhance activity, or to enhance cellular distribution, or to enhance cellular uptake, such modifications may consist of modified internucleoside linkages, modified nucleic acid bases, modified sugars and/or chemical linkage the siRNA to one or more moieties or conjugates. The nucleotide sequences are selected according to siRNA designing rules that give an improved reduction of the TARGET sequences compared to nucleotide sequences that do not comply with these siRNA designing rules (For a discussion of these rules and examples of the preparation of siRNA, WO 2004/094636, and US 2003/0198627, are hereby incorporated by reference).

The present invention also relates to compositions, and methods using said compositions, comprising a DNA expression vector capable of expressing a polynucleotide capable of increasing functional activity of CF-associated mutant CFTR and described hereinabove as an expression inhibition agent.

A particular aspect of these compositions and methods relates to the down-regulation or blocking of the expression of the TARGET by the induced expression of a polynucleotide encoding an intracellular binding protein that is capable of selectively interacting with the TARGET. An intracellular binding protein includes any protein capable of selectively interacting, or binding, with the polypeptide in the cell in which it is expressed and neutralizing the function of the polypeptide. Preferably, the intracellular binding protein is a neutralizing antibody or a fragment of a neutralizing antibody having binding affinity to an epitope of a TARGET selected from the group consisting of SEQ ID NO: 30-55. More preferably, the intracellular binding protein is a single chain antibody.

A particular embodiment of this composition comprises the expression-inhibiting agent selected from the group consisting of antisense RNA, antisense oligodeoxynucleotide (ODN), a ribozyme that cleaves the polyribonucleotide coding for a TARGET selected from the group consisting of SEQ ID NO: 30-55, and a small interfering RNA (siRNA) that is sufficiently homologous to a portion of the polyribonucleotide coding for a TARGET selected from the group consisting of SEQ ID NO: 30-55, such that the siRNA interferes with the translation of the TARGET polyribonucleotide to the TARGET polypeptide.

The polynucleotide expressing the expression-inhibiting agent, or a polynucleotide expressing the TARGET polypeptide in cells, is particularly included within a vector. The polynucleic acid is operably linked to signals enabling expression of the nucleic acid sequence and is introduced into a cell utilizing, preferably, recombinant vector constructs, which will express the antisense nucleic acid once the vector is introduced into the cell. A variety of viral-based systems are available, including adenoviral, retroviral, adeno-associated viral, lentiviral, herpes simplex viral or a sendaiviral vector systems, and all may be used to introduce and express polynucleotide sequence for the expression-inhibiting agents or the polynucleotide expressing the TARGET polypeptide in the target cells.

Particularly, the viral vectors used in the methods of the present invention are replication defective. Such replication defective vectors will usually pack at least one region that is necessary for the replication of the virus in the infected cell. These regions can either be eliminated (in whole or in part), or be rendered non-functional by any technique known to a person skilled in the art. These techniques include the total removal, substitution, partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome, which are necessary for encapsidating, the viral particles.

In a preferred embodiment, the viral element is derived from an adenovirus. Preferably, the vehicle includes an adenoviral vector packaged into an adenoviral capsid, or a functional part, derivative, and/or analogue thereof. Adenovirus biology is also comparatively well known on the molecular level. Many tools for adenoviral vectors have been and continue to be developed, thus making an adenoviral capsid a preferred vehicle for incorporating in a library of the invention. An adenovirus is capable of infecting a wide variety of cells. However, different adenoviral serotypes have different preferences for cells. To combine and widen the target cell population that an adenoviral capsid of the invention can enter in a preferred embodiment, the vehicle includes adenoviral fiber proteins from at least two adenoviruses. Preferred adenoviral fiber protein sequences are serotype 17, 45 and 51. Techniques or construction and expression of these chimeric vectors are disclosed in US 2003/0180258 and US 2004/0071660, hereby incorporated by reference.

In a preferred embodiment, the nucleic acid derived from an adenovirus includes the nucleic acid encoding an adenoviral late protein or a functional part, derivative, and/or analogue thereof. An adenoviral late protein, for instance an adenoviral fiber protein, may be favorably used to target the vehicle to a certain cell or to induce enhanced delivery of the vehicle to the cell. Preferably, the nucleic acid derived from an adenovirus encodes for essentially all adenoviral late proteins, enabling the formation of entire adenoviral capsids or functional parts, analogues, and/or derivatives thereof. Preferably, the nucleic acid derived from an adenovirus includes the nucleic acid encoding adenovirus E2A or a functional part, derivative, and/or analogue thereof. Preferably, the nucleic acid derived from an adenovirus includes the nucleic acid encoding at least one E4-region protein or a functional part, derivative, and/or analogue thereof, which facilitates, at least in part, replication of an adenoviral derived nucleic acid in a cell. The adenoviral vectors used in the examples of this application are exemplary of the vectors useful in the present method of treatment invention.

Certain embodiments of the present invention use retroviral vector systems. Retroviruses are integrating viruses that infect dividing cells, and their construction is known in the art. Retroviral vectors can be constructed from different types of retrovirus, such as, MoMuLV ("murine Moloney leukemia virus") MSV ("murine Moloney sarcoma virus"), HaSV ("Harvey sarcoma virus"); SNV ("spleen necrosis virus"); RSV ("Rous sarcoma virus") and Friend virus. Lentiviral vector systems may also be used in the practice of the present invention.

In other embodiments of the present invention, adeno-associated viruses ("AAV") are utilized. The AAV viruses are DNA viruses of relatively small size that integrate, in a stable and site-specific manner, into the genome of the infected cells. They are able to infect a wide spectrum of cells without inducing any effects on cellular growth, morphology or differentiation, and they do not appear to be involved in human pathologies.

In the vector construction, the polynucleotide agents of the present invention may be linked to one or more regulatory regions. Selection of the appropriate regulatory region or regions is a routine matter, within the level of ordinary skill in the art. Regulatory regions include promoters, and may include enhancers, suppressors, etc.

Promoters that may be used in the expression vectors of the present invention include both constitutive promoters and regulated (inducible) promoters. The promoters may be prokaryotic or eukaryotic depending on the host. Among the prokaryotic (including bacteriophage) promoters useful for practice of this invention are lac, lacZ, T3, T7, lambda $P_r$, $P_1$, and trp promoters. Among the eukaryotic (including viral) promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells, or Flt and Flk promoters active in endothelial cells), including animal transcriptional control regions, which exhibit tissue specificity and have been utilized in transgenic animals: elastase I gene control region which is active in pancreatic acinar cells (Swift, et al. (1984) Cell 38:639-46; Ornitz, et al. (1986) Cold Spring Harbor Symp. Quant. Biol. 50:399-409; MacDonald, (1987) Hepatology 7:425-515); insulin gene control region which is active in pancreatic beta cells (Hanahan, (1985) Nature 315:115-22), immunoglobulin gene control region which is active in lymphoid cells (Grosschedl, et al. (1984) Cell 38:647-58; Adames, et al. (1985) Nature 318:533-8; Alexander, et al. (1987) Mol. Cell. Biol. 7:1436-44), mouse mammary tumor virus control region which is active in testicular, breast, lymphoid and mast cells (Leder, et al. (1986) Cell 45:485-95), albumin gene control region which is active in liver (Pinkert, et al. (1987) Genes and Devel. 1:268-76), alpha-fetoprotein gene control region which is active in liver (Krumlauf, et al. (1985) Mol. Cell. Biol., 5:1639-48; Hammer, et al. (1987) Science 235:53-8), alpha 1-antitrypsin gene control region which is active in the liver (Kelsey, et al. (1987) Genes and Devel., 1: 161-71), beta-globin gene control region which is active in myeloid cells (Mogram, et al. (1985) Nature 315: 338-40; Kollias, et al. (1986) Cell 46:89-94), myelin basic protein gene control region which is active in oligodendrocyte cells in the brain (Readhead, et al. (1987) Cell 48:703-12), myosin light chain-2 gene control region which is active in skeletal muscle (Sani, (1985) Nature 314.283-6), and gonadotropic releasing hormone gene control region which is active in the hypothalamus (Mason, et al. (1986) Science 234:1372-8).

Other promoters which may be used in the practice of the invention include promoters which are preferentially activated in dividing cells, promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters. Further promoters which may be of use in the practice of the invention include promoters which are active and/or expressed in lung cells, or in epithelial cells, particularly in airway or brochial epithelial cells.

Additional vector systems include the non-viral systems that facilitate introduction of polynucleotide agents into a patient. For example, a DNA vector encoding a desired sequence can be introduced in vivo by lipofection. Synthetic cationic lipids designed to limit the difficulties encountered with liposome-mediated transfection can be used to prepare liposomes for in vivo transfection of a gene encoding a marker (Felgner, et. al. (1987) Proc. Natl. Acad. Sci. USA 84:7413-7); see Mackey, et al. (1988) Proc. Natl. Acad. Sci. USA 85:8027-31; Ulmer, et al. (1993) Science 259:1745-8). The use of cationic lipids may promote encapsulation of negatively charged nucleic acids, and also promote fusion with negatively charged cell membranes (Felgner and Ringold, (1989) Nature 337:387-8). Particularly useful lipid compounds and compositions for transfer of nucleic acids are described in International Patent Publications WO 95/18863 and WO 96/17823, and in U.S. Pat. No. 5,459,127. The use of lipofection to introduce exogenous genes into the specific organs in vivo has certain practical advantages and directing transfection to particular cell types would be particularly advantageous in a tissue with cellular heterogeneity, for example, pancreas, liver, kidney, and the brain. Lipids may be chemically coupled to other molecules for the purpose of targeting. Targeted peptides, e.g., hormones or neurotransmitters, and proteins for example, antibodies, or non-peptide molecules could be coupled to liposomes chemically. Other molecules are also useful for facilitating transfection of a nucleic acid in vivo, for example, a cationic oligopeptide (e.g., International Patent Publication WO 95/21931), peptides derived from DNA binding proteins (e.g., International Patent Publication WO 96/25508), or a cationic polymer (e.g., International Patent Publication WO 95/21931).

It is also possible to introduce a DNA vector in vivo as a naked DNA plasmid (see U.S. Pat. Nos. 5,693,622, 5,589,466 and 5,580,859). Naked DNA vectors for therapeutic purposes can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wilson, et al. (1992) J. Biol. Chem. 267:963-7; Wu and Wu, (1988) J. Biol. Chem. 263: 14621-4; Hartmut, et al. Canadian Patent Application No. 2,012,311, filed Mar. 15, 1990; Williams, et al (1991). Proc. Natl. Acad. Sci. USA 88:2726-30). Receptor-mediated DNA delivery approaches can also be used (Curiel, et al. (1992) Hum. Gene Ther. 3:147-54; Wu and Wu, (1987) J. Biol. Chem. 262:4429-32).

The present invention also provides biologically compatible, CF-associated mutant CFTR inducing compositions comprising an effective amount of one or more compounds identified as TARGET inhibitors, and/or the expression-inhibiting agents as described hereinabove.

A biologically compatible composition is a composition, that may be solid, liquid, gel, or other form, in which the compound, polynucleotide, vector, and antibody of the invention is maintained in an active form, e.g., in a form able to effect a biological activity. For example, a compound of the invention would have inverse agonist or antagonist activity on the TARGET; a nucleic acid would be able to replicate, translate a message, or hybridize to a complementary mRNA of the TARGET; a vector would be able to transfect a target cell and express the antisense, antibody, ribozyme or siRNA as described hereinabove; an antibody would bind a the TARGET polypeptide domain.

A particular biologically compatible composition is an aqueous solution that is buffered using, e.g., Tris, phosphate, or HEPES buffer, containing salt ions. Usually the concentration of salt ions will be similar to physiological levels. Biologically compatible solutions may include stabilizing agents and preservatives. In a more preferred embodiment, the biocompatible composition is a pharmaceutically acceptable composition. Such compositions can be formulated for administration by topical, oral, parenteral, intranasal, subcutaneous, and intraocular, routes. Parenteral administration is meant to include intravenous injection, intramuscular injection, intra-arterial injection or infusion techniques. The composition may be administered parenterally in dosage unit formulations containing standard, well-known non-toxic physiologically acceptable carriers, adjuvants and vehicles as desired.

A particular embodiment of the present composition invention is a pharmaceutical composition comprising a therapeutically effective amount of an expression-inhibiting agent as described hereinabove, in admixture with a pharmaceutically acceptable carrier. Another preferred embodiment is a pharmaceutical composition for the treatment or prevention of a disease involving a decrease in functional activity of CF-associated mutant CFTR, or a susceptibility to the condition, comprising an effective amount of the TARGET antagonist or inverse agonist, its pharmaceutically acceptable salts, hydrates, solvates, or prodrugs thereof in admixture with a pharmaceutically acceptable carrier.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical compositions for oral use can be prepared by combining active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate. Dragee cores may be used in conjunction with suitable coatings, such as concentrated sugar solutions, which may also contain gum arabic, talc, polyvinyl-pyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Preferred sterile injectable preparations can be a solution or suspension in a non-toxic parenterally acceptable solvent or diluent. Examples of pharmaceutically acceptable carriers are saline, buffered saline, isotonic saline (e.g. monosodium or disodium phosphate, sodium, potassium; calcium or magnesium chloride, or mixtures of such salts), Ringer's solution, dextrose, water, sterile water, glycerol, ethanol, and combinations thereof 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The agents or compositions of the invention may be combined for administration with or embedded in polymeric carrier(s), biodegradable or biomimetic matrices or in a scaffold. The carrier, matrix or scaffold may be of any material that will allow composition to be incorporated and expressed and will be compatible with the addition of cells or in the presence of cells. Particularly, the carrier matrix or scaffold is predominantly non-immunogenic and is biodegradable. Examples of biodegradable materials include, but are not limited to, polyglycolic acid (PGA), polylactic acid (PLA), hyaluronic acid, catgut suture material, gelatin, cellulose, nitrocellulose, collagen, albumin, fibrin, alginate, cotton, or other naturally-occurring biodegradable materials. It may be preferable to sterilize the matrix or scaffold material prior to administration or implantation, e.g., by treatment with ethylene oxide or by gamma irradiation or irradiation with an electron beam. In addition, a number of other materials may be used to form the scaffold or framework structure, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), polymers of hydroxy acids such as polylactic acid (PLA), polyglycolic acid (PGA), and polylactic acid-glycolic acid (PLGA), polyorthoesters, polyanhydrides, polyphosphazenes, and a variety of polyhydroxyalkanoates, and combinations thereof. Matrices suitable include a polymeric mesh or sponge and a polymeric hydrogel. In the particular embodiment, the matrix is biodegradable over a time period of less than a year, more particularly less than six months, most particularly over two to ten weeks. The polymer composition, as well as method of manufacture, can be used to determine the rate of degradation. For example, mixing increasing amounts of polylactic acid with polyglycolic acid decreases the degradation time. Meshes of polyglycolic acid that can be used can be obtained commercially, for instance, from surgical supply companies (e.g., Ethicon, N.J.). In general, these polymers are at least partially soluble in aqueous solutions, such as water, buffered salt solutions, or aqueous alcohol solutions, that have charged side groups, or a monovalent ionic salt thereof.

The composition medium can also be a hydrogel, which is prepared from any biocompatible or non-cytotoxic homo- or hetero-polymer, such as a hydrophilic polyacrylic acid polymer that can act as a drug absorbing sponge. Certain of them, such as, in particular, those obtained from ethylene and/or propylene oxide are commercially available. A hydrogel can be deposited directly onto the surface of the tissue to be treated, for example during surgical intervention.

Embodiments of pharmaceutical compositions of the present invention comprise a replication defective recombinant viral vector encoding the polynucleotide inhibitory agent of the present invention and a transfection enhancer, such as poloxamer. An example of a poloxamer is Poloxamer 407, which is commercially available (BASF, Parsippany, N.J.) and is a non-toxic, biocompatible polyol. A poloxamer impregnated with recombinant viruses may be deposited directly on the surface of the tissue to be treated, for example during a surgical intervention. Poloxamer possesses essentially the same advantages as hydrogel while having a lower viscosity.

The active expression-inhibiting agents may also be entrapped in microcapsules prepared, for example, by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1980) 16th edition, Osol, A. Ed.

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

As defined above, therapeutically effective dose means that amount of protein, polynucleotide, peptide, or its antibodies, agonists or antagonists, which ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, and it can be expressed as the ratio, $LD_{50}/ED_{50}$. Pharmaceutical compositions that exhibit large therapeutic indices are preferred. The data obtained from cell culture assays and animal studies are used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The pharmaceutical compositions according to this invention may be administered to a subject by a variety of methods. They may be added directly to target tissues, complexed with cationic lipids, packaged within liposomes, or delivered to target cells by other methods known in the art. Localized administration to the desired tissues may be done by direct injection, transdermal absorption, catheter, infusion pump or stent. The DNA, DNA/vehicle complexes, or the recombinant virus particles are locally administered to the site of treatment. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery. Examples of ribozyme delivery and administration are provided in Sullivan et al. WO 94/02595.

Antibodies according to the invention may be delivered as a bolus only, infused over time or both administered as a bolus and infused over time. Those skilled in the art may employ different formulations for polynucleotides than for proteins. Similarly, delivery of polynucleotides or polypeptides will be specific to particular cells, conditions, locations, etc.

As discussed hereinabove, recombinant viruses may be used to introduce DNA encoding polynucleotide agents useful in the present invention. Recombinant viruses according to the invention are generally formulated and administered in the form of doses of between about $10^4$ and about $10^{14}$ pfu. In the case of AAVs and adenoviruses, doses of from about $10^6$ to about $10^{11}$ pfu are preferably used. The term pfu ("plaque-forming unit") corresponds to the infective power of a suspension of virions and is determined by infecting an appropriate cell culture and measuring the number of plaques formed. The techniques for determining the pfu titre of a viral solution are well documented in the prior art.

In one aspect the present invention provides methods of preventing and/or treating disorders involving ER-associated protein misfolding, said methods comprising administering to a subject a therapeutically effective amount of an agent as disclosed herein. In a particular embodiment, the agent is selected from an expression-inhibiting agent and an antibody.

In a further aspect the present invention provides a method of preventing and/or treating a disease characterized by abnormal trafficking of a disease associated protein, said method comprising administering to a subject a therapeutically effective amount of an agent as disclosed herein. In a particular embodiment, the agent is selected from an expression-inhibiting agent and an antibody.

In a particular aspect, the present invention provides a method of preventing and/or treating Cystic Fibrosis, said method comprising administering to a subject a a therapeutically effective amount of an agent as disclosed herein. In a particular embodiment, the agent is selected from an expression-inhibiting agent and an antibody.

A further aspect of the invention relates to a method of treating or preventing a disease involving a decrease in CF-associated mutant CFTR function, comprising administering to said subject a therapeutically effective amount of an agent as disclosed herein. In a particular embodiment, the agent is selected from an expression-inhibiting agent and an antibody.

The invention also relates to the use of an agent as described above for the preparation of a medicament for treating or preventing a disease involving ER-associated protein misfolding. In a particular embodiment, the disease is characterised by abnormal trafficking of a disease-associated protein. In a particular embodiment of the present invention the disease is selected from Cystic Fibrosis, Parkinson's Disease, Gaucher's Disease, Nephrogenic diabetes insipidus, Emphysema and Liver Disease (alpha-1-antitrypsin deficiency), Maple syrup urine disease, Fabry's disease, Hypogonadotropic hypogonadism, Hyperinsulinemic hypoglycemia, beta-Galactosidosis, Wilson disease, Long QT syndrome, Retinitis pigmentosa, transthyretin-linked amyloidosis, Alzheimer's Disease, Prion disease, and inclusion body myositis. In a further embodiment of the present invention the disease is cystic fibrosis.

The invention also relates to the use of an agent as described above for the preparation of a medicament for treating or preventing an airway epithelial or brochial inflammatory disease, including asthma or COPD.

The present invention also provides a method of treating and/or preventing a disease involving ER-associated protein misfolding said method comprising administering, to a subject suffering from, or susceptible to, a disease involving ER-associated protein misfolding, a pharmaceutical composition or compound as described herein, particularly a therapeutically effective amount of an agent which inhibits the expression or activity of a TARGET as identified herein. In one embodiment, the disease is characterized by abnormal trafficking of a disease-associated protein. In a further embodiment the disease is selected from cystic fibrosis, Parkinson's disease, Gaucher's disease, nephrogenic diabetes insipidus, emphysema and liver disease (alpha-1-antitrypsin deficiency), Maple syrup urine disease, Fabry's disease, hypogonadotropic hypogonadism, hyperinsulinemic hypoglycemia, beta-galactosidosis, Wilson's disease, long QT syndrome, retinitis pigmentosa, transthyretin-linked amyloidosis, Alzheimer's Disease, Prion disease, and inclusion body myositis. In a further embodiment of the present invention the disease is cystic fibrosis.

The present invention also provides a method of treating and/or preventing asthma and COPD said method comprising administering, to a subject suffering from or susceptible to, asthma and COPD a pharmaceutical composition or an agent as described herein.

The invention also relates to an agent or a pharmaceutical composition as described above for use in the treatment and/or prevention of a disease involving ER-associated protein misfolding. In a particular embodiment, the disease is characterised by abnormal trafficking of a disease-associated protein. In a particular embodiment of the present invention the disease is selected from cystic fibrosis, Parkinson's disease, Gaucher's disease, nephrogenic diabetes insipidus, emphysema and liver disease (alpha-1-antitrypsin deficiency), Maple syrup urine disease, Fabry's disease, hypogonadotropic hypogonadism, hyperinsulinemic hypoglycemia, beta-galactosidosis, Wilson's disease, long QT syndrome, retinitis pigmentosa, transthyretin-linked amyloidosis, Alzheimer's disease, Prion disease, and inclusion body myositis. In a further embodiment of the present invention the disease is cystic fibrosis.

The invention also relates to an agent or a pharmaceutical composition as described above for use in the treatment and/or prevention of an airway epithelial or brochial inflammatory disease, including asthma or COPD.

Administration of the agent or pharmaceutical composition of the present invention to the subject patient includes both self-administration and administration by another person. The patient may be in need of treatment for an existing disease or medical condition, or may desire prophylactic treatment to prevent or reduce the risk for diseases and medical conditions characterized by ER-associated protein misfolding. The agent of the present invention may be delivered to the subject patient orally, transdermally, via inhalation, injection, nasally, rectally or via a sustained release formulation.

Still another aspect of the invention relates to a method for diagnosing a pathological condition involving ER-associated protein misfolding, comprising determining the amount of a polypeptide comprising an amino acid sequence selected from the group consisting of SEQ ID NO: 30-55 in a biological sample, and comparing the amount with the amount of the polypeptide in a healthy subject, wherein an increase of the amount of polypeptide compared to the healthy subject is indicative of the presence of the pathological condition. In one embodiment, the disease is characterized by abnormal trafficking of a disease-associated protein. In a further embodiment the disease is selected from cystic fibrosis, Parkinson's disease, Gaucher's disease, nephrogenic diabetes insipidus, emphysema and liver disease (alpha-1-antitrypsin deficiency), Maple syrup urine disease, Fabry's disease, hypogonadotropic hypogonadism, hyperinsulinemic hypoglycemia, beta-galactosidosis, Wilson's disease, long QT syndrome, retinitis pigmentosa, transthyretin-linked amyloidosis, Alzheimer's disease, Prion disease, and inclusion body myositis. In a particular embodiment, said method may be used to diagnose a decrease in CF-associated mutant CFTR functionality or a susceptibility to the condition in a subject. In a further embodiment of the present invention the disease is cystic fibrosis.

Still another aspect of the invention relates to a method for diagnosing a pathological condition involving ER-associated protein misfolding, comprising determining the activity of a polypeptide comprising an amino acid sequence selected from the group consisting of SEQ ID NO: 30-55 in a biological sample, and comparing the activity with the activity of the polypeptide in a healthy subject, wherein an increase of the activity of polypeptide compared to the healthy subject is indicative of the presence of the pathological condition. In one embodiment, the disease is characterized by abnormal trafficking of a disease-associated protein. In an embodiment, the disease is characterized by abnormal folding of a disease-associated protein. In an embodiment, the disease is characterized by misfolding and degradation of a disease-associated protein. In a further embodiment the disease is selected from cystic fibrosis, Parkinson's disease, Gaucher's disease, nephrogenic diabetes insipidus, emphysema and liver disease (alpha-1-antitrypsin deficiency), Maple syrup urine disease, Fabry's disease, hypogonadotropic hypogonadism, hyperinsulinemic hypoglycemia, beta-galactosidosis, Wilson's disease, long QT syndrome, retinitis pigmentosa, transthyretin-linked amyloidosis, Alzheimer's disease, Prion disease, and inclusion body myositis. In a particular embodiment, said method may be used to diagnose a decrease in CF-associated mutant CFTR functionality or a susceptibility to the condition in a subject. In a further embodiment of the present invention the disease is cystic fibrosis.

Still another aspect of the invention relates to a method for diagnosing a pathological condition involving ER-associated protein misfolding, comprising determining the nucleic acid sequence of at least one of the genes of SEQ ID NO: 1-29 within the genomic DNA of a subject; comparing the sequence with the nucleic acid sequence obtained from a database and/or a healthy subject; and identifying any difference(s) related to the onset or prevalence of the pathological conditions disclosed herein.

The polypeptides or the polynucleotides of the present invention employed in the methods described herein may be free in solution, affixed to a solid support, borne on a cell surface, or located intracellularly. To perform the methods it is feasible to immobilize either the polypeptide of the present invention or the compound to facilitate separation of complexes from uncomplexed forms of the polypeptide, as well as to accommodate automation of the assay. Interaction (e.g., binding of) of the polypeptide of the present invention with a compound can be accomplished in any vessel suitable for containing the reactants. Examples of such vessels include microtitre plates, test tubes, and microcentrifuge tubes. In one embodiment, a fusion protein can be provided which adds a domain that allows the polypeptide to be bound to a matrix. For example, the polypeptide of the present invention can be "His" tagged, and subsequently adsorbed onto Ni-NTA microtitre plates, or ProtA fusions with the polypeptides of the present invention can be adsorbed to IgG, which are then combined with the cell lysates (e.g., $^{(35)}$S-labelled) and the candidate compound, and the mixture incubated under conditions favorable for complex formation (e.g., at physiological conditions for salt and pH). Following incubation, the plates are washed to remove any unbound label, and the matrix is immobilized. The amount of radioactivity can be determined directly, or in the supernatant after dissociation of the complexes. Alternatively, the complexes can be dissociated from the matrix, separated by SDS-PAGE, and the level of the protein binding to the protein of the present invention quantitated from the gel using standard electrophoretic techniques.

Other techniques for immobilizing protein on matrices can also be used in the method of identifying compounds. For example, either the polypeptide of the present invention or the compound can be immobilized utilizing conjugation of biotin and streptavidin. Biotinylated protein molecules of the present invention can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptides of the present invention but which do not interfere with binding of the polypeptide to the compound can be derivatized to the wells of the plate, and the polypeptide of the present invention can be trapped in the wells by antibody conjugation. As described above, preparations of a labeled candidate compound are incubated in the wells of the plate presenting the polypeptide of the present invention, and the amount of complex trapped in the well can be quantitated.

The polynucleotides encoding the TARGET polypeptides are identified as SEQ ID NO: 1-29. The present inventors show herein that transfection of mammalian cells with Ad-siRNAs targeting these genes increases the functional activity of CF-associated mutant CFTR.

The invention is further illustrated in the following figures and examples.

EXPERIMENTAL SECTION

Example 1

Development of a High-Throughput Screening Method for CFTR-Dependent Halide Flux 1.1 Principal of the Assay Cystic Fibrosis Transmembrane Conductance Regulator (CFTR), by its chloride channel function, plays a key role in chloride secretion and water balance in epithelia throughout the body. Other halides such as iodide also make use of CFTR. Accordingly, an assay to monitor CFTR-halide flux by using a reporter protein, halide-sensitive fluorescent protein YFP, is developed to measure the functional activity of CFTR. Cells expressing this reporter protein show enhanced fluorescence quenching of YFP by extracellular isomolar iodide solutions in the presence of activated CFTR. This is caused by the increased flux of iodide across the plasma membrane by CFTR. The fluorescence quenching is measured on a fluorescence plate reader.

1.2 Development of the Assay

Human lung epithelial cells are isolated from a ΔF508-CFTR patient, obtained after informed consent. These cells are stably transfected with ΔF508-CFTR expression plasmids and are named CFBE41o-cells (Gruenert et al., 2004). This is a preferred cell model because it is of human origin and derived from the primary organ suffering from the effect of the CF-associated mutations. Targets identified in human model systems are commonly considered to have lower attrition as compared to targets identified in models from different species, which have naturally diverged from humans during evolution. CFBE41o-cells are cultured on tissue culture grade plastic, coated with 0.1 mg/mL bovine serum albumin (BSA), 0.03 mg/mL bovine collagen type 1 and 0.01 mg/mL human fibronectin. CFBE41o-cells are cultured in MEM containing 10% Fetal Bovine Serum, 2 mM glutamine, 100 IU/mL penicilline, 0.1 mg/mL streptomycine sulfate and 0.5 mg/mL hygromycin B at 37° C., 5% $CO_2$ in a humidified chamber. For high-throughput screening, 96-well plates are seeded with 1,000 cells per well.

As discussed above, measuring halide channel activity in cells expressing CFTR represents the preferred method for measuring the functional activity of CF-associated mutant CFTR. Halide channel activity is measured using the reporter, halide-sensitive fluorescent protein YFP (Galietta et al., 2001a).

To efficiently express the halide-sensitive fluorescent protein YFP in CFBE41o-cells, the reporter cDNA is synthesized and cloned in adenoviral adapter plasmids. dE1/dE2A (deleted for adenoviral genes E1 and E2A) adenoviruses are generated from these adapter plasmids by co-transfection of the helper plasmid pWEAd5AflII-rITR.dE2A in PER.E2A packaging cells, as described in WO99/64582.

In order to specifically assess the activity of ΔF508-CFTR, this protein is expressed, or as a positive control, the wild-type CFTR is expressed, from adenoviral vectors. ΔF508-CFTR cDNA or the wild-type CFTR cDNA (GenBank accession number NM_000492) (SEQ ID NO: 101) is cloned in adenoviral adapter plasmids to produce adenoviral vectors.

To determine the optimal conditions for adenoviral transduction, several conditions for the expression of the YFP halide reporter are tested. An experiment is performed where increasing amounts of adenoviral vectors as defined by virus particles per cell (VPU) are used to transduce CFBE41o-cells. VPU is determined by quantitative PCR, and is defined as adenoviral particles per ml according to (Ma et al., 2001). Three days after transduction of the fluorescent halide reporter, transduction efficiency is measured using fluorescent activated cell sorting (FACS) (Becton Dickinson FACS-calibur) with excitation at 488 nm. The outcome of such an experiment is shown in FIGS. 1A and 1B. In this experiment, CFBE41o-cells are transduced with increasing VPU of adenovirus without a cDNA (empty), enhanced Green Fluorescent Protein (eGFP) as a positive control, and the YFP halide-sensitive fluorescent protein (YFP). Three days after transduction, cells are detached with trypsin, fixed and analysed with FACS (10,000 cells are counted).

As can be seen in FIGS. 1A and 1B, adenovirus without a cDNA represents the background fluorescence in the cells (2.14% at VPU 500 and 2.85% at VPU 2000). eGFP transduction results in 93.3% and 97.4% positive cells at VPU 500 and VPU 2000 respectively. YFP transduction results in 84.2% and 93.4% positive cells at VPU 500 and VPU 2000 respectively. YFP transduction at VPU 2000 results in significantly stronger fluorescent signal compared to VPU 500 (62.6 versus 27.5 respectively). Thus, transduction with the adenoviral YFP reporter at VPU 2000 is the preferred method.

Example 2

Validation of the CFTR-Dependent Halide Flux Assay

In this example, it is shown that the halide-sensitive reporter expressed in CFBE41o-cells can monitor functional activity of CFTR. CFBE41o-cells are transduced with the YFP fluorescent halide reporter adenoviral vector at a VPU of 2000 viral particles per cell, together with adenoviral vectors expressing ΔF508-CFTR, or as a positive control the wild-type CFTR. Three days after transduction, wells are washed two times with phosphate-buffered saline (PBS: 137 mM NaCl, 2.7 mM KCl, 10 mM $Na_2HPO_4$, 1.76 mM $KH_2PO_4$ at pH 7.4), and incubated in 40 microliter of PBS containing 10 microM forskolin and 100 microM genistein for 5 minutes. Forskolin and genistein have been shown to activate CFTR activity (Hwang et al., 1997), and are used here to pre-activate any existing CFTR. Plates are read in a fluorescent plate reader, equipped with injectors for the delivery of reagents to the well (Perkin-Elmer Envision 2102). Each well is read for 2 seconds at 485/530 nm (excitation/emission) prior to the addition of 110 microliter iodide-containing buffer (137 mM NaI, 2.7 mM KCl, 10 mM $Na_2HPO_4$, 1.76 mM $KH_2PO_4$ at pH 7.4). Fluorescent reading is continued for an additional 12 sec, sampling every 200 msec.

Figure 2:
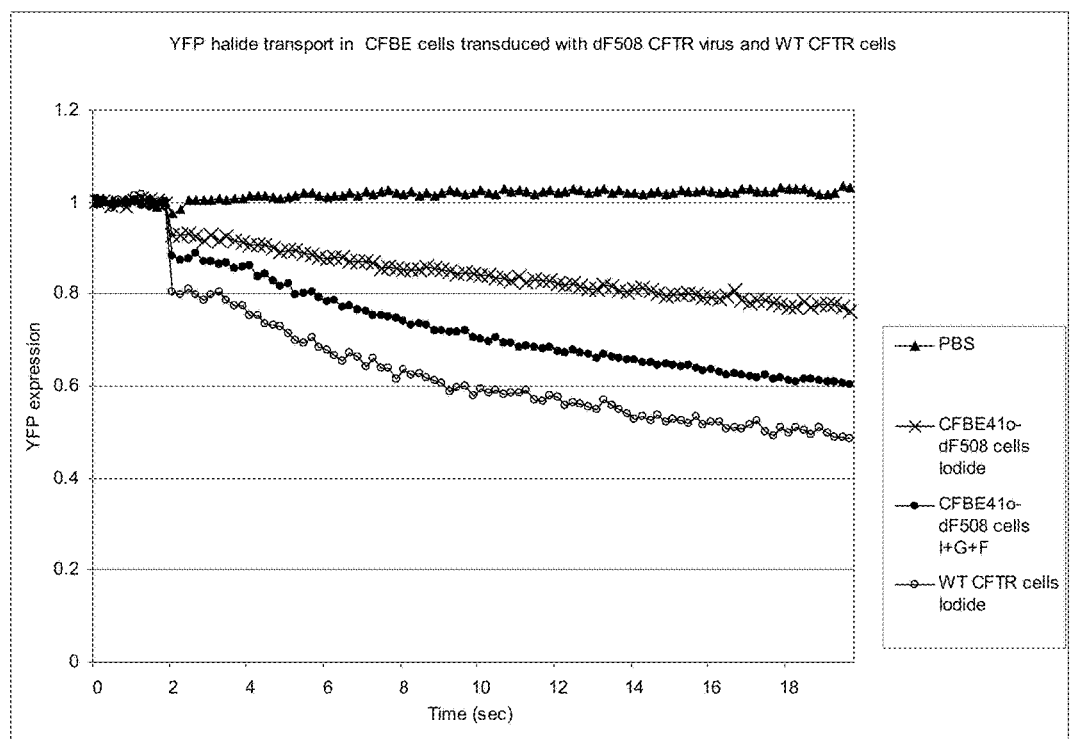
FIG. 2: YFP halide transport in CFBE cells transduced with ΔF508 CFTR virus and wild type CFTR cells

FIG. 2 shows results of such an experiment. Injection of PBS does not quench YFP fluorescence in ΔF508-CFTR expressing cells. In contrast, injection of iodide results in a slow quenching of fluorescence, where the slope of the curve indicates the rate of halide flux. A minimal increase in halide flux is observed after pre-incubation with forskolin and genistein, indicating that ΔF508-CFTR is activated by this combination. Furthermore, a much stronger increase in YFP fluorescence quenching is observed when the wild-type CFTR protein is expressed. These results confirm that this assay measures CFTR-dependent halide flux, and that the ΔF508-CFTR has reduced activity compared to the wild-type protein. Thus, quenching of YFP in the presence of ΔF508-CFTR is a specific measure of CFTR activity and can be used to identify correctors of defect ΔF508 CFTR activity in a high throughput screen.

Example 3

Screening of 11330 "Ad-siRNAs" in the CFTR-Dependent Halide Flux Assay

The CFTR-Dependent Halide Flux Assay, the development of which is described in Example 1, has been screened against an arrayed collection of 11,330 different recombinant adenoviruses mediating the expression of shRNAs in CFBE41o-cells. These shRNAs cause a reduction in expression levels of genes that contain homologous sequences by a mechanism known as RNA interference (RNAi). The 11330 Ad-siRNAs contained in the arrayed collection target 5046 different transcripts. On average, every transcript is targeted by 2 to 3 independent Ad-siRNAs. The screening assay followed the following time-course: CFBE41o-cells were seeded at 1000 cells per well in 96-well plates (transparent bottom, black sides). One day after seeding, an aliquot of the Ad-siRNA was applied to each well. Four days after seeding, each well received an aliquot of adenovirus expressing ΔF508-CFTR and an aliquot of adenovirus expressing YFP. Seven days after seeding, the YFP assay was performed as described in Example 2.

Figure 3:
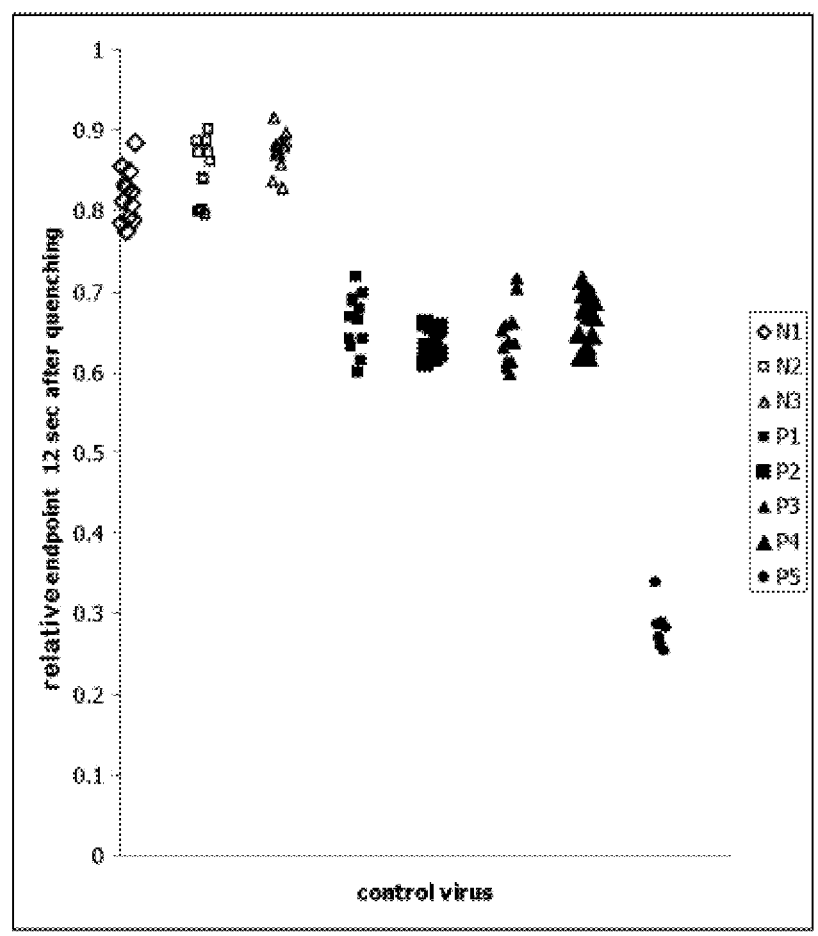
FIG. 3: Example of a control plate during Ad-siRNA screening

For every batch of Ad-siRNA plates, control plates were screened that contain control viruses that are produced under the same conditions as the SilenceSelect® adenoviral collection. The viruses include sets of negative control viruses (N1 (Ad5-empty_KD)), N2 (Ad5-empty_KD), N3 (no virus)), together with positive control viruses (P1 (Ad5-STX8_v5_KD)), P2 (Ad5-STX8_v5_KD), P3 (Ad5-BCAP31_v3_KD), P4 (Ad5-BCAP31_v3_KD)), P5 (Ad5-CFTR_v5_KI)). Every well of a virus plate contains 150 μL of virus crude lysate. A representative example of the performance of a plate tested with the screening protocol described above is shown in FIG. 3. In this figure, the calculated relative 12 sec endpoint of iodide-mediated quenching of the YFP reporter detected upon performing the assay for every recombinant adenovirus on the plate is shown (as defined by the average of the last three data-points divided by the average of the pre-injection baseline fluorescence).

For analysis of the screening of 11,330 Ad-siRNAs, data from the fluorescent plate reader is exported and analyzed using perl scripts and the R statistical package as follows:
1) Mean baseline fluorescence (prior to iodide injection) is calculated (YFP expression level).
2) Data are normalized against the baseline (set at 1).
3) Wells are excluded when more than 10% of the data points are above baseline.
4) Based on the input parameters, the curve fit is performed using the R statistics program for analysis. It will include the baseline at t=tinj, and use the rest of the data points until t=14s.
5) The exponential decay (y=a*e-bx+c) curve fit requires initial values for variables. Therefore, the script loops through different combinations of initial values, until it finds the optimal curve fit.
6) The slope at t=tinj is returned by determining the derivative of the function (initial slope).
7) The average of the three last data points (t=14 sec) is determined and calculated relative to baseline (endpoint). This value ranges from 1 (no quenching) to 0 (complete quenching of YFP).

Figure 4:
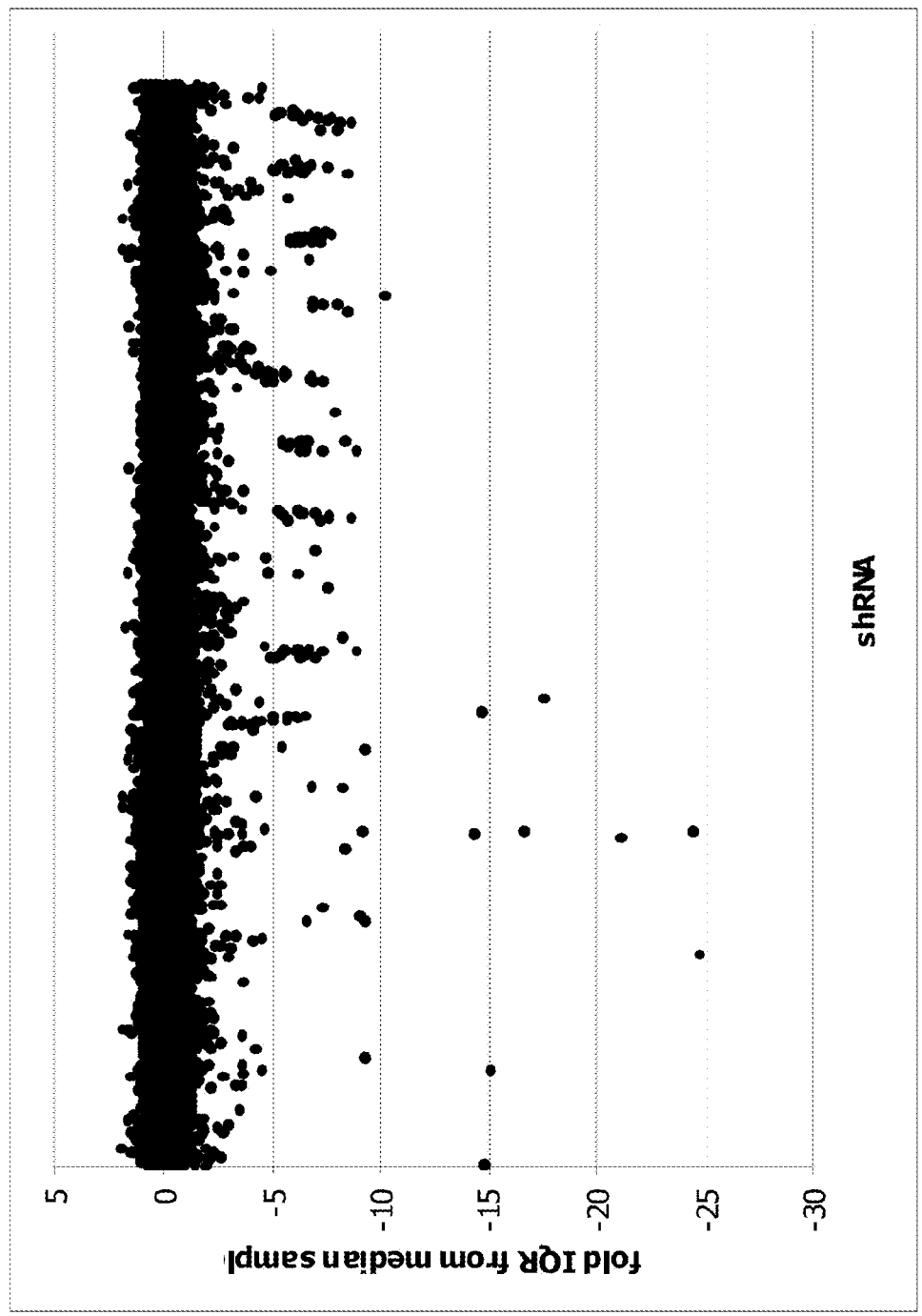
FIG. 4: High-throughput screening data on 11,330 Ad-siRNAs in the CFTR-Dependent Halide Flux Assay.

Identification of hits was performed both on the calculated 12-sec endpoint and the calculated initial slope. These values were expressed in fold standard deviation of the samples on the 96-well plate relative to the mean of the samples on the 96-well plate. When either of these values exceeds the cutoff value (defined as 1.5 fold the standard deviation below the sample mean), a Ad-siRNA virus is marked as a hit. An overview of the screening data is shown in FIG. 4, with hits below −1.5. The screen of 11,330 Ad-siRNAs procedure yielded 753 hits.

Example 4

Rescreen of the Primary Hits Using Independent Repropagation Material

To confirm the results of the identified Ad-siRNA in the CFTR-Dependent Halide Flux Assay, the following approach may be taken: the Ad-siRNA hits are repropagated using PerC6 cells (Crucell, Leiden, The Netherlands) at a 96-well plate level, followed by retesting in the CFTR-Dependent Halide Flux Assay. First, tubes containing the crude lysates of the identified hit Ad-siRNA's samples are picked from the SilenceSelect® collection and rearranged in 96 well plates together with negative/positive controls. As the tubes are labeled with a barcode (Screenmates™, Matrix technologies), quality checks are performed on the rearranged plates. To propagate the rearranged hit viruses, 40,000 PerC6.E2A cells are seeded in 200 microL of DMEM containing 10% non-heat inactivated FBS into each well of a 96 well plate and incubated overnight at 39° C. in a humidified incubator at 10% $CO_2$. Subsequently, 2 microL of crude lysate from the hit Ad-siRNA's rearranged in the 96 well plates as indicated above is added to the PerC6.E2A cells using a 96 well dispenser. The plates may then be incubated at 34° C. in a humidified incubator at 10% $CO_2$ for 5 to 10 days. After this period, the repropagation plates are frozen at −20° C., provided that complete CPE (cytopathic effect) could be seen. The propagated Ad-siRNAs are rescreened in the CFTR-Dependent Halide Flux Assay.

Data analysis for each of the rescreen is performed as follows. For every plate the average and standard deviation is calculated for the negative controls and may be used to convert each data point into a "cutoff value" that indicates the difference between the sample and the average of all negatives in terms of standard deviation of all negatives. Threshold settings for the rescreen were −2 fold standard deviation from the mean of the negative controls. At this cut-off, 315 Ad-siRNAs are again positive in the CFTR-Dependent Halide Flux Assay. Data for the TARGETs of the present invention are shown in Table 3 below, the halide flux is expressed as the fold stdev from the mean of the negative controls.

TABLE 3

Efficacy of the restoration of CFTR-dependent halide flux in CFBE41o-relevant to the present expression-inhibitory agent invention

| TARGET Gene Symbol | SEQ ID NO: DNA | Forskolin-Genistein induced halide flux in CFBE41o- |
|---|---|---|
| UGT3A2 | 2 | −5.485 |
| PHGDH | 3 | −6.495 |
| B3GNT3 | 4 | −4.495 |
| PPIH | 5 | −11.49 |
| CELSR3 | 6 | −2.16 |
| MC2R | 7 | −9.81 |
| MAS1L | 8 | −3.93 |
| LRRK2 | 9 | −5.865 |
| NLRP1 | 10, 11, 12, 13, 14 | −7.195 |
| PMS1 | 15, 16, 17 | −5.065 |
| MAK | 18 | −4.645 |
| CPD | 19 | −7.04 |
| CST7 | 20 | −3.87 |
| DUSP5 | 21 | −3.39 |
| PTPRG | 22 | −4.41 |
| IL6R | 23, 24 | −5.595 |
| GHR | 25 | −4.425 |
| CSF3 | 26, 27, 28 | −6.36 |
| SPNS1 | 29 | −7.025 |
| STX8_v5 | positive control | −6.9963 |
| BCAP31_v3 | positive control | −5.45241 |
| wild-type CFTR_v5 | positive control | −25.1772 |

A quality control of target Ad-siRNAs is performed as follows: Target Ad-siRNAs are propagated using derivatives of PERC6.E2A cells (Crucell, Leiden, The Netherlands) in 96-well plates, followed by sequencing the siRNAs encoded by the target Ad-siRNA viruses. PERC6.E2A cells are seeded in 96 well plates at a density of 40,000 cells/well in 180 µL PER.E2A medium. Cells are then incubated overnight at 39° C. in a 10% $CO_2$ humidified incubator. One day later, cells are infected with 1 µL of crude cell lysate from SilenceSelect® stocks containing target Ad-siRNAs. Cells are incubated further at 34° C., 10% $CO_2$ until appearance of cytopathic effect (as revealed by the swelling and rounding up of the cells, typically 7 days post infection). The supernatant is collected, and the virus crude lysate is treated with proteinase K by adding to 4 µL Lysis buffer (1× Expand High Fidelity buffer with MgCl2 (Roche Molecular Biochemicals, Cat. No 1332465) supplemented with 1 mg/mL proteinase K (Roche Molecular Biochemicals, Cat No 745 723) and 0.45% Tween-20 (Roche Molecular Biochemicals, Cat No 1335465) to 12 µL crude lysate in sterile PCR tubes. These tubes are incubated at 55° C. for 2 hours followed by a 15 minutes inactivation step at 95° C. For the PCR reaction, 1 µL lysate is added to a PCR master mix composed of 5 µL 10× Expand High Fidelity buffer with MgCl2, 0.5 µL of dNTP mix (10 mM for each dNTP), 1 µL of "Forward primer" (10 mM stock, sequence: 5' CCG TTT ACG TGG AGA CTC GCC 3' (SEQ. ID NO: 102), 1 µL of "Reverse Primer" (10 mM stock, sequence: 5' CCC CCA CCT TAT ATA TAT TCT TTC C 3') (SEQ. ID NO: 103), 0.2 µL of Expand High Fidelity DNA polymerase (3.5 U/µL, Roche Molecular Biochemicals) and 41.3 µL of H2O. PCR is performed in a PE Biosystems GeneAmp PCR system 9700 as follows: the PCR mixture (50 µL in total) is incubated at 95° C. for 5 minutes; each cycle runs at 95° C. for 15 sec., 55° C. for 30 sec., 68° C. for 4 minutes, and is repeated for 35 cycles. A final incubation at 68° C. is performed for 7 minutes. For sequencing analysis, the siRNA constructs expressed by the target adenoviruses are amplified by PCR using primers complementary to vector sequences flanking the SapI site of the pIPspAdapt6-U6 plasmid. The sequence of the PCR fragments is determined and compared with the expected sequence. All sequences are found to be identical to the expected sequence.

Example 5

Analysis of the Expression Levels for Certain Targets Identified in Human Primary Bronchial Epithelial Cells and Human Lung Expression levels for certain identified targets are determined in different isolates of lung epithelial cells as follows.

Microarray data from human lung large airway epithelia, non-smoker, non-COPD (Carolan et al., 2006) is downloaded from the NCBI website (http://www.ncbi.nlm.nih.gov/entrez/query.fcgi?db=gds&term=GSE5060[Accession] &cmd=search) and analyzed for expression of the HITS. Hits expressed in each of the samples present on these arrays ($p<0.05$) are considered expressed. All other hits are subsequently analyzed using real-time gene expression analysis as follows.

Two RNA samples from human total lung (either adult or fetal) are obtained from a commercial supplier (Stratagene). These samples will be referred to as "human lung".

Cultured primary bronchial epithelial cell isolates are obtained from Cell Applications Inc. (#502-05a, cryopreserved at first passage), from the University of Genova (Galieta lab, Genove, Italy) or from cultured CFBE41o-cells (human lung epithelial cells stably transfected with ΔF508-CFTR expression plasmids as described above) are utilized. Total RNA is extracted using the "RNAeasy Total RNA Isolation kit" (Qiagen).

The concentration of RNA in each sample is fluorimetrically quantified. A similar amount of RNA from each preparation is reverse transcribed into first strand cDNA with the "Taqman reverse transcription kit" from Applied Biosystems. Briefly, 300 ng RNA is included per 50 µL reaction mix containing 125 pmol of random hexamers, 25 U Rnase inhibitor, 62.5 U Multiscribe reverse transcriptase, 5 mM $MgCl_2$ and 0.5 mM of each dNTP. The reaction mixture is incubated at 25° C. for 10 minutes, followed by 30 minutes incubation at 48° C. and heat inactivation (5 minutes 95° C.) of the reverse transcriptase in a thermocycler (Dyad, MJ Research). Reactions are immediately chilled to 4° C. at the end of the program. To avoid multiple freeze/thaw cycles of the obtained cDNA, the different samples are pooled in 96-well plates, aliquoted and stored at −20° C.

Real-time PCR reactions are performed and monitored using the "ABI PRISM 7000 Sequence Detection System Instrument" (Applied Biosystems). Pre-designed, gene-specific Taqman probe and primer sets for quantitative gene expression are purchased from Applied Biosystems as part of the "Assays on Demand" Gene expression products. These commercially available kits are quality checked by the supplier and allow quantitative determination of the amount of target cDNA in the sample. The "Assays on Demand" gene expression products are used according to the protocol delivered by the supplier. The PCR mixture consisted of 1× "Taqman Universal PCR Mastermix no AmpErase UNG" and 1× "Taqman Gene Expression Assay on Demand mix" and 5 uL of the retro-transcription reaction product (1-40 ng of RNA converted into cDNA) in a total volume of 25 uL. After an initial denaturation step at 95° C. for 10 minutes, the cDNA products are amplified with 40 cycles consisting of 95° C. for 15 sec, and 60° C. for 1 minute. To normalize for variability in the initial quantities of cDNA between different samples, amplification reactions with the same cDNA are performed for the housekeeping gene GAPDH using the pre-developed "Assays on demand" primer set and Taqman probe mix and "Taqman Universal PCR Mastermix" (all Applied Biosystems) according to the manufacturer's instructions. Threshold cycle values (Ct), for example, the cycle number at which the amount of amplified gene of interest reached a fixed threshold are determined for each sample. A HIT is considered as expressed if the Ct value obtained for this hit is lower than 35 in at least one of the available human lung isolate and at least one of the cultured human bronchial epithelial (HBE) samples. This analysis of 315 hits yielded 210 genes expressed in bronchial epithelium.

TABLE 4

Expression of the targets in lung epithelial tissue

| TARGET Gene Symbol | SEQ ID NO: DNA | microarray (p-value) | lung Q-PCR (Ct) | HBE Q-PCR (Ct) | CFBE Q-PCR (Ct) |
|---|---|---|---|---|---|
| UGT3A2 | 2 | N/A | 37.255 | 38.18667 | 33.89 |
| PHGDH | 3 | 0.030273 | N/A | N/A | N/A |
| B3GNT3 | 4 | 0.00415 | N/A | N/A | N/A |
| PPIH | 5 | 0.00415 | N/A | N/A | N/A |
| CELSR3 | 6 | 0.081337 | 32.895 | 32.03 | 29.14 |
| MC2R | 7 | 0.466064 | 35.565 | 40 | 31.695 |
| MAS1L | 8 | 0.760937 | 33.2125 | 40 | 30.605 |
| LRRK2 | 9 | 0.303711 | 27.435 | 33.435 | 35.35 |
| NLRP1 | 10, 11, 12, 13, 14 | 0.888428 | 28.195 | 27.60667 | 27.97 |
| PMS1 | 15, 16, 17 | 0.000244 | N/A | N/A | N/A |
| MAK | 18 | 0.000244 | N/A | N/A | N/A |
| CPD | 19 | 0.000244 | N/A | N/A | N/A |
| CST7 | 20 | 0.533936 | 26.355 | 40 | 31.32 |
| DUSP5 | 21 | 0.000244 | N/A | N/A | N/A |
| PTPRG | 22 | 0.030273 | N/A | N/A | N/A |
| IL6R | 23, 24 | 0.00415 | N/A | N/A | N/A |
| GHR | 25 | 0.001953 | N/A | N/A | N/A |
| CSF3 | 26, 27, 28 | 0.544587 | 31.705 | 30.01 | 37.66 |
| SPNS1 | 29 | 0.018555 | N/A | N/A | N/A |

Example 6

"On Target Analysis" Using KD Viruses

To strengthen the validation of a hit, it is helpful to recapitulate its effect using a completely independent siRNA targeting the same target gene through a different sequence. This analysis is called the "on target analysis". In practice, this was done by designing multiple new shRNA oligonucleotides against the target using a specialised algorithm previously described, and incorporating these into adenoviruses, according to WO 03/020931. After virus production, these viruses were arrayed in 96 well plates, together with positive and negative control viruses. On average, 6 new independent Ad-siRNA's have been produced for a set of targets. One independent repropagation of these virus plates was then performed as described above for the rescreen in Example 4. The plates produced in this repropagation was tested in biological duplicate in the YFP assay at 3 MOIS according to the protocol described (Example 2). Ad-siRNA's mediating an increase in the quenching of the YFP reporter above the set cutoff value in at least 1 were nominated as hits scoring in the "on target analysis". The cutoff value in these experiments was defined as the average over the negative controls+2 times the standard deviation over the negative controls. Through this exercise, 141 hits were identified with at least two active shRNAs (range: 2-6, average: 2.46). These hits are considered "on target", and proceeded to the next validation experiment.

Example 7

Analysis of the Cell-Surface Expression of ΔF508 CFTR

A further validation of the correction of ΔF508 CFTR is the expression of this protein on the cell surface as measured by cell-surface biotinylation (Prince et al., 1994). This analysis allows a more quantitative measurement of the levels of restoration of cell-surface expressed ΔF508 CFTR, as well as the glycosylation status of the ΔF508 CFTR protein (Cheng et al., 1990). A preferred effect of a HIT would be increased cell-surface expression of ΔF508 CFTR, and especially "band C" (Cheng et al., 1990), fully glycosylated ΔF508 CFTR. The assay to measure cell surface expression of ΔF508-CFTR is performed in the following fashion: CFBE41o-cells are seeded in 60 mm cell culture dishes coated with 0.1 mg/mL bovine serum albumin (BSA), 0.03 mg/mL bovine collagen type 1 and 0.01 mg/mL human fibronectin. CFBE41o-cells are cultured in MEM containing 10% Fetal Bovine Serum, 2 mM glutamine, 100 IU/mL penicillin, 0.1 mg/mL streptomycine sulfate and 0.5 mg/mL hygromycin B at 37° C., 5% $CO_2$ in a humidified chamber. One day after seeding, an aliquot of the Ad-siRNA is applied to each well. Four days after seeding, each well receives an aliquot of adenovirus expressing ΔF508-CFTR. Seven days after seeding, the cell cultures are exposed to 10 microM forskolin and 100 microM genistein for 15 min at 37° C. The cells are washed three times in PBS pH 8 to which 1 mM $MgCl_2$ and 0.1 mM $CaCl_2$ are added at 0° C., and 1.5 ml of 0.5 mg/mL sulfo-NHS-SS-biotin (Pierce #21328) diluted in PBS pH 8 supplemented with 1 mM $MgCl_2$ and 0.1 mM $CaCl_2$ is added to the cell cultures. The cell culture dishes are gently rocked for 30 min at 4° C. Cell cultures are washed three times in PBS containing 1% bovine serum albumin at 0° C. and one with PBS at 0° C. Cells are scraped from the plastic in PBS at 0° C. and transferred to 1.5 mL Eppendorf tubes. The cells are harvested by centrifugation at 4° C., 20,000 g for 1 min. Cells are lysed in 270 microl of RIPA buffer (1% Triton X100, 150 mM NaCl, 25 mM Tris-Cl pH7.4, 0.005% sodium deoxycholate, protease inhibitor cocktail (Roche #11873580001) at 2 mg/mL and 0.3 mM Pefablock SC (Roche #11429868001)) for 15 min at 0° C. After centrifugation for 20 min at 20,000 g, the supernatant is transferred to an Eppendorf tube containing 30 microL of pre-washed 50% v/v NeutrAvidin agarose resin beads (Thermo Scientific #29200) in RIPA buffer. The supernatant is incubated with the avidin beads for 16 hrs at 4° C. with gentle rocking. Beads are harvested by centrifugation at 4° C., 20,000 g for 20 sec and washed twice with RIPA buffer, twice with (25 mM Tris-Cl pH 7.4, 150 mM NaCl, 1% Triton X100) at 0° C. and twice with (25 mM Tris-Cl pH 7.4, 150 mM NaCl) at 0° C. Beads are harvested by centrifugation at 4° C., 20,000 g for 20 sec and resuspended in 15 microl of (24 mM Tris-Cl pH 6.8, 4% glycerol, 50 mM dithiotreitol, 0.04% bromophenol-blue) and incubated for 20 min at 37° C. The supernatant is analyzed on Western blots (BioRad Criterion XT gels, 3-8% polyacrylamide #3450131). Western blots are probed with a rat antibody raised against CFTR (monoclonal 3G11), an antibody against a protein not expressed on the cell surface as a negative control (anti laminA, Sigma #L1293) and an antibody against a protein constitutively expressed on the cell surface as a positive control (E-cadherin, Abcam #ab1416). Secondary antibodies are: ECLTM anti-rabbit IgG, HRP-Linked whole Ab (from donkey) (GE Healthcare #NA934-1), ImmunoPure Goat Anti-Rat IgG, HRP conjugated (Thermo Scientific #31470), ImmunoPure Goat Anti-Mouse IgG, HRP conjugated (Thermo Scientific #31430). Development of the blots is performed with enhanced chemiluminescence on a Biorad ChemiDoc XRS. Quantification of the cell surface expression of ΔF508 CFTR was performed with Biorad Quantity One software.

Positive and negative controls for the biotinylation include incubation of cell culture at 27° C. for 48 hrs to correct misfolding and trafficking of ΔF508 CFTR, and omission of Ad-siRNAs respectively. No signal is detected when the biotinylation reagent was omitted. The cell surface expression of ΔF508 CFTR is quantitated relative to the signal obtained without Ad-siRNAs (relative to the E-cadherin signal, and set at 0) and the signal obtained at 27° C. for 48 hrs (relative to the E-cadherin signal, and set at 1). Quantification is performed both for band B ΔF508 CFTR (core glycosylated) and band C ΔF508 CFTR (fully glycosylated). The analysis of 142 hits yields 19 TARGETS that show expression of band C ΔF508 CFTR and band B ΔF508 CFTR on the cell surface of CFBE41o-cells upon Ad-siRNAs-mediated knock-down of that TARGET. These TARGETS are listed in Table 1.

TABLE 5

Cell surface exprerssion of CFTR ΔF508 in CFBE41o-cell culture upon TARGET Ad-siRNA application

| TARGET Gene Symbol | SEQ ID NO: DNA | CFTRΔF508 cell surface expression | C-band/B-band ratio |
|---|---|---|---|
| UGT3A2 | 2 | 0.906 | 0.278 |
| PHGDH | 3 | 0.573 | 0.173 |
| B3GNT3 | 4 | 0.113 | 0.121 |
| PPIH | 5 | 0.408 | 0.176 |
| CELSR3 | 6 | 2.179 | 0.213 |
| MC2R | 7 | 1.082 | 0.412 |
| MAS1L | 8 | 0.179 | 0.289 |
| LRRK2 | 9 | 1.293 | 0.280 |
| NLRP1 | 10, 11, 12, 13, 14 | 0.761 | 0.718 |
| PMS1 | 15, 16, 17 | 0.461 | 0.284 |
| MAK | 18 | 0.201 | 0.309 |
| CPD | 19 | 1.294 | 0.220 |
| CST7 | 20 | 0.740 | 0.238 |
| DUSP5 | 21 | 1.219 | 0.241 |
| PTPRG | 22 | 0.380 | 0.139 |
| IL6R | 23, 24 | 1.135 | 0.294 |
| GHR | 25 | 0.576 | 0.241 |
| CSF3 | 26, 27, 28 | 1.663 | 0.223 |
| SPNS1 | 29 | 0.276 | 0.305 |
| low temperature rescue | positive control | 1.000 | 0.754 |

Example 8

Analysis of the Trans-Epithelial Chloride Flux in CFTR ΔF508 Homozygous Primary Bronchial Epithelial Cells A further validation of the correction of ΔF508 CFTR is the correction of trans-epithelial chloride transport in primary bronchial epithelial cell cultures from a CF patient, grown in a filter support. These well-differentiated primary human bronchial epithelial cell cultures derived from CF patients homozygous for the ΔF508 CFTR mutation show a residual forskolin and genistein-stimulated chloride flux that is less than 2% of non-CF control cell cultures. A standard drug addition protocol (Devor et al., 2000) can be used to detect transepithelial currents due to CFTR. Short-circuit current ($I_{sc}$) across HBE primary cultures can be measured as described (Myerburg et al., 2006; Myerburg et al., 2008). Cells cultured on filter supports are mounted in modified Ussing chambers, and the cultures are continuously short-circuited with an automatic voltage clamp (Physiological Instruments, San Diego, Calif.). The basolateral bathing solution composition is: 120 mM NaCl, 25 mM NaHCO$_3$, 3.3 mM KH$_2$PO$_4$, 0.8 mM K$_2$HPO$_4$, 1.2 mN MgCl$_2$, 1.2 mM CaCl$_2$, and 10 mM glucose. A basal-to-apical Cl gradient can be imposed by reducing the NaCl concentration of the apical bathing solution by replacing NaCl with equimolar Na-gluconate. The chambers are maintained at 37° C. and gassed continuously with a mixture of 95% O$_2$-5% CO$_2$ which fixed the pH at 7.4. Following a 5 min equilibration period, the baseline $I_{sc}$ is recorded. Sodium currents are blocked by addition of the epithelial sodium channel (ENaC) blocker, amiloride (10 μM), to the apical bath. Subsequently, the cAMP agonist-forskolin (10 μM, Sigma), the CFTR potentiator-genistein (50 μM, Sigma), and the CFTR channel blocker—CFTRinh-172 (10 μM; Calbiochem, San Diego, Calif.) are added sequentially, at the current steady-state, to determine cAMP-stimulated CFTR currents. Addition of the CFTR inhibitor CFTRinh-172 is done to show specificity of ion flux through CFTR (Ma et al., 2002). Using this analysis, the transepithelial currents associated with knockdown of the targets are shown in Table 6. Each of these targets shows a significant increase in chloride transport across the epithelial monolayer. Interestingly, the level of CFTR response can reach up to 20% of wild-type CFTR-mediated currents, suggesting a clinically meaningful level of CFTR channel activity (Sheppard et al., 1993).

TABLE 6

Efficacy of the restoration of chloride transport in primary CF bronchial epithelial cell culture relevant to the present expression-inhibitory agent invention

| TARGET Gene Symbol | SEQ ID NO: DNA | Forskolin-Genistein induced chloride flux in CF primary epithelial cells compared to control cells (non-CF) |
|---|---|---|
| UGT3A2 | 2 | 22.9% |
| PHGDH | 3 | 6.6% |
| B3GNT3 | 4 | 4.7% |
| PPIH | 5 | 9.1% |
| CELSR3 | 6 | 11.8% |
| MC2R | 7 | 6.8% |
| MAS1L | 8 | 6.6% |
| LRRK2 | 9 | 15.9% |
| NLRP1 | 10, 11, 12, 13, 14 | 9.0% |
| PMS1 | 15, 16, 17 | 9.3% |
| MAK | 18 | 9.5% |
| CPD | 19 | 14.8% |
| CST7 | 20 | 10.7% |
| DUSP5 | 21 | 15.5% |
| PTPRG | 22 | 10.7% |
| IL6R | 23, 24 | 19.9% |
| GHR | 25 | 11.6% |
| CSF3 | 26, 27, 28 | 9.4% |
| SPNS1 | 29 | 13.4% |

In the table above the knock-down sequence corresponding to SEQ 57 was used, which demonstrates a specific effect with UGT3A2. However due to the close homology and the high level of sequence identity between UGT3A2 and UGT3A1 it would be expected that a knock down of UGT3A1 would have a similar effect on the restoration of chloride transport in primary CF bronchial epithelial cells.

REFERENCES

Antonin, W., C. Holroyd, D. Fasshauer, S. Pabst, G. F. Von Mollard, and R. Jahn. 2000. A SNARE complex mediating fusion of late endosomes defines conserved properties of SNARE structure and function. *Embo J.* 19:6453-64.

Bilan, F., V. Thoreau, M. Nacfer, R. Derand, C. Norez, A. Cantereau, M. Garcia, F. Becq, and A. Kitzis. 2004. Syntaxin 8 impairs trafficking of cystic fibrosis transmembrane conductance regulator (CFTR) and inhibits its channel activity. *J Cell Sci.* 117:1923-35.

Carolan, B. J., A. Heguy, B. G. Harvey, P. L. Leopold, B. Ferris, and R. G. Crystal. 2006. Up-regulation of expression of the ubiquitin carboxyl-terminal hydrolase L1 gene in human airway epithelium of cigarette smokers. *Cancer Res.* 66:10729-40.

Cheng, S. H., R. J. Gregory, J. Marshall, S. Paul, D. W. Souza, G. A. White, C. R. O'Riordan, and A. E. Smith. 1990. Defective intracellular transport and processing of CFTR is the molecular basis of most cystic fibrosis. *Cell.* 63:827-34.

Denning, G. M., M. P. Anderson, J. F. Amara, J. Marshall, A. E. Smith, and M. J. Welsh. 1992. Processing of mutant cystic fibrosis transmembrane conductance regulator is temperature-sensitive. *Nature.* 358:761-4.

Devor, D. C., Bridges, R. J., and Pilewski, J. M. (2000). Pharmacological modulation of ion transport across wild-type and DeltaF508 CFTR-expressing human bronchial epithelia. Am J Physiol Cell Physiol 279, C461-479.

Fischer, D. F., A. K. Scaffidi, S. Griffioen, M. Roseboom, and R. A. Janssen. 2006. Identification of novel drug targets to treat cystic fibrosis using adenoviral knock-down technology. *Ped Pulmonol.* 41:Suppl. 29, p. 209.

Galietta, L. J., P. M. Haggie, and A. S. Verkman. 2001a. Green fluorescent protein-based halide indicators with improved chloride and iodide affinities. *FEBS Lett.* 499:220-4.

Galietta, L. V., S. Jayaraman, and A. S. Verkman. 2001b. Cell-based assay for high-throughput quantitative screening of CFTR chloride transport agonists. *Am J Physiol Cell Physiol.* 281:C1734-42.

Gruenert, D. C., M. Willems, J. J. Cassiman, and R. A. Frizzell. 2004. Established cell lines used in cystic fibrosis research. *J Cyst Fibros.* 3 Suppl 2:191-6.

Guggino, W. B., and B. A. Stanton. 2006. New insights into cystic fibrosis: molecular switches that regulate CFTR. *Nat Rev Mol Cell Biol.* 7:426-36.

Hwang, T. C., F. Wang, I. C. Yang, and W. W. Reenstra. 1997. Genistein potentiates wild-type and delta F508-CFTR channel activity. *Am J Physiol.* 273:C988-98.

Lambert, G., B. Becker, R. Schreiber, A. Boucherot, M. Reth, and K. Kunzelmann. 2001. Control of Cystic Fibrosis Transmembrane Conductance Regulator Expression by BAP31. *J Biol. Chem.* 276:20340-20345.

Li, H., D. N. Sheppard, and M. J. Hug. 2004. Transepithelial electrical measurements with the Ussing chamber. *J Cyst Fibros.* 3 Suppl 2:123-6.

Ma, L., H. A. Bluyssen, M. De Raeymaeker, V. Laurysens, N. van der Beek, H. Pavliska, A. J. van Zonneveld, P. Tomme, and H. H. van Es. 2001. Rapid determination of adenoviral vector titers by quantitative real-time PCR. *J Virol Methods.* 93:181-8.

Ma, T., Thiagarajah, J. R., Yang, H., Sonawane, N. D., Folli, C., Galietta, L. J., and Verkman, A. S. (2002). Thiazolidinone CFTR inhibitor identified by high-throughput screening blocks cholera toxin-induced intestinal fluid secretion. J Clin Invest 110, 1651-1658.

Myerburg, M. M., Butterworth, M. B., McKenna, E. E., Peters, K. W., Frizzell, R. A., Kleyman, T. R., and Pilewski, J. M. (2006). Airway surface liquid volume regulates ENaC by altering the serine protease-protease inhibitor balance: a mechanism for sodium hyperabsorption in cystic fibrosis. J Biol Chem 281, 27942-27949.

Myerburg, M. M., McKenna, E. E., Luke, C. J., Frizzell, R. A., Kleyman, T. R., and Pilewski, J. M. (2008). Prostasin expression is regulated by airway surface liquid volume and is increased in cystic fibrosis. Am J Physiol Lung Cell Mol Physiol 294, L932-941.

Prince, L. S., R. B. Workman, Jr., and R. B. Marchase. 1994. Rapid endocytosis of the cystic fibrosis transmembrane conductance regulator chloride channel. *Proc Natl Acad Sci USA.* 91:5192-6.

Quinton, P. M. 1990. Cystic fibrosis: a disease in electrolyte transport. *Faseb J.* 4:2709-17.

Riordan, J. R., J. M. Rommens, B. Kerem, N. Alon, R. Rozmahel, Z. Grzelczak, J. Zielenski, S. Lok, N. Playsic, J. L. Chou, M. L. Drumm, M. C. Ianuzzi, F. C. Collins, and L.-C. Tsui. 1989. Identification of the cystic fibrosis gene: cloning and characterization of complementary DNA. *Science.* 245:1066-73.

Rowe, S. M., S. Miller, and E. J. Sorscher. 2005. Cystic fibrosis. *N Engl J Med.* 352:1992-2001.

Sheppard, D. N., Rich, D. P., Ostedgaard, L. S., Gregory, R. J., Smith, A. E., and Welsh, M. J. (1993). Mutations in CFTR associated with mild-disease-form Cl-channels with altered pore properties. Nature 362, 160-164.

Thoreau, V., T. Berges, I. Callebaut, Z. Guillier-Gencik, L. Gressin, A. Bernheim, F. Karst, J. P. Mornon, A. Kitzis, and J. C. Chomel. 1999. Molecular cloning, expression analysis, and chromosomal localization of human syntaxin 8 (STX8). *Biochem Biophys Res Commun.* 257:577-83.

Ulloa-Aguirre, A., J. A. Janovick, S. P. Brothers, and P. M. Conn. 2004. Pharmacologic rescue of conformationally-defective proteins: implications for the treatment of human disease. *Traffic.* 5:821-37.

All publications, including but not limited to patents and patent applications, cited in this specification are herein incorporated by reference as if each individual publication were specifically and individually indicated to be incorporated by reference herein as though fully set forth.

From the foregoing description, various modifications and changes in the compositions and methods of this invention will occur to those skilled in the art. All such modifications coming within the scope of the appended claims are intended to be included therein.

We claim:

1. An in vitro method for identifying a compound that increases the functional activity of CF-associated mutant CFTR, comprising:

(a) contacting a compound with a polypeptide comprising an amino acid sequence selected from the group consisting of SEQ ID NO: 33, and fragments thereof, wherein said polypeptide is in an in vitro cell-free preparation;

(b) measuring the binding affinity of said compound to said polypeptide;
(c) contacting a population of mammalian cells expressing said polypeptide, wherein the cells also express a CF-associated mutant CFTR, with the compound that exhibits binding affinity; and
(d) identifying a compound that increases the functional activity of the CF-associated mutant CFTR.

2. The method of claim 1, wherein the method is used to identify compounds that promote migration of CF-associated mutant CFTR ΔF508-CFTR to the plasma membrane.

3. An in vitro method for identifying a compound that increases the functional activity of CF-associated mutant CFTR, comprising:
   a) contacting a compound with a polypeptide comprising an amino acid sequence selected from the group consisting of SEQ ID NO: 33, and fragments thereof, or with a nucleic acid encoding said polypeptide;
   b) measuring activity or expression of said polypeptide;
   c) contacting a population of mammalian cells expressing said polypeptide, wherein the cells also express a CF-associated mutant CFTR, with the compound that significantly inhibits the expression or activity of the polypeptide; and
   d) identifying the compound that increases the functional activity of CF-associated mutant CFTR.

4. The method according to claim 1 or 3, which additionally comprises the step of comparing the compound to be tested to a control.

5. The method according to claim 4, wherein said control is where the polypeptide or nucleic acid has not been contacted with said compound.

6. The method according to claim 4 wherein said control is a population of mammalian cells that does not express said polypeptide.

7. The method according to claim 1 or 3, wherein said compound is selected from the group consisting of compounds of a commercially available screening library and compounds having binding affinity for a polypeptide comprising an amino acid sequence of SEQ ID NO: 33.

8. The method according to claim 1 or 3, wherein said compound is a peptide in a phage display library or an antibody fragment library.

9. The method of claim 1 or 3 wherein the CF-associated mutant CFTR is ΔF508-CFTR.

10. The method of claim 3, wherein the method is used to identify compounds that promote migration of CF-associated mutant CFTR ΔF508-CFTR to the plasma membrane.

\* \* \* \* \*